US012496360B2

(12) United States Patent
Roy et al.

(10) Patent No.: US 12,496,360 B2
(45) Date of Patent: *Dec. 16, 2025

(54) GENE EDITING-BASED METHOD OF ATTENUATING THE BETA-AMYLOID PATHWAY

(71) Applicant: Wisconsin Alumni Research Foundation, Madison, WI (US)

(72) Inventors: Subhojit Roy, Madison, WI (US); Jichao Sun, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 275 days.

This patent is subject to a terminal disclaimer.

(21) Appl. No.: 18/319,042

(22) Filed: May 17, 2023

(65) Prior Publication Data

US 2023/0293732 A1 Sep. 21, 2023

Related U.S. Application Data

(60) Continuation of application No. 17/494,457, filed on Oct. 5, 2021, now Pat. No. 11,701,436, which is a division of application No. 16/251,970, filed on Jan. 18, 2019, now Pat. No. 11,173,216.

(60) Provisional application No. 62/618,694, filed on Jan. 18, 2018.

(51) Int. Cl.

| | |
|---|---|
| ***A61K 48/00*** | (2006.01) |
| ***A61K 9/00*** | (2006.01) |
| ***A61P 25/28*** | (2006.01) |
| ***C07K 14/47*** | (2006.01) |
| ***C12N 9/22*** | (2006.01) |
| ***C12N 15/10*** | (2006.01) |
| ***C12N 15/90*** | (2006.01) |

(52) U.S. Cl.

CPC ........ *A61K 48/0066* (2013.01); *A61K 9/0019* (2013.01); *A61K 48/0008* (2013.01); *A61K 48/0058* (2013.01); *A61K 48/0075* (2013.01); *A61P 25/28* (2018.01); *C07K 14/4711* (2013.01); *C12N 9/22* (2013.01); *C12N 15/102* (2013.01); *C12N 15/907* (2013.01); *C12N 2310/20* (2017.05); *C12N 2740/16043* (2013.01); *C12N 2750/14143* (2013.01)

(58) Field of Classification Search

None

See application file for complete search history.

(56) References Cited

U.S. PATENT DOCUMENTS 11,173,216 B2 11/2021 Roy et al.
11,701,436 B2 * 7/2023 Roy ........................ A61P 25/28 424/93.2
2016/0175462 A1 * 6/2016 Zhang ................ A61K 48/0058 514/44 R
2017/0240888 A1 * 8/2017 Tremblay ............. C12N 15/113
2019/0216950 A1 7/2019 Roy et al.
2022/0023444 A1 1/2022 Roy et al.

FOREIGN PATENT DOCUMENTS

WO 0173002 A2 10/2001

OTHER PUBLICATIONS

Aime, P. et al.; Trib3 Is Elevated in Parkinson's Disease and Mediates Death in Parkinson's Disease Models: Journal of Neuroscience, vol. 35; 2015; pp. 10731-10749, doi:10.1523/JNEUROSCI.0614-15.2015.

Banks, W.; "From blood-brain barrier to blood-brain interface: new opportunities for CNS drug delivery"; Nature Reviews, vol. 15; 2016; pp. 275-292.

Beckett, C., et al.; Nuclear signalling by membrane protein intracellular domains: the AICD enigma; Cell Signal, vol. 24; 2012; pp. 402-409; doi:10.1016/j.cellsig.2011.10.007.

Brinkman, E. K. et al.; "Easy quantitative assessment of genome editing by sequence trace decomposition"; Nucleic Acids Research vol. 42, e168; 2014; doi:10.1093/nar/gku936.

Carlson-Stevermer, J. et al. "Assembly of CRISPR ribonucleoproteins with biotinylated oligonucleotides via an RNA aptamer for precise gene editing"; Nat Commun, vol. 8, 1711; 2017; doi: 10.1038/s41467-017-01875-9.

Chakrabarty, P. et al.; "Capsid serotype and timing of injection determines AAV transduction in the neonatal mice prain"; PLoS One, vol. 8, e67680; 2013; doi:10.1371/journal.pone.0067680.

Chow, V. W., et al.; "An overview of APP processing enzymes and products" Neuromolecular Med, vol. 12; 2010; pp. 1-12; doi:10.1007/s12017-009-8104-z.

Citron, M. et al.; "Generation of amyloid beta protein from its precursor is sequence specific"; Neuron, vol. 14; 1995; pp. 661-670; doi:0896-6273(95)90323-2.

Das, U. et al.; "Activity-induced convergence of APP and BACE-1 in acidic microdomains via an endocytosis-dependent pathway"; Neuron, vol. 79; 2013; pp. 447-460, doi:10.1016/j.neuron.2013.05.035.

Das, U. et al.; "Visualizing APP and BACE-1 approximation in neurons yields insight into the amyloidogenic pathway" Nat Neurosci, vol. 19; 2016; pp. 55-64; doi:10.1038/nn.4188.

(Continued)

*Primary Examiner* — Brian Whiteman
*Assistant Examiner* — Khaleda B Hasan
(74) *Attorney, Agent, or Firm* — Karen A. LeCuyer; DeWitt LLP

(57) ABSTRACT

Described herein are CRISPR/Cas9 constructs designed for the C-terminal truncation of human amyloid precursor protein (APP) as well as methods of making and using such a construct.

6 Claims, 53 Drawing Sheets
(37 of 53 Drawing Sheet(s) Filed in Color)
Specification includes a Sequence Listing.

(56) References Cited

OTHER PUBLICATIONS

De Strooper, B. et al.; "The Cellular Phase of Alzheimer's Disease"; Cell, vol. 164; 2016; pp. 603-615.
Deverman, B. et al.; "Cre-dependent selection yields AAV variants for widespread gene transfer to the adult brain"; Nature Biotechnology, vol. 34, Issue No. 2; 2016; pp. 204-209.
Deyts, C. et al.; "APP Receptor? To Be or Not To Be"; Trends in Pharmacological Sciences, vol. 37; 2016; pp. 390-411, doi:10.1016/j.tips.2016.01.005.
Doench, J. et al.; "Optimized sgRNA design to maximize activity and minimize off-target effects of CRISPR-Cas9"; Nature Biotechnology, vol. 34, Issue No. 2; 2016; pp. 184-191 doi:10.1037/nbt3437.
Fellmann, C. et al.; "Cornerstones of CRISPR-Cas in drug discovery and therapy"; Nat Rev Drug Discov, vol. 16; 2017; pp. 89-100; doi:10.1038/nrd.2016.238.
Fol, R. et al. "Viral gene transfer of APPsalpha rescues synaptic failure in an Alzheimer's disease mouse model"; Acta Neuropathol, vol. 131; 2016; pp. 247-266; doi:10.1007/s00401-015-1498-9.
Fu, Y. et al.; "Improving CRISPR-Cas nuclease specificity using truncated guide RNAs"; Nature Biotechnology, vol. 32, Issue No. 3; 2014; pp. 279-284.
Guo, W. et al.; "Fragile X Proteins FMRP and FXR2P Control Synaptic GluA1 Expression and Neuronal Maturation via Distinct Mechanisms"; Cell Rep, vol. 11; 2015; pp. 1651-1666; doi:10.1016/j.celrep.2015.05.013.
Gyorgy, B. et al.; "CRISPR/Cas9 Mediated Disruption of the Swedish APP Allele as a Therapeutic Approach for Early-Onset Alzheimer's Disease"; Mol Ther Nucleic Acids, vol. 11; 2018; pp. 429-440, doi:10.1016/j.omtn.2018.03.007.
Haass, C. et al.; "Soluble protein oligomers in neurodegeneration: lessons from the Alzheimer's amyloid β-peptide"; Molecular Cell Biology, vol. 8; 2007; pp. 101-112.
Haass, C. et al.; "Trafficking and Proteolytic Processing of APP"; Cold Spring Harbor Perspectives in Medicine, vol. 2, Issue No. 5; 2012; pp. 1-25.
Hampel, H. et al.; "The future of Alzheimer's disease: The next 10 years"; Progress in Neurobiology, vol. 95; 2011; pp. 718-728.
Hardy, J. et al.; "The Amyloid Hypothesis of Alzheimer's Disease: Progress and Problems on the Road to Therapeutics"; Science, vol. 297; 2002; pp. 353-355.
Hendriks, L. et al.; "Presenile dementia and cerebral haemorrhage linked to a mutation at codon 692 of the β-amyloid precursor protein gene"; Nature Genetics, vol. 1; 1992; pp. 218-221.
Hocquemiller, M. et al.; "Adeno-Associated Virus-Based Gene Therapy for CNS Diseases"; Human Gene Therapy, vol. 27, Issue No. 7; 2016; pp. 478-496.
International Search Report and Written Opinion for International Application PCT/US2019/014249; International Filing Date: Jan. 18, 2019; Date of Mailing: May 21, 2019; 16 pages.
Joung, J. et al.; "Genome-scale CRISPR-Cas9 knockout and transcriptional activation screening"; Nat Protoc, vol. 12; 2017; pp. 828-863; doi:10.1038/nprot.2017.016.
Kim, J. Y.; "Widespread Neuronal Transduction of the Rodent CNS via Neonatal Viral Injection"; Methods Mol Biol, vol. 1382; 2016; pp. 239-250; doi:10.1007/978-1-4939-3271-9_17.
Komor, A. et al.; "CRISPR-Based Technologies for the Manipulation of Eukaryotic Genomes"; Cell, vol. 168; 2017; pp. 20-36.
Koo, E. H. et al.; "Evidence that production and release of amyloid beta-protein involves the endocytic pathway"; J Biol Chem, vol. 269; 1994; pp. 17386-17389.
Kuscu, C. et al.; "Genome-wide analysis reveals characteristics of off-target sites bound by the Cas9 endonuclease"; Nature Biotechnology, vol. 32, Issue No. 7; 2014; pp. 677-683.
Lai, A., et al.; "Characterization of sorting signals in the beta-amyloid precursor protein cytoplasmic domain"; J Biol Chem, vol. 270; 1995; pp. 3565-3573.
Lee, M. S. et al.; "APP processing is regulated by cytoplasmic phosphorylation"; J Cell Biol, vol. 163; 2003; pp. 83-95; doi:10.1083/jcb.200301115.
Liu, Y. et al.; "Brain-targeting gene delivery and cellular internalization mechanisms for modified rabies virus glycoprotein RVG29 nanoparticles"; Biomaterials, vol. 30; 2009; pp. 4195-4202.
Luo, S. et al.; "Water Soluble Poly(histamine acrylamide) with Superior Buffer Capacity Mediates Efficient and Nontoxic In Vitro Gene Transfection"; Journal of Polymer Science Part A: Polymer Chemistry, vol. 49; 2011; pp. 3366-3373.
McMahon, M. A. et al.; "Gene therapy: Gene-editing therapy for neurological disease"; Nat Rev Neurol, vol. 13; 2017; pp. 7-9; doi:10.1038/nmneurol.2016.190.
Mendell, J. et al.; "Single-Dose Gene-Replacement Therapy for Spinal Muscular Atrophy"; The New England Journal of Medicine, vol. 377, Issue No. 18; 2017; pp. 1713-1722.
Mockett, B. G. et al.; "Therapeutic Potential of Secreted Amyloid Precursor Protein APPsalpha"; Front Mol Neurosci, vol. 10; 2017; pp. 30; doi:10.3389/fnmol.2017.00030.
Morel, E. et al.; "Phosphatidylinositol-3-phosphate regulates sorting and processing of amyloid precursor protein through the endosomal system"; Nat Commun, vol. 4, Issue No. 2250; 2013; doi:10.1038/ncomms3250.
Muller, U. C. et al.; "Physiological functions of APP family proteins"; Cold Spring Harb Perspect Med, vol. 2, a006288; 2012; doi:10.1101/cshperspect.a006288.
Muller, U. C., et al.; "Not just amyloid: physiological functions of the amyloid precursor protein family"; Nat Rev Neurosci, vol. 18; 2017; pp. 281-298, doi:10.1038/nrn.2017.29.
Musiek, E. et al.; "Three dimensions of the amyloid hypothesis: time, space and 'wingmen'"; Nature Neuroscience, vol. 18; 2015; pp. 800-806.
Nitsch, et al.; "Release of Alzheimer amyloid precursor derivatives stimulated by activation of muscarinic acetylcholine receptors"; Science, vol. 258; 1992; pp. 304-307.
O'Brien, R. J. et al.; "Amyloid precursor protein processing and Alzheimer's disease"; Annu Rev Neurosci, vol. 34; 2011; 185-204, doi:10.1146/annurev-neuro-061010-113613.
Paquet, D. et al.; "Efficient introduction of specific homozygous and heterozygous mutations using CRISPR/Cas9"; Nature, vol. 533, 125-129; 2016; doi:10.1038/nature17664.
Pardossi, et al.; "The physiology of the beta-amyloid precursor protein intracellular domain AICD"; J Neurochem, vol. 120, Suppl 1; 2012; pp. 109-124; doi:10.1111/j.1471-4159.2011.07475.x.
Park, C. Y. et al.; "Reversion of FMR1 Methylation and Silencing by Editing the Triplet Repeats in Fragile X iPSC-Derived Neurons"; Cell Rep, vol. 13; 2015; pp. 234-241; doi:10.1016/j.celrep.2015.08.084.
Passini, M. A. et al.; "Widespread gene delivery and structure-specific patterns of expression in the brain after intraventricular injections of neonatal mice with an adeno-associated virus vector"; J Virol, vol. 75; 2001; pp. 12382-12392; doi:10.1128/JVI.75.24.12382-12392.2001.
Perez, R. G. et al.; "Mutagenesis identifies new signals for beta-amyloid precursor protein endocytosis, turnover, and the generation of secreted fragments, including Abeta42"; J Biol Chem, vol. 274; 1999; pp. 18851-18856.
Perrin, et al.; "Multimodal techniques for diagnosis and prognosis of Alzheimer's disease"; Nature, vol. 461, Issue No. 7266; pp. 916-922, (2009).
Putnam, D. et al.; "Polymer-based gene delivery with low cytotoxicity by a unique balance of side-chain termini"; PNAS, vol. 98, Issue No. 3; 2001; pp. 1200-1205.
Ran, F. et al.; "Genome engineering using the CRISPR-Cas9 system"; Nature Protocols, vol. 8, Issue No. 11; 2013; pp. 2281-2308.
Richter, M. C. et al.; "Distinct in vivo roles of secreted APP ectodomain variants APPsalpha and APPsbeta in regulation of spine density, synaptic plasticity, and cognition"; EMBO J, vol. 37; 2018; doi:10.15252/embj.201798335.
Ring, S. et al.; "The secreted beta-amyloid precursor protein ectodomain APPs alpha is sufficient to rescue the anatomical, behavioral, and

(56) References Cited

OTHER PUBLICATIONS electrophysiological abnormalities of APP-deficient mice"; J Neurosci, vol. 27; 2007; pp. 7817-7826; doi:10.1523/JNEUROSCI.1026-07.2007.

Rohn, T. et al.; "The Potential of CRISPR/Cas9 Gene Editing as a Treatment Strategy for Alzheimer's Disease"; Journal of Alzheimer's Disease and Parkinsonism, vol. 8, Issue No. 3; 2018; 12 pages; doi:10.4172/2161-0460.1000439.

Sander, J. D. et al.; "CRISPR-Cas systems for editing, regulating and targeting genomes"; Nat Biotechnol, vol. 32; 2014; pp. 347-355; doi:10.1038/nbt.2842.

Sanjana, N. E., et al.; "Improved vectors and genome-wide libraries for CRISPR screening"; Nat Methods, vol. 11; 2014; pp. 783-784; doi:10.1038/nmeth.3047.

Schwartz, M. et al.; "Human pluripotent stem cell-derived neural constructs for predicting neural toxicity"; PNAS, vol. 112, Issue No. 40; 2015; pp. 12516-12521.

Scott, D. et al.; "A Pathologic Cascade Leading to Synaptic Dysfunction in α-Synuclein-Induced Neurodegeneration"; The Journal of Neuroscience, vol. 30, Issue No. 24; 2010; pp. 8083-8095.

Scott, D. et al.; "Mechanistic Logic Underlying the Axonal Transport of Cytosolic Proteins"; Neuron, vol. 70, Issue No. 3; 2011; pp. 441-454.

Shrestha, R. et al.; "Endosomal escape and siRNA delivery with cationic shell crosslinked knedel-like nanoparticles with tunable buffering capcities"; Biomaterials, vol. 33, Issue No. 33; 2012; pp. 8557-8568.

Sisodia, S. S.; "Beta-amyloid precursor protein cleavage by a membrane-bound protease"; Proc Natl Acad Sci U S A, vol. 89; 1992; pp. 6075-6079.

Sun, J. et al.; "CRISPR/Cas9 editing of APP C-terminus attenuates β-cleavage and promotes α-cleavage"; Nature Communications, vol. 10, Issue No. 1; 2019; 11 pages; doi:10.1038/s41467-018-07971-8.

Sun, J. et al.; "The physical approximation of APP and BACE-1: A key event in alzheimer's disease pathogenesis"; Dev Neurobiol, vol. 78; 2018; pp. 340-347, doi:10.1002/dneu.22556.

Swiech, L. et al.; "In vivo interrogation of gene function in the mammalian brain using CRISPR-Cas9"; Nat Biotechnol, vol. 33; 2015; pp. 102-106; doi:10.1038/nbt.3055.

Tang, Y. et al.; "Early and selective impairments in axonal transport kinetics of synaptic cargoes induced by soluble amyloid beta-protein oligomers"; Traffic , vol. 13; 2012; pp. 681-693; doi:10.1111/j.1600-0854.2012.01340.x.

Thinakaran, G. et al.; "Amyloid precursor protein trafficking, processing, and function"; J Biol Chem, vol. 283; 2008; pp. 29615-29619; doi:10.1074/jbc.R800019200.

Topol, A., et al.; "A guide to generating and using hiPSC derived NPCs for the study of neurological diseases"; J Vis Exp, e52495; 2015; doi:10.3791/52495.

Ubelmann, F. et al.; "Bin1 and CD2AP polarise the endocytic generation of beta-amyloid"; EMBO Rep, vol. 18; 2017; pp. 102-122, doi:10.15252/embr.201642738.

Vassar, R. et al.; "Function, therapeutic potential and cell biology of BACE proteases: current status and future prospects"; J Neurochem, vol. 130; 2014; pp. 4-28, doi:10.1111/jnc.12715.

Vassar, R. et al.; "The β-Secretase Enzyme BACE in Health and Alzheimer's Disease: Regulation, Cell Biology, Function, and Therapeutic Potential"; The Journal of Neuroscience, vol. 29, Issue No. 41; 2009 pp. 12787-12794.

Veres, A. et al.; "Low Incidence of Off-Target Mutations in Individual CRISPR-Cas9 and TALEN Targeted Human Stem Cell Clones Detected by Whole-Genome Sequencing"; Cell Stem Cell, vol. 15, Issue No. 1; 2014; pp. 27-30.

Vickers, J. et al.; "A Vaccine Against Alzheimer's Disease: Developments to Date"; Drugs and Aging, vol. 19, Issue No. 7; 2002; pp. 487-494.

Wang, L. et al.; "α-Synuclein Multimers Clusters Synaptic Vesicles and Attenuate Recycling"; Current Biology: CB, vol. 24, Issue No. 19; 2014; pp. 2319-2326.

Wiley, D. et al.; "Transcytosis and brain uptake of transferrin-containing nanoparticles by tuning avidity to transferrin receptor"; PNAS, vol. 110, Issue No. 21; 2013; pp. 8662-8667.

Yang, S. et al.; "CRISPR/Cas9-mediated gene editing ameliorates neurotoxicity in mouse model of Huntington's disease"; J Clin Invest, vol. 127; 2017; pp. 2719-2724; doi:10.1172/JCI92087.

Zeitler, B. et al.; "Sustained Tau Reduction via Zinc Finger Protein Transcription Factors as a Potential Next-Generation Therapy for Alzheimer's Disease and Other Tauopathies"; available online at https://d1io3yog0oux5.cloudfront.net/sangamo/files/documents/051017.Zeitler.ZFP-TFs.tau.Final.pdf, retrieved Jun. 28, 2021; 18 pages.

Alzheimer's Association Report: 2014 Alzheimer's disease facts and figures, Alzheimer's & Dementia, 10 (2014) e47-e92, section 2.2.4.2.

* cited by examiner

FIGS. 2A-2H CONTINUED f.

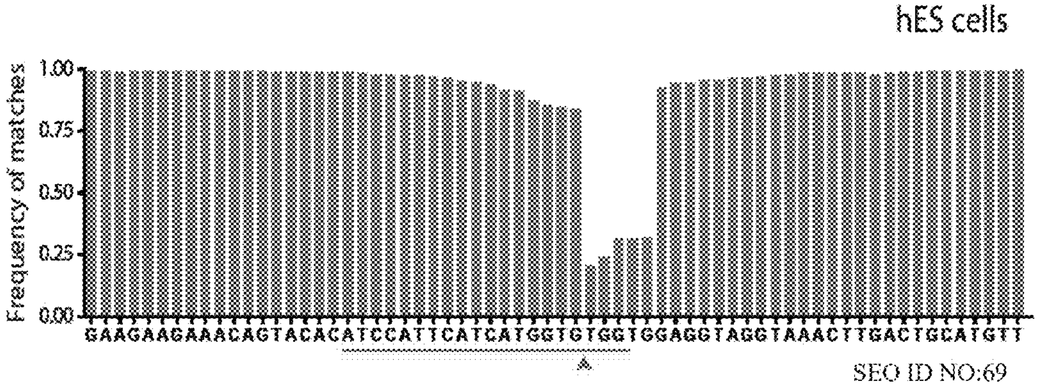

g.

| | Sequence | Freq (%) | |
|---|---|---|---|
| WT | AACAGTACACATCCATTCATCATGGTGTGGTGGAGGTAGGTAAAC | | SEQ ID NO:70 |
| C1 | AACAGTACACATCCATTCATCATGGTG------GAGGTAGGTAAAC | 81.8 | SEQ ID NO:71 |
| C2 | AACAGTACACATCCATTCATCATGGTG--GTGGAGGTAGGTAAAC | 0.3 | SEQ ID NO:72 |
| C3 | AACAGTACACATCCATTCATCAT----TGGTGGAGGTAGGTAAAC | 0.2 | SEQ ID NO:73 |
| C4 | AACAGTACACATCCATTCATCATGGTG-GGTGGAGGTAGGTAAAC | 0.2 | SEQ ID NO:74 |
| C5 | AACAGTACACATCCATTCATC------TGGTGGAGGTAGGTAAAC | 0.2 | SEQ ID NO:75 |

Mutated locus h.

Human APP translation (hES)

| | Sequence | Freq (%) | |
|---|---|---|---|
| WT | GGVVIATVIVITLVMLKKKQYTSIHHGVVEVDAAVTPEERHLSKMQ...(stop) | | SEQ ID NO:76 |
| C1 | GGVVIATVIVITLVMLKKKQYTSIHHG[illegible] (stop) | 81.8 | SEQ ID NO:77 |
| C2 | GGVVIATVIVITLVMLKKKQYTSIHHG[illegible] (stop) | 0.3 | SEQ ID NO:78 |
| C3 | GGVVIATVIVITLVMLKKKQYTSIHH-...60 missense aa(stop) | 0.2 | SEQ ID NO:79 |
| C4 | GGVVIATVIVITLVMLKKKQYTSIHHG...60 missense aa(stop) | 0.2 | SEQ ID NO:80 |
| C5 | GGVVIATVIVITLVMLKKKQYTSIH--LVEVDAAVTPEEPHLSKMQ...(stop) | 0.2 | SEQ ID NO:81 |

659

FIGS. 3A-3G CONTINUED
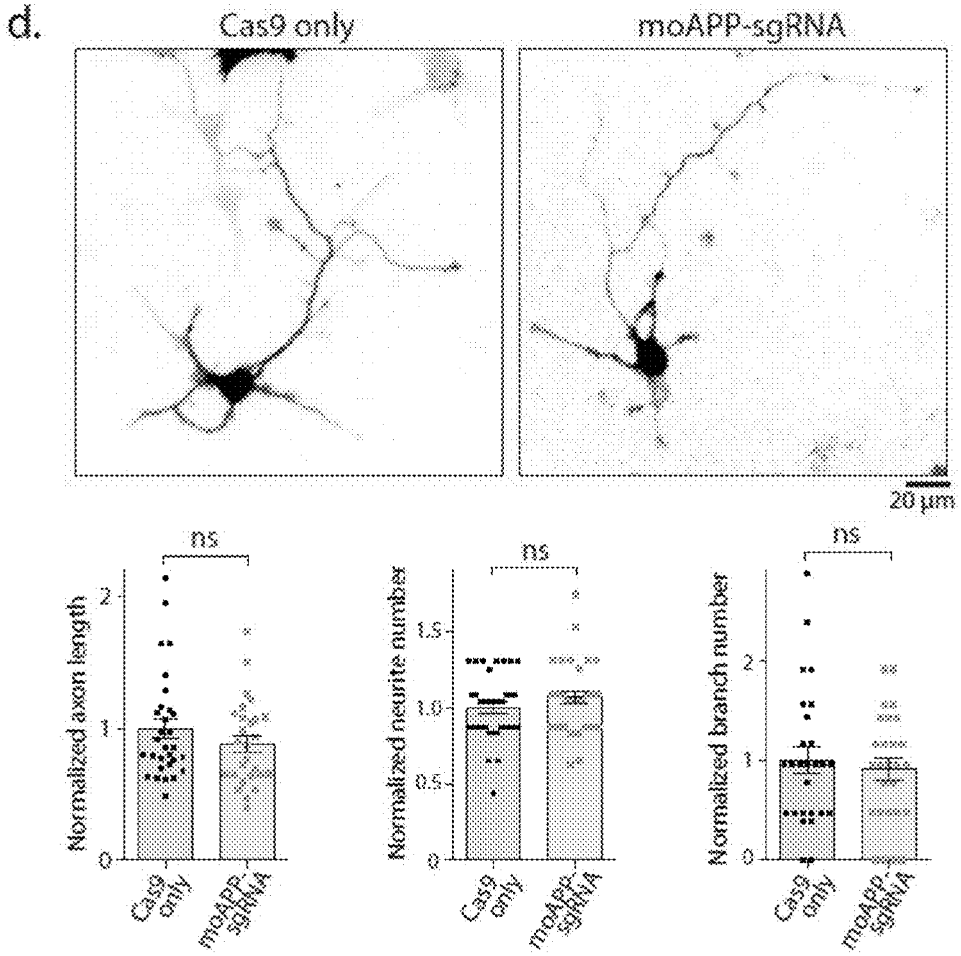
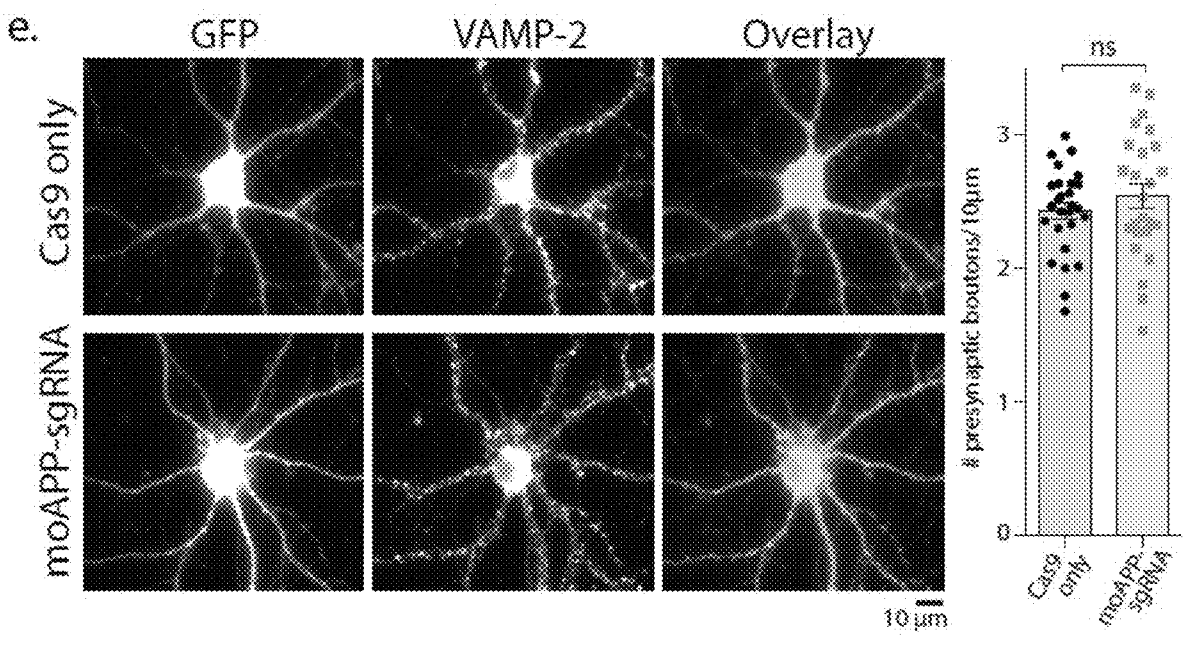

FIGS. 3A-3G CONTINUED
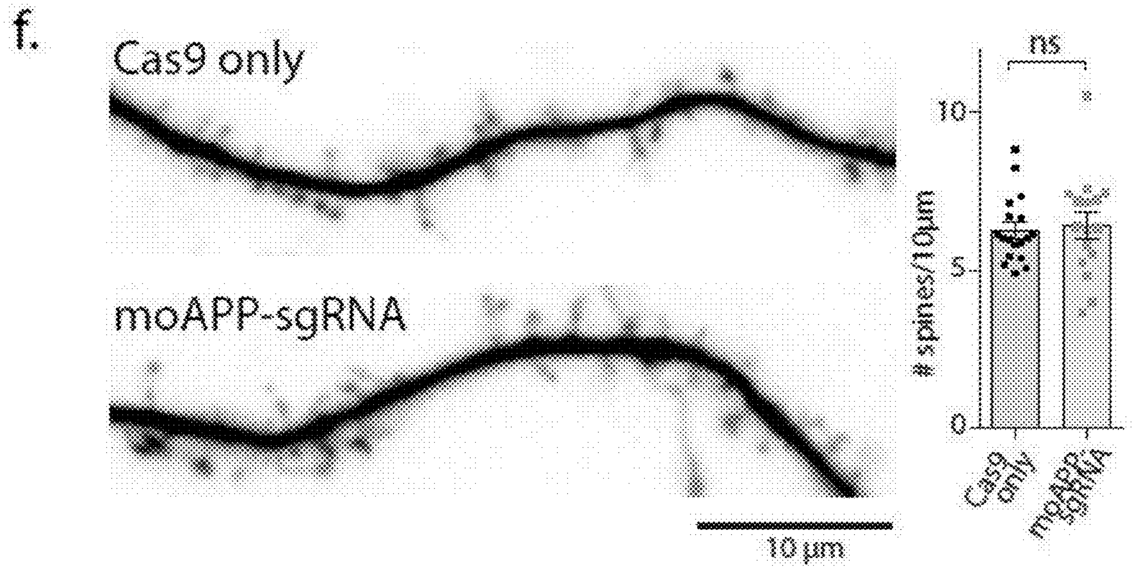
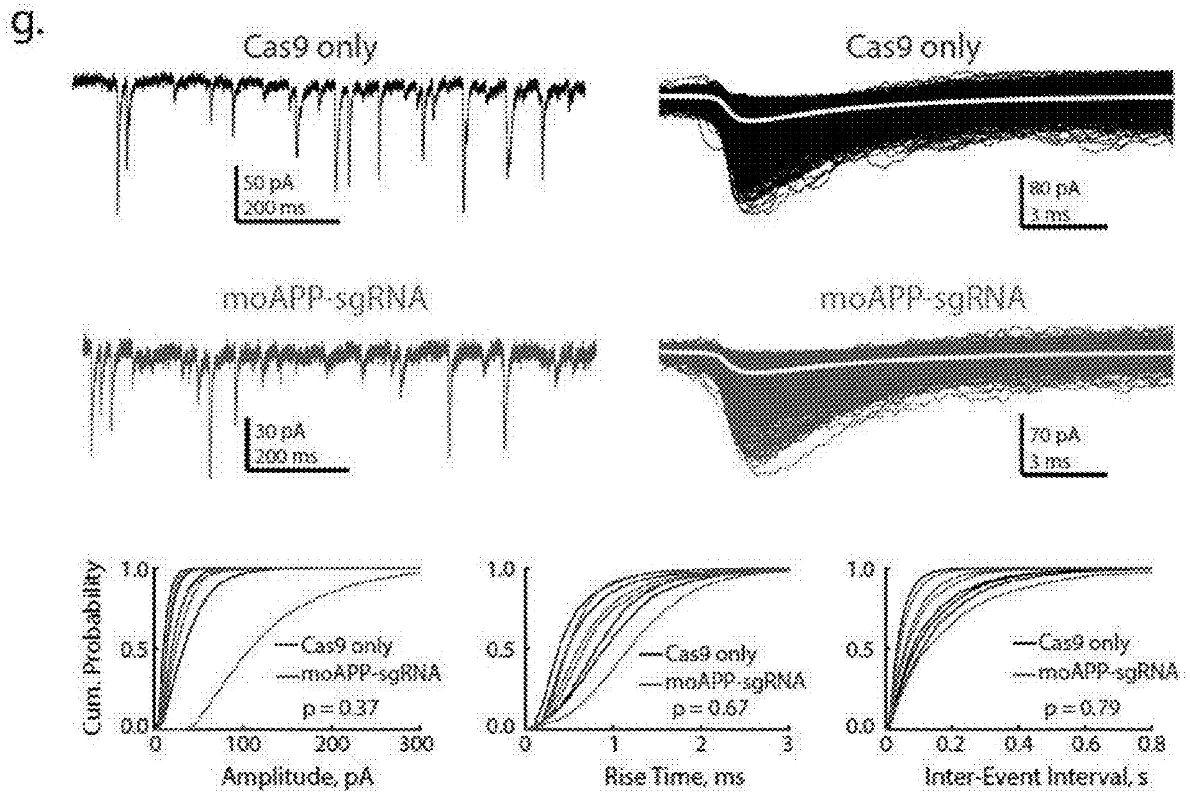

FIGS. 4A-4G
a. Hippocampal AAV9 injections (schematic)
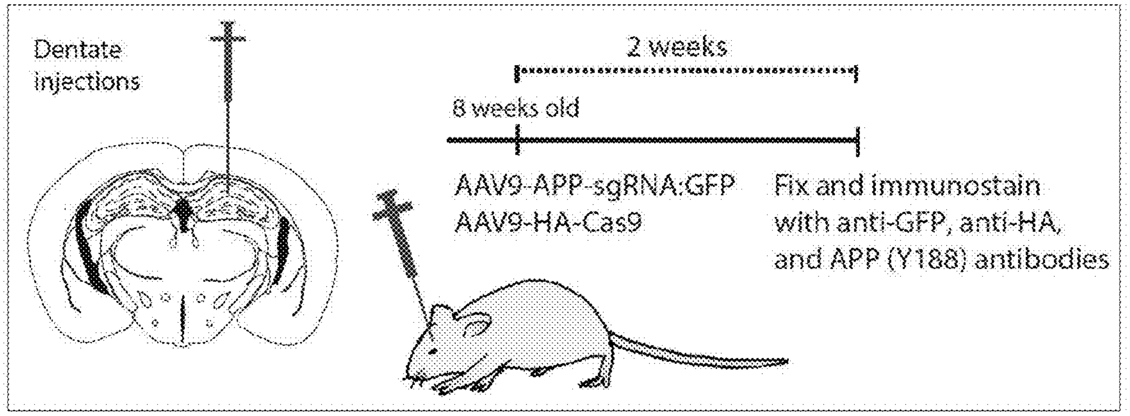
b.
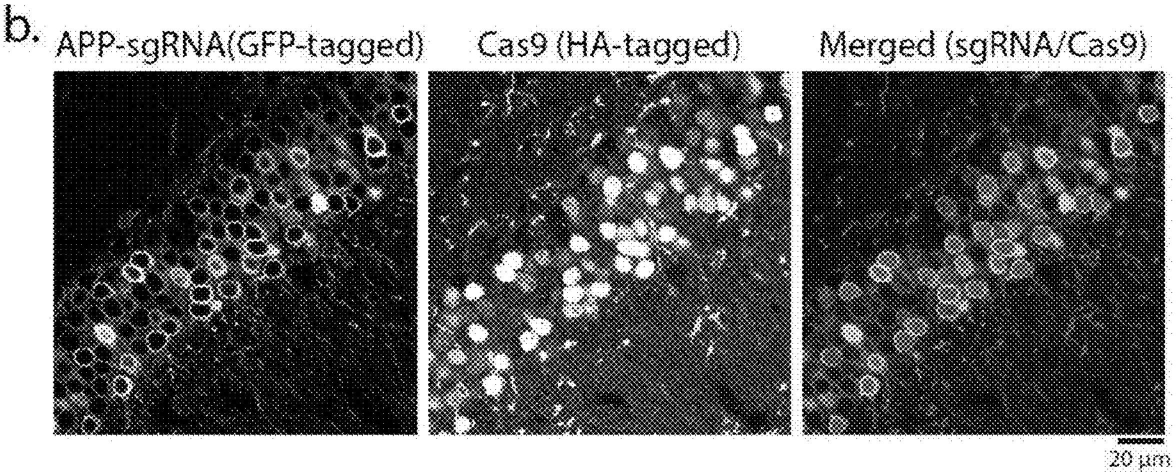

FIGS. 4A-4G CONTINUED
e. ICV AAV9 injections (schematic)
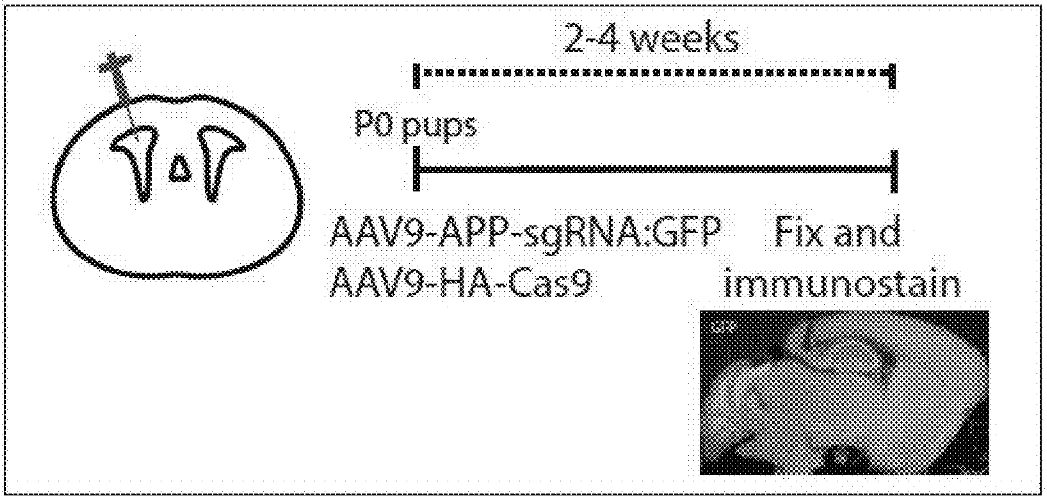
f. APP (Y188) staining
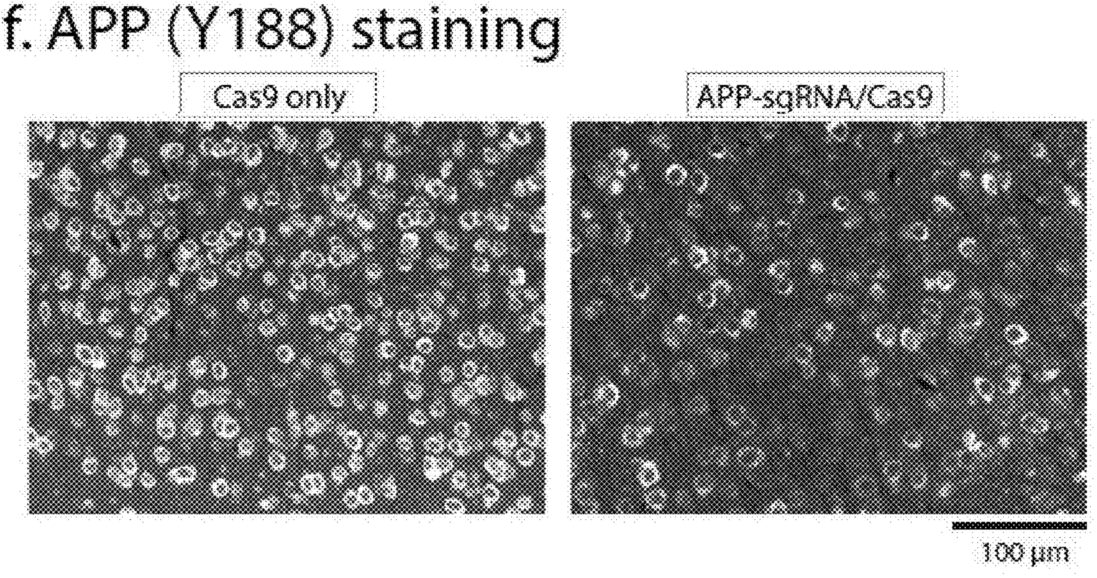
g.
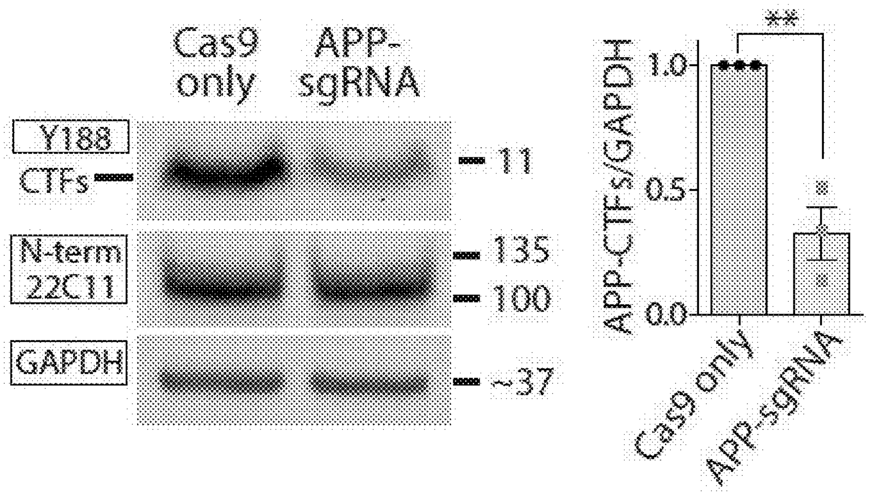

FIGS. 6A-6E CONTINUED
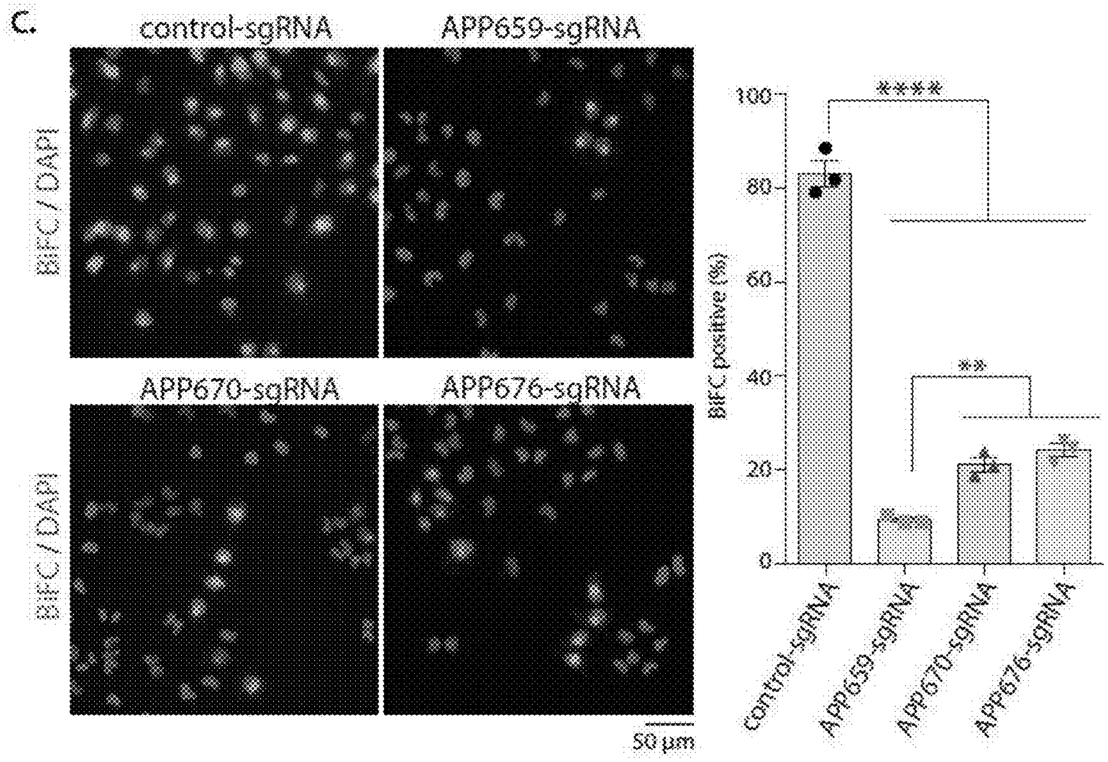
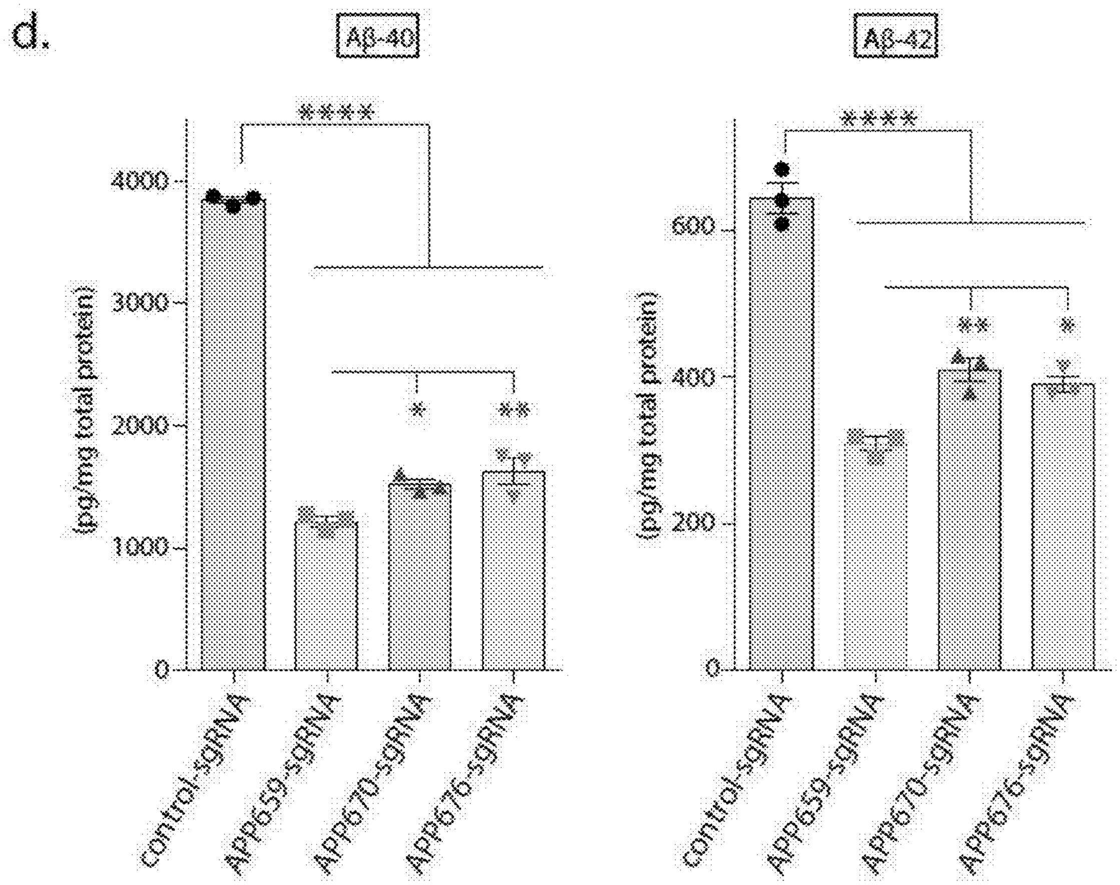

FIGS. 6A-6E CONTINUED e. Left

HEK APP659-sgRNA

Human APP genomic sequence

| | | Freq (%) | |
|---|---|---|---|
| WT | AACAGTACACATCCATTCATCATGGTGTGGTGGAGGTAGGTAAAC | | SEQ ID NO:83 |
| C1 | AACAGTACACATCCATTCATCATGGTG-----GAGGTAGGTAAAC | 42.9 | SEQ ID NO:84 |
| C2 | AACAGTACACATCCATTCATCATGGTG--GTGGAGGTAGGTAAAC | 10.2 | SEQ ID NO:85 |
| C3 | AACAGTACACATCCATTCATCATGGTG-GGTGGAGGTAGGTAAAC | 3.6 | SEQ ID NO:86 |
| C4 | AACAGTACACATCCATTCATCAT----TGGTGGAGGTAGGTAAAC | 2.3 | SEQ ID NO:87 |
| C5 | AACAGTACACATCCATTCATCATG---TGGTGGAGGTAGGTAAAC | 1.9 | SEQ ID NO:88 |

Mutated locus: C1–C5

HEK APP670-sgRNA

Human APP genomic sequence

| | | Freq (%) | |
|---|---|---|---|
| WT | TGCTGCATCTTGGACAGGTGGCGCTCCTCTGGGGTGACAGCGGCG | | SEQ ID NO:89 |
| C1 | TGCTGCATCTTGGACAGGTGGCGCTCCNTCTGGGGTGACAGCGGCG | 17.8 | SEQ ID NO:90 |
| C2 | TGCTGCATCTTGGACAGGTGGCGCT---TCTGGGGTGACAGCGGCG | 12.5 | SEQ ID NO:91 |
| C3 | TGCTGCATCTTGGACAGGTGGC------TCTGGGGTGACAGCGGCG | 8.4 | SEQ ID NO:92 |
| C4 | TGCTGCATCTTGGACAGGTGGCGC---TCTGGGGTGACAGCGGCG | 8.1 | SEQ ID NO:93 |
| C5 | TGCTGCATCTTGGACAGGTGGCGCTC-TCTGGGGTGACAGCGGCG | 5.7 | SEQ ID NO:94 |

Mutated locus: C1–C5

HEK APP676-sgRNA

Human APP genomic sequence

| | | Freq (%) | |
|---|---|---|---|
| WT | TTGGATTTTCGTAGCCGTTCTGCTGCATCTTGGACAGGTGGCGCT | | SEQ ID NO:95 |
| C1 | TTGGATTTTCGTAGCCGTTCTGCTGCANTCTTGGACAGGTGGCGCT | 24.1 | SEQ ID NO:96 |
| C2 | TTGGATTTTCGTAGCCGTTCT---------TGGACAGGTGGCGCT | 19.2 | SEQ ID NO:97 |
| C3 | TTGGATTTTCGTAGCCGTTCTGCTGC-TCTTGGACAGGTGGCGCT | 8.8 | SEQ ID NO:98 |
| C4 | TTGGATTTTCGTAGCCGTTCTGCT---TCTTGGACAGGTGGCGCT | 8.4 | SEQ ID NO:99 |
| C5 | TTGGATTTTCGTAGCCGTTCT------TCTTGGACAGGTGGCGCT | 4.4 | SEQ ID NO:100 |

Mutated locus: C1–C5

FIGS. 6A-6E CONTINUED e. CONTINUED Right

Human APP translational products

| | | Freq (%) | |
|---|---|---|---|
| WT | GGVVIATVIVITLVMLKKKQYTSIHHGVVEVDAAVTPEERHLSKMQ...(stop) | | SEQ ID NO:101 |
| C1 | GGVVIATVIVITLVMLKKKQYTSIHHG (stop) | 42.9 | SEQ ID NO:102 |
| C2 | GGVVIATVIVITLVMLKKKQYTSIHHG (stop) | 10.2 | SEQ ID NO:103 |
| C3 | GGVVIATVIVITLVMLKKKQYTSIHHG...60 missense aa (stop) | 3.6 | SEQ ID NO:104 |
| C4 | GGVVIATVIVITLVMLKKKQYTSIHH-...60 missense aa (stop) | 2.3 | SEQ ID NO:105 |
| C5 | GGVVIATVIVITLVMLKKKQYTSIHH-VVEVDAAVTPEERHLSKMQ...(stop) | 1.9 | SEQ ID NO:106 |

659

Human APP translational products

| | | Freq (%) | |
|---|---|---|---|
| WT | KKQYTSIHHGVVEVDAAVTPEERHLSKMQQNGYENPTYKFFEQMQN (stop) | | SEQ ID NO:107 |
| C1 | KKQYTSIHHGVVEVDAAVTP D/E APPVQDAAERLKKSNLQVL (stop) | 17.8 | SEQ ID NO:108 |
| C2 | KKQYTSIHHGVVEVDAAVTPEAPPVQDAAERLKKSNLQVL (stop) | 12.5 | SEQ ID NO:109 |
| C3 | KKQYTSIHHGVVEVDAAVTPEPPVQDAAERLKKSNLQVL (stop) | 8.4 | SEQ ID NO:110 |
| C4 | KKQYTSIHHGVVEVDAAVTPE-RHLSKMQQNGYENPTYKFFEQMQN (stop) | 8.1 | SEQ ID NO:111 |
| C5 | KKQYTSIHHGVVEVDAAVTP...50 missense aa (stop) | 5.7 | SEQ ID NO:112 |

670

Human APP translational products

| | | Freq (%) | |
|---|---|---|---|
| WT | KKQYTSIHHGVVEVDAAVTPEERHLSKMQQNGYENPTYKFFEQMQN (stop) | | SEQ ID NO:107 |
| C1 | KKQYTSIHHGVVEVDAAVTPEERHLSK...14 missense aa (stop) | 24.1 | SEQ ID NO:113 |
| C2 | KKQYTSIHHGVVEVDAAVTPEERHLSK---NGYENPTYKFFEQMQN (stop) | 19.2 | SEQ ID NO:114 |
| C3 | KKQYTSIHHGVVEVDAAVTPEERHLSK...43 missense aa (stop) | 8.8 | SEQ ID NO:115 |
| C4 | KKQYTSIHHGVVEVDAAVTPEERHLSK-QNGYENPTYKFFEQMQN (stop) | 8.4 | SEQ ID NO:116 |
| C5 | KKQYTSIHHGVVEVDAAVTPEERHLSK--NGYENPTYKFFEQMQN (stop) | 4.4 | SEQ ID NO:117 |

676

FIGS. 7A-7D CONTINUED
C.
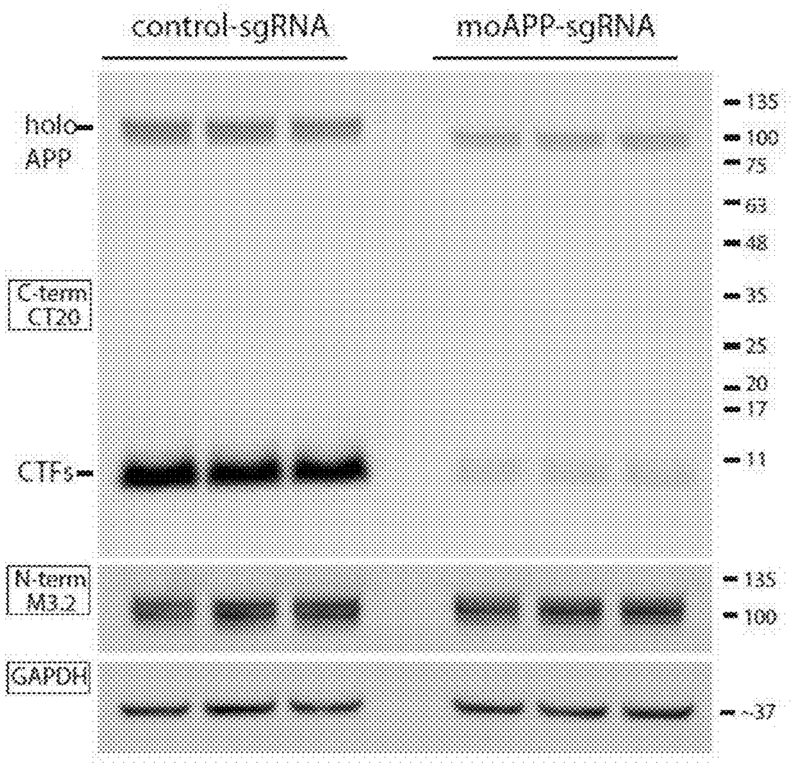
d. Mouse translational products (post-editing)
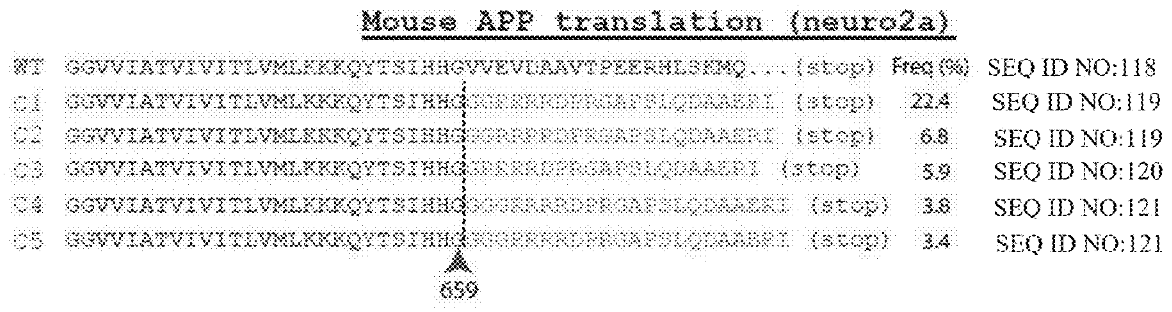

FIGS. 8A-8G
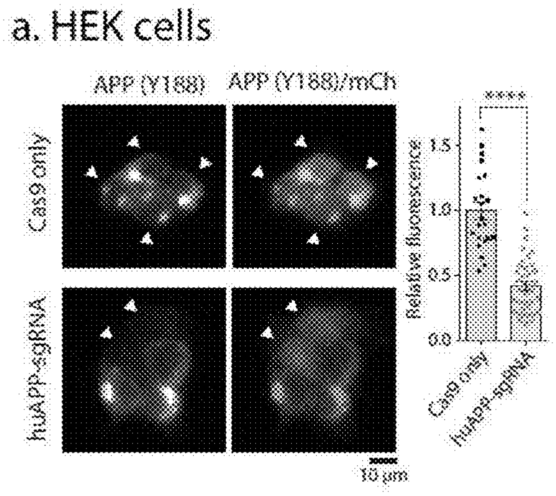
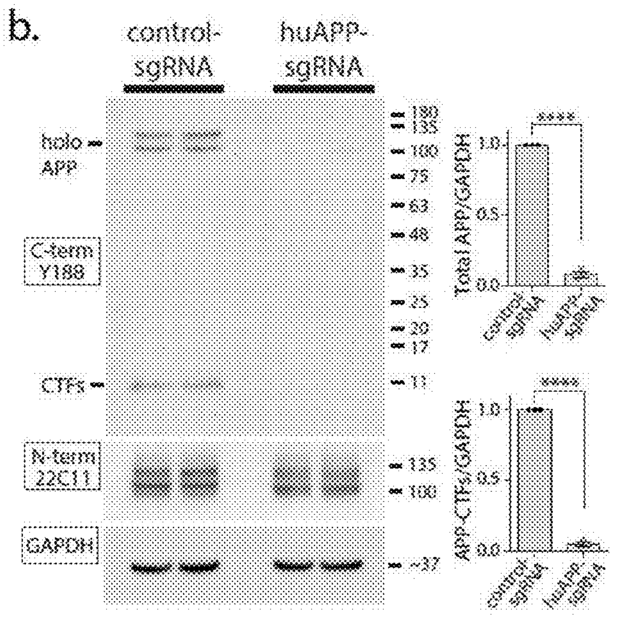
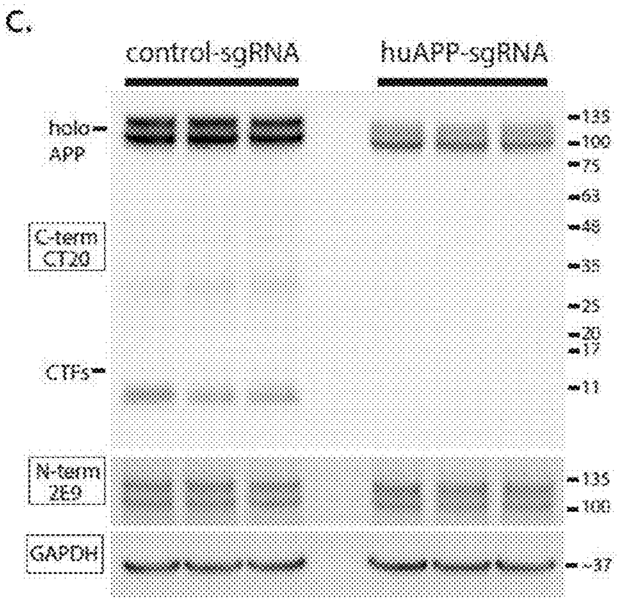

FIGS. 8A-8G CONTINUED
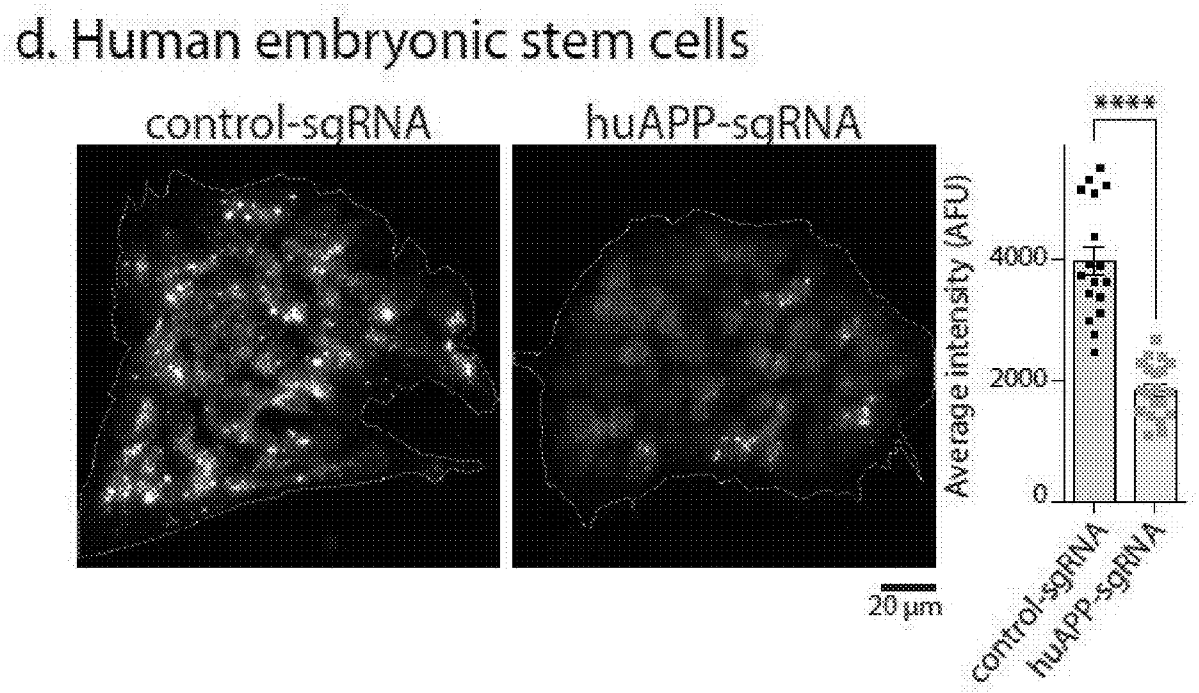
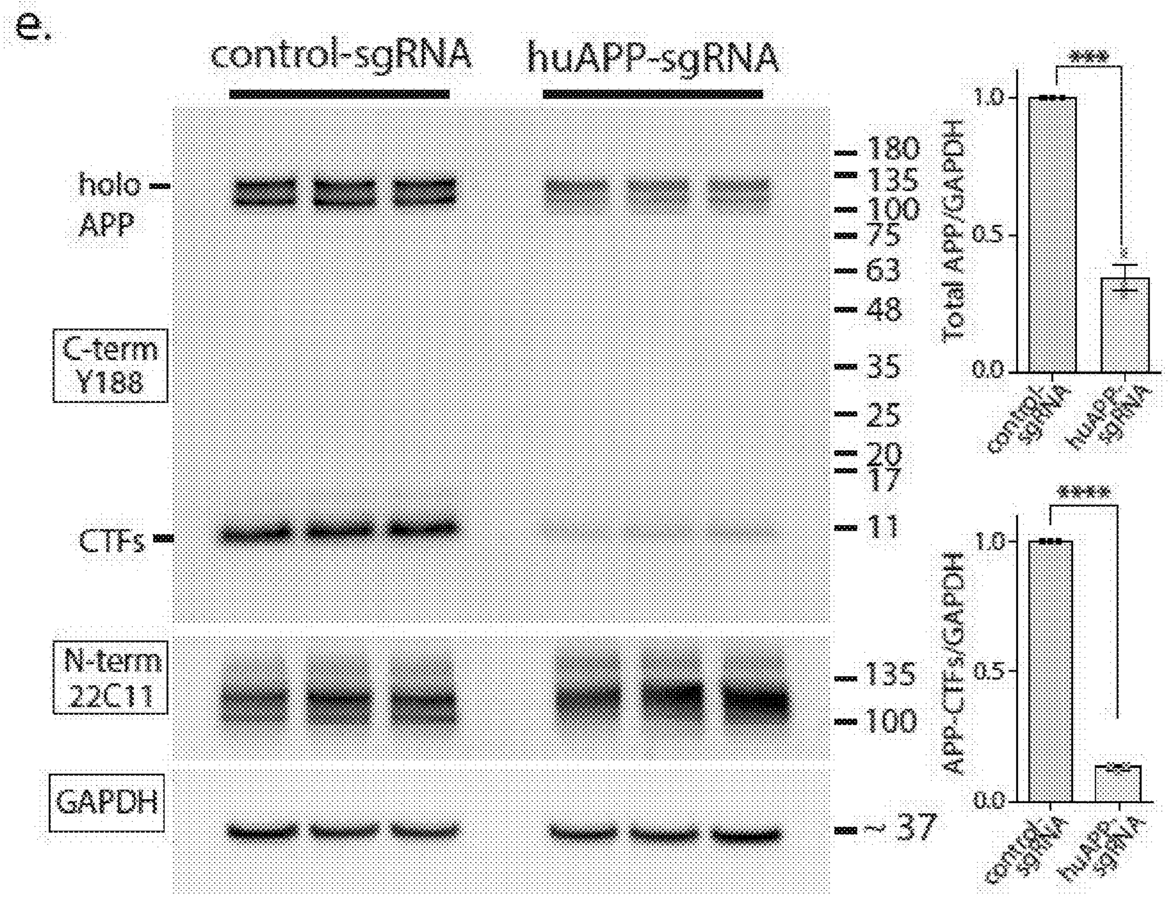

FIGS. 8A-8G CONTINUED
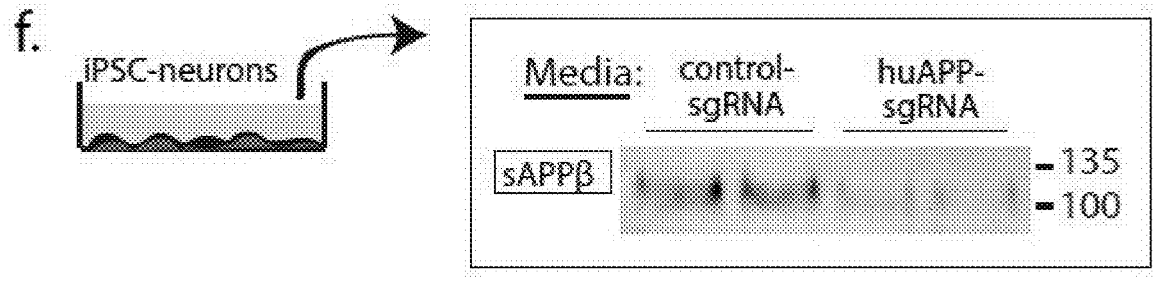
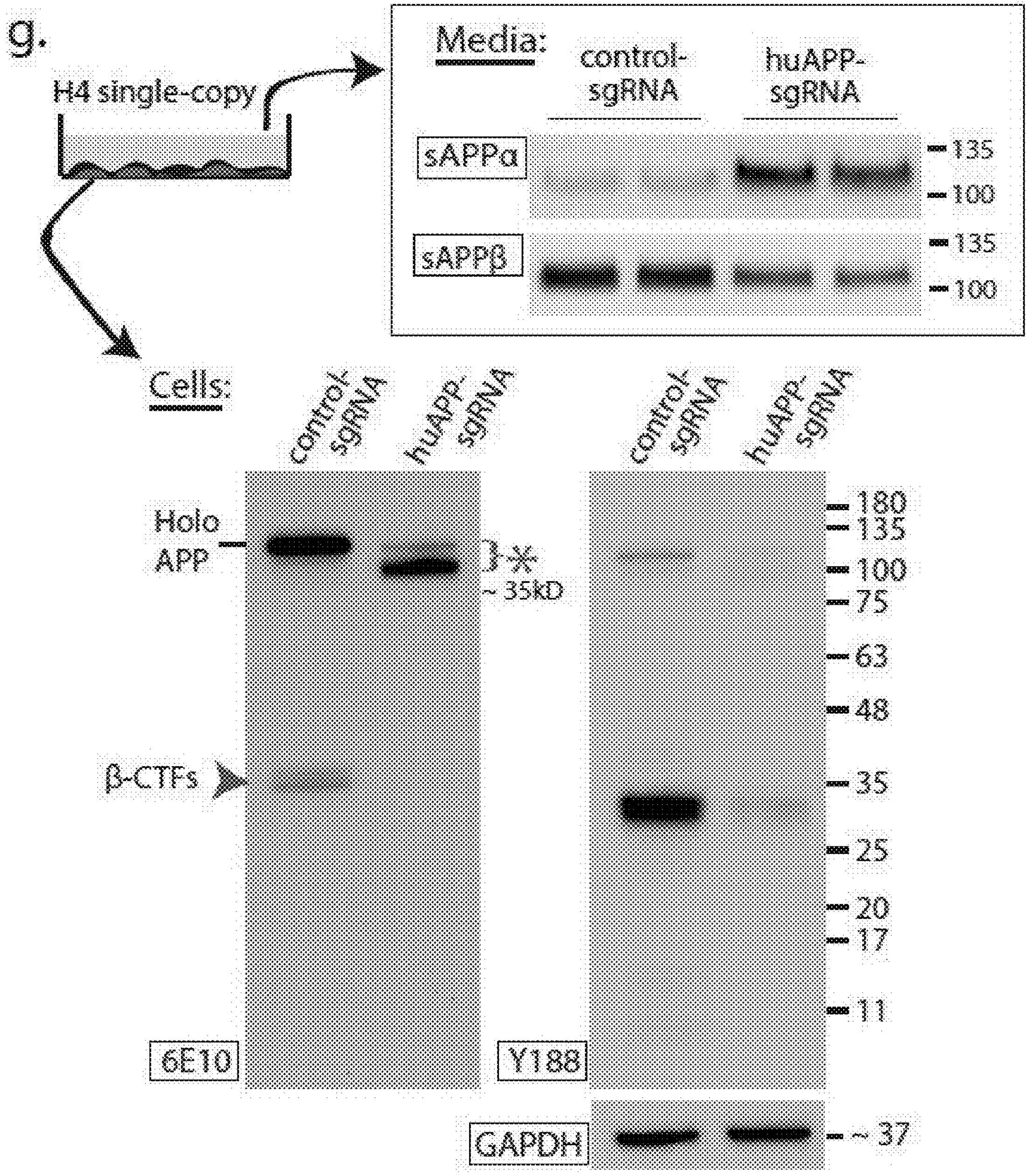

FIGS. 10A-10G a. Off-target sites

| | | Sequence | Location | Coding region | |
|---|---|---|---|---|---|
| Mouse | OT1 | GTCCATCCATCATGGCCTGG | chr18:+82500985 | No | SEQ ID NO:122 |
| | OT2 | TTCCATCCATCATGGCTTGG | chr15:+83079515 | No | SEQ ID NO:123 |
| | OT3 | GTCCCTCCATCATGGCCTGG | chr8:+54570804 | No | SEQ ID NO:124 |
| | OT4 | GGCCATCATTCATGGCGTGG | chr12:-30225859 | No | SEQ ID NO:125 |
| | OT5 | ATAAATATATCATGGCGTGG | chr2:+85075854 | No | SEQ ID NO:126 |
| | | | | | |
| Human | OT1 | CTCCCTTCATCTTGGTGTGG | chr17:+42059975 | No | SEQ ID NO:127 |
| | OT2 | ATGCAATCAGCATGGTGTGG | chr11:+45935195 | Yes, PHF21A | SEQ ID NO:128 |
| | OT3 | TTCTGTTCAGCATGGTGTGG | chr19:+13830088 | No | SEQ ID NO:129 |
| | OT4 | TTAAATTCAACATGGTGTGG | chrX:+78686020 | No | SEQ ID NO:130 |
| | OT5 | AGCCATTTATCAAGGTGTGG | chr8:+61517706 | No | SEQ ID NO:131 |

b.

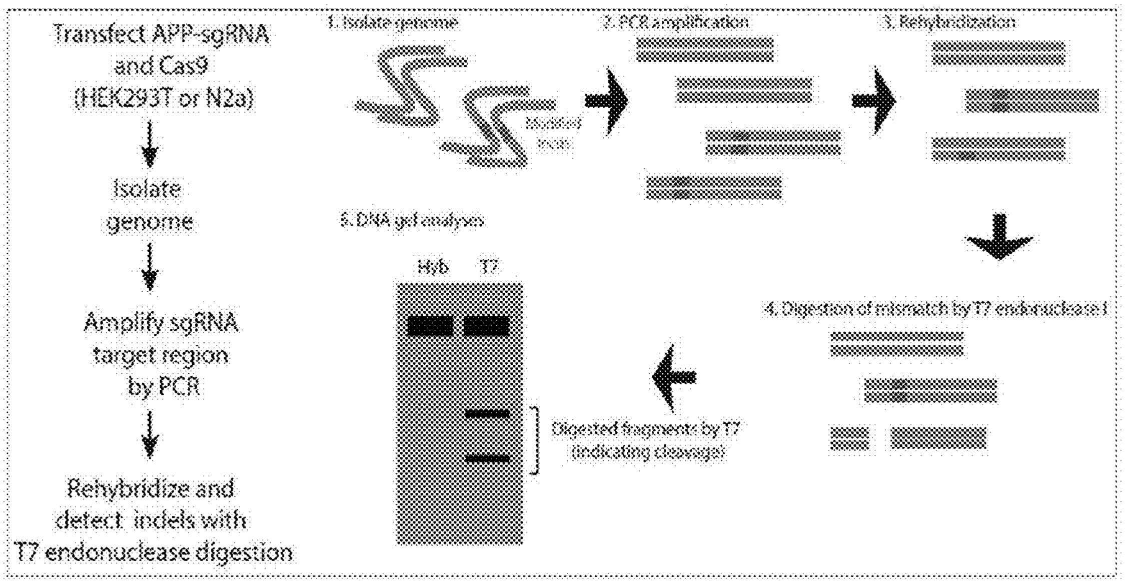

FIGS. 10A-10G CONTINUED

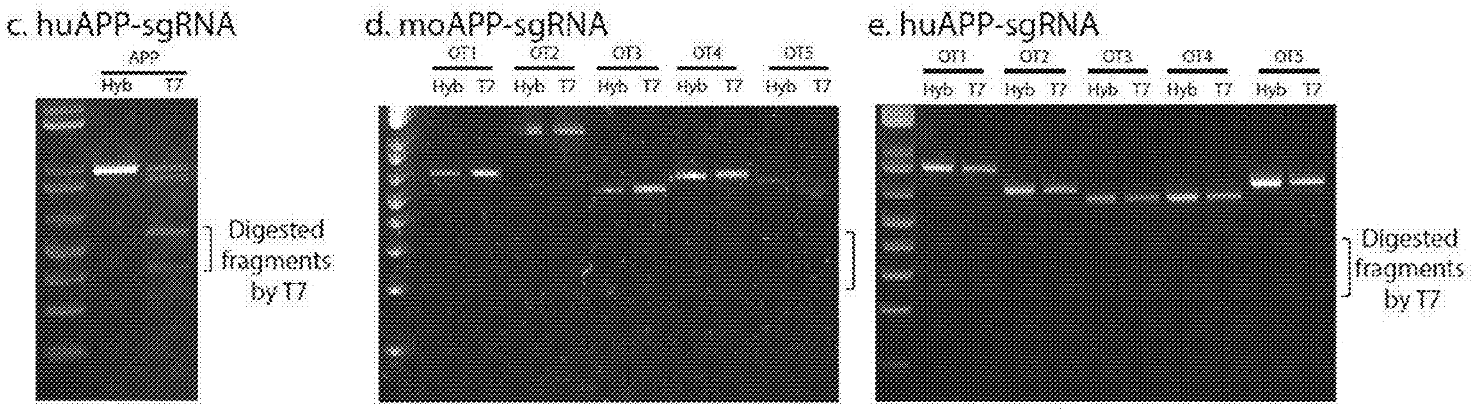

f. PAM/targeting sequence allignment of APP and APLP 1/2

SEQ ID NO:132 Mouse APP atccatccatcatggcgtggtgg
SEQ ID NO:133 Mouse APLP1 gactatcagccatggagtggtgg Mouse APP atccatccatcatggcgtggtgg SEQ ID NO:134
Mouse APLP2 caccatcagccacgggattgtgg SEQ ID NO:135

SEQ ID NO:136 Human APP atccattcatcatggtgtggtgg
SEQ ID NO:137 Human APLP1 ggctatcagccatggcgtggtgg Human APP atccattcatcatggtgtggtgg SEQ ID NO:138
Human APLP2 caccatcagccacgggatcgtgg SEQ ID NO:139

FIGS. 11A-11C
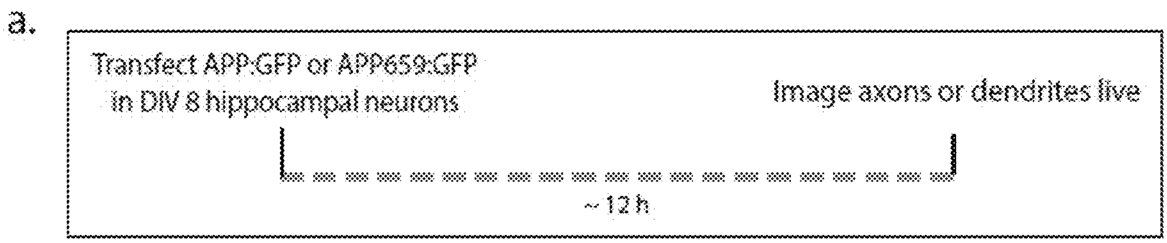
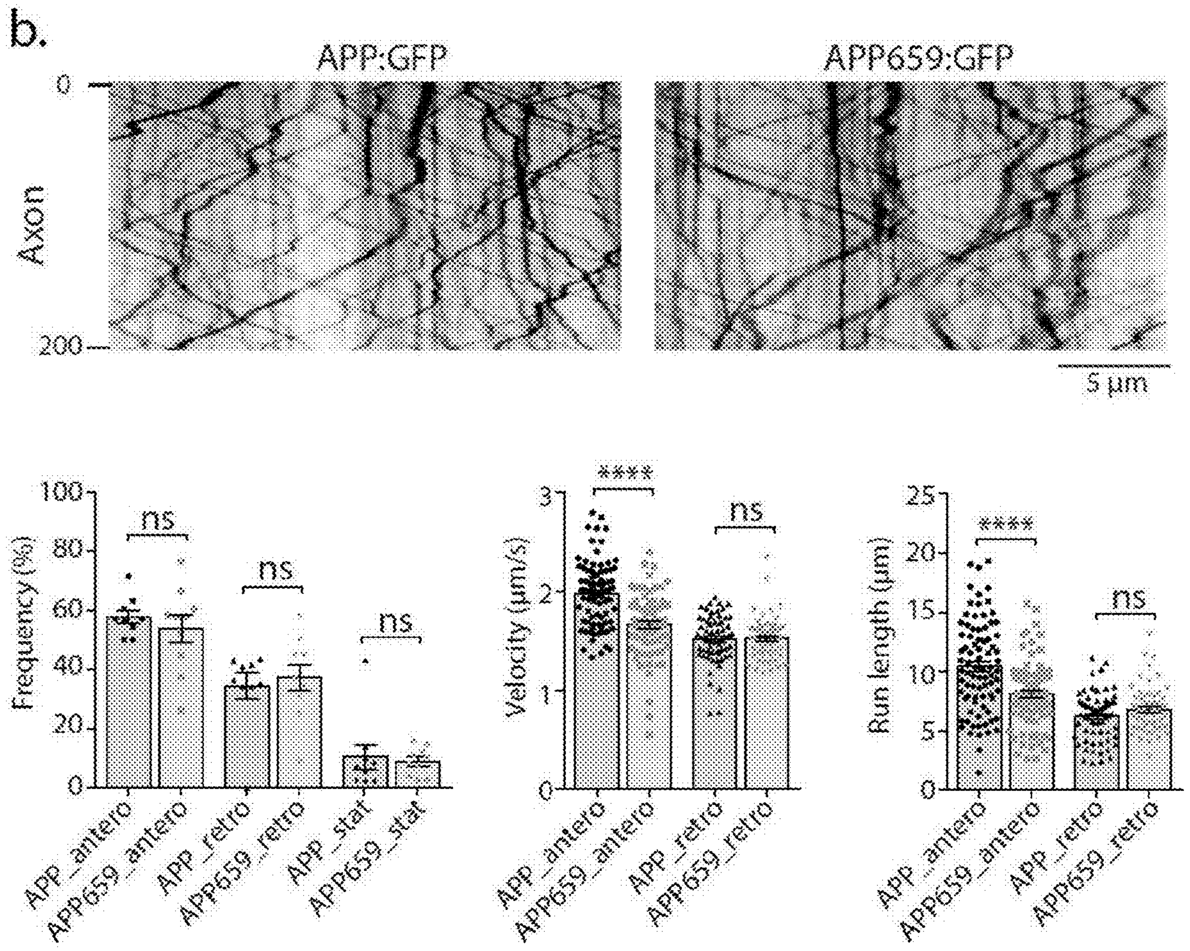

FIG. 13

>human APP (nucleotide sequence SEQ ID NO:11, amino acid sequence SEQ ID NO:12)

```
atgctgcccggtttggcactgctcctgctggccgcctggacggctcgggcgctggaggta
 M  L  P  G  L  A  L  L  L  L  A  A  W  T  A  R  A  L  E  V
cccactgatggtaatgctggcctgctggctgaaccccagattgccatgttctgtggcaga
 P  T  D  G  N  A  G  L  L  A  E  P  Q  I  A  M  F  C  G  R
ctgaacatgcacatgaatgtccagaatgggaagtgggattcagatccatcagggaccaaa
 L  N  M  H  M  N  V  Q  N  G  K  W  D  S  D  P  S  G  T  K
acctgcattgataccaaggaaggcatcctgcagtattgccaagaagtctaccctgaactg
 T  C  I  D  T  K  E  G  I  L  Q  Y  C  Q  E  V  Y  P  E  L
cagatcaccaatgtggtagaagccaaccaaccagtgaccatccagaactggtgcaagcgg
 Q  I  T  N  V  V  E  A  N  Q  P  V  T  I  Q  N  W  C  K  R
ggccgcaagcagtgcaagacccatccccactttgtgattccctaccgctgcttagttggt
 G  R  K  Q  C  K  T  H  P  H  F  V  I  P  Y  R  C  L  V  G
gagtttgtaagtgatgcccttctcgttcctgacaagtgcaaattcttacaccaggagagg
 E  F  V  S  D  A  L  L  V  P  D  K  C  K  F  L  H  Q  E  R
atggatgtttgcgaaactcatcttcactggcacaccgtcgccaaagagacatgcagtgag
 M  D  V  C  E  T  H  L  H  W  H  T  V  A  K  E  T  C  S  E
aagagtaccaacttgcatgactacggcatgttgctgccctgcggaattgacaagttccga
 K  S  T  N  L  H  D  Y  G  M  L  L  P  C  G  I  D  K  F  R
ggggtagagtttgtgtgttgcccactggctgaagaaagtgacaatgtggattctgctgat
 G  V  E  F  V  C  C  P  L  A  E  E  S  D  N  V  D  S  A  D
gcggaggaggatgactcggatgtctggtggggcggagcagacacagactatgcagatggg
 A  E  E  D  D  S  D  V  W  W  G  G  A  D  T  D  Y  A  D  G
agtgaagacaaagtagtagaagtagcagaggaggaagaagtggctgaggtggaagaagaa
 S  E  D  K  V  V  E  V  A  E  E  E  E  V  A  E  V  E  E  E
gaagccgatgatgacgaggacgatgaggatggtgatgaggtagaggaagaggctgaggaa
 E  A  D  D  D  E  D  D  E  D  G  D  E  V  E  E  E  A  E  E
ccctacgaagaagccacagagagaaccaccagcattgccaccaccaccaccaccaccaca
 P  Y  E  E  A  T  E  R  T  T  S  I  A  T  T  T  T  T  T  T
gagtctgtggaagaggtggttcgagttcctacaacagcagccagtacccctgatgccgtt
 E  S  V  E  E  V  V  R  V  P  T  T  A  A  S  T  P  D  A  V
gacaagtatctcgagacacctggggatgagaatgaacatgcccatttccagaaagccaaa
 D  K  Y  L  E  T  P  G  D  E  N  E  H  A  H  F  Q  K  A  K
gagaggcttgaggccaagcaccgagagagaatgtcccaggtcatgagagaatgggaagag
 E  R  L  E  A  K  H  R  E  R  M  S  Q  V  M  R  E  W  E  E
gcagaacgtcaagcaaagaacttgcctaaagctgataagaaggcagttatccagcatttc
 A  E  R  Q  A  K  N  L  P  K  A  D  K  K  A  V  I  Q  H  F
caggagaaagtggaatctttggaacaggaagcagccaacgagagacagcagctggtggag
 Q  E  K  V  E  S  L  E  Q  E  A  A  N  E  R  Q  Q  L  V  E
acacacatggccagagtggaagccatgctcaatgaccgccgccgcctggccctggagaac
 T  H  M  A  R  V  E  A  M  L  N  D  R  R  R  L  A  L  E  N
tacatcaccgctctgcaggctgttcctcctcggcctcgtcacgtgttcaatatgctaaag
 Y  I  T  A  L  Q  A  V  P  P  R  P  R  H  V  F  N  M  L  K
aagtatgtccgcgcagaacagaaggacagacagcacaccctaaagcatttcgagcatgtg
 K  Y  V  R  A  E  Q  K  D  R  Q  H  T  L  K  H  F  E  H  V
cgcatggtggatcccaagaaagccgctcagatccggtcccaggttatgacacacctccgt
 R  M  V  D  P  K  K  A  A  Q  I  R  S  Q  V  M  T  H  L  R
gtgatttatgagcgcatgaatcagtctctctccctgctctacaacgtgcctgcagtggcc
 V  I  Y  E  R  M  N  Q  S  L  S  L  L  Y  N  V  P  A  V  A
gaggagattcaggatgaagttgatgagctgcttcagaaagagcaaaactattcagatgac
 E  E  I  Q  D  E  V  D  E  L  L  Q  K  E  Q  N  Y  S  D  D
gtcttggccaacatgattagtgaaccaaggatcagttacggaaacgatgctctcatgcca
 V  L  A  N  M  I  S  E  P  R  I  S  Y  G  N  D  A  L  M  P
tctttgaccgaaacgaaaaccaccgtggagctccttcccgtgaatggagagttcagcctg
```

FIG. 13 CONTINUED

```
 S   L   T   E   T   K   T   T   V   E   L   L   P   V   N   G   E   F   S   L
gacgatctccagccgtggcattcttttggggctgactctgtgccagccaacacagaaaac
 D   D   L   Q   P   W   H   S   F   G   A   D   S   V   P   A   N   T   E   N
gaagttgagcctgttgatgcccgccctgctgccgaccgaggactgaccactcgaccaggt
 E   V   E   P   V   D   A   R   P   A   A   D   R   G   L   T   T   R   P   G
tctgggttgacaaatatcaagacggaggagatctctgaagtgaagatggatgcagaattc
 S   G   L   T   N   I   K   T   E   E   I   S   E   V   K   M   D   A   E   F
cgacatgactcaggatatgaagttcatcatcaaaaattggtgttctttgcagaagatgtg
 R   H   D   S   G   Y   E   V   H   H   Q   K   L   V   F   F   A   E   D   V
ggttcaaacaaaggtgcaatcattggactcatggtgggcggtgttgtcatagcgacagtg
 G   S   N   K   G   A   I   I   G   L   M   V   G   G   V   V   I   A   T   V
atcgtcatcaccttggtgatgctgaagaagaaacagtacac[illegible]
 I   V   I   T   L   V   M   L   K   K   K   Q   Y   T   S   I   H   H   G   V
[illegible]tggaggttgacgccgctgtcacccc[illegible]
 V   E   V   D   A   A   V   T   P   E   E   R   H   L   S   K   M   Q   Q   N
[illegible]gaaaatcca[illegible]gatgcagaactag
 G   Y   E   N   P   T   Y   K   F   F   E   Q   M   Q   N   -
```

Sense:

659 gRNA

Antisense:

669 gRNA 676 gRNA 686 gRNA

670 gRNA

\>mouse APP (nucleotide sequence SEQ ID NO:13, amino acid sequence SEQ ID NO:14)

```
atgctgcccagcttggcactgctcctgctggccgcctggacggttcgggctctggaggta
 M   L   P   S   L   A   L   L   L   L   A   A   W   T   V   R   A   L   E   V
cccactgatggcaacgccgggctgctggcagaaccccagatcgccatgttctgtggtaaa
 P   T   D   G   N   A   G   L   L   A   E   P   Q   I   A   M   F   C   G   K
ctcaacatgcacatgaatgtgcagaatggaaagtgggagtcagacccgtcagggaccaaa
 L   N   M   H   M   N   V   Q   N   G   K   W   E   S   D   P   S   G   T   K
acctgcattggcaccaaggagggcatcttgcagtactgccaagaggtctaccctgaactg
 T   C   I   G   T   K   E   G   I   L   Q   Y   C   Q   E   V   Y   P   E   L
cagatcacaaacgtggtggaagccaaccagccagtgaccatccagaactggtgcaagcgg
 Q   I   T   N   V   V   E   A   N   Q   P   V   T   I   Q   N   W   C   K   R
ggccgcaagcagtgcaagacacacacccacatcgtgattccttaccgttgcctagttggt
 G   R   K   Q   C   K   T   H   T   H   I   V   I   P   Y   R   C   L   V   G
gagtttgtgagcgacgcccttctcgtgcccgacaagtgcaagttcctacaccaggagcgg
 E   F   V   S   D   A   L   L   V   P   D   K   C   K   F   L   H   Q   E   R
atggatgtttgtgagacccatcttcactggcacaccgtcgccaaagagacatgcagcgag
 M   D   V   C   E   T   H   L   H   W   H   T   V   A   K   E   T   C   S   E
aagagcactaacttgcacgactatggcatgctgctgccctgcggcatcgacaagttccga
 K   S   T   N   L   H   D   Y   G   M   L   L   P   C   G   I   D   K   F   R
ggggtagagtttgtatgctgcccgttggccgaggaaagcgacagcgtggattctgcggat
 G   V   E   F   V   C   C   P   L   A   E   E   S   D   S   V   D   S   A   D
gcagaggaggatgactctgatgtctggtggggtggagcggacacagactacgctgatggc
 A   E   E   D   D   S   D   V   W   W   G   G   A   D   T   D   Y   A   D   G
ggtgaagacaaagtagtagaagtcgccgaagaggaggaagtggctgatgttgaggaagag
 G   E   D   K   V   V   E   V   A   E   E   E   E   V   A   D   V   E   E   E
gaagctgatgatgatgaggatgtggaggatggggacgaggtggaggaggaggccgaggag
 E   A   D   D   D   E   D   V   E   D   G   D   E   V   E   E   E   A   E   E
```

FIG. 13 CONTINUED

```
ccctacgaagaggccaccgagagaacaaccagcactgccaccaccaccacaaccaccact
 P   Y   E   E   A   T   E   R   T   T   S   T   A   T   T   T   T   T   T   T
gagtccgtggaggaggtggtccgagttcccacgacagcagccagcacccccgacgccgtc
 E   S   V   E   E   V   V   R   V   P   T   T   A   A   S   T   P   D   A   V
gacaagtacctggagacacccggggacgagaacgagcatgcccatttccagaaagccaaa
 D   K   Y   L   E   T   P   G   D   E   N   E   H   A   H   F   Q   K   A   K
gagaggctggaagccaagcaccgagagagaatgtcccaggtcatgagagaatgggaagag
 E   R   L   E   A   K   H   R   E   R   M   S   Q   V   M   R   E   W   E   E
gcagagcgtcaagccaagaacttgcccaaagctgacaagaaggccgttatccagcatttc
 A   E   R   Q   A   K   N   L   P   K   A   D   K   K   A   V   I   Q   H   F
caggagaaagtggaatctctggaacaggaagcagccaatgagagacagcagcttgtagag
 Q   E   K   V   E   S   L   E   Q   E   A   A   N   E   R   Q   Q   L   V   E
acacacatggccagagttgaagccatgctcaatgaccgccgccgcctggccctcgagaat
 T   H   M   A   R   V   E   A   M   L   N   D   R   R   R   L   A   L   E   N
tacatcactgcactgcaggcggtgcccccaaggcctcatcatgtgttcaacatgctgaag
 Y   I   T   A   L   Q   A   V   P   P   R   P   H   H   V   F   N   M   L   K
aagtacgtccgtgcggagcagaaagacagacagcacaccctaaagcattttgaacatgtg
 K   Y   V   R   A   E   Q   K   D   R   Q   H   T   L   K   H   F   E   H   V
cgcatggtggaccccaagaaagctgctcagatccggtcccaggttatgacacacctccgt
 R   M   V   D   P   K   K   A   A   Q   I   R   S   Q   V   M   T   H   L   R
gtgatctacgagcgcatgaaccagtctctgtccctgctctacaatgtccctgcggtggct
 V   I   Y   E   R   M   N   Q   S   L   S   L   L   Y   N   V   P   A   V   A
gaggagattcaagatgaagtcgatgagctgcttcagaaggagcagaactactccgacgat
 E   E   I   Q   D   E   V   D   E   L   L   Q   K   E   Q   N   Y   S   D   D
gtcttggccaacatgatcagtgagcccagaatcagctacggaaacgacgctctcatgcct
 V   L   A   N   M   I   S   E   P   R   I   S   Y   G   N   D   A   L   M   P
tcgctgacggaaaccaagaccaccgtggagctccttcccgtgaatggggaattcagcctg
 S   L   T   E   T   K   T   T   V   E   L   L   P   V   N   G   E   F   S   L
gatgacctccagccgtggcacccttttggggtggactctgtgccagccaataccgaaaat
 D   D   L   Q   P   W   H   P   F   G   V   D   S   V   P   A   N   T   E   N
gaagtcgagcctgttgacgccccgcccgctgctgaccgaggactgaccactcgaccaggt
 E   V   E   P   V   D   A   P   P   A   A   D   R   G   L   T   T   R   P   G
tctgggctgacaaacatcaagacggaagagatctcggaagtgaagatggatgcagaattc
 S   G   L   T   N   I   K   T   E   E   I   S   E   V   K   M   D   A   E   F
ggacatgattcaggatttgaagtccgccatcaaaaactggtgttctttgctgaagatgtg
 G   H   D   S   G   F   E   V   R   H   Q   K   L   V   F   F   A   E   D   V
ggttcgaacaaaggcgccatcatcggactcatggtgggcggcgttgtcatagcaaccgtg
 G   S   N   K   G   A   I   I   G   L   M   V   G   G   V   V   I   A   T   V
attgtcatcaccctggtgatgttgaagaagaaacagtacac[illegible]
 I   V   I   T   L   V   M   L   K   K   K   Q   Y   T   S   I   H   H   G   V
[illegible]tggaggtcgacgccgccgtgacccc[illegible]
 V   E   V   D   A   A   V   T   P   E   E   R   H   L   S   K   M   Q   Q   N
[illegible]gagaatcca[illegible]aatgcagaactaa
 G   Y   E   N   P   T   Y   K   F   F   E   Q   M   Q   N   ~
```

Sense:
659 gRNA
Antisense:
670 gRNA
676 gRNA
686 gRNA
670 gRNA

FIG. 13 CONTINUED

>mouse APP (nucleotide sequence SEQ ID NO:13, amino acid sequence SEQ ID NO:14)

```
atgctgcccagcttggcactgctcctgctggccgcctggacggttcgggctctggaggta
 M  L  P  S  L  A  L  L  L  L  A  A  W  T  V  R  A  L  E  V
cccactgatggcaacgctggcctgctggcagaaccccagatcgccatgttctgtggtaaa
 P  T  D  G  N  A  G  L  L  A  E  P  Q  I  A  M  F  C  G  K
ctcaacatgcacatgaatgtgcagaatgggaagtgggagtcagacccgtcagggaccaaa
 L  N  M  H  M  N  V  Q  N  G  K  W  E  S  D  P  S  G  T  K
acctgcattggcaccaaggagggcatcttgcagtactgccaagaggtctaccctgaactg
 T  C  I  G  T  K  E  G  I  L  Q  Y  C  Q  E  V  Y  P  E  L
cagatcacaaacgtggtggaagccaaccagccagtgaccatccagaactggtgcaagcgg
 Q  I  T  N  V  V  E  A  N  Q  P  V  T  I  Q  N  W  C  K  R
ggccgcaagcagtgcaagacacacacccacatcgtgattccttaccgttgcctagttggt
 G  R  K  Q  C  K  T  H  T  H  I  V  I  P  Y  R  C  L  V  G
gagtttgtgagcgatgcccttctcgtgcctgacaagtgcaagttcctacaccaggagcgg
 E  F  V  S  D  A  L  L  V  P  D  K  C  K  F  L  H  Q  E  R
atggatgtttgtgagacccatcttcactggcacaccgtcgccaaagagacatgcagcgag
 M  D  V  C  E  T  H  L  H  W  H  T  V  A  K  E  T  C  S  E
aagagcactaacttgcacgactatggcatgctgctgccctgcggcatcgacaagttccga
 K  S  T  N  L  H  D  Y  G  M  L  L  P  C  G  I  D  K  F  R
ggggtagagtttgtatgctgcccgttggccgaggaaagcgacagcgtggattctgcggat
 G  V  E  F  V  C  C  P  L  A  E  E  S  D  S  V  D  S  A  D
gcagaggaggatgactctgatgtctggtggggtggagcggacacagactacgctgatggc
 A  E  E  D  D  S  D  V  W  W  G  G  A  D  T  D  Y  A  D  G
ggtgaagacaaggtcgtagaagtcgcagaggaggaagaagtggctgatgttgaggaagag
 G  E  D  K  V  V  E  V  A  E  E  E  E  V  A  D  V  E  E  E
gaagctgatgatgatgaggatgtggaggatggggacgaggtggaggaggaggccgaggag
 E  A  D  D  D  E  D  V  E  D  G  D  E  V  E  E  E  A  E  E
ccctacgaagaggccaccgagagaacaaccagcactgccaccaccaccaccaccaccact
 P  Y  E  E  A  T  E  R  T  T  S  T  A  T  T  T  T  T  T  T
gagtccgtggaggaggtggtccgagttcccacgacagcagccagcaccccggacgccgtc
 E  S  V  E  E  V  V  R  V  P  T  T  A  A  S  T  P  D  A  V
gacaagtacctggagacacccggggacgagaacgagcatgcccatttccagaaagccaaa
 D  K  Y  L  E  T  P  G  D  E  N  E  H  A  H  F  Q  K  A  K
gagaggctggaagccaagcaccgagagagaatgtcccaggtcatgagagaatgggaagag
 E  R  L  E  A  K  H  R  E  R  M  S  Q  V  M  R  E  W  E  E
gcagagcgtcaagccaagaacttgcccaaagctgacaagaaggccgttatccagcatttc
 A  E  R  Q  A  K  N  L  P  K  A  D  K  K  A  V  I  Q  H  F
caggagaaagtggaatctctggaacaggaagcagccaatgagagacagcagcttgtagag
 Q  E  K  V  E  S  L  E  Q  E  A  A  N  E  R  Q  Q  L  V  E
acacacatggccagagttgaagccatgctcaatgaccgccgccgcctggccctggagaat
 T  H  M  A  R  V  E  A  M  L  N  D  R  R  R  L  A  L  E  N
tacatcactgcactgcaggcggtgcccccaaggcctcatcatgtgttcaacatgctgaag
 Y  I  T  A  L  Q  A  V  P  P  R  P  H  H  V  F  N  M  L  K
aagtacgtccgtgcggagcagaaagacagacagcacaccctaaagcatttcgaacatgtg
 K  Y  V  R  A  E  Q  K  D  R  Q  H  T  L  K  H  F  E  H  V
cgcatggtggaccccaagaaagctgctcagatccggtcccaggttatgacacacctccgt
 R  M  V  D  P  K  K  A  A  Q  I  R  S  Q  V  M  T  H  L  R
gtgatttatgagcgcatgaaccagtctctctccctgctctacaacgtccctgcggtggcc
 V  I  Y  E  R  M  N  Q  S  L  S  L  L  Y  N  V  P  A  V  A
gaggagattcaagatgaagtcgatgagctgcttcagaaggagcagaactactccgacgat
 E  E  I  Q  D  E  V  D  E  L  L  Q  K  E  Q  N  Y  S  D  D
gtcttggccaacatgatcagtgagcccagaatcagctacggaaacgacgctctcatgcct
 V  L  A  N  M  I  S  E  P  R  I  S  Y  G  N  D  A  L  M  P
tcgctgacggaaaccaagaccaccgtggagcttcttcccgtgaatggggagttcagcctg
 S  L  T  E  T  K  T  T  V  E  L  L  P  V  N  G  E  F  S  L
gatgacctccagccgtggcactcttttggggctgactctgtgccagccaacacagaaaac
 D  D  L  Q  P  W  H  S  F  G  A  D  S  V  P  A  N  T  E  N
gaagtcgagcctgttgatgcccgccccgctgccgaccgaggactgaccactcgaccaggt
 E  V  E  P  V  D  A  R  P  A  A  D  R  G  L  T  T  R  P  G
tctgggctgacaaacatcaagacggaagagatctcggaagtgaagatggatgcagaattc
 S  G  L  T  N  I  K  T  E  E  I  S  E  V  K  M  D  A  E  F
ggacatgattcaggatttgaagtccgccatcaaaaactggtgttctttgctgaagatgtg
 G  H  D  S  G  F  E  V  R  H  Q  K  L  V  F  F  A  E  D  V
ggttcgaacaaaggcgccatcatcggactcatggtgggcggcgttgtcatagcaaccgtg
 G  S  N  K  G  A  I  I  G  L  M  V  G  G  V  V  I  A  T  V
attgtcatcaccctggtgatgttgaagaagaaacagtacacatccatccatcatggcgtg
 I  V  I  T  L  V  M  L  K  K  K  Q  Y  T  S  I  H  H  G  V
gtggaggtcgacgccgctgtgaccccagaggagcgccatctctccaagatgcagcagaac
 V  E  V  D  A  A  V  T  P  E  E  R  H  L  S  K  M  Q  Q  N
ggatatgagaatccaacttacaagttctttgagcaaatgcagaactaa
 G  Y  E  N  P  T  Y  K  F  F  E  Q  M  Q  N  -
```

653 gRNA
669 gRNA
670 gRNA
676 gRNA
686 gRNA

FIG. 13 CONTINUED

>human APP

```
atgctgcccggtttggcactgctcctgctggccgcctggacggctcgggcgctggaggta
 M  L  P  G  L  A  L  L  L  L  A  A  W  T  A  R  A  L  E  V
cccactgatggtaatgctggcctgctggctgaaccccagattgccatgttctgtggcaga
 P  T  D  G  N  A  G  L  L  A  E  P  Q  I  A  M  F  C  G  R
ctgaacatgcacatgaatgtccagaatgggaagtgggattcagatccatcagggaccaaa
 L  N  M  H  M  N  V  Q  N  G  K  W  D  S  D  P  S  G  T  K
acctgcattgataccaaggaaggcatcctgcagtattgccaagaagtctaccctgaactg
 T  C  I  D  T  K  E  G  I  L  Q  Y  C  Q  E  V  Y  P  E  L
cagatcaccaatgtggtagaagccaaccaaccagtgaccatccagaactggtgcaagcgg
 Q  I  T  N  V  V  E  A  N  Q  P  V  T  I  Q  N  W  C  K  R
ggccgcaagcagtgcaagacccatccccactttgtgattccctaccgctgcttagttggt
 G  R  K  Q  C  K  T  H  P  H  F  V  I  P  Y  R  C  L  V  G
gagtttgtaagtgatgcccttctcgttcctgacaagtgcaaattcttacaccaggagagg
 E  F  V  S  D  A  L  L  V  P  D  K  C  K  F  L  H  Q  E  R
atggatgtttgcgaaactcatcttcactggcacaccgtcgccaaagagacatgcagtgag
 M  D  V  C  E  T  H  L  H  W  H  T  V  A  K  E  T  C  S  E
aagagtaccaacttgcatgactacggcatgttgctgccctgcggaattgacaagttccga
 K  S  T  N  L  H  D  Y  G  M  L  L  P  C  G  I  D  K  F  R
ggggtagagtttgtgtgttgcccactggctgaagaaagtgacaatgtggattctgctgat
 G  V  E  F  V  C  C  P  L  A  E  E  S  D  N  V  D  S  A  D
gcggaggaggatgactcggatgtctggtggggcggagcagacacagactatgcagatggg
 A  E  E  D  D  S  D  V  W  W  G  G  A  D  T  D  Y  A  D  G
agtgaagacaaagtagtagaagtagcagaggaggaagaagtggctgaggtggaagaagaa
 S  E  D  K  V  V  E  V  A  E  E  E  E  V  A  E  V  E  E  E
gaagccgatgatgacgaggacgatgaggatggtgatgaggtagaggaagaggctgaggaa
 E  A  D  D  D  E  D  D  E  D  G  D  E  V  E  E  E  A  E  E
ccctacgaagaagccacagagagaaccaccagcattgccaccaccaccaccaccaccaca
 P  Y  E  E  A  T  E  R  T  T  S  I  A  T  T  T  T  T  T  T
gagtctgtggaagaggtggttcgagttcctacaacagcagccagtacccctgatgccgtt
 E  S  V  E  E  V  V  R  V  P  T  T  A  A  S  T  P  D  A  V
gacaagtatctcgagacacctggggatgagaatgaacatgcccatttccagaaagccaaa
 D  K  Y  L  E  T  P  G  D  E  N  E  H  A  H  F  Q  K  A  K
gagaggcttgaggccaagcaccgagagagaatgtcccaggtcatgagagaatgggaagag
 E  R  L  E  A  K  H  R  E  R  M  S  Q  V  M  R  E  W  E  E
gcagaacgtcaagcaaagaacttgcctaaagctgataagaaggcagttatccagcatttc
 A  E  R  Q  A  K  N  L  P  K  A  D  K  K  A  V  I  Q  H  F
caggagaaagtggaatctttggaacaggaagcagccaacgagagacagcagctggtggag
 Q  E  K  V  E  S  L  E  Q  E  A  A  N  E  R  Q  Q  L  V  E
acacacatggccagagtggaagccatgctcaatgaccgccgccgcctggccctggagaac
 T  H  M  A  R  V  E  A  M  L  N  D  R  R  R  L  A  L  E  N
tacatcaccgctctgcaggctgttcctcctcggcctcgtcacgtgttcaatatgctaaag
 Y  I  T  A  L  Q  A  V  P  P  R  P  R  H  V  F  N  M  L  K
aagtatgtccgcgcagaacagaaggacagacagcacaccctaaagcatttcgagcatgtg
 K  Y  V  R  A  E  Q  K  D  R  Q  H  T  L  K  H  F  E  H  V
cgcatggtggatcccaagaaagccgctcagatccggtcccaggttatgacacacctccgt
 R  M  V  D  P  K  K  A  A  Q  I  R  S  Q  V  M  T  H  L  R
gtgatttatgagcgcatgaatcagtctctctccctgctctacaacgtgcctgcagtggcc
 V  I  Y  E  R  M  N  Q  S  L  S  L  L  Y  N  V  P  A  V  A
gaggagattcaggatgaagttgatgagctgcttcagaaagagcaaaactattcagatgac
 E  E  I  Q  D  E  V  D  E  L  L  Q  K  E  Q  N  Y  S  D  D
gtcttggccaacatgattagtgaaccaaggatcagttacggaaacgatgctctcatgcca
 V  L  A  N  M  I  S  E  P  R  I  S  Y  G  N  D  A  L  M  P
tctttgaccgaaacgaaaaccaccgtggagctccttcccgtgaatggagagttcagcctg
 S  L  T  E  T  K  T  T  V  E  L  L  P  V  N  G  E  F  S  L
gacgatctccagccgtggcattcttttggggctgactctgtgccagccaacacagaaaac
 D  D  L  Q  P  W  H  S  F  G  A  D  S  V  P  A  N  T  E  N
gaagttgagcctgttgatgcccgccctgctgccgaccgaggactgaccactcgaccaggt
 E  V  E  P  V  D  A  R  P  A  A  D  R  G  L  T  T  R  P  G
tctgggttgacaaatatcaagacggaggagatctctgaagtgaagatggatgcagaattc
 S  G  L  T  N  I  K  T  E  E  I  S  E  V  K  M  D  A  E  F
cgacatgactcaggatatgaagttcatcatcaaaaattggtgttctttgcagaagatgtg
 R  H  D  S  G  Y  E  V  H  H  Q  K  L  V  F  F  A  E  D  V
ggttcaaacaaaggtgcaatcattggactcatggtgggcggtgttgtcatagcgacagtg
 G  S  N  K  G  A  I  I  G  L  M  V  G  G  V  V  I  A  T  V
atcgtcatcaccttggtgatgctgaagaagaaacagtacacatccattcatcatggtgtg
 I  V  I  T  L  V  M  L  K  K  K  Q  Y  T  S  I  H  H  G  V
gtggaggttgacgccgctgtcaccccagaggagcgccacctgtccaagatgcagcagaac
 V  E  V  D  A  A  V  T  P  E  E  R  H  L  S  K  M  Q  Q  N
ggctacgaaaatccaacctacaagttctttgagcagatgcagaactag
 G  Y  E  N  P  T  Y  K  F  F  E  Q  M  Q  N  *
```

(nucleotide sequence SEQ ID NO:11, amino acid sequence SEQ ID NO:12)

653 gRNA
669 gRNA
670 gRNA
676 gRNA
686 gRNA

FIG. 14

>SpCas9 (SEQ ID NO:15)
ATGGGTATCCACGGAGTCCCAGCAGCCGACAAGAAGTACAGCATCGGCCTGGACAT
CGGCACCAACTCTGTGGGCTGGGCCGTGATCACCGACGAGTACAAGGTGCCCAGCA
AGAAATTCAAGGTGCTGGGCAACACCGACCGGCACAGCATCAAGAAGAACCTGATC
GGAGCCCTGCTGTTCGACAGCGGCGAAACAGCCGAGGCCACCCGGCTGAAGAGAAC
CGCCAGAAGAAGATACACCAGACGGAAGAACCGGATCTGCTATCTGCAAGAGATCT
TCAGCAACGAGATGGCCAAGGTGGACGACAGCTTCTTCCACAGACTGGAAGAGTCC
TTCCTGGTGGAAGAGGATAAGAAGCACGAGCGGCACCCCATCTTCGGCAACATCGT
GGACGAGGTGGCCTACCACGAGAAGTACCCCACCATCTACCACCTGAGAAAGAAAC
TGGTGGACAGCACCGACAAGGCCGACCTGCGGCTGATCTATCTGGCCCTGGCCCAC
ATGATCAAGTTCCGGGGCCACTTCCTGATCGAGGGCGACCTGAACCCCGACAACAG
CGACGTGGACAAGCTGTTCATCCAGCTGGTGCAGACCTACAACCAGCTGTTCGAGG
AAAACCCCATCAACGCCAGCGGCGTGGACGCCAAGGCCATCCTGTCTGCCAGACTG
AGCAAGAGCAGACGGCTGGAAAATCTGATCGCCCAGCTGCCCGGCGAGAAGAAGA
ATGGCCTGTTCGGAAACCTGATTGCCCTGAGCCTGGGCCTGACCCCCAACTTCAAGA
GCAACTTCGACCTGGCCGAGGATGCCAAACTGCAGCTGAGCAAGGACACCTACGAC
GACGACCTGGACAACCTGCTGGCCCAGATCGGCGACCAGTACGCCGACCTGTTTCTG
GCCGCCAAGAACCTGTCCGACGCCATCCTGCTGAGCGACATCCTGAGAGTGAACAC
CGAGATCACCAAGGCCCCCCTGAGCGCCTCTATGATCAAGAGATACGACGAGCACC
ACCAGGACCTGACCCTGCTGAAAGCTCTCGTGCGGCAGCAGCTGCCTGAGAAGTAC
AAAGAGATTTTCTTCGACCAGAGCAAGAACGGCTACGCCGGCTACATTGACGGCGG
AGCCAGCCAGGAAGAGTTCTACAAGTTCATCAAGCCCATCCTGGAAAAGATGGACG
GCACCGAGGAACTGCTCGTGAAGCTGAACAGAGAGGACCTGCTGCGGAAGCAGCG
GACCTTCGACAACGGCAGCATCCCCCACCAGATCCACCTGGGAGAGCTGCACGCCA
TTCTGCGGCGGCAGGAAGATTTTTACCCATTCCTGAAGGACAACCGGGAAAAGATC
GAGAAGATCCTGACCTTCCGCATCCCCTACTACGTGGGCCCTCTGGCCAGGGGAAAC
AGCAGATTCGCCTGGATGACCAGAAAGAGCGAGGAAACCATCACCCCCTGGAACTT
CGAGGAAGTGGTGGACAAGGGCGCTTCCGCCCAGAGCTTCATCGAGCGGATGACCA
ACTTCGATAAGAACCTGCCCAACGAGAAGGTGCTGCCCAAGCACAGCCTGCTGTAC
GAGTACTTCACCGTGTATAACGAGCTGACCAAAGTGAAATACGTGACCGAGGGAAT
GAGAAAGCCCGCCTTCCTGAGCGGCGAGCAGAAAAAGGCCATCGTGGACCTGCTGT
TCAAGACCAACCGGAAAGTGACCGTGAAGCAGCTGAAAGAGGACTACTTCAAGAAA
ATCGAGTGCTTCGACTCCGTGGAAATCTCCGGCGTGGAAGATCGGTTCAACGCCTCC
CTGGGCACATACCACGATCTGCTGAAAATTATCAAGGACAAGGACTTCCTGGACAA
TGAGGAAAACGAGGACATTCTGGAAGATATCGTGCTGACCCTGACACTGTTTGAGG
ACAGAGAGATGATCGAGGAACGGCTGAAAACCTATGCCCACCTGTTCGACGACAAA
GTGATGAAGCAGCTGAAGCGGCGGAGATACACCGGCTGGGGCAGGCTGAGCCGGA
AGCTGATCAACGGCATCCGGGACAAGCAGTCCGGCAAGACAATCCTGGATTTCCTG
AAGTCCGACGGCTTCGCCAACAGAAACTTCATGCAGCTGATCCACGACGACAGCCT

FIG. 14 CONTINUED

GACCTTTAAAGAGGACATCCAGAAAGCCCAGGTGTCCGGCCAGGGCGATAGCCTGC
ACGAGCACATTGCCAATCTGGCCGGCAGCCCCGCCATTAAGAAGGGCATCCTGCAG
ACAGTGAAGGTGGTGGACGAGCTCGTGAAAGTGATGGGCCGGCACAAGCCCGAGA
ACATCGTGATCGAAATGGCCAGAGAGAACCAGACCACCCAGAAGGGACAGAAGAA
CAGCCGCGAGAGAATGAAGCGGATCGAAGAGGGCATCAAAGAGCTGGGCAGCCAG
ATCCTGAAAGAACACCCCGTGGAAAACACCCAGCTGCAGAACGAGAAGCTGTACCT
GTACTACCTGCAGAATGGGCGGGATATGTACGTGGACCAGGAACTGGACATCAACC
GGCTGTCCGACTACGATGTGGACCATATCGTGCCTCAGAGCTTTCTGAAGGACGACT
CCATCGACAACAAGGTGCTGACCAGAAGCGACAAGAACCGGGGCAAGAGCGACAA
CGTGCCCTCCGAAGAGGTCGTGAAGAAGATGAAGAACTACTGGCGGCAGCTGCTGA
ACGCCAAGCTGATTACCCAGAGAAAGTTCGACAATCTGACCAAGGCCGAGAGAGGC
GGCCTGAGCGAACTGGATAAGGCCGGCTTCATCAAGAGACAGCTGGTGGAAACCCG
GCAGATCACAAAGCACGTGGCACAGATCCTGGACTCCCGGATGAACACTAAGTACG
ACGAGAATGACAAGCTGATCCGGGAAGTGAAAGTGATCACCCTGAAGTCCAAGCTG
GTGTCCGATTTCCGGAAGGATTTCCAGTTTTACAAAGTGCGCGAGATCAACAACTAC
CACCACGCCCACGACGCCTACCTGAACGCCGTCGTGGGAACCGCCCTGATCAAAAA
GTACCCTAAGCTGGAAAGCGAGTTCGTGTACGGCGACTACAAGGTGTACGACGTGC
GGAAGATGATCGCCAAGAGCGAGCAGGAAATCGGCAAGGCTACCGCCAAGTACTTC
TTCTACAGCAACATCATGAACTTTTTCAAGACCGAGATTACCCTGGCCAACGGCGAG
ATCCGGAAGCGGCCTCTGATCGAGACAAACGGCGAAACCGGGGAGATCGTGTGGGA
TAAGGGCCGGGATTTTGCCACCGTGCGGAAAGTGCTGAGCATGCCCCAAGTGAATA
TCGTGAAAAAGACCGAGGTGCAGACAGGCGGCTTCAGCAAAGAGTCTATCCTGCCC
AAGAGGAACAGCGATAAGCTGATCGCCAGAAAGAAGGACTGGGACCCTAAGAAGT
ACGGCGGCTTCGACAGCCCCACCGTGGCCTATTCTGTGCTGGTGGTGGCCAAAGTGG
AAAAGGGCAAGTCCAAGAAACTGAAGAGTGTGAAAGAGCTGCTGGGGATCACCATC
ATGGAAAGAAGCAGCTTCGAGAAGAATCCCATCGACTTTCTGGAAGCCAAGGGCTA
CAAAGAAGTGAAAAAGGACCTGATCATCAAGCTGCCTAAGTACTCCCTGTTCGAGC
TGGAAAACGGCCGGAAGAGAATGCTGGCCTCTGCCGGCGAACTGCAGAAGGGAAA
CGAACTGGCCCTGCCCTCCAAATATGTGAACTTCCTGTACCTGGCCAGCCACTATGA
GAAGCTGAAGGGCTCCCCCGAGGATAATGAGCAGAAACAGCTGTTTGTGGAACAGC
ACAAGCACTACCTGGACGAGATCATCGAGCAGATCAGCGAGTTCTCCAAGAGAGTG
ATCCTGGCCGACGCTAATCTGGACAAAGTGCTGTCCGCCTACAACAAGCACCGGGA
TAAGCCCATCAGAGAGCAGGCCGAGAATATCATCCACCTGTTTACCCTGACCAATCT
GGGAGCCCCTGCCGCCTTCAAGTACTTTGACACCACCATCGACCGGAAGAGGTACA
CCAGCACCAAAGAGGTGCTGGACGCCACCCTGATCCACCAGAGCATCACCGGCCTG
TACGAGACACGGATCGACCTGTCTCAGCTGGGAGGCGACAAAAGGCCGGCGGCCAC
GAAAAAGGCCGGCCAGGCAAAAAAGAAAAAG

FIG. 15

APP 659 gRNA Cas9 vector (SEQ ID NO:17)

CCCCACGAGGGCCTATTTCCCATGATTCCTTCATATTTGCATATACGATACAAGGCT
GTTAGAGAGATAATTGGAATTAATTTGACTGTAAACACAAAGATATTAGTACAAAA
TACGTGACGTAGAAAGTAATAATTTCTTGGGTAGTTTGCAGTTTTAAAATTATGTTTT
AAAATGGACTATCATATGCTTACCGTAACTTGAAAGTATTTCGATTTCTTGGCTTTAT
ATATCTTGTGGAAAGGACGAAACACCG*atccattcatcatggtgtgg*GTTTTAGAGCTAGAAAT
AGCAAGTTAAAATAAGGCTAGTCCGTTATCAACTTGAAAAAGTGGCACCGAGTCGG
TGCTTTTTTGTTTTAGAGCTAGAAATAGCAAGTTAAAATAAGGCTAGTCCGTTTTTAG
CGCGTGCGCCAATTCTGCAGACAAATGGCTCTAGAGGTACCCGTTACATAACTTACG
GTAAATGGCCCGCCTGGCTGACCGCCCAACGACCCCCGCCCATTGACGTCAATAGTA
ACGCCAATAGGGACTTTCCATTGACGTCAATGGGTGGAGTATTTACGGTAAACTGCC
CACTTGGCAGTACATCAAGTGTATCATATGCCAAGTACGCCCCCTATTGACGTCAAT
GACGGTAAATGGCCCGCCTGGCATTGTGCCCAGTACATGACCTTATGGGACTTTCCT
ACTTGGCAGTACATCTACGTATTAGTCATCGCTATTACCATGGTCGAGGTGAGCCCC
ACGTTCTGCTTCACTCTCCCCATCTCCCCCCCCTCCCCACCCCCAATTTTGTATTTATT
TATTTTTTAATTATTTTGTGCAGCGATGGGGGCGGGGGGGGGGGGGGGGCGCGCGC
CAGGCGGGGCGGGGCGGGGCGAGGGGCGGGGCGGGGCGAGGCGGAGAGGTGCGG
CGGCAGCCAATCAGAGCGGCGCGCTCCGAAAGTTTCCTTTTATGGCGAGGCGGCGG
CGGCGGCGGCCCTATAAAAAGCGAAGCGCGCGGCGGGCGGGAGTCGCTGCGACGCT
GCCTTCGCCCCGTGCCCCGCTCCGCCGCCGCCTCGCGCCGCCCGCCCCGGCTCTGAC
TGACCGCGTTACTCCCACAGGTGAGCGGGCGGGACGGCCCTTCTCCTCCGGGCTGTA
ATTAGCTGAGCAAGAGGTAAGGGTTTAAGGGATGGTTGGTTGGTGGGGTATTAATG
TTTAATTACCTGGAGCACCTGCCTGAAATCACTTTTTTTCAGGTTGGACCGGTGCCAC
CATGGACTATAAGGACCACGACGGAGACTACAAGGATCATGATATTGATTACAAAG
ACGATGACGATAAGATGGCCCCAAAGAAGAAGCGGAAGGTCGGTATCCACGGAGTC
CCAGCAGCCGACAAGAAGTACAGCATCGGCCTGGACATCGGCACCAACTCTGTGGG
CTGGGCCGTGATCACCGACGAGTACAAGGTGCCCAGCAAGAAATTCAAGGTGCTGG
GCAACACCGACCGGCACAGCATCAAGAAGAACCTGATCGGAGCCCTGCTGTTCGAC
AGCGGCGAAACAGCCGAGGCCACCCGGCTGAAGAGAACCGCCAGAAGAAGATACA
CCAGACGGAAGAACCGGATCTGCTATCTGCAAGAGATCTTCAGCAACGAGATGGCC
AAGGTGGACGACAGCTTCTTCCACAGACTGGAAGAGTCCTTCCTGGTGGAAGAGGA
TAAGAAGCACGAGCGGCACCCCATCTTCGGCAACATCGTGGACGAGGTGGCCTACC
ACGAGAAGTACCCCACCATCTACCACCTGAGAAAGAAACTGGTGGACAGCACCGAC
AAGGCCGACCTGCGGCTGATCTATCTGGCCCTGGCCCACATGATCAAGTTCCGGGGC
CACTTCCTGATCGAGGGCGACCTGAACCCCGACAACAGCGACGTGGACAAGCTGTT
CATCCAGCTGGTGCAGACCTACAACCAGCTGTTCGAGGAAAACCCCATCAACGCCA
GCGGCGTGGACGCCAAGGCCATCCTGTCTGCCAGACTGAGCAAGAGCAGACGGCTG
GAAAATCTGATCGCCCAGCTGCCCGGCGAGAAGAAGAATGGCCTGTTCGGAAACCT

FIG. 15 CONTINUED

GATTGCCCTGAGCCTGGGCCTGACCCCCAACTTCAAGAGCAACTTCGACCTGGCCGA
GGATGCCAAACTGCAGCTGAGCAAGGACACCTACGACGACGACCTGGACAACCTGC
TGGCCCAGATCGGCGACCAGTACGCCGACCTGTTTCTGGCCGCCAAGAACCTGTCCG
ACGCCATCCTGCTGAGCGACATCCTGAGAGTGAACACCGAGATCACCAAGGCCCCC
CTGAGCGCCTCTATGATCAAGAGATACGACGAGCACCACCAGGACCTGACCCTGCT
GAAAGCTCTCGTGCGGCAGCAGCTGCCTGAGAAGTACAAAGAGATTTTCTTCGACC
AGAGCAAGAACGGCTACGCCGGCTACATTGACGGCGGAGCCAGCCAGGAAGAGTTC
TACAAGTTCATCAAGCCCATCCTGGAAAAGATGGACGGCACCGAGGAACTGCTCGT
GAAGCTGAACAGAGAGGACCTGCTGCGGAAGCAGCGGACCTTCGACAACGGCAGC
ATCCCCCACCAGATCCACCTGGGAGAGCTGCACGCCATTCTGCGGCGGCAGGAAGA
TTTTTACCCATTCCTGAAGGACAACCGGGAAAAGATCGAGAAGATCCTGACCTTCCG
CATCCCCTACTACGTGGGCCCTCTGGCCAGGGGAAACAGCAGATTCGCCTGGATGA
CCAGAAAGAGCGAGGAAACCATCACCCCCTGGAACTTCGAGGAAGTGGTGGACAA
GGGCGCTTCCGCCCAGAGCTTCATCGAGCGGATGACCAACTTCGATAAGAACCTGC
CCAACGAGAAGGTGCTGCCCAAGCACAGCCTGCTGTACGAGTACTTCACCGTGTAT
AACGAGCTGACCAAAGTGAAATACGTGACCGAGGGAATGAGAAAGCCCGCCTTCCT
GAGCGGCGAGCAGAAAAAGGCCATCGTGGACCTGCTGTTCAAGACCAACCGGAAA
GTGACCGTGAAGCAGCTGAAAGAGGACTACTTCAAGAAAATCGAGTGCTTCGACTC
CGTGGAAATCTCCGGCGTGGAAGATCGGTTCAACGCCTCCCTGGGCACATACCACG
ATCTGCTGAAAATTATCAAGGACAAGGACTTCCTGGACAATGAGGAAAACGAGGAC
ATTCTGGAAGATATCGTGCTGACCCTGACACTGTTTGAGGACAGAGAGATGATCGA
GGAACGGCTGAAAACCTATGCCCACCTGTTCGACGACAAAGTGATGAAGCAGCTGA
AGCGGCGGAGATACACCGGCTGGGGCAGGCTGAGCCGGAAGCTGATCAACGGCATC
CGGGACAAGCAGTCCGGCAAGACAATCCTGGATTTCCTGAAGTCCGACGGCTTCGC
CAACAGAAACTTCATGCAGCTGATCCACGACGACAGCCTGACCTTTAAAGAGGACA
TCCAGAAAGCCCAGGTGTCCGGCCAGGGCGATAGCCTGCACGAGCACATTGCCAAT
CTGGCCGGCAGCCCCGCCATTAAGAAGGGCATCCTGCAGACAGTGAAGGTGGTGGA
CGAGCTCGTGAAAGTGATGGGCCGGCACAAGCCCGAGAACATCGTGATCGAAATGG
CCAGAGAGAACCAGACCACCCAGAAGGGACAGAAGAACAGCCGCGAGAGAATGAA
GCGGATCGAAGAGGGCATCAAAGAGCTGGGCAGCCAGATCCTGAAAGAACACCCC
GTGGAAAACACCCAGCTGCAGAACGAGAAGCTGTACCTGTACTACCTGCAGAATGG
GCGGGATATGTACGTGGACCAGGAACTGGACATCAACCGGCTGTCCGACTACGATG
TGGACCATATCGTGCCTCAGAGCTTTCTGAAGGACGACTCCATCGACAACAAGGTGC
TGACCAGAAGCGACAAGAACCGGGGCAAGAGCGACAACGTGCCCTCCGAAGAGGT
CGTGAAGAAGATGAAGAACTACTGGCGGCAGCTGCTGAACGCCAAGCTGATTACCC
AGAGAAAGTTCGACAATCTGACCAAGGCCGAGAGAGGCGGCCTGAGCGAACTGGAT
AAGGCCGGCTTCATCAAGAGACAGCTGGTGGAAACCCGGCAGATCACAAAGCACGT
GGCACAGATCCTGGACTCCCGGATGAACACTAAGTACGACGAGAATGACAAGCTGA
TCCGGGAAGTGAAAGTGATCACCCTGAAGTCCAAGCTGGTGTCCGATTTCCGGAAG
GATTTCCAGTTTTACAAAGTGCGCGAGATCAACAACTACCACCACGCCCACGACGCC

FIG. 15 CONTINUED

TACCTGAACGCCGTCGTGGGAACCGCCCTGATCAAAAAGTACCCTAAGCTGGAAAG
CGAGTTCGTGTACGGCGACTACAAGGTGTACGACGTGCGGAAGATGATCGCCAAGA
GCGAGCAGGAAATCGGCAAGGCTACCGCCAAGTACTTCTTCTACAGCAACATCATG
AACTTTTTCAAGACCGAGATTACCCTGGCCAACGGCGAGATCCGGAAGCGGCCTCT
GATCGAGACAAACGGCGAAACCGGGGAGATCGTGTGGGATAAGGGCCGGGATTTTG
CCACCGTGCGGAAAGTGCTGAGCATGCCCCAAGTGAATATCGTGAAAAAGACCGAG
GTGCAGACAGGCGGCTTCAGCAAAGAGTCTATCCTGCCCAAGAGGAACAGCGATAA
GCTGATCGCCAGAAAGAAGGACTGGGACCCTAAGAAGTACGGCGGCTTCGACAGCC
CCACCGTGGCCTATTCTGTGCTGGTGGTGGCCAAAGTGGAAAAGGGCAAGTCCAAG
AAACTGAAGAGTGTGAAAGAGCTGCTGGGGATCACCATCATGGAAAGAAGCAGCTT
CGAGAAGAATCCCATCGACTTTCTGGAAGCCAAGGGCTACAAAGAAGTGAAAAAGG
ACCTGATCATCAAGCTGCCTAAGTACTCCCTGTTCGAGCTGGAAAACGGCCGGAAG
AGAATGCTGGCCTCTGCCGGCGAACTGCAGAAGGGAAACGAACTGGCCCTGCCCTC
CAAATATGTGAACTTCCTGTACCTGGCCAGCCACTATGAGAAGCTGAAGGGCTCCCC
CGAGGATAATGAGCAGAAACAGCTGTTTGTGGAACAGCACAAGCACTACCTGGACG
AGATCATCGAGCAGATCAGCGAGTTCTCCAAGAGAGTGATCCTGGCCGACGCTAAT
CTGGACAAAGTGCTGTCCGCCTACAACAAGCACCGGGATAAGCCCATCAGAGAGCA
GGCCGAGAATATCATCCACCTGTTTACCCTGACCAATCTGGGAGCCCCTGCCGCCTT
CAAGTACTTTGACACCACCATCGACCGGAAGAGGTACACCAGCACCAAAGAGGTGC
TGGACGCCACCCTGATCCACCAGAGCATCACCGGCCTGTACGAGACACGGATCGAC
CTGTCTCAGCTGGGAGGCGACAAAAGGCCGGCGGCCACGAAAAAGGCCGGCCAGG
CAAAAAAGAAAAAGCTTGAGGGCAGAGGAAGTCTGCTAACATGCGGTGACGTGGA
GGAGAATCCCGGCCCTGCTAGCATGGTGAGCAAGGGCGAGGAGGATAACATGGCCA
TCATCAAGGAGTTCATGCGCTTCAAGGTGCACATGGAGGGCTCCGTGAACGGCCAC
GAGTTCGAGATCGAGGGCGAGGGCGAGGGCCGCCCCTACGAGGGCACCCAGACCG
CCAAGCTGAAGGTGACCAAGGGTGGCCCCCTGCCCTTCGCCTGGGACATCCTGTCCC
CTCAGTTCATGTACGGCTCCAAGGCCTACGTGAAGCACCCCGCCGACATCCCCGACT
ACTTGAAGCTGTCCTTCCCCGAGGGCTTCAAGTGGGAGCGCGTGATGAACTTCGAGG
ACGGCGGCGTGGTGACCGTGACCCAGGACTCCTCCCTGCAGGACGGCGAGTTCATC
TACAAGGTGAAGCTGCGCGGCACCAACTTCCCCTCAGACGGCCCCGTAATGCAGAA
GAAAACCATGGGCTGGGAGGCCTCCTCCGAGCGGATGTACCCCGAGGACGGCGCCC
TGAAGGGCGAGATCAAGCAGAGGCTGAAGCTGAAGGACGGCGGCCACTACGACGC
TGAGGTCAAGACCACCTACAAGGCCAAGAAGCCCGTGCAGCTGCCCGGCGCCTACA
ACGTCAACATCAAGTTGGACATCACCTCCCACAACGAGGACTACACCATCGTGGAA
CAGTACGAACGCGCCGAGGGCCGCCACTCCACCGGCGGCATGGACGAGCTGTACAA
GTAAGAATTCCTAGAGCTCGCTGATCAGCCTCGACTGTGCCTTCTAGTTGCCAGCCA
TCTGTTGTTTGCCCCTCCCCCGTGCCTTCCTTGACCCTGGAAGGTGCCACTCCCACTG
TCCTTTCCTAATAAAATGAGGAAATTGCATCGCATTGTCTGAGTAGGTGTCATTCTAT
TCTGGGGGGTGGGGTGGGGCAGGACAGCAAGGGGGAGGATTGGGAAGAGAATAGC
AGGCATGCTGGGGAGCGGCCGCAGGAACCCCTAGTGATGGAGTTGGCCACTCCCTC

FIG. 15 CONTINUED

TCTGCGCGCTCGCTCGCTCACTGAGGCCGGGCGACCAAAGGTCGCCCGACGCCCGG
GCTTTGCCCGGGCGGCCTCAGTGAGCGAGCGAGCGCGCAGCTGCCTGCAGGGGCGC
CTGATGCGGTATTTTCTCCTTACGCATCTGTGCGGTATTTCACACCGCATACGTCAAA
GCAACCATAGTACGCGCCCTGTAGCGGCGCATTAAGCGCGGCGGGTGTGGTGGTTA
CGCGCAGCGTGACCGCTACACTTGCCAGCGCCCTAGCGCCCGCTCCTTTCGCTTTCTT
CCCTTCCTTTCTCGCCACGTTCGCCGGCTTTCCCCGTCAAGCTCTAAATCGGGGGCTC
CCTTTAGGGTTCCGATTTAGTGCTTTACGGCACCTCGACCCCAAAAAACTTGATTTG
GGTGATGGTTCACGTAGTGGGCCATCGCCCTGATAGACGGTTTTTCGCCCTTTGACG
TTGGAGTCCACGTTCTTTAATAGTGGACTCTTGTTCCAAACTGGAACAACACTCAAC
CCTATCTCGGGCTATTCTTTTGATTTATAAGGGATTTTGCCGATTTCGGCCTATTGGT
TAAAAAATGAGCTGATTTAACAAAAATTTAACGCGAATTTTAACAAAATATTAACGT
TTACAATTTTATGGTGCACTCTCAGTACAATCTGCTCTGATGCCGCATAGTTAAGCCA
GCCCCGACACCCGCCAACACCCGCTGACGCGCCCTGACGGGCTTGTCTGCTCCCGGC
ATCCGCTTACAGACAAGCTGTGACCGTCTCCGGGAGCTGCATGTGTCAGAGGTTTTC
ACCGTCATCACCGAAACGCGCGAGACGAAAGGGCCTCGTGATACGCCTATTTTTATA
GGTTAATGTCATGATAATAATGGTTTCTTAGACGTCAGGTGGCACTTTTCGGGGAAA
TGTGCGCGGAACCCCTATTTGTTTATTTTTCTAAATACATTCAAATATGTATCCGCTC
ATGAGACAATAACCCTGATAAATGCTTCAATAATATTGAAAAAGGAAGAGTATGAG
TATTCAACATTTCCGTGTCGCCCTTATTCCCTTTTTTGCGGCATTTTGCCTTCCTGTTT
TTGCTCACCCAGAAACGCTGGTGAAAGTAAAAGATGCTGAAGATCAGTTGGGTGCA
CGAGTGGGTTACATCGAACTGGATCTCAACAGCGGTAAGATCCTTGAGAGTTTTCGC
CCCGAAGAACGTTTTCCAATGATGAGCACTTTTAAAGTTCTGCTATGTGGCGCGGTA
TTATCCCGTATTGACGCCGGGCAAGAGCAACTCGGTCGCCGCATACACTATTCTCAG
AATGACTTGGTTGAGTACTCACCAGTCACAGAAAAGCATCTTACGGATGGCATGAC
AGTAAGAGAATTATGCAGTGCTGCCATAACCATGAGTGATAACACTGCGGCCAACT
TACTTCTGACAACGATCGGAGGACCGAAGGAGCTAACCGCTTTTTTGCACAACATGG
GGGATCATGTAACTCGCCTTGATCGTTGGGAACCGGAGCTGAATGAAGCCATACCA
AACGACGAGCGTGACACCACGATGCCTGTAGCAATGGCAACAACGTTGCGCAAACT
ATTAACTGGCGAACTACTTACTCTAGCTTCCCGGCAACAATTAATAGACTGGATGGA
GGCGGATAAAGTTGCAGGACCACTTCTGCGCTCGGCCCTTCCGGCTGGCTGGTTTAT
TGCTGATAAATCTGGAGCCGGTGAGCGTGGAAGCCGCGGTATCATTGCAGCACTGG
GGCCAGATGGTAAGCCCTCCCGTATCGTAGTTATCTACACGACGGGGAGTCAGGCA
ACTATGGATGAACGAAATAGACAGATCGCTGAGATAGGTGCCTCACTGATTAAGCA
TTGGTAACTGTCAGACCAAGTTTACTCATATATACTTTAGATTGATTTAAAACTTCAT
TTTTAATTTAAAAGGATCTAGGTGAAGATCCTTTTTGATAATCTCATGACCAAAATC
CCTTAACGTGAGTTTTCGTTCCACTGAGCGTCAGACCCCGTAGAAAAGATCAAAGGA
TCTTCTTGAGATCCTTTTTTTCTGCGCGTAATCTGCTGCTTGCAAACAAAAAAACCAC
CGCTACCAGCGGTGGTTTGTTTGCCGGATCAAGAGCTACCAACTCTTTTTCCGAAGG
TAACTGGCTTCAGCAGAGCGCAGATACCAAATACTGTCCTTCTAGTGTAGCCGTAGT
TAGGCCACCACTTCAAGAACTCTGTAGCACCGCCTACATACCTCGCTCTGCTAATCC

FIG. 15 CONTINUED

TGTTACCAGTGGCTGCTGCCAGTGGCGATAAGTCGTGTCTTACCGGGTTGGACTCAA
GACGATAGTTACCGGATAAGGCGCAGCGGTCGGGCTGAACGGGGGGTTCGTGCACA
CAGCCCAGCTTGGAGCGAACGACCTACACCGAACTGAGATACCTACAGCGTGAGCT
ATGAGAAAGCGCCACGCTTCCCGAAGGGAGAAAGGCGGACAGGTATCCGGTAAGC
GGCAGGGTCGGAACAGGAGAGCGCACGAGGGAGCTTCCAGGGGGAAACGCCTGGT
ATCTTTATAGTCCTGTCGGGTTTCGCCACCTCTGACTTGAGCGTCGATTTTTGTGATG
CTCGTCAGGGGGGCGGAGCCTATGGAAAAACGCCAGCAACGCGGCCTTTTTACGGT
TCCTGGCCTTTTGCTGGCCTTTTGCTCACATGT

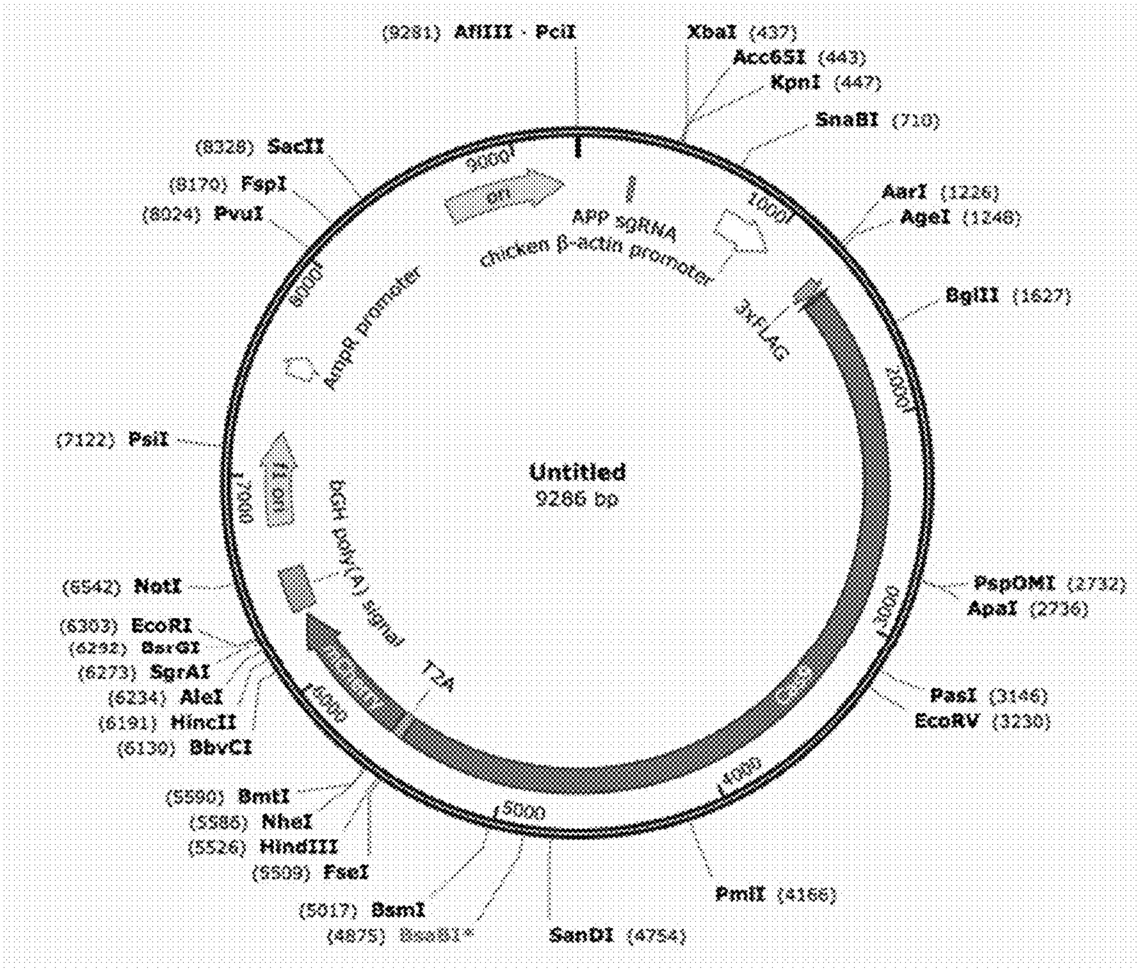

FIG. 16

PX551 Cas9 vector (SEQ ID NO:18)

cctgcaggcagctgcgcgctcgctcgctcactgaggccgcccgggcaaagcccgggcgtcgggcgacctttggtcgcccggcctcagt
gagcgagcgagcgcgcagagagggagtggccaactccatcactaggggttcctgcggcctctagaaagcttAGCTGAATGGG
GTCCGCCTCTTTTCCCTGCCTAAACAGACAGGAACTCCTGCCAATTGAGGGCGTCAC
CGCTAAGGCTCCGCCCCAGCCTGGGCTCCACAACCAATGAAGGGTAATCTCGACAA
AGAGCAAGGGGTGGGGCGCGGGCGCGCAGGTGCAGCAGCACACAGGCTGGTCGGG
AGGGCGGGGCGCGACGTCTGCCGTGCGGGGTCCCGGCATCGGTTGCGCGCaccggtgcca
ccatgtacccatacgatgttccagattacgcttcgccgaagaaaaagcgcaaggtcgaagcgtccgacaagaagtacagcatcggcctgg
acatcggcaccaactctgtgggctgggccgtgatcaccgacgagtacaaggtgcccagcaagaaattcaaggtgctgggcaacaccgac
cggcacagcatcaagaagaacctgatcggagccctgctgttcgacagcggcgaaacagccgaggccacccggctgaagagaaccgcc
agaagaagatacaccagacggaagaaccggatctgctatctgcaagagatcttcagcaacgagatggccaaggtggacgacagcttcttc
cacagactggaagagtccttcctggtggaagaggataagaagcacgagcggcaccccatcttcggcaacatcgtggacgaggtggccta
ccacgagaagtaccccaccatctaccacctgagaaagaaactggtggacagcaccgacaaggccgacctgcggctgatctatctggccct
ggcccacatgatcaagttccggggccacttcctgatcgagggcgacctgaaccccgacaacagcgacgtggacaagctgttcatccagct
ggtgcagacctacaaccagctgttcgaggaaaaccccatcaacgccagcggcgtggacgccaaggccatcctgtctgccagactgagca
agagcagacggctggaaaatctgatcgcccagctgcccggcgagaagaagaatggcctgttcggcaacctgattgccctgagcctgggc
ctgacccccaacttcaagagcaacttcgacctggccgaggatgccaaactgcagctgagcaaggacacctacgacgacgacctggacaa
cctgctggcccagatcggcgaccagtacgccgacctgtttctggccgccaagaacctgtccgacgccatcctgctgagcgacatcctgag
agtgaacaccgagatcaccaaggcccccctgagcgcctctatgatcaagagatacgacgagcaccaccaggacctgaccctgctgaaag
ctctcgtgcggcagcagctgcctgagaagtacaaagagattttcttcgaccagagcaagaacggctacgccggctacattgacggcggag
ccagccaggaagagttctacaagttcatcaagcccatcctggaaaagatggacggcaccgaggaactgctcgtgaagctgaacagagag
gacctgctgcggaagcagcggaccttcgacaacggcagcatcccccaccagatccacctgggagagctgcacgccattctgcggcggc
aggaagatttttacccattcctgaaggacaaccgggaaaagatcgagaagatcctgaccttccgcatcccctactacgtgggccctctggcc
aggggaaacagcagattcgcctggatgaccagaaagagcgaggaaaccatcaccccctggaacttcgaggaagtggtggacaagggc
gcttccgcccagagcttcatcgagcggatgaccaacttcgataagaacctgcccaacgagaaggtgctgcccaagcacagcctgctgtac
gagtacttcaccgtgtataacgagctgaccaaagtgaaatacgtgaccgagggaatgagaaagcccgccttcctgagcggcgagcagaa
aaaggccatcgtggacctgctgttcaagaccaaccggaaagtgaccgtgaagcagctgaaagaggactacttcaagaaaatcgagtgctt
cgactccgtggaaatctccggcgtggaagatcggttcaacgcctccctgggcacataccacgatctgctgaaaattatcaaggacaaggac
ttcctggacaatgaggaaaacgaggacattctggaagatatcgtgctgaccctgacactgtttgaggacagagagatgatcgaggaacggc
tgaaaacctatgcccacctgttcgacgacaaagtgatgaagcagctgaagcggcggagatacaccggctggggcaggctgagccggaa
gctgatcaacggcatccgggacaagcagtccggcaagacaatcctggatttcctgaagtccgacggcttcgccaacagaaacttcatgca
gctgatccacgacgacagcctgacctttaaagaggacatccagaaagcccaggtgtccggccagggcgatagcctgcacgagcacattg
ccaatctggccggcagccccgccattaagaagggcatcctgcagacagtgaaggtggtggacgagctcgtgaaagtgatgggccggca
caagcccgagaacatcgtgatcgaaatggccagagagaaccagaccacccagaagggacagaagaacagccgcgagagaatgaagc
ggatcgaagagggcatcaaagagctgggcagccagatcctgaaagaacaccccgtggaaaacacccagctgcagaacgagaagctgt
acctgtactacctgcagaatgggcgggatatgtacgtggaccaggaactggacatcaaccggctgtccgactacgatgtggaccatatcgt
gcctcagagctttctgaaggacgactccatcgacaacaaggtgctgaccagaagcgacaagaaccggggcaagagcgacaacgtgccc
tccgaagaggtcgtgaagaagatgaagaactactggcggcagctgctgaacgccaagctgattacccagagaaagttcgacaatctgacc

FIG. 16 CONTINUED aaggccgagagaggcggcctgagcgaactggataaggccggcttcatcaagagacagctggtggaaacccggcagatcacaaagcac
gtggcacagatcctggactcccggatgaacactaagtacgacgagaatgacaagctgatccgggaagtgaaagtgatcaccctgaagtcc
aagctggtgtccgatttccggaaggatttccagttttacaaagtgcgcgagatcaacaactaccaccacgcccacgacgcctacctgaacgc
cgtcgtgggaaccgccctgatcaaaaagtaccctaagctggaaagcgagttcgtgtacggcgactacaaggtgtacgacgtgcggaagat
gatcgccaagagcgagcaggaaatcggcaaggctaccgccaagtacttcttctacagcaacatcatgaactttttcaagaccgagattaccc
tggccaacggcgagatccggaagcggcctctgatcgagacaaacggcgaaaccggggagatcgtgtgggataagggccgggattttgc
caccgtgcggaaagtgctgagcatgccccaagtgaatatcgtgaaaaagaccgaggtgcagacaggcggcttcagcaaagagtctatcct
gcccaagaggaacagcgataagctgatcgccagaaagaaggactgggaccctaagaagtacggcggcttcgacagccccaccgtggc
ctattctgtgctggtggtggccaaagtggaaaagggcaagtccaagaaactgaagagtgtgaaagagctgctggggatcaccatcatgga
aagaagcagcttcgagaagaatcccatcgactttctggaagccaagggctacaaagaagtgaaaaaggacctgatcatcaagctgcctaa
gtactccctgttcgagctggaaaacggccggaagagaatgctggcctctgccggcgaactgcagaagggaaacgaactggccctgccct
ccaaatatgtgaacttcctgtacctggccagccactatgagaagctgaagggctcccccgaggataatgagcagaaacagctgtttgtgga
acagcacaagcactacctggacgagatcatcgagcagatcagcgagttctccaagagagtgatcctggccgacgctaatctggacaaagt
gctgtccgcctacaacaagcaccgggataagcccatcagagagcaggccgagaatatcatccacctgtttaccctgaccaatctgggagc
ccctgccgccttcaagtactttgacaccaccatcgaccggaagaggtacaccagcaccaaagaggtgctggacgccaccctgatccacca
gagcatcaccggcctgtacgagacacggatcgacctgtctcagctgggaggcgacagccccaagaagaagagaaaggtggaggccag
ctaagaattcAATAAAAGATCTTTATTTTCATTAGATCTGTGTGTTGGTTTTTTGTGTgcggcc
gcaggaacccctagtgatggagttggccactccctctctgcgcgctcgctcgctcactgaggccgggcgaccaaaggtcgcccgacgcc
cgggctttgcccgggcggcctcagtgagcgagcgagcgcgcagctgcctgcaggggcgcctgatgcggtattttctccttacgcatctgtg
cggtatttcacaccgcatacgtcaaagcaaccatagtacgcgccctgtagcggcgcattaagcgcggcgggtgtggtggttacgcgcagc
gtgaccgctacacttgccagcgccctagcgcccgctcctttcgctttcttcccttcctttctcgccacgttcgccggctttccccgtcaagctcta
aatcgggggctccctttagggttccgatttagtgctttacggcacctcgaccccaaaaaacttgatttgggtgatggttcacgtagtgggccat
cgccctgatagacggtttttcgccctttgacgttggagtccacgttctttaatagtggactcttgttccaaactggaacaacactcaaccctatct
cgggctattcttttgatttataagggattttgccgatttcggcctattggttaaaaaatgagctgatttaacaaaaatttaacgcgaattttaacaaa
atattaacgtttacaatttatggtgcactctcagtacaatctgctctgatgccgcatagttaagccagccccgacacccgccaacacccgctg
acgcgccctgacgggcttgtctgctcccggcatccgcttacagacaagctgtgaccgtctccgggagctgcatgtgtcagaggttttcaccg
tcatcaccgaaacgcgcgagacgaaagggcctcgtgatacgcctatttttataggttaatgtcatgataataatggtttcttagacgtcaggtg
gcacttttcggggaaatgtgcgcggaacccctatttgtttatttttctaaatacattcaaatatgtatccgctcatgagacaataaccctgataaat
gcttcaataatattgaaaaaggaagagtatgagtattcaacatttccgtgtcgcccttattcccttttttgcggcattttgccttcctgtttttgctcac
ccagaaacgctggtgaaagtaaaagatgctgaagatcagttgggtgcacgagtgggttacatcgaactggatctcaacagcggtaagatcc
ttgagagttttcgccccgaagaacgttttccaatgatgagcacttttaaagttctgctatgtggcgcggtattatcccgtattgacgccgggcaa
gagcaactcggtcgccgcatacactattctcagaatgacttggttgagtactcaccagtcacagaaaagcatcttacggatggcatgacagta
agagaattatgcagtgctgccataaccatgagtgataacactgcggccaacttacttctgacaacgatcggaggaccgaaggagctaaccg
cttttttgcacaacatgggggatcatgtaactcgccttgatcgttgggaaccggagctgaatgaagccataccaaacgacgagcgtgacacc
acgatgcctgtagcaatggcaacaacgttgcgcaaactattaactggcgaactacttactctagcttcccggcaacaattaatagactggatg
gaggcggataaagttgcaggaccacttctgcgctcggcccttccggctggctggtttattgctgataaatctggagccggtgagcgtggaag
ccgcggtatcattgcagcactggggccagatggtaagccctcccgtatcgtagttatctacacgacggggagtcaggcaactatggatgaa
cgaaatagacagatcgctgagataggtgcctcactgattaagcattggtaactgtcagaccaagtttactcatatatactttagattgatttaaaa
cttcatttttaatttaaaaggatctaggtgaagatcctttttgataatctcatgaccaaaatcccttaacgtgagttttcgttccactgagcgtcaga
ccccgtagaaaagatcaaaggatcttcttgagatcctttttttctgcgcgtaatctgctgcttgcaaacaaaaaaaccaccgctaccagcggtg

FIG. 16 CONTINUED gtttgtttgccggatcaagagctaccaactctttttccgaaggtaactggcttcagcagagcgcagataccaaatactgtccttctagtgtagcc
gtagttaggccaccacttcaagaactctgtagcaccgcctacatacctcgctctgctaatcctgttaccagtggctgctgccagtggcgataa
gtcgtgtcttaccgggttggactcaagacgatagttaccggataaggcgcagcggtcgggctgaacggggggttcgtgcacacagcccag
cttggagcgaacgacctacaccgaactgagatacctacagcgtgagctatgagaaagcgccacgcttcccgaagggagaaaggcggac
aggtatccggtaagcggcagggtcggaacaggagagcgcacgagggagcttccagggggaaacgcctggtatctttatagtcctgtcgg
gtttcgccacctctgacttgagcgtcgatttttgtgatgctcgtcaggggggcggagcctatggaaaaacgccagcaacgcggcctttttacg
gttcctggccttttgctggccttttgctcacatgt

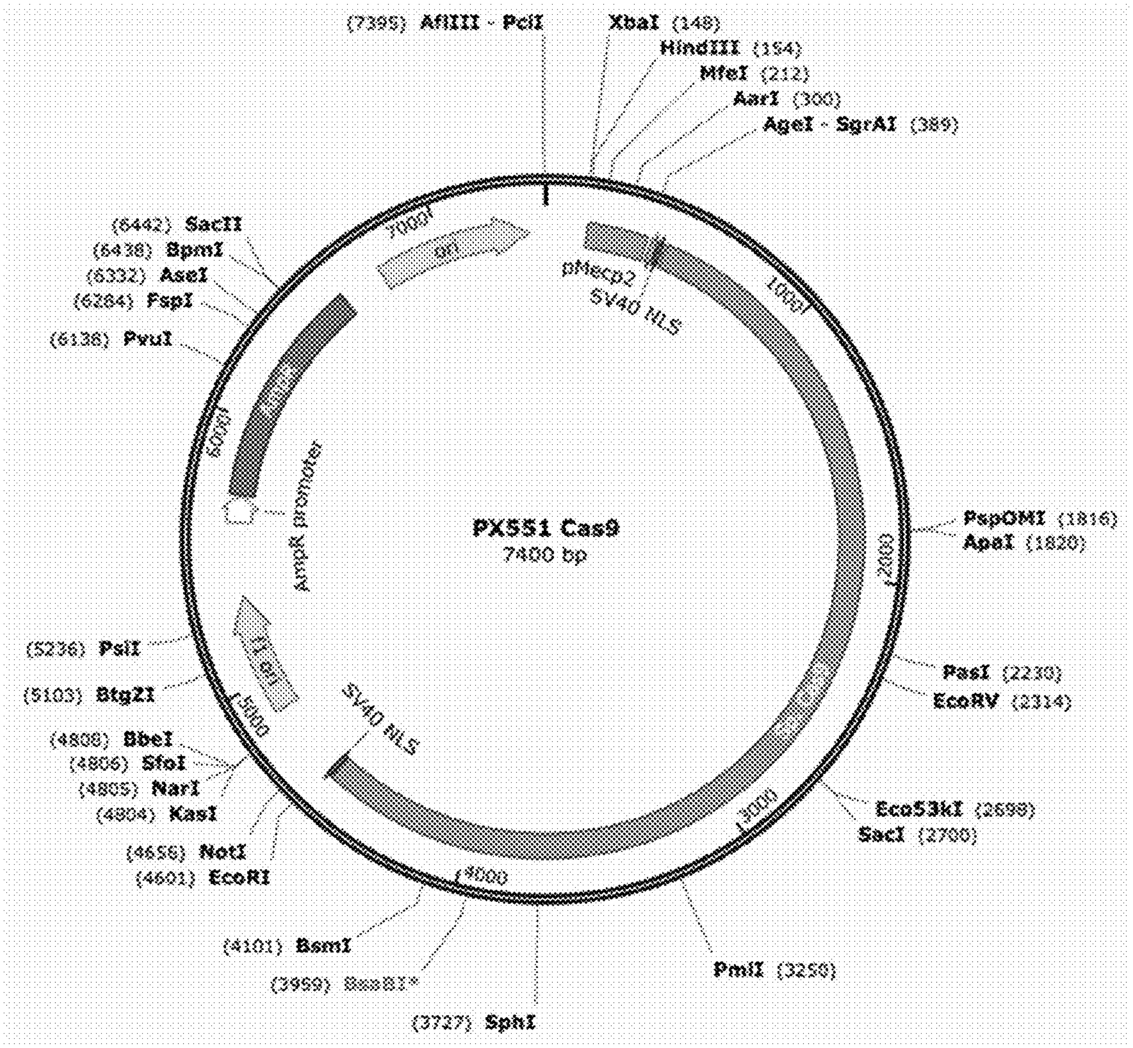

FIG. 17

PX552 APP sgRNA vector (SEQ ID NO:19)

cctgcaggcagctgcgcgctcgctcgctcactgaggccgcccgggcaaagcccgggcgtcgggcgacctttggtcgcccggcctcagtgagcgagc
gagcgcgcagagagggagtggccaactccatcactaggggttcctgcggccgcacgcgtgagggcctatttcccatgattccttcatatttgcatatacg
atacaaggctgttagagagataattggaattaatttgactgtaaacacaaagatattagtacaaaatacgtgacgtagaaagtaataatttcttgggtagtttgc
agttttaaaattatgttttaaaatggactatcatatgcttaccgtaacttgaaagtatttcgatttcttggctttatatatcttGTGGAAAGGACGAAA
CACCATCCATCCATCATGGCGTGGGTTttagagctaGAAAtagcaagttaaaataaggctagtccgttatcaacttgaaaaag
tggcaccgagtcggtgcTTTTTTtctagactgcagagggccctgcgtatgagtgcaagtgggttttaggaccaggatgaggcggggtgggggtgc
ctacctgacgaccgaccccgacccactggacaagcacccaacccccattccccaaattgcgcatcccctatcagagagggggaggggaaacaggatg
cggcgaggcgcgtgcgcactgccagcttcagcaccgcggacagtgccttcgcccccgcctggcggcgcgcgccaccgccgcctcagcactgaagg
cgcgctgacgtcactcgccggtcccccgcaaactccccttcccggccaccttggtcgcgtccgcgccgccgccggcccagccggaccgcaccacgc
gaggcgcgagataggggggcacgggcgcgaccatctgcgctgcggcgccggcgactcagcgctgcctcagtctgcggtgggcagcggaggagtc
gtgtcgtgcctgagagcgcagtcgagaaggtaccggatcctctagagtcgacgccaccatggtgagcaagggcgaggagctgttcaccggggtggtg
cccatcctggtcgagctggacggcgacgtaaacggccacaagttcagcgtgtccggcgagggcgagggcgatgccacctacggcaagctgaccctg
aagttcatctgcaccaccggcaagctgcccgtgccctggcccaccctcgtgaccaccctgacctacggcgtgcagtgcttcagccgctaccccgaccac
atgaagcagcacgacttcttcaagtccgccatgcccgaaggctacgtccaggagcgcaccatcttcttcaaggacgacggcaactacaagacccgcgc
cgaggtgaagttcgagggcgacaccctggtgaaccgcatcgagctgaagggcatcgacttcaaggaggacggcaacatcctggggcacaagctgga
gtacaactacaacagccacaacgtctatatcatggccgacaagcagaagaacggcatcaaggtgaacttcaagatccgccacaacatcgaggacggca
gcgtgcagctcgccgaccactaccagcagaacacccccatcggcgacggccccgtgctgctgcccgacaaccactacctgagcacccagtccgccct
gagcaaagaccccaacgagaagcgcgatcacatggtcctgctggagttcgtgaccgccgccgggatcactctcggcatggacgagctgtacaagtcc
ggactcagatctcgagaggaggaggaggagacagacagcaggatgccccacctcgacagccccggcagctcccagccgagacgctccttcctctca
agggtgatcagggcagcgctaccgttgcagctgcttctgctgctgctgctgctcctggcctgcctgctacctgcctctgaagatgactacagctgcaccca
ggccaacaactttgcccgatccttctaccccatgctgcggtacaccaacgggccacctcccacctaggaattcgatatcaagcttatcgataccgagcgct
gctcgagagatctacgggtggcatccctgtgacccctccccagtgcctctcctggccctggaagttgccactccagtgcccaccagccttgtcctaataaa
attaagttgcatcattttgtctgactaggtgtccttctataatattatggggtggaggggggtggtatggagcaaggggcaagttgggaagacaacctgtag
ggcctgcggggtctattgggaaccaagctggagtgcagtggcacaatcttggctcactgcaatctccgcctcctgggttcaagcgattctcctgcctcagc
ctcccgagttgttgggattccaggcatgcatgaccaggctcagctaatttttgtttttttggtagagacggggtttcaccatattggccaggctggtctccaact
cctaatctcaggtgatctacccaccttggcctcccaaattgctgggattacaggcgtgaaccactgctcccttccctgtccttctgattttgtaggtaaccacg
tgcggaccgagcggccgcaggaacccctagtgatggagttggccactccctctctgcgcgctcgctcgctcactgaggccgggcgaccaaaggtcgc
ccgacgcccgggctttgcccgggcggcctcagtgagcgagcgagcgcgcagctgcctgcaggggcgcctgatgcggtattttctccttacgcatctgt
gcggtatttcacaccgcatacgtcaaagcaaccatagtacgcgccctgtagcggcgcattaagcgcggcgggtgtggtggttacgcgcagcgtgaccg
ctacacttgccagcgccctagcgcccgctcctttcgctttcttcccttcctttctcgccacgttcgccggctttccccgtcaagctctaaatcgggggctccctt
tagggttccgatttagtgctttacggcacctcgaccccaaaaaacttgatttgggtgatggttcacgtagtgggccatcgccctgatagacggtttttcgccct
ttgacgttggagtccacgttctttaatagtggactcttgttccaaactggaacaacactcaaccctatctcgggctattcttttgatttataagggattttgccgat
ttcggcctattggttaaaaaatgagctgatttaacaaaaatttaacgcgaattttaacaaaatattaacgtttacaattttatggtgcactctcagtacaatctgct
ctgatgccgcatagttaagccagccccgacacccgccaacacccgctgacgcgccctgacgggcttgtctgctcccggcatccgcttacagacaagct
gtgaccgtctccgggagctgcatgtgtcagaggttttcaccgtcatcaccgaaacgcgcgagacgaaagggcctcgtgatacgcctatttttataggttaat
gtcatgataataatggtttcttagacgtcaggtggcacttttcggggaaatgtgcgcggaacccctatttgtttatttttctaaatacattcaaatatgtatccgct
catgagacaataaccctgataaatgcttcaataatattgaaaaaggaagagtatgagtattcaacatttccgtgtcgcccttattcccttttttgcggcattttgc
cttcctgtttttgctcacccagaaacgctggtgaaagtaaaagatgctgaagatcagttgggtgcacgagtgggttacatcgaactggatctcaacagcggt
aagatccttgagagttttcgccccgaagaacgttttccaatgatgagcacttttaaagttctgctatgtggcgcggtattatcccgtattgacgccgggcaag
agcaactcggtcgccgcatacactattctcagaatgacttggttgagtactcaccagtcacagaaaagcatcttacggatggcatgacagtaagagaattat
gcagtgctgccataaccatgagtgataacactgcggccaacttacttctgacaacgatcggaggaccgaaggagctaaccgcttttttgcacaacatggg

FIG. 17 CONTINUED ggatcatgtaactcgccttgatcgttgggaaccggagctgaatgaagccataccaaacgacgagcgtgacaccacgatgcctgtagcaatggcaacaa
cgttgcgcaaactattaactggcgaactacttactctagcttcccggcaacaattaatagactggatggaggcggataaagttgcaggaccacttctgcgct
cggcccttccggctggctggtttattgctgataaatctggagccggtgagcgtgggtctcgcggtatcattgcagcactggggccagatggtaagccctc
ccgtatcgtagttatctacacgacggggagtcaggcaactatggatgaacgaaatagacagatcgctgagataggtgcctcactgattaagcattggtaac
tgtcagaccaagtttactcatatatactttagattgatttaaaacttcatttttaatttaaaaggatctaggtgaagatcctttttgataatctcatgaccaaaatccc
ttaacgtgagttttcgttccactgagcgtcagaccccgtagaaaagatcaaaggatcttcttgagatcctttttttctgcgcgtaatctgctgcttgcaaacaaa
aaaaccaccgctaccagcggtggtttgtttgccggatcaagagctaccaactctttttccgaaggtaactggcttcagcagagcgcagataccaaatactg
tccttctagtgtagccgtagttaggccaccacttcaagaactctgtagcaccgcctacatacctcgctctgctaatcctgttaccagtggctgctgccagtgg
cgataagtcgtgtcttaccgggttggactcaagacgatagttaccggataaggcgcagcggtcgggctgaacggggggttcgtgcacacagcccagctt
ggagcgaacgacctacaccgaactgagatacctacagcgtgagctatgagaaagcgccacgcttcccgaagggagaaaggcggacaggtatccggt
aagcggcagggtcggaacaggagagcgcacgagggagcttccagggggaaacgcctggtatctttatagtcctgtcgggtttcgccacctctgacttga
gcgtcgatttttgtgatgctcgtcaggggggcggagcctatggaaaaacgccagcaacgcggcctttttacggttcctggccttttgctggccttttgctcac
atgt

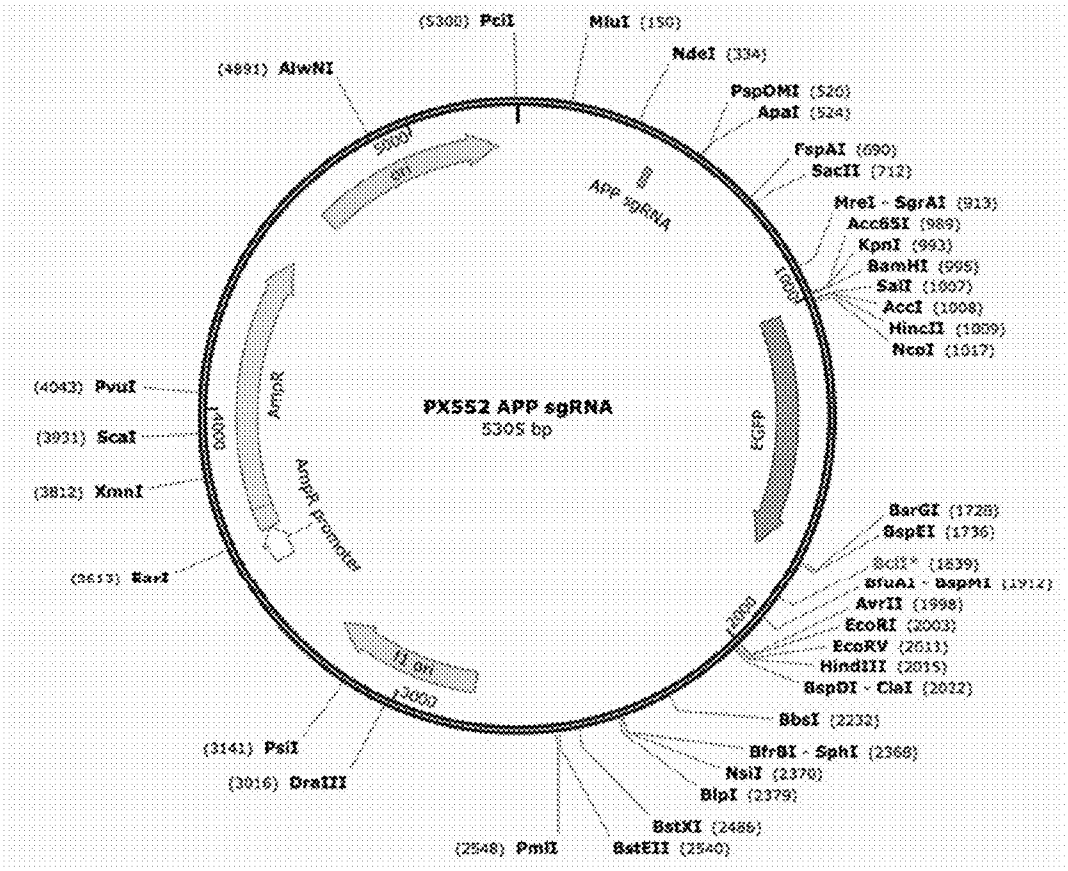

FIG. 18

LentiCRISPRv2 APP sgRNA vector (SEQ ID NO:20)

tgatgcggttttggcagtacatcaatgggcgtggatagcggtttgactcacggggatttccaagtctccaccccattgacgtcaatgggagttt
gttttggcaccaaaatcaacgggactttccaaaatgtcgtaacaactccgccccattgacgcaaatgggcggtaggcgtgtacggtgggag
gtctatataagcagcgcgttttgcctgtactgggtctctctggttagaccagatctgagcctgggagctctctggctaactagggaacccactg
cttaagcctcaataaagcttgccttgagtgcttcaagtagtgtgtgcccgtctgttgtgtgactctggtaactagagatccctcagacccttttagt
cagtgtggaaaatctctagcagtggcgcccgaacagggacttgaaagcgaaagggaaaccagaggagctctctcgacgcaggactcgg
cttgctgaagcgcgcacggcaagaggcgaggggcggcgactggtgagtacgccaaaaattttgactagcggaggctagaaggagaga
gatgggtgcgagagcgtcagtattaagcgggggagaattagatcgcgatgggaaaaaattcggttaaggccagggggaaagaaaaaata
taaattaaaacatatagtatgggcaagcagggagctagaacgattcgcagttaatcctggcctgttagaaacatcagaaggctgtagacaaa
tactgggacagctacaaccatcccttcagacaggatcagaagaacttagatcattatataatacagtagcaaccctctattgtgtgcatcaaag
gatagagataaaagacaccaaggaagctttagacaagatagaggaagagcaaaacaaaagtaagaccaccgcacagcaagcggccgct
gatcttcagacctggaggaggagatatgagggacaattggagaagtgaattatataaatataaagtagtaaaaattgaaccattaggagtag
cacccaccaaggcaaagagaagagtggtgcagagagaaaaaagagcagtgggaataggagctttgttccttgggttcttgggagcagca
ggaagcactatgggcgcagcgtcaatgacgctgacggtacaggccagacaattattgtctggtatagtgcagcagcagaacaatttgctga
gggctattgaggcgcaacagcatctgttgcaactcacagtctggggcatcaagcagctccaggcaagaatcctggctgtggaaagatacct
aaaggatcaacagctcctggggatttggggttgctctggaaaactcatttgcaccactgctgtgccttggaatgctagttggagtaataaatct
ctggaacagatttggaatcacacgacctggatggagtgggacagagaaattaacaattacacaagcttaatacactccttaattgaagaatcg
caaaaccagcaagaaaagaatgaacaagaattattggaattagataaatgggcaagtttgtggaattggtttaacataacaaattggctgtggt
atataaaattattcataatgatagtaggaggcttggtaggtttaagaatagtttttgctgtactttctatagtgaatagagttaggcagggatattca
ccattatcgtttcagacccacctcccaaccccgaggggacccgacaggcccgaaggaatagaagaagaaggtggagagagagacaga
gacagatccattcgattagtgaacggatcggcactgcgtgcgccaattctgcagacaaatggcagtattcatccacaattttaaaagaaaagg
ggggattggggggtacagtgcaggggaaagaatagtagacataatagcaacagacatacaaactaaagaattacaaaaacaaattacaaa
aattcaaaattttcgggtttattacagggacagcagagatccagtttggttaattaaggtaccgagggcctatttcccatgattccttcatatttgc
atatacgatacaaggctgttagagagataattagaattaatttgactgtaaacacaaagatattagtacaaaatacgtgacgtagaaagtaataa
tttcttgggtagtttgcagttttaaaattatgttttaaaatggactatcatatgcttaccgtaacttgaaagtatttcgatttcttggctttatatatcttG
TGGAAAGGACGAAACACCgatccattcatcatggtgtgggttttagagctaGAAAtagcaagttaaaataaggctagtc
cgttatcaacttgaaaaagtggcaccgagtcggtgcTTTTTTgaattcgctagctaggtcttgaaaggagtgggaattggctccggtgc
ccgtcagtgggcagagcgcacatcgcccacagtccccgagaagttggggggaggggtcggcaattgatccggtgcctagagaaggtgg
cgcggggtaaactgggaaagtgatgtcgtgtactggctccgcctttttcccgagggtgggggagaaccgtatataagtgcagtagtcgccg
tgaacgttctttttcgcaacgggtttgccgccagaacacaggaccggttctagagcgctgccaccATGGACAAGAAGTACA
GCATCGGCCTGGACATCGGCACCAACTCTGTGGGCTGGGCCGTGATCACCGACGAG
TACAAGGTGCCCAGCAAGAAATTCAAGGTGCTGGGCAACACCGACCGGCACAGCAT
CAAGAAGAACCTGATCGGAGCCCTGCTGTTCGACAGCGGCGAAACAGCCGAGGCCA
CCCGGCTGAAGAGAACCGCCAGAAGAAGATACACCAGACGGAAGAACCGGATCTG
CTATCTGCAAGAGATCTTCAGCAACGAGATGGCCAAGGTGGACGACAGCTTCTTCCA
CAGACTGGAAGAGTCCTTCCTGGTGGAAGAGGATAAGAAGCACGAGCGGCACCCCA
TCTTCGGCAACATCGTGGACGAGGTGGCCTACCACGAGAAGTACCCCACCATCTACC
ACCTGAGAAAGAAACTGGTGGACAGCACCGACAAGGCCGACCTGCGGCTGATCTAT

FIG. 18 CONTINUED

CTGGCCCTGGCCCACATGATCAAGTTCCGGGGCCACTTCCTGATCGAGGGCGACCTG
AACCCCGACAACAGCGACGTGGACAAGCTGTTCATCCAGCTGGTGCAGACCTACAA
CCAGCTGTTCGAGGAAAACCCCATCAACGCCAGCGGCGTGGACGCCAAGGCCATCC
TGTCTGCCAGACTGAGCAAGAGCAGACGGCTGGAAAATCTGATCGCCCAGCTGCCC
GGCGAGAAGAAGAATGGCCTGTTCGGAAACCTGATTGCCCTGAGCCTGGGCCTGAC
CCCCAACTTCAAGAGCAACTTCGACCTGGCCGAGGATGCCAAACTGCAGCTGAGCA
AGGACACCTACGACGACGACCTGGACAACCTGCTGGCCCAGATCGGCGACCAGTAC
GCCGACCTGTTTCTGGCCGCCAAGAACCTGTCCGACGCCATCCTGCTGAGCGACATC
CTGAGAGTGAACACCGAGATCACCAAGGCCCCCCTGAGCGCCTCTATGATCAAGAG
ATACGACGAGCACCACCAGGACCTGACCCTGCTGAAAGCTCTCGTGCGGCAGCAGC
TGCCTGAGAAGTACAAAGAGATTTTCTTCGACCAGAGCAAGAACGGCTACGCCGGC
TACATTGACGGCGGAGCCAGCCAGGAAGAGTTCTACAAGTTCATCAAGCCCATCCT
GGAAAAGATGGACGGCACCGAGGAACTGCTCGTGAAGCTGAACAGAGAGGACCTG
CTGCGGAAGCAGCGGACCTTCGACAACGGCAGCATCCCCCACCAGATCCACCTGGG
AGAGCTGCACGCCATTCTGCGGCGGCAGGAAGATTTTTACCCATTCCTGAAGGACAA
CCGGGAAAAGATCGAGAAGATCCTGACCTTCCGCATCCCCTACTACGTGGGCCCTCT
GGCCAGGGGAAACAGCAGATTCGCCTGGATGACCAGAAAGAGCGAGGAAACCATC
ACCCCCTGGAACTTCGAGGAAGTGGTGGACAAGGGCGCTTCCGCCCAGAGCTTCAT
CGAGCGGATGACCAACTTCGATAAGAACCTGCCCAACGAGAAGGTGCTGCCCAAGC
ACAGCCTGCTGTACGAGTACTTCACCGTGTATAACGAGCTGACCAAAGTGAAATAC
GTGACCGAGGGAATGAGAAAGCCCGCCTTCCTGAGCGGCGAGCAGAAAAAGGCCA
TCGTGGACCTGCTGTTCAAGACCAACCGGAAAGTGACCGTGAAGCAGCTGAAAGAG
GACTACTTCAAGAAAATCGAGTGCTTCGACTCCGTGGAAATCTCCGGCGTGGAAGAT
CGGTTCAACGCCTCCCTGGGCACATACCACGATCTGCTGAAAATTATCAAGGACAA
GGACTTCCTGGACAATGAGGAAAACGAGGACATTCTGGAAGATATCGTGCTGACCC
TGACACTGTTTGAGGACAGAGAGATGATCGAGGAACGGCTGAAAACCTATGCCCAC
CTGTTCGACGACAAAGTGATGAAGCAGCTGAAGCGGCGGAGATACACCGGCTGGGG
CAGGCTGAGCCGGAAGCTGATCAACGGCATCCGGGACAAGCAGTCCGGCAAGACA
ATCCTGGATTTCCTGAAGTCCGACGGCTTCGCCAACAGAAACTTCATGCAGCTGATC
CACGACGACAGCCTGACCTTTAAAGAGGACATCCAGAAAGCCCAGGTGTCCGGCCA
GGGCGATAGCCTGCACGAGCACATTGCCAATCTGGCCGGCAGCCCCGCCATTAAGA
AGGGCATCCTGCAGACAGTGAAGGTGGTGGACGAGCTCGTGAAAGTGATGGGCCGG
CACAAGCCCGAGAACATCGTGATCGAAATGGCCAGAGAGAACCAGACCACCCAGA
AGGGACAGAAGAACAGCCGCGAGAGAATGAAGCGGATCGAAGAGGGCATCAAAGA
GCTGGGCAGCCAGATCCTGAAAGAACACCCCGTGGAAAACACCCAGCTGCAGAACG
AGAAGCTGTACCTGTACTACCTGCAGAATGGGCGGGATATGTACGTGGACCAGGAA
CTGGACATCAACCGGCTGTCCGACTACGATGTGGACCATATCGTGCCTCAGAGCTTT
CTGAAGGACGACTCCATCGACAACAAGGTGCTGACCAGAAGCGACAAGAACCGGG
GCAAGAGCGACAACGTGCCCTCCGAAGAGGTCGTGAAGAAGATGAAGAACTACTGG
CGGCAGCTGCTGAACGCCAAGCTGATTACCCAGAGAAAGTTCGACAATCTGACCAA

FIG. 18 CONTINUED

GGCCGAGAGAGGCGGCCTGAGCGAACTGGATAAGGCCGGCTTCATCAAGAGACAG
CTGGTGGAAACCCGGCAGATCACAAAGCACGTGGCACAGATCCTGGACTCCCGGAT
GAACACTAAGTACGACGAGAATGACAAGCTGATCCGGGAAGTGAAAGTGATCACCC
TGAAGTCCAAGCTGGTGTCCGATTTCCGGAAGGATTTCCAGTTTTACAAAGTGCGCG
AGATCAACAACTACCACCACGCCCACGACGCCTACCTGAACGCCGTCGTGGGAACC
GCCCTGATCAAAAAGTACCCTAAGCTGGAAAGCGAGTTCGTGTACGGCGACTACAA
GGTGTACGACGTGCGGAAGATGATCGCCAAGAGCGAGCAGGAAATCGGCAAGGCT
ACCGCCAAGTACTTCTTCTACAGCAACATCATGAACTTTTTCAAGACCGAGATTACC
CTGGCCAACGGCGAGATCCGGAAGCGGCCTCTGATCGAGACAAACGGCGAAACCGG
GGAGATCGTGTGGGATAAGGGCCGGGATTTTGCCACCGTGCGGAAAGTGCTGAGCA
TGCCCCAAGTGAATATCGTGAAAAAGACCGAGGTGCAGACAGGCGGCTTCAGCAAA
GAGTCTATCCTGCCCAAGAGGAACAGCGATAAGCTGATCGCCAGAAAGAAGGACTG
GGACCCTAAGAAGTACGGCGGCTTCGACAGCCCCACCGTGGCCTATTCTGTGCTGGT
GGTGGCCAAAGTGGAAAAGGGCAAGTCCAAGAAACTGAAGAGTGTGAAAGAGCTG
CTGGGGATCACCATCATGGAAAGAAGCAGCTTCGAGAAGAATCCCATCGACTTTCT
GGAAGCCAAGGGCTACAAAGAAGTGAAAAAGGACCTGATCATCAAGCTGCCTAAGT
ACTCCCTGTTCGAGCTGGAAAACGGCCGGAAGAGAATGCTGGCCTCTGCCGGCGAA
CTGCAGAAGGGAAACGAACTGGCCCTGCCCTCCAAATATGTGAACTTCCTGTACCTG
GCCAGCCACTATGAGAAGCTGAAGGGCTCCCCCGAGGATAATGAGCAGAAACAGCT
GTTTGTGGAACAGCACAAGCACTACCTGGACGAGATCATCGAGCAGATCAGCGAGT
TCTCCAAGAGAGTGATCCTGGCCGACGCTAATCTGGACAAAGTGCTGTCCGCCTACA
ACAAGCACCGGGATAAGCCCATCAGAGAGCAGGCCGAGAATATCATCCACCTGTTT
ACCCTGACCAATCTGGGAGCCCCTGCCGCCTTCAAGTACTTTGACACCACCATCGAC
CGGAAGAGGTACACCAGCACCAAAGAGGTGCTGGACGCCACCCTGATCCACCAGAG
CATCACCGGCCTGTACGAGACACGGATCGACCTGTCTCAGCTGGGAGGCGACAAGC
GACCTGCCGCCACAAAGAAGGCTGGACAGGCTAAGAAGAAGAAAGATTACAAAGA
CGATGACGATAAGGGATCCGGCGCAACAAACTTCTCTCTGCTGAAACAAGCCGGAG
ATGTCGAAGAGAATCCTGGACCGACCGAGTACAAGCCCACGGTGCGCCTCGCCACC
CGCGACGACGTCCCCAGGGCCGTACGCACCCTCGCCGCCGCGTTCGCCGACTACCCC
GCCACGCGCCACACCGTCGATCCGGACCGCCACATCGAGCGGGTCACCGAGCTGCA
AGAACTCTTCCTCACGCGCGTCGGGCTCGACATCGGCAAGGTGTGGGTCGCGGACG
ACGGCGCCGCGGTGGCGGTCTGGACCACGCCGGAGAGCGTCGAAGCGGGGGCGGT
GTTCGCCGAGATCGGCCCGCGCATGGCCGAGTTGAGCGGTTCCCGGCTGGCCGCGC
AGCAACAGATGGAAGGCCTCCTGGCGCCGCACCGGCCCAAGGAGCCCGCGTGGTTC
CTGGCCACCGTCGGAGTCTCGCCCGACCACCAGGGCAAGGGTCTGGGCAGCGCCGT
CGTGCTCCCCGGAGTGGAGGCGGCCGAGCGCGCCGGGGTGCCCGCCTTCCTGGAGA
CCTCCGCGCCCCGCAACCTCCCCTTCTACGAGCGGCTCGGCTTCACCGTCACCGCCG
ACGTCGAGGTGCCCGAAGGACCGCGCACCTGGTGCATGACCCGCAAGCCCGGTGCC
TGAACGCGTTAAGTCGACAATCAACCTCTGGATTACAAAATTTGTGAAAGATTGACT
GGTATTCTTAACTATGTTGCTCCTTTTACGCTATGTGGATACGCTGCTTTAATGCCTT

FIG. 18 CONTINUED

TGTATCATGCTATTGCTTCCCGTATGGCTTTCATTTTCTCCTCCTTGTATAAATCCTGG
TTGCTGTCTCTTTATGAGGAGTTGTGGCCCGTTGTCAGGCAACGTGGCGTGGTGTGC
ACTGTGTTTGCTGACGCAACCCCCACTGGTTGGGGCATTGCCACCACCTGTCAGCTC
CTTTCCGGGACTTTCGCTTTCCCCCTCCCTATTGCCACGGCGGAACTCATCGCCGCCT
GCCTTGCCCGCTGCTGGACAGGGGCTCGGCTGTTGGGCACTGACAATTCCGTGGTGT
TGTCGGGGAAATCATCGTCCTTTCCTTGGCTGCTCGCCTGTGTTGCCACCTGGATTCT
GCGCGGGACGTCCTTCTGCTACGTCCCTTCGGCCCTCAATCCAGCGGACCTTCCTTCC
CGCGGCCTGCTGCCGGCTCTGCGGCCTCTTCCGCGTCTTCGCCTTCGCCCTCAGACG
AGTCGGATCTCCCTTTGGGCCGCCTCCCCGCGTCGACTTTAAGACCAATGACTTACA
AGGCAGCTGTAGATCTTAGCCACTTTTTAAAAGAAAAGGGGGGACTGGAAGGGCTA
ATTCACTCCCAACGAAGACAAGATCTGCTTTTTGCTTGTACTGGGTCTCTCTGGTTAG
ACCAGATCTGAGCCTGGGAGCTCTCTGGCTAACTAGGGAACCCACTGCTTAAGCCTC
AATAAAGCTTGCCTTGAGTGCTTCAAGTAGTGTGTGCCCGTCTGTTGTGTGACTCTG
GTAACTAGAGATCCCTCAGACCCTTTTAGTCAGTGTGGAAAATCTCTAGCAGggcccgttt
aaacccgctgatcagcctcgactgtgccttctagttgccagccatctgttgtttgcccctcccccgtgccttccttgaccctggaaggtgccact
cccactgtcctttcctaataaaatgaggaaattgcatcgcattgtctgagtaggtgtcattctattctggggggtggggtggggcaggacagc
aagggggaggattgggaagacaatagcaggcatgctggggatgcggtgggctctatggcttctgaggcggaaagaaccagctggggct
ctagggggtatccccacgcgccctgtagcggcgcattaagcgcggcgggtgtggtggttacgcgcagcgtgaccgctacacttgccagc
gccctagcgcccgctcctttcgctttcttcccttcctttctcgccacgttcgccggctttccccgtcaagctctaaatcgggggctccctttaggg
ttccgatttagtgctttacggcacctcgaccccaaaaaacttgattagggtgatggttcacgtagtgggccatcgccctgatagacggtttttcg
ccctttgacgttggagtccacgttctttaatagtggactcttgttccaaactggaacaacactcaaccctatctcggtctattcttttgatttataag
ggattttgccgatttcggcctattggttaaaaaatgagctgatttaacaaaaatttaacgcgaattaattctgtggaatgtgtgtcagttagggtgt
ggaaagtccccaggctccccagcaggcagaagtatgcaaagcatgcatctcaattagtcagcaaccaggtgtggaaagtccccaggctcc
ccagcaggcagaagtatgcaaagcatgcatctcaattagtcagcaaccatagtcccgcccctaactccgcccatcccgcccctaactccgc
ccagttccgcccattctccgccccatggctgactaattttttttatttatgcagaggccgaggccgcctctgcctctgagctattccagaagtagt
gaggaggcttttttggaggcctaggcttttgcaaaaagctcccgggagcttgtatatccatttcggatctgatcagcacgtgttgacaattaat
catcggcatagtatatcggcatagtataatacgacaaggtgaggaactaaaccatggccaagttgaccagtgccgttccggtgctcaccgc
gcgcgacgtcgccggagcggtcgagttctggaccgaccggctcgggttctcccgggacttcgtggaggacgacttcgccggtgtggtcc
gggacgacgtgaccctgttcatcagcgcggtccaggaccaggtggtgccggacaacaccctggcctgggtgtgggtgcgcggcctgga
cgagctgtacgccgagtggtcggaggtcgtgtccacgaacttccgggacgcctccgggccggccatgaccgagatcggcgagcagccg
tgggggcgggagttcgccctgcgcgacccggccggcaactgcgtgcacttcgtggccgaggagcaggactgacacgtgctacgagattt
cgattccaccgccgccttctatgaaaggttgggcttcggaatcgttttccgggacgccggctggatgatcctccagcgcggggatctcatgc
tggagttcttcgcccaccccaacttgtttattgcagcttataatggttacaaataaagcaatagcatcacaaatttcacaaataaagcatttttttca
ctgcattctagttgtggtttgtccaaactcatcaatgtatcttatcatgtctgtataccgtcgacctctagctagagcttggcgtaatcatggtcata
gctgtttcctgtgtgaaattgttatccgctcacaattccacacaacatacgagccggaagcataaagtgtaaagcctggggtgcctaatgagt
gagctaactcacattaattgcgttgcgctcactgcccgctttccagtcgggaaacctgtcgtgccagctgcattaatgaatcggccaacgcgc
ggggagaggcggtttgcgtattgggcgctcttccgcttcctcgctcactgactcgctgcgctcggtcgttcggctgcggcgagcggtatcag
ctcactcaaaggcggtaatacggttatccacagaatcaggggataacgcaggaaagaacatgtgagcaaaaggccagcaaaaggccag
gaaccgtaaaaaggccgcgttgctggcgtttttccataggctccgcccccctgacgagcatcacaaaaatcgacgctcaagtcagaggtgg
cgaaacccgacaggactataaagataccaggcgtttccccctggaagctccctcgtgcgctctcctgttccgaccctgccgcttaccggata

FIG. 18 CONTINUED cctgtccgcctttctcccttcgggaagcgtggcgctttctcatagctcacgctgtaggtatctcagttcggtgtaggtcgttcgctccaagctgg
gctgtgtgcacgaaccccccgttcagcccgaccgctgcgccttatccggtaactatcgtcttgagtccaacccggtaagacacgacttatcg
ccactggcagcagccactggtaacaggattagcagagcgaggtatgtaggcggtgctacagagttcttgaagtggtggcctaactacggct
acactagaagaacagtatttggtatctgcgctctgctgaagccagttaccttcggaaaaagagttggtagctcttgatccggcaaacaaacca
ccgctggtagcggtggtttttttgtttgcaagcagcagattacgcgcagaaaaaaaggatctcaagaagatcctttgatcttttctacggggtct
gacgctcagtggaacgaaaactcacgttaagggattttggtcatgagattatcaaaaaggatcttcacctagatccttttaaattaaaaatgaag
ttttaaatcaatctaaagtatatatgagtaaacttggtctgacagttaccaatgcttaatcagtgaggcacctatctcagcgatctgtctatttcgtt
catccatagttgcctgactccccgtcgtgtagataactacgatacgggagggcttaccatctggccccagtgctgcaatgataccgcgagac
ccacgctcaccggctccagatttatcagcaataaaccagccagccggaagggccgagcgcagaagtggtcctgcaactttatccgcctcc
atccagtctattaattgttgccgggaagctagagtaagtagttcgccagttaatagtttgcgcaacgttgttgccattgctacaggcatcgtggt
gtcacgctcgtcgtttggtatggcttcattcagctccggttcccaacgatcaaggcgagttacatgatcccccatgttgtgcaaaaaagcggtt
agctccttcggtcctccgatcgttgtcagaagtaagttggccgcagtgttatcactcatggttatggcagcactgcataattctcttactgtcatg
ccatccgtaagatgcttttctgtgactggtgagtactcaaccaagtcattctgagaatagtgtatgcggcgaccgagttgctcttgcccggcgt
caatacgggataataccgcgccacatagcagaactttaaaagtgctcatcattggaaaacgttcttcggggcgaaaactctcaaggatcttac
cgctgttgagatccagttcgatgtaacccactcgtgcacccaactgatcttcagcatcttttactttcaccagcgtttctgggtgagcaaaaaca
ggaaggcaaaatgccgcaaaaaagggaataagggcgacacggaaatgttgaatactcatactcttcctttttcaatattattgaagcatttatc
agggttattgtctcatgagcggatacatatttgaatgtatttagaaaaataaacaaataggggttccgcgcacatttccccgaaaagtgccacct
gacgtcgacggatcgggagatctcccgatcccctatggtgcactctcagtacaatctgctctgatgccgcatagttaagccagtatctgctcc
ctgcttgtgtgttggaggtcgctgagtagtgcgcgagcaaaatttaagctacaacaaggcaaggcttgaccgacaattgcatgaagaatctg
cttagggttaggcgttttgcgctgcttcgcgatgtacgggccagatatacgcgttgacattgattattgactagttattaatagtaatcaattacgg
ggtcattagttcatagcccatatatggagttccgcgttacataacttacggtaaatggcccgcctggctgaccgcccaacgacccccgcccat
tgacgtcaataatgacgtatgttcccatagtaacgccaatagggactttccattgacgtcaatgggtggagtatttacggtaaactgcccacttg
gcagtacatcaagtgtatcatatgccaagtacgccccctattgacgtcaatgacggtaaatggcccgcctggcattatgcccagtacatgacc
ttatgggactttcctacttggcagtacatctacgtattagtcatcgctattaccatgg

SEQUENCE LISTING

```
Sequence total quantity: 138
SEQ ID NO: 1            moltype = DNA  length = 20
FEATURE                 Location/Qualifiers
misc_feature            1..20
                        note = synthetic
```

-continued

```
source                  1..20
                        mol_type = other DNA
                        organism = synthetic construct
SEQUENCE: 1
atccattcat catggtgtgg                                              20

SEQ ID NO: 2            moltype = DNA  length = 20
FEATURE                 Location/Qualifiers
misc_feature            1..20
                        note = synthetic
source                  1..20
                        mol_type = other DNA
                        organism = synthetic construct
SEQUENCE: 2
tggacaggtg gcgctcctct                                              20

SEQ ID NO: 3            moltype = DNA  length = 20
FEATURE                 Location/Qualifiers
misc_feature            1..20
                        note = synthetic
source                  1..20
                        mol_type = other DNA
                        organism = synthetic construct
SEQUENCE: 3
ttggacaggt ggcgctcctc                                              20

SEQ ID NO: 4            moltype = DNA  length = 20
FEATURE                 Location/Qualifiers
misc_feature            1..20
                        note = synthetic
source                  1..20
                        mol_type = other DNA
                        organism = synthetic construct
SEQUENCE: 4
gtagccgttc tgctgcatct                                              20

SEQ ID NO: 5            moltype = DNA  length = 20
FEATURE                 Location/Qualifiers
misc_feature            1..20
                        note = synthetic
source                  1..20
                        mol_type = other DNA
                        organism = synthetic construct
SEQUENCE: 5
tgctcaaaga acttgtaggt                                              20

SEQ ID NO: 6            moltype = DNA  length = 20
FEATURE                 Location/Qualifiers
misc_feature            1..20
                        note = synthetic
source                  1..20
                        mol_type = other DNA
                        organism = synthetic construct
SEQUENCE: 6
atccatccat catggcgtgg                                              20

SEQ ID NO: 7            moltype = DNA  length = 20
FEATURE                 Location/Qualifiers
misc_feature            1..20
                        note = synthetic
source                  1..20
                        mol_type = other DNA
                        organism = synthetic construct
SEQUENCE: 7
tggagagatg gcgctcctct                                              20

SEQ ID NO: 8            moltype = DNA  length = 20
FEATURE                 Location/Qualifiers
misc_feature            1..20
                        note = synthetic
source                  1..20
                        mol_type = other DNA
                        organism = synthetic construct
SEQUENCE: 8
ttggagagat ggcgctcctc                                              20

SEQ ID NO: 9            moltype = DNA  length = 20
FEATURE                 Location/Qualifiers
misc_feature            1..20
```

```
                        note = synthetic
source                  1..20
                        mol_type = other DNA
                        organism = synthetic construct
SEQUENCE: 9
atatccgttc tgctgcatct                                              20

SEQ ID NO: 10           moltype = DNA  length = 20
FEATURE                 Location/Qualifiers
misc_feature            1..20
                        note = synthetic
source                  1..20
                        mol_type = other DNA
                        organism = synthetic construct
SEQUENCE: 10
tgctcaaaga acttgtaagt                                              20

SEQ ID NO: 11           moltype = DNA  length = 2088
FEATURE                 Location/Qualifiers
source                  1..2088
                        mol_type = genomic DNA
                        organism = Homo sapiens
SEQUENCE: 11
atgctgcccg gtttggcact gctcctgctg gccgcctgga cggctcgggc gctggaggta  60
cccactgatg gtaatgctgg cctgctggct gaaccccaga ttgccatgtt ctgtggcaga  120
ctgaacatgc acatgaatgt ccagaatggg aagtgggatt cagatccatc agggaccaaa  180
acctgcattg ataccaagga aggcatcctg cagtattgcc aagaagtcta ccctgaactg  240
cagatcacca atgtggtaga agccaaccaa ccagtgacca tccagaactg gtgcaagcgg  300
ggccgcaagc agtgcaagac ccatccccac tttgtgattc cctaccgctg cttagttggt  360
gagtttgtaa gtgatgccct tctcgttcct gacaagtgca aattcttaca ccaggagagg  420
atggatgttt gcgaaactca tcttcactgg cacaccgtcg ccaaagagac atgcagtgag  480
aagagtacca acttgcatga ctacggcatg ttgctgccct gcggaattga caagttccga  540
ggggtagagt ttgtgtgttg cccactggct gaagaaagtg acaatgtgga ttctgctgat  600
gcggaggagg atgactcgga tgtctggtgg ggcggagcag acacagacta tgcagatggg  660
agtgaagaca aagtagtaga agtagcagag gaggaagaag tggctgaggt ggaagaagaa  720
gaagccgatg atgacgagga cgatgaggat ggtgatgagg tagaggaaga ggctgaggaa  780
ccctacgaag aagccacaga gagaaccacc agcattgcca ccaccaccac caccaccaca  840
gagtctgtgg aagaggtggt tcgagttcct acaacagcag ccagtacccc tgatgccgtt  900
gacaagtatc tcgagacacc tggggatgag aatgaacatg cccatttcca gaaagccaaa  960
gagaggcttg aggccaagca ccgagagaga atgtcccagg tcatgagaga atgggaagag  1020
gcagaacgtc aagcaaagaa cttgcctaaa gctgataaga aggcagttat ccagcatttc  1080
caggagaaag tggaatcttt ggaacaggaa gcagccaacg agagacagca gctggtggag  1140
acacacatgg ccagagtgga agccatgctc aatgaccgcc gccgcctggc cctggagaac  1200
tacatcaccg ctctgcaggc tgttcctcct cggcctcgtc acgtgttcaa tatgctaaag  1260
aagtatgtcc gcgcagaaca gaaggacaga cagcacaccc taaagcattt cgagcatgtg  1320
cgcatggtgg atcccaagaa agccgctcag atccggtccc aggttatgac acacctccgt  1380
gtgatttatg agcgcatgaa tcagtctctc tccctgctct acaacgtgcc tgcagtggcc  1440
gaggagattc aggatgaagt tgatgagctg cttcagaaag agcaaaacta ttcagatgac  1500
gtcttggcca acatgattag tgaaccaagg atcagttacg gaaacgatgc tctcatgcca  1560
tctttgaccg aaacgaaaac caccgtggag ctccttcccg tgaatggaga gttcagcctg  1620
gacgatctcc agccgtggca ttcttttggg gctgactctg tgccagccaa cacagaaaac  1680
gaagttgagc ctgttgatgc ccgccctgct gccgaccgag gactgaccac tcgaccaggt  1740
tctgggttga caaatatcaa gacggaggag atctctgaag tgaagatgga tgcagaattc  1800
cgacatgact caggatatga agttcatcat caaaaattgg tgttctttgc agaagatgtg  1860
ggttcaaaca aaggtgcaat cattggactc atggtgggcg gtgttgtcat agcgacagtg  1920
atcgtcatca ccttggtgat gctgaagaag aaacagtaca catccattca tcatggtgtg  1980
gtggaggttg acgccgctgt caccccagag gagcgccacc tgtccaagat gcagcagaac  2040
ggctacgaaa atccaaccta caagttcttt gagcagatgc agaactag               2088

SEQ ID NO: 12           moltype = AA  length = 695
FEATURE                 Location/Qualifiers
source                  1..695
                        mol_type = protein
                        organism = Homo sapiens
SEQUENCE: 12
MLPGLALLLL AAWTARALEV PTDGNAGLLA EPQIAMFCGR LNMHMNVQNG KWDSDPSGTK  60
TCIDTKEGIL QYCQEVYPEL QITNVVEANQ PVTIQNWCKR GRKQCKTHPH FVIPYRCLVG  120
EFVSDALLVP DKCKFLHQER MDVCETHLHW HTVAKETCSE KSTNLHDYGM LLPCGIDKFR  180
GVEFVCCPLA EESDNVDSAD AEEDDSDVWW GGADTDYADG SEDKVVEVAE EEEVAEVEEE  240
EADDDEDDED GDEVEEEAEE PYEEATERTT SIATTTTTTT ESVEEVVRVP TTAASTPDAV  300
DKYLETPGDE NEHAHFQKAK ERLEAKHRER MSQVMREWEE AERQAKNLPK ADKKAVIQHF  360
QEKVESLEQE AANERQQLVE THMARVEAML NDRRRLALEN YITALQAVPP RPRHVFNMLK  420
KYVRAEQKDR QHTLKHFEHV RMVDPKKAAQ IRSQVMTHLR VIYERMNQSL SLLYNVPAVA  480
EEIQDEVDEL LQKEQNYSDD VLANMISEPR ISYGNDALMP SLTETKTTVE LLPVNGEFSL  540
DDLQPWHSFG ADSVPANTEN EVEPVDARPA ADRGLTTRPG SGLTNIKTEE ISEVKMDAEF  600
RHDSGYEVHH QKLVFFAEDV GSNKGAIIGL MVGGVVIATV IVITLVMLKK KQYTSIHHGV  660
VEVDAAVTPE ERHLSKMQQN GYENPTYKFF EQMQN                             695

SEQ ID NO: 13           moltype = DNA  length = 2088
```

```
FEATURE                Location/Qualifiers
source                 1..2088
                       mol_type = genomic DNA
                       organism = Mus musculus
SEQUENCE: 13
atgctgccca gcttggcact gctcctgctg gccgcctgga cggttcgggc tctggaggta  60
cccactgatg gcaacgccgg gctgctggca gaaccccaga tcgccatgtt ctgtggtaaa  120
ctcaacatgc acatgaatgt gcagaatgga aagtgggagt cagacccgtc agggaccaaa  180
acctgcattg gcaccaagga gggcatcttg cagtactgcc aagaggtcta ccctgaactg  240
cagatcacaa acgtggtgga agccaaccag ccagtgacca tccagaactg gtgcaagcgg  300
ggccgcaagc agtgcaagac acacacccac atcgtgattc cttaccgttg cctagttggt  360
gagtttgtga gcgacgccct tctcgtgccc gacaagtgca agttcctaca ccaggagcgg  420
atggatgttt gtgagaccca tcttcactgg cacaccgtcg ccaaagagac atgcagcgag  480
aagagcacta acttgcacga ctatggcatg ctgctgccct gcggcatcga caagttccga  540
ggggtagagt ttgtatgctg cccgttggcc gaggaaagcg acagcgtgga ttctgcggat  600
gcagaggagg atgactctga tgtctggtgg ggtggagcgg acacagacta cgctgatggc  660
ggtgaagaca aagtagtaga agtcgccgaa gaggaggaag tggctgatgt tgaggaagag  720
gaagctgatg atgatgagga tgtggaggat ggggacgagg tggaggagga ggccgaggag  780
ccctacgaag aggccaccga gagaacaacc agcactgcca ccaccaccac aaccaccact  840
gagtccgtgg aggaggtggt ccgagttccc acgacagcag ccagcacccc cgacgccgtc  900
gacaagtacc tggagacacc cggggacgag aacgagcatg cccatttcca gaaagccaaa  960
gagaggctgg aagccaagca ccgagagaga atgtcccagg tcatgagaga atgggaagag  1020
gcagagcgtc aagccaagaa cttgcccaaa gctgacaaga aggccgttat ccagcatttc  1080
caggagaaag tggaatctct ggaacaggaa gcagccaatg agagacagca gcttgtagag  1140
acacacatgg ccagagttga agccatgctc aatgaccgcc gccgcctggc cctcgagaat  1200
tacatcactg cactgcaggc ggtgccccca aggcctcatc atgtgttcaa catgctgaag  1260
aagtacgtcc gtgcggagca gaaagacaga cagcacaccc taaagcattt tgaacatgtg  1320
cgcatggtgg accccaagaa agctgctcag atccggtccc aggttatgac acacctccgt  1380
gtgatctacg agcgcatgaa ccagtctctg tccctgctct acaatgtccc tgcggtggct  1440
gaggagattc aagatgaagt cgatgagctg cttcagaagg agcagaacta ctccgacgat  1500
gtcttggcca acatgatcag tgagcccaga atcagctacg gaaacgacgc tctcatgcct  1560
tcgctgacgg aaaccaagac caccgtggag ctccttcccg tgaatgggga attcagcctg  1620
gatgacctcc agccgtggca ccctttttggg gtggactctg tgccagccaa taccgaaaat  1680
gaagtcgagc ctgttgacgc ccgcccccgct gctgaccgag gactgaccac tcgaccaggt  1740
tctgggctga caaacatcaa gacggaagag atctcggaag tgaagatgga tgcagaattc  1800
ggacatgatt caggatttga agtccgccat caaaaactgg tgttctttgc tgaagatgtg  1860
ggttcgaaca aaggcgccat catcggactc atggtgggcg gcgttgtcat agcaaccgtg  1920
attgtcatca ccctggtgat gttgaagaag aaacagtaca catccatcca tcatggcgtg  1980
gtggaggtcg acgccgccgt gaccccagag gagcgccatc tctccaagat gcagcagaac  2040
ggatatgaga atccaactta caagttcttt gagcaaatgc agaactaa             2088

SEQ ID NO: 14          moltype = AA  length = 695
FEATURE                Location/Qualifiers
source                 1..695
                       mol_type = protein
                       organism = Mus musculus
SEQUENCE: 14
MLPSLALLLL AAWTVRALEV PTDGNAGLLA EPQIAMFCGK LNMHMNVQNG KWESDPSGTK  60
TCIGTKEGIL QYCQEVYPEL QITNVVEANQ PVTIQNWCKR GRKQCKTHTH IVIPYRCLVG  120
EFVSDALLVP DKCKFLHQER MDVCETHLHW HTVAKETCSE KSTNLHDYGM LLPCGIDKFR  180
GVEFVCCPLA EESDSVDSAD AEEDDSDVWW GGADTDYADG GEDKVVEVAE EEEVADVEEE  240
EADDDEDVED GDEVEEEAEE PYEEATERTT STATTTTTTT ESVEEVVRVP TTAASTPDAV  300
DKYLETPGDE NEHAHFQKAK ERLEAKHRER MSQVMREWEE AERQAKNLPK ADKKAVIQHF  360
QEKVESLEQE AANERQQLVE THMARVEAML NDRRRLALEN YITALQAVPP RPHHVFNMLK  420
KYVRAEQKDR QHTLKHFEHV RMVDPKKAAQ IRSQVMTHLR VIYERMNQSL SLLYNVPAVA  480
EEIQDEVDEL LQKEQNYSDD VLANMISEPR ISYGNDALMP SLTETKTTVE LLPVNGEFSL  540
DDLQPWHPFG VDSVPANTEN EVEPVDARPA ADRGLTTRPG SGLTNIKTEE ISEVKMDAEF  600
GHDSGFEVRH QKLVFFAEDV GSNKGAIIGL MVGGVVIATV IVITLVMLKK KQYTSIHHGV  660
VEVDAAVTPE ERHLSKMQQN GYENPTYKFF EQMQN                            695

SEQ ID NO: 15          moltype = DNA  length = 4176
FEATURE                Location/Qualifiers
source                 1..4176
                       mol_type = genomic DNA
                       organism = Streptococcus pyogenes
SEQUENCE: 15
atgggtatcc acggagtccc agcagccgac aagaagtaca gcatcggcct ggacatcggc  60
accaactctg tgggctgggc cgtgatcacc gacgagtaca aggtgcccag caagaaattc  120
aaggtgctgg gcaacaccga ccggcacagc atcaagaaga acctgatcgg agccctgctg  180
ttcgacagcg gcgaaacagc cgaggccacc cggctgaaga gaaccgccag aagaagatac  240
accagacgga agaaccggat ctgctatctg caagagatct tcagcaacga gatggccaag  300
gtggacgaca gcttcttcca cagactggaa gagtccttcc tggtggaaga ggataagaag  360
cacgagcggc accccatctt cggcaacatc gtggacgagg tggcctacca cgagaagtac  420
cccaccatct accacctgag aaagaaactg gtggacagca ccgacaaggc cgacctgcgg  480
ctgatctatc tggccctggc ccacatgatc aagttccggg gccacttcct gatcgagggc  540
gacctgaacc ccgacaacag cgacgtggac aagctgttca tccagctggt gcagacctac  600
aaccagctgt tcgaggaaaa ccccatcaac gccagcggcg tggacgccaa ggccatcctg  660
tctgccagac tgagcaagag cagacggctg gaaaatctga tcgcccagct gcccggcgag  720
aagaagaatg gcctgttcgg aaacctgatt gccctgagcc tgggcctgac ccccaacttc  780
```

-continued

```
aagagcaact tcgacctggc cgaggatgcc aaactgcagc tgagcaagga cacctacgac  840
gacgacctgg acaacctgct ggcccagatc ggcgaccagt acgccgacct gtttctggcc  900
gccaagaacc tgtccgacgc catcctgctg agcgacatcc tgagagtgaa caccgagatc  960
accaaggccc ccctgagcgc ctctatgatc aagagatacg acgagcacca ccaggacctg  1020
accctgctga aagctctcgt gcggcagcag ctgcctgaga agtacaaaga gatttttcttc  1080
gaccagagca agaacggcta cgccggctac attgacggcg gagccagcca ggaagagttc  1140
tacaagttca tcaagcccat cctggaaaag atggacggca ccgaggaact gctcgtgaag  1200
ctgaacagag aggacctgct gcggaagcag cggaccttcg acaacggcag catcccccac  1260
cagatccacc tgggagagct gcacgccatt ctgcggcggc aggaagattt ttacccattc  1320
ctgaaggaca accgggaaaa gatcgagaag atcctgacct tccgcatccc ctactacgtg  1380
ggccctctgg ccaggggaaa cagcagattc gcctggatga ccagaaagag cgaggaaacc  1440
atcaccccct ggaacttcga ggaagtggtg gacaagggcg cttccgccca gagcttcatc  1500
gagcggatga ccaacttcga taagaacctg cccaacgaga aggtgctgcc caagcacagc  1560
ctgctgtacg agtacttcac cgtgtataac gagctgacca aagtgaaata cgtgaccgag  1620
ggaatgagaa agcccgcctt cctgagcggc gagcagaaaa aggccatcgt ggacctgctg  1680
ttcaagacca accggaaagt gaccgtgaag cagctgaaag aggactactt caagaaaatc  1740
gagtgcttcg actccgtgga aatctccggc gtggaagatc ggttcaacgc ctccctgggc  1800
acataccacg atctgctgaa aattatcaag gacaaggact tcctggacaa tgaggaaaac  1860
gaggacattc tggaagatat cgtgctgacc ctgacactgt ttgaggacag agagatgatc  1920
gaggaacggc tgaaaaccta tgcccacctg ttcgacgaca aagtgatgaa gcagctgaag  1980
cggcggagat acaccggctg gggcaggctg agccggaagc tgatcaacgg catccgggac  2040
aagcagtccg gcaagacaat cctggatttc ctgaagtccg acggcttcgc caacagaaac  2100
ttcatgcagc tgatccacga cgacagcctg acctttaaag aggacatcca gaaagcccag  2160
gtgtccggcc agggcgatag cctgcacgag cacattgcca atctggccgg cagccccgcc  2220
attaagaagg gcatcctgca gacagtgaag gtggtggacg agctcgtgaa agtgatgggc  2280
cggcacaagc ccgagaacat cgtgatcgaa atggccagag agaaccagac cacccagaag  2340
ggacagaaga acagccgcga gagaatgaag cggatcgaag agggcatcaa agagctgggc  2400
agccagatcc tgaaagaaca ccccgtggaa aacacccagc tgcagaacga gaagctgtac  2460
ctgtactacc tgcagaatgg gcgggatatg tacgtggacc aggaactgga catcaaccgg  2520
ctgtccgact acgatgtgga ccatatcgtg cctcagagct ttctgaagga cgactccatc  2580
gacaacaagg tgctgaccag aagcgacaag aaccggggca agagcgacaa cgtgccctcc  2640
gaagaggtcg tgaagaagat gaagaactac tggcggcagc tgctgaacgc caagctgatt  2700
acccagagaa agttcgacaa tctgaccaag gccgagagag gcggcctgag cgaactggat  2760
aaggccggct tcatcaagag acagctggtg gaaacccggc agatcacaaa gcacgtggca  2820
cagatcctgg actcccggat gaacactaag tacgacgaga atgacaagct gatccgggaa  2880
gtgaaagtga tcaccctgaa gtccaagctg gtgtccgatt tccggaagga tttccagttt  2940
tacaaagtgc gcgagatcaa caactaccac cacgcccacg acgcctacct gaacgccgtc  3000
gtgggaaccg ccctgatcaa aaagtaccct aagctggaaa gcgagttcgt gtacggcgac  3060
tacaaggtgt acgacgtgcg gaagatgatc gccaagagcg agcaggaaat cggcaaggct  3120
accgccaagt acttcttcta cagcaacatc atgaactttt tcaagaccga gattaccctg  3180
gccaacggcg agatccggaa gcggcctctg atcgagacaa acggcgaaac cggggagatc  3240
gtgtgggata agggccggga ttttgccacc gtgcggaaag tgctgagcat gccccaagtg  3300
aatatcgtga aaaagaccga ggtgcagaca ggcggcttca gcaaagagtc tatcctgccc  3360
aagaggaaca gcgataagct gatcgccaga aagaaggact gggaccctaa gaagtacggc  3420
ggcttcgaca gccccaccgt ggcctattct gtgctggtgg tggccaaagt ggaaaagggc  3480
aagtccaaga aactgaagag tgtgaaagag ctgctgggga tcaccatcat ggaaagaagc  3540
agcttcgaga agaatcccat cgactttctg gaagccaagg gctacaaaga agtgaaaaag  3600
gacctgatca tcaagctgcc taagtactcc ctgttcgagc tggaaaacgg ccggaagaga  3660
atgctggcct ctgccggcga actgcagaag ggaaacgaac tggccctgcc ctccaaatat  3720
gtgaacttcc tgtacctggc cagccactat gagaagctga agggctcccc cgaggataat  3780
gagcagaaac agctgtttgt ggaacagcac aagcactacc tggacgagat catcgagcag  3840
atcagcgagt tctccaagag agtgatcctg gccgacgcta atctggacaa agtgctgtcc  3900
gcctacaaca agcaccggga taagcccatc agagagcagg ccgagaatat catccacctg  3960
tttaccctga ccaatctggg agcccctgcc gccttcaagt actttgacac caccatcgac  4020
cggaagaggt acaccagcac caaagaggtg ctggacgcca ccctgatcca ccagagcatc  4080
accggcctgt acgagacacg gatcgacctg tctcagctgg gaggcgacaa aaggccggcg  4140
gccacgaaaa aggccggcca ggcaaaaaag aaaaag                          4176
```

```
SEQ ID NO: 16          moltype = DNA  length = 80
FEATURE                Location/Qualifiers
misc_feature           1..80
                       note = synthetic
source                 1..80
                       mol_type = other DNA
                       organism = synthetic construct
SEQUENCE: 16
gttttagagc tagaaatagc aagttaaaat aaggctagtc cgttatcaac ttgaaaaagt  60
ggcaccgagt cggtgctttt                                            80
```

```
SEQ ID NO: 17          moltype = DNA  length = 9286
FEATURE                Location/Qualifiers
misc_feature           1..9286
                       note = synthetic
source                 1..9286
                       mol_type = other DNA
                       organism = synthetic construct
SEQUENCE: 17
ccccacgagg gcctatttcc catgattcct tcatatttgc atatacgata caaggctgtt  60
agagagataa ttggaattaa tttgactgta aacacaaaga tattagtaca aaatacgtga  120
```

```
cgtagaaagt aataatttct tgggtagttt gcagttttaa aattatgttt taaaatggac  180
tatcatatgc ttaccgtaac ttgaaagtat ttcgatttct tggctttata tatcttgtgg  240
aaaggacgaa acaccgatcc attcatcatg gtgtgggttt tagagctaga aatagcaagt  300
taaaataagg ctagtccgtt atcaacttga aaaagtggca ccgagtcggt gcttttttgt  360
tttagagcta gaaatagcaa gttaaaataa ggctagtccg tttttagcgc gtgcgccaat  420
tctgcagaca aatggctcta gaggtacccg ttacataact tacggtaaat ggcccgcctg  480
gctgaccgcc caacgacccc cgcccattga cgtcaatagt aacgccaata gggactttcc  540
attgacgtca atgggtggag tatttacggt aaactgccca cttggcagta catcaagtgt  600
atcatatgcc aagtacgccc cctattgacg tcaatgacgg taaatggccc gcctggcatt  660
gtgcccagta catgacctta tggcacttcc ctacttggca gtacatctac gtattagtca  720
tcgctattac catggtcgag gtgagcccca cgttctgctt cactctcccc atctcccccc  780
cctccccacc cccaattttg tatttattta ttttttaatt attttgtgca gcgatggggg  840
cggggggggg ggggggggcgc gcgccaggcg gggcggggcg gggcgagggg cggggcgggg  900
cgaggcggag aggtgcggcg gcagccaatc agagcggcgc gctccgaaag tttcctttta  960
tggcgaggcg gcggcggcgg cggccctata aaaagcgaag cgcgcggcgg gcgggagtcg  1020
ctgcgacgct gccttcgccc cgtgccccgc tccgccgccg cctcgcgccg cccgccccgg  1080
ctctgactga ccgcgttact cccacaggtg agcgggcggg acggcccttc tcctccgggc  1140
tgtaattagc tgagcaagag gtaagggttt aagggatggt tggttggtgg ggtattaatg  1200
tttaattacc tggagcacct gcctgaaatc actttttttc aggttggacc ggtgccacca  1260
tggactataa ggaccacgac ggagactaca aggatcatga tattgattac aaagacgatg  1320
acgataagat ggccccaaag aagaagcgga aggtcggtat ccacggagtc ccagcagccg  1380
acaagaagta cagcatcggc ctggacatcg gcaccaactc tgtgggctgg gccgtgatca  1440
ccgacgagta caaggtgccc agcaagaaat tcaaggtgct gggcaacacc gaccggcaca  1500
gcatcaagaa gaacctgatc ggagccctgc tgttcgacag cggcgaaaca gccgaggcca  1560
cccggctgaa gagaaccgcc agaagaagat acaccagacg gaagaaccgg atctgctatc  1620
tgcaagagat cttcagcaac gagatggcca aggtggacga cagcttcttc cacagactgg  1680
aagagtcctt cctggtggaa gaggataaga agcacgagcg gcaccccatc ttcggcaaca  1740
tcgtggacga ggtggcctac cacgagaagt accccaccat ctaccacctg agaaagaaac  1800
tggtggacag caccgacaag gccgacctgc ggctgatcta tctggccctg gcccacatga  1860
tcaagttccg gggccacttc ctgatcgagg gcgacctgaa ccccgacaac agcgacgtgg  1920
acaagctgtt catccagctg gtgcagacct acaaccagct gttcgaggaa aaccccatca  1980
acgccagcgg cgtggacgcc aaggccatcc tgtctgccag actgagcaag agcagacggc  2040
tggaaaatct gatcgcccag ctgcccggcg agaagaagaa tggcctgttc ggaaacctga  2100
ttgccctgag cctgggcctg acccccaact tcaagagcaa cttcgacctg gccgaggatg  2160
ccaaactgca gctgagcaag gacacctacg acgacgacct ggacaacctg ctggcccaga  2220
tcggcgacca gtacgccgac ctgtttctgg ccgccaagaa cctgtccgac gccatcctgc  2280
tgagcgacat cctgagagtg aacaccgaga tcaccaaggc ccccctgagc gcctctatga  2340
tcaagagata cgacgagcac caccaggacc tgaccctgct gaaagctctc gtgcggcagc  2400
agctgcctga gaagtacaaa gagattttct tcgaccagag caagaacggc tacgccggct  2460
acattgacgg cggagccagc caggaagagt tctacaagtt catcaagccc atcctggaaa  2520
agatggacgg caccgaggaa ctgctcgtga agctgaacag agaggacctg ctgcggaagc  2580
agcggacctt cgacaacggc agcatccccc accagatcca cctgggagag ctgcacgcca  2640
ttctgcggcg gcaggaagat ttttacccat tcctgaagga caaccgggaa aagatcgaga  2700
agatcctgac cttccgcatc ccctactacg tgggccctct ggccagggga aacagcagat  2760
tcgcctggat gaccagaaag agcgaggaaa ccatcacccc ctggaacttc gaggaagtgg  2820
tggacaaggg cgcttccgcc cagagcttca tcgagcggat gaccaacttc gataagaacc  2880
tgcccaacga gaaggtgctg cccaagcaca gcctgctgta cgagtacttc accgtgtata  2940
acgagctgac caaagtgaaa tacgtgaccg agggaatgag aaagcccgcc ttcctgagcg  3000
gcgagcagaa aaaggccatc gtggacctgc tgttcaagac caaccggaaa gtgaccgtga  3060
agcagctgaa agaggactac ttcaagaaaa tcgagtgctt cgactccgtg gaaatctccg  3120
gcgtggaaga tcggttcaac gcctccctgg gcacatacca cgatctgctg aaaattatca  3180
aggacaagga cttcctggac aatgaggaaa acgaggacat tctggaagat atcgtgctga  3240
ccctgacact gtttgaggac agagagatga tcgaggaacg gctgaaaacc tatgcccacc  3300
tgttcgacga caaagtgatg aagcagctga agcggcggag atacaccggc tggggcaggc  3360
tgagccggaa gctgatcaac ggcatccggg acaagcagtc cggcaagaca atcctggatt  3420
tcctgaagtc cgacggcttc gccaacagaa acttcatgca gctgatccac gacgacagcc  3480
tgacctttaa agaggacatc cagaaagccc aggtgtccgg ccagggcgat agcctgcacg  3540
agcacattgc caatctggcc ggcagccccg ccattaagaa gggcatcctg cagacagtga  3600
aggtggtgga cgagctcgtg aaagtgatgg gccggcacaa gcccgagaac atcgtgatcg  3660
aaatggccag agagaaccag accacccaga agggacagaa gaacagccgc gagagaatga  3720
agcggatcga agagggcatc aaagagctgg gcagccagat cctgaaagaa caccccgtgg  3780
aaaacaccca gctgcagaac gagaagctgt acctgtacta cctgcagaat gggcgggata  3840
tgtacgtgga ccaggaactg gacatcaacc ggctgtccga ctacgatgtg gaccatatcg  3900
tgcctcagag ctttctgaag gacgactcca tcgacaacaa ggtgctgacc agaagcgaca  3960
agaaccgggg caagagcgac aacgtgccct ccgaagaggt cgtgaagaag atgaagaact  4020
actggcggca gctgctgaac gccaagctga ttacccagag aaagttcgac aatctgacca  4080
aggccgagag aggcggcctg agcgaactgg ataaggccgg cttcatcaag agacagctgg  4140
tggaaacccg gcagatcaca aagcacgtgg cacagatcct ggactcccgg atgaacacta  4200
agtacgacga gaatgacaag ctgatccggg aagtgaaagt gatcaccctg aagtccaagc  4260
tggtgtccga tttccggaag gatttccagt tttacaaagt gcgcgagatc aacaactacc  4320
accacgccca cgacgcctac ctgaacgccg tcgtgggaac cgccctgatc aaaaagtacc  4380
ctaagctgga aagcgagttc gtgtacggcg actacaaggt gtacgacgtg cggaagatga  4440
tcgccaagag cgagcaggaa atcggcaagg ctaccgccaa gtacttcttc tacagcaaca  4500
tcatgaactt tttcaagacc gagattaccc tggccaacgg cgagatccgg aagcggcctc  4560
tgatcgagac aaacggcgaa accggggaga tcgtgtggga taagggccgg gattttgcca  4620
ccgtgcggaa agtgctgagc atgccccaag tgaatatcgt gaaaaagacc gaggtgcaga  4680
caggcggctt cagcaaagag tctatcctgc ccaagaggaa cagcgataag ctgatcgcca  4740
gaaagaagga ctgggaccct aagaagtacg gcggcttcga cagccccacc gtggcctatt  4800
ctgtgctggt ggtggccaaa gtggaaaagg gcaagtccaa gaaactgaag agtgtgaaag  4860
```

-continued

```
agctgctggg gatcaccatc atggaaagaa gcagcttcga gaagaatccc atcgactttc  4920
tggaagccaa gggctacaaa gaagtgaaaa aggacctgat catcaagctg cctaagtact  4980
ccctgttcga gctggaaaac ggccggaaga gaatgctggc ctctgccggc gaactgcaga  5040
agggaaacga actggccctg ccctccaaat atgtgaactt cctgtacctg gccagccact  5100
atgagaagct gaagggctcc cccgaggata atgagcagaa acagctgttt gtggaacagc  5160
acaagcacta cctggacgag atcatcgagc agatcagcga gttctccaag agagtgatcc  5220
tggccgacgc taatctggac aaagtgctgt ccgcctacaa caagcaccgg gataagccca  5280
tcagagagca ggccgagaat atcatccacc tgtttaccct gaccaatctg ggagcccctg  5340
ccgccttcaa gtactttgac accaccatcg accggaagag gtacaccagc accaaagagg  5400
tgctggacgc caccctgatc caccagagca tcaccggcct gtacgagaca cggatcgacc  5460
tgtctcagct gggaggcgac aaaaggccgg cggccacgaa aaaggccggc caggcaaaaa  5520
agaaaaagct tgagggcaga ggaagtctgc taacatgcgg tgacgtggag gagaatcccg  5580
gccctgctag catggtgagc aagggcgagg aggataacat ggccatcatc aaggagttca  5640
tgcgcttcaa ggtgcacatg gagggctccg tgaacggcca cgagttcgag atcgagggcg  5700
agggcgaggg ccgcccctac gagggcaccc agaccgccaa gctgaaggtg accaagggtg  5760
gcccccctgcc cttcgcctgg gacatcctgt cccctcagtt catgtacggc tccaaggcct  5820
acgtgaagca ccccgccgac atccccgact acttgaagct gtccttcccc gagggcttca  5880
agtgggagcg cgtgatgaac ttcgaggacg gcggcgtggt gaccgtgacc caggactcct  5940
ccctgcagga cggcgagttc atctacaagg tgaagctgcg cggcaccaac ttcccctcag  6000
acggccccgt aatgcagaag aaaaccatgg gctgggaggc ctcctccgag cggatgtacc  6060
ccgaggacgg cgccctgaag ggcgagatca agcagaggct gaagctgaag gacggcggcc  6120
actacgacgc tgaggtcaag accacctaca aggccaagaa gcccgtgcag ctgcccggcg  6180
cctacaacgt caacatcaag ttggacatca cctcccacaa cgaggactac accatcgtgg  6240
aacagtacga acgcgccgag ggccgccact ccaccggcgg catggacgag ctgtacaagt  6300
aagaattcct agagctcgct gatcagcctc gactgtgcct tctagttgcc agccatctgt  6360
tgtttgcccc tcccccgtgc cttccttgac cctggaaggt gccactccca ctgtcctttc  6420
ctaataaaat gaggaaattg catcgcattg tctgagtagg tgtcattcta ttctgggggg  6480
tggggtgggg caggacagca agggggagga ttgggaagag aatagcaggc atgctgggga  6540
gcggccgcag gaacccctag tgatggagtt ggccactccc tctctgcgcg ctcgctcgct  6600
cactgaggcc gggcgaccaa aggtcgcccg acgcccgggc tttgcccggg cggcctcagt  6660
gagcgagcga gcgcgcagct gcctgcaggg gcgcctgatg cggtattttc tccttacgca  6720
tctgtgcggt atttcacacc gcatacgtca aagcaaccat agtacgcgcc ctgtagcggc  6780
gcattaagcg cggcgggtgt ggtggttacg cgcagcgtga ccgctacact tgccagcgcc  6840
ctagcgcccg ctcctttcgc tttcttccct tcctttctcg ccacgttcgc cggctttccc  6900
cgtcaagctc taaatcgggg gctcccttta gggttccgat ttagtgcttt acggcacctc  6960
gaccccaaaa aacttgattt gggtgatggt tcacgtagtg ggccatcgcc ctgatagacg  7020
gtttttcgcc ctttgacgtt ggagtccacg ttctttaata gtggactctt gttccaaact  7080
ggaacaacac tcaaccctat ctcgggctat tcttttgatt tataagggat tttgccgatt  7140
tcggcctatt ggttaaaaaa tgagctgatt taacaaaaat ttaacgcgaa ttttaacaaa  7200
atattaacgt ttacaatttt atggtgcact ctcagtacaa tctgctctga tgccgcatag  7260
ttaagccagc cccgacaccc gccaacaccc gctgacgcgc cctgacgggc ttgtctgctc  7320
ccggcatccg cttacagaca agctgtgacc gtctccggga gctgcatgtg tcagaggttt  7380
tcaccgtcat caccgaaacg cgcgagacga aagggcctcg tgatacgcct atttttatag  7440
gttaatgtca tgataataat ggtttcttag acgtcaggtg gcacttttcg gggaaatgtg  7500
cgcggaaccc ctatttgttt atttttctaa atacattcaa atatgtatcc gctcatgaga  7560
caataaccct gataaatgct tcaataatat tgaaaaagga agagtatgag tattcaacat  7620
ttccgtgtcg cccttattcc cttttttgcg gcattttgcc ttcctgtttt tgctcaccca  7680
gaaacgctgg tgaaagtaaa agatgctgaa gatcagttgg gtgcacgagt gggttacatc  7740
gaactggatc tcaacagcgg taagatcctt gagagttttc gccccgaaga acgttttcca  7800
atgatgagca cttttaaagt tctgctatgt ggcgcggtat tatcccgtat tgacgccggg  7860
caagagcaac tcggtcgccg catacactat tctcagaatg acttggttga gtactcacca  7920
gtcacagaaa agcatcttac ggatggcatg acagtaagag aattatgcag tgctgccata  7980
accatgagtg ataacactgc ggccaactta cttctgacaa cgatcggagg accgaaggag  8040
ctaaccgctt ttttgcacaa catgggggat catgtaactc gccttgatcg ttgggaaccg  8100
gagctgaatg aagccatacc aaacgacgag cgtgacacca cgatgcctgt agcaatggca  8160
acaacgttgc gcaaactatt aactggcgaa ctacttactc tagcttcccg gcaacaatta  8220
atagactgga tggaggcgga taaagttgca ggaccacttc tgcgctcggc ccttccggct  8280
ggctggttta ttgctgataa atctggagcc ggtgagcgtg gaagccgcgg tatcattgca  8340
gcactggggc cagatggtaa gccctcccgt atcgtagtta tctacacgac ggggagtcag  8400
gcaactatgg atgaacgaaa tagacagatc gctgagatag gtgcctcact gattaagcat  8460
tggtaactgt cagaccaagt ttactcatat atactttaga ttgatttaaa acttcatttt  8520
taatttaaaa ggatctaggt gaagatcctt tttgataatc tcatgaccaa aatcccttaa  8580
cgtgagtttt cgttccactg agcgtcagac cccgtagaaa agatcaaagg atcttcttga  8640
gatccttttt ttctgcgcgt aatctgctgc ttgcaaacaa aaaaaccacc gctaccagcg  8700
gtggtttgtt tgccggatca agagctacca actctttttc cgaaggtaac tggcttcagc  8760
agagcgcaga taccaaatac tgtccttcta gtgtagccgt agttaggcca ccacttcaag  8820
aactctgtag caccgcctac atacctcgct ctgctaatcc tgttaccagt ggctgctgcc  8880
agtggcgata agtcgtgtct taccgggttg gactcaagac gatagttacc ggataaggcg  8940
cagcggtcgg gctgaacggg gggttcgtgc acacagccca gcttggagcg aacgacctac  9000
accgaactga gatacctaca gcgtgagcta tgagaaagcg ccacgcttcc cgaagggaga  9060
aaggcggaca ggtatccggt aagcggcagg gtcggaacag gagagcgcac gagggagctt  9120
ccagggggaa acgcctggta tctttatagt cctgtcgggt ttcgccacct ctgacttgag  9180
cgtcgatttt tgtgatgctc gtcagggggg cggagcctat ggaaaaacgc cagcaacgcg  9240
gcctttttac ggttcctggc cttttgctgg ccttttgctc acatgt                 9286
```

```
SEQ ID NO: 18           moltype = DNA  length = 7400
FEATURE                 Location/Qualifiers
misc_feature            1..7400
                        note = synthetic
```

```
source                  1..7400
                        mol_type = other DNA
                        organism = synthetic construct
SEQUENCE: 18
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc tgcggcctct agaaagctta gctgaatggg gtccgcctct  180
tttccctgcc taaacagaca ggaactcctg ccaattgagg gcgtcaccgc taaggctccg  240
ccccagcctg ggctccacaa ccaatgaagg gtaatctcga caaagagcaa ggggtggggc  300
gcgggcgcgc aggtgcagca gcacacaggc tggtcgggag ggcggggcgc gacgtctgcc  360
gtgcggggtc ccggcatcgg ttgcgcgcac cggtgccacc atgtacccat acgatgttcc  420
agattacgct tcgccgaaga aaaagcgcaa ggtcgaagcg tccgacaaga agtacagcat  480
cggcctggac atcggcacca actctgtggg ctgggccgtg atcaccgacg agtacaaggt  540
gcccagcaag aaattcaagg tgctgggcaa caccgaccgg cacagcatca agaagaacct  600
gatcggagcc ctgctgttcg acagcggcga aacagccgag gccacccggc tgaagagaac  660
cgccagaaga agatacacca gacggaagaa ccggatctgc tatctgcaag agatcttcag  720
caacgagatg gccaaggtgg acgacagctt cttccacaga ctggaagagt ccttcctggt  780
ggaagaggat aagaagcacg agcggcaccc catcttcggc aacatcgtgg acgaggtggc  840
ctaccacgag aagtacccca ccatctacca cctgagaaag aaactggtgg acagcaccga  900
caaggccgac ctgcggctga tctatctggc cctggcccac atgatcaagt tccggggcca  960
cttcctgatc gagggcgacc tgaaccccga caacagcgac gtggacaagc tgttcatcca  1020
gctggtgcag acctacaacc agctgttcga ggaaaacccc atcaacgcca gcggcgtgga  1080
cgccaaggcc atcctgtctg ccagactgag caagagcaga cggctggaaa atctgatcgc  1140
ccagctgccc ggcgagaaga agaatggcct gttcggcaac ctgattgccc tgagcctggg  1200
cctgaccccc aacttcaaga gcaacttcga cctggccgag gatgccaaac tgcagctgag  1260
caaggacacc tacgacgacg acctggacaa cctgctggcc cagatcggcg accagtacgc  1320
cgacctgttt ctggccgcca agaacctgtc cgacgccatc ctgctgagcg acatcctgag  1380
agtgaacacc gagatcacca aggcccccct gagcgcctct atgatcaaga gatacgacga  1440
gcaccaccag gacctgaccc tgctgaaagc tctcgtgcgg cagcagctgc ctgagaagta  1500
caaagagatt ttcttcgacc agagcaagaa cggctacgcc ggctacattg acggcggagc  1560
cagccaggaa gagttctaca agttcatcaa gcccatcctg gaaaagatgg acggcaccga  1620
ggaactgctc gtgaagctga acagagagga cctgctgcgg aagcagcgga ccttcgacaa  1680
cggcagcatc ccccaccaga tccacctggg agagctgcac gccattctgc ggcggcagga  1740
agatttttac ccattcctga aggacaaccg ggaaaagatc gagaagatcc tgaccttccg  1800
catcccctac tacgtgggcc ctctggccag gggaaacagc agattcgcct ggatgaccag  1860
aaagagcgag gaaaccatca cccccctggaa cttcgaggaa gtggtggaca agggcgcttc  1920
cgcccagagc ttcatcgagc ggatgaccaa cttcgataag aacctgccca acgagaaggt  1980
gctgcccaag cacagcctgc tgtacgagta cttcaccgtg tataacgagc tgaccaaagt  2040
gaaatacgtg accgagggaa tgagaaagcc cgccttcctg agcggcgagc agaaaaaggc  2100
catcgtggac ctgctgttca agaccaaccg gaaagtgacc gtgaagcagc tgaaagagga  2160
ctacttcaag aaaatcgagt gcttcgactc cgtggaaatc tccggcgtgg aagatcggtt  2220
caacgcctcc ctgggcacat accacgatct gctgaaaatt atcaaggaca aggacttcct  2280
ggacaatgag gaaaacgagg acattctgga agatatcgtg ctgaccctga cactgtttga  2340
ggacagagag atgatcgagg aacggctgaa aacctatgcc cacctgttcg acgacaaagt  2400
gatgaagcag ctgaagcggc ggagatacac cggctggggc aggctgagcc ggaagctgat  2460
caacggcatc cgggacaagc agtccggcaa gacaatcctg gatttcctga agtccgacgg  2520
cttcgccaac agaaacttca tgcagctgat ccacgacgac agcctgacct ttaaagagga  2580
catccagaaa gcccaggtgt ccggccaggg cgatagcctg cacgagcaca ttgccaatct  2640
ggccggcagc cccgccatta agaagggcat cctgcagaca gtgaaggtgg tggacgagct  2700
cgtgaaagtg atgggccggc acaagcccga gaacatcgtg atcgaaatgg ccagagagaa  2760
ccagaccacc cagaagggac agaagaacag ccgcgagaga atgaagcgga tcgaagaggg  2820
catcaaagag ctgggcagcc agatcctgaa agaacacccc gtggaaaaca cccagctgca  2880
gaacgagaag ctgtacctgt actacctgca gaatgggcgg gatatgtacg tggaccagga  2940
actggacatc aaccggctgt ccgactacga tgtggaccat atcgtgcctc agagctttct  3000
gaaggacgac tccatcgaca acaaggtgct gaccagaagc gacaagaacc ggggcaagag  3060
cgacaacgtg ccctccgaag aggtcgtgaa gaagatgaag aactactggc ggcagctgct  3120
gaacgccaag ctgattaccc agagaaagtt cgacaatctg accaaggccg agagaggcgg  3180
cctgagcgaa ctggataagg ccggcttcat caagagacag ctggtggaaa cccggcagat  3240
cacaaagcac gtggcacaga tcctggactc ccggatgaac actaagtacg acgagaatga  3300
caagctgatc cgggaagtga aagtgatcac cctgaagtcc aagctggtgt ccgatttccg  3360
gaaggatttc cagttttaca aagtgcgcga gatcaacaac taccaccacg cccacgacgc  3420
ctacctgaac gccgtcgtgg gaaccgccct gatcaaaaag taccctaagc tggaaagcga  3480
gttcgtgtac ggcgactaca aggtgtacga cgtgcggaag atgatcgcca agagcgagca  3540
ggaaatcggc aaggctaccg ccaagtactt cttctacagc aacatcatga actttttcaa  3600
gaccgagatt accctggcca acggcgagat ccggaagcgg cctctgatcg agacaaacgg  3660
cgaaaccggg gagatcgtgt gggataaggg ccgggatttt gccaccgtgc ggaaagtgct  3720
gagcatgccc caagtgaata tcgtgaaaaa gaccgaggtg cagacaggcg gcttcagcaa  3780
agagtctatc ctgcccaaga ggaacagcga taagctgatc gccagaaaga aggactggga  3840
ccctaagaag tacggcggct tcgacagccc caccgtggcc tattctgtgc tggtggtggc  3900
caaagtggaa aagggcaagt ccaagaaact gaagagtgtg aaagagctgc tggggatcac  3960
catcatggaa agaagcagct tcgagaagaa tcccatcgac tttctggaag ccaagggcta  4020
caaagaagtg aaaaaggacc tgatcatcaa gctgcctaag tactccctgt tcgagctgga  4080
aaacggccgg aagagaatgc tggcctctgc cggcgaactg cagaagggaa acgaactggc  4140
cctgccctcc aaatatgtga acttcctgta cctggccagc cactatgaga agctgaaggg  4200
ctcccccgag gataatgagc agaaacagct gtttgtggaa cagcacaagc actacctgga  4260
cgagatcatc gagcagatca gcgagttctc caagagagtg atcctggccg acgctaatct  4320
ggacaaagtg ctgtccgcct acaacaagca ccgggataag cccatcagag agcaggccga  4380
gaatatcatc cacctgttta ccctgaccaa tctgggagcc cctgccgcct tcaagtactt  4440
tgacaccacc atcgaccgga agaggtacac cagcaccaaa gaggtgctgg acgccaccct  4500
```

-continued

```
gatccaccag agcatcaccg gcctgtacga gacacggatc gacctgtctc agctgggagg  4560
cgacagcccc aagaagaaga gaaaggtgga ggccagctaa gaattcaata aaagatcttt  4620
attttcatta gatctgtgtg ttggtttttt gtgtgcggcc gcaggaaccc ctagtgatgg  4680
agttggccac tccctctctg cgcgctcgct cgctcactga ggccgggcga ccaaaggtcg  4740
cccgacgccc gggctttgcc cgggcggcct cagtgagcga gcgagcgcgc agctgcctgc  4800
aggggcgcct gatgcggtat tttctcctta cgcatctgtg cggtatttca caccgcatac  4860
gtcaaagcaa ccatagtacg cgccctgtag cggcgcatta agcgcggcgg gtgtggtggt  4920
tacgcgcagc gtgaccgcta cacttgccag cgccctagcg cccgctcctt tcgctttctt  4980
cccttccttt ctcgccacgt tcgccggctt tccccgtcaa gctctaaatc gggggctccc  5040
tttagggttc cgatttagtg ctttacggca cctcgacccc aaaaaacttg atttgggtga  5100
tggttcacgt agtgggccat cgccctgata gacggttttt cgccctttga cgttggagtc  5160
cacgttcttt aatagtggac tcttgttcca aactggaaca acactcaacc ctatctcggg  5220
ctattctttt gatttataag ggattttgcc gatttcggcc tattggttaa aaaatgagct  5280
gatttaacaa aaatttaacg cgaattttaa caaaatatta acgtttacaa ttttatggtg  5340
cactctcagt acaatctgct ctgatgccgc atagttaagc cagccccgac acccgccaac  5400
acccgctgac gcgccctgac gggcttgtct gctcccggca tccgcttaca gacaagctgt  5460
gaccgtctcc gggagctgca tgtgtcagag gttttcaccg tcatcaccga aacgcgcgag  5520
acgaaagggc ctcgtgatac gcctattttt ataggttaat gtcatgataa taatggtttc  5580
ttagacgtca ggtggcactt ttcggggaaa tgtgcgcgga acccctattt gtttattttt  5640
ctaaatacat tcaaatatgt atccgctcat gagacaataa ccctgataaa tgcttcaata  5700
atattgaaaa aggaagagta tgagtattca acatttccgt gtcgccctta ttcccttttt  5760
tgcggcattt tgccttcctg tttttgctca cccagaaacg ctggtgaaag taaaagatgc  5820
tgaagatcag ttgggtgcac gagtgggtta catcgaactg gatctcaaca gcggtaagat  5880
ccttgagagt tttcgccccg aagaacgttt tccaatgatg agcactttta aagttctgct  5940
atgtggcgcg gtattatccc gtattgacgc cgggcaagag caactcggtc gccgcataca  6000
ctattctcag aatgacttgg ttgagtactc accagtcaca gaaaagcatc ttacggatgg  6060
catgacagta agagaattat gcagtgctgc cataaccatg agtgataaca ctgcggccaa  6120
cttacttctg acaacgatcg gaggaccgaa ggagctaacc gcttttttgc acaacatggg  6180
ggatcatgta actcgccttg atcgttggga accggagctg aatgaagcca taccaaacga  6240
cgagcgtgac accacgatgc ctgtagcaat ggcaacaacg ttgcgcaaac tattaactgg  6300
cgaactactt actctagctt cccggcaaca attaatagac tggatggagg cggataaagt  6360
tgcaggacca cttctgcgct cggcccttcc ggctggctgg tttattgctg ataaatctgg  6420
agccggtgag cgtggaagcc gcggtatcat tgcagcactg gggccagatg gtaagccctc  6480
ccgtatcgta gttatctaca cgacggggag tcaggcaact atggatgaac gaaatagaca  6540
gatcgctgag ataggtgcct cactgattaa gcattggtaa ctgtcagacc aagtttactc  6600
atatatactt tagattgatt taaaacttca tttttaattt aaaaggatct aggtgaagat  6660
cctttttgat aatctcatga ccaaaatccc ttaacgtgag ttttcgttcc actgagcgtc  6720
agaccccgta gaaaagatca aaggatcttc ttgagatcct ttttttctgc gcgtaatctg  6780
ctgcttgcaa acaaaaaaac caccgctacc agcggtggtt tgtttgccgg atcaagagct  6840
accaactctt tttccgaagg taactggctt cagcagagcg cagataccaa atactgtcct  6900
tctagtgtag ccgtagttag gccaccactt caagaactct gtagcaccgc ctacatacct  6960
cgctctgcta atcctgttac cagtggctgc tgccagtggc gataagtcgt gtcttaccgg  7020
gttggactca agacgatagt taccggataa ggcgcagcgg tcgggctgaa cggggggttc  7080
gtgcacacag cccagcttgg agcgaacgac ctacaccgaa ctgagatacc tacagcgtga  7140
gctatgagaa agcgccacgc ttcccgaagg gagaaaggcg gacaggtatc cggtaagcgg  7200
cagggtcgga acaggagagc gcacgaggga gcttccaggg ggaaacgcct ggtatcttta  7260
tagtcctgtc gggtttcgcc acctctgact tgagcgtcga tttttgtgat gctcgtcagg  7320
ggggcggagc ctatggaaaa acgccagcaa cgcggccttt ttacggttcc tggccttttg  7380
ctggcctttt gctcacatgt                                              7400

SEQ ID NO: 19          moltype = DNA  length = 5305
FEATURE                Location/Qualifiers
misc_feature           1..5305
                       note = synthetic
source                 1..5305
                       mol_type = other DNA
                       organism = synthetic construct
SEQUENCE: 19
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc tgcggccgca cgcgtgaggg cctatttccc atgattcctt  180
catatttgca tatacgatac aaggctgtta gagagataat tggaattaat ttgactgtaa  240
acacaaagat attagtacaa aatacgtgac gtagaaagta ataatttctt gggtagtttg  300
cagttttaaa attatgtttt aaaatggact atcatatgct taccgtaact tgaaagtatt  360
tcgatttctt ggctttatat atcttgtgga aaggacgaaa caccatccat ccatcatggc  420
gtgggtttta gagctagaaa tagcaagtta aaataaggct agtccgttat caacttgaaa  480
aagtggcacc gagtcggtgc ttttttttcta gactgcagag ggccctgcgt atgagtgcaa  540
gtgggtttta ggaccaggat gaggcggggt gggggtgcct acctgacgac cgaccccgac  600
ccactggaca agcacccaac ccccattccc caaattgcgc atcccctatc agagaggggg  660
aggggaaaca ggatgcggcg aggcgcgtgc gcactgccag cttcagcacc gcggacagtg  720
ccttcgcccc cgcctggcgg cgcgcgccac cgccgcctca gcactgaagg cgcgctgacg  780
tcactcgccg gtcccccgca aactcccctt cccggccacc ttggtcgcgt ccgcgccgcc  840
gccggcccag ccggaccgca ccacgcgagg cgcgagatag gggggcacgg gcgcgaccat  900
ctgcgctgcg gcgccggcga ctcagcgctg cctcagtctg cggtgggcag cggaggagtc  960
gtgtcgtgcc tgagagcgca gtcgagaagg taccggatcc tctagagtcg acgccaccat  1020
ggtgagcaag ggcgaggagc tgttcaccgg ggtggtgccc atcctggtcg agctggacgg  1080
cgacgtaaac ggccacaagt tcagcgtgtc cggcgagggc gagggcgatg ccacctacgg  1140
caagctgacc ctgaagttca tctgcaccac cggcaagctg cccgtgccct ggcccaccct  1200
cgtgaccacc ctgacctacg gcgtgcagtg cttcagccgc taccccgacc acatgaagca  1260
```

```
gcacgacttc ttcaagtccg ccatgcccga aggctacgtc caggagcgca ccatcttctt  1320
caaggacgac ggcaactaca agacccgcgc cgaggtgaag ttcgagggcg acaccctggt  1380
gaaccgcatc gagctgaagg gcatcgactt caaggaggac ggcaacatcc tggggcacaa  1440
gctggagtac aactacaaca gccacaacgt ctatatcatg gccgacaagc agaagaacgg  1500
catcaaggtg aacttcaaga tccgccacaa catcgaggac ggcagcgtgc agctcgccga  1560
ccactaccag cagaacaccc ccatcggcga cggccccgtg ctgctgcccg acaaccacta  1620
cctgagcacc cagtccgccc tgagcaaaga ccccaacgag aagcgcgatc acatggtcct  1680
gctggagttc gtgaccgccg ccgggatcac tctcggcatg gacgagctgt acaagtccgg  1740
actcagatct cgagaggagg aggaggagac agacagcagg atgccccacc tcgacagccc  1800
cggcagctcc cagccgagac gctccttcct ctcaagggtg atcagggcag cgctaccgtt  1860
gcagctgctt ctgctgctgc tgctgctcct ggcctgcctg ctacctgcct ctgaagatga  1920
ctacagctgc acccaggcca acaactttgc ccgatccttc taccccatgc tgcggtacac  1980
caacgggcca cctcccacct aggaattcga tatcaagctt atcgataccg agcgctgctc  2040
gagagatcta cgggtggcat ccctgtgacc cctccccagt gcctctcctg gccctggaag  2100
ttgccactcc agtgcccacc agccttgtcc taataaaatt aagttgcatc attttgtctg  2160
actaggtgtc cttctataat attatggggt ggaggggggt ggtatggagc aaggggcaag  2220
ttgggaagac aacctgtagg gcctgcgggg tctattggga accaagctgg agtgcagtgg  2280
cacaatcttg gctcactgca atctccgcct cctgggttca agcgattctc ctgcctcagc  2340
ctcccgagtt gttgggattc caggcatgca tgaccaggct cagctaattt ttgttttttt  2400
ggtagagacg gggtttcacc atattggcca ggctggtctc caactcctaa tctcaggtga  2460
tctacccacc ttggcctccc aaattgctgg gattacaggc gtgaaccact gctcccttcc  2520
ctgtccttct gattttgtag gtaaccacgt gcggaccgag cggccgcagg aacccctagt  2580
gatggagttg gccactccct ctctgcgcgc tcgctcgctc actgaggccg ggcgaccaaa  2640
ggtcgcccga cgcccgggct ttgcccgggc ggcctcagtg agcgagcgag cgcgcagctg  2700
cctgcagggg cgcctgatgc ggtattttct ccttacgcat ctgtgcggta tttcacaccg  2760
catacgtcaa agcaaccata gtacgcgccc tgtagcggcg cattaagcgc ggcgggtgtg  2820
gtggttacgc gcagcgtgac cgctacactt gccagcgccc tagcgcccgc tcctttcgct  2880
ttcttccctt cctttctcgc cacgttcgcc ggctttcccc gtcaagctct aaatcggggg  2940
ctccctttag ggttccgatt tagtgcttta cggcacctcg accccaaaaa acttgatttg  3000
ggtgatggtt cacgtagtgg gccatcgccc tgatagacgg tttttcgccc tttgacgttg  3060
gagtccacgt tctttaatag tggactcttg ttccaaactg gaacaacact caaccctatc  3120
tcgggctatt cttttgattt ataagggatt ttgccgattt cggcctattg gttaaaaaat  3180
gagctgattt aacaaaaatt taacgcgaat tttaacaaaa tattaacgtt tacaatttta  3240
tggtgcactc tcagtacaat ctgctctgat gccgcatagt taagccagcc ccgacacccg  3300
ccaacacccg ctgacgcgcc ctgacgggct tgtctgctcc cggcatccgc ttacagacaa  3360
gctgtgaccg tctccgggag ctgcatgtgt cagaggtttt caccgtcatc accgaaacgc  3420
gcgagacgaa agggcctcgt gatacgccta tttttatagg ttaatgtcat gataataatg  3480
gtttcttaga cgtcaggtgg cacttttcgg ggaaatgtgc gcggaacccc tatttgttta  3540
tttttctaaa tacattcaaa tatgtatccg ctcatgagac aataaccctg ataaatgctt  3600
caataatatt gaaaaaggaa gagtatgagt attcaacatt tccgtgtcgc ccttattccc  3660
ttttttgcgg cattttgcct tcctgttttt gctcacccag aaacgctggt gaaagtaaaa  3720
gatgctgaag atcagttggg tgcacgagtg ggttacatcg aactggatct caacagcggt  3780
aagatccttg agagttttcg ccccgaagaa cgttttccaa tgatgagcac ttttaaagtt  3840
ctgctatgtg gcgcggtatt atcccgtatt gacgccgggc aagagcaact cggtcgccgc  3900
atacactatt ctcagaatga cttggttgag tactcaccag tcacagaaaa gcatcttacg  3960
gatggcatga cagtaagaga attatgcagt gctgccataa ccatgagtga taacactgcg  4020
gccaacttac ttctgacaac gatcggagga ccgaaggagc taaccgcttt tttgcacaac  4080
atgggggatc atgtaactcg ccttgatcgt tgggaaccgg agctgaatga agccatacca  4140
aacgacgagc gtgacaccac gatgcctgta gcaatggcaa caacgttgcg caaactatta  4200
actggcgaac tacttactct agcttcccgg caacaattaa tagactggat ggaggcggat  4260
aaagttgcag gaccacttct gcgctcggcc cttccggctg gctggtttat tgctgataaa  4320
tctggagccg gtgagcgtgg gtctcgcggt atcattgcag cactggggcc agatggtaag  4380
ccctcccgta tcgtagttat ctacacgacg gggagtcagg caactatgga tgaacgaaat  4440
agacagatcg ctgagatagg tgcctcactg attaagcatt ggtaactgtc agaccaagtt  4500
tactcatata tactttagat tgatttaaaa cttcattttt aatttaaaag gatctaggtg  4560
aagatccttt ttgataatct catgaccaaa atcccttaac gtgagttttc gttccactga  4620
gcgtcagacc ccgtagaaaa gatcaaagga tcttcttgag atcctttttt tctgcgcgta  4680
atctgctgct tgcaaacaaa aaaaccaccg ctaccagcgg tggtttgttt gccggatcaa  4740
gagctaccaa ctctttttcc gaaggtaact ggcttcagca gagcgcagat accaaatact  4800
gtccttctag tgtagccgta gttaggccac cacttcaaga actctgtagc accgcctaca  4860
tacctcgctc tgctaatcct gttaccagtg gctgctgcca gtggcgataa gtcgtgtctt  4920
accgggttgg actcaagacg atagttaccg gataaggcgc agcggtcggg ctgaacgggg  4980
ggttcgtgca cacagcccag cttggagcga acgacctaca ccgaactgag atacctacag  5040
cgtgagctat gagaaagcgc cacgcttccc gaagggagaa aggcggacag gtatccggta  5100
agcggcaggg tcggaacagg agagcgcacg agggagcttc caggggggaaa cgcctggtat  5160
ctttatagtc ctgtcgggtt tcgccacctc tgacttgagc gtcgattttt gtgatgctcg  5220
tcaggggggc ggagcctatg gaaaaacgcc agcaacgcgg cctttttacg gttcctggcc  5280
ttttgctggc cttttgctca catgt                                        5305
```

```
SEQ ID NO: 20           moltype = DNA  length = 13013
FEATURE                 Location/Qualifiers
misc_feature            1..13013
                        note = synthetic
source                  1..13013
                        mol_type = other DNA
                        organism = synthetic construct
SEQUENCE: 20
tgatgcggtt ttggcagtac atcaatgggc gtggatagcg gtttgactca cggggatttc  60
caagtctcca ccccattgac gtcaatggga gtttgttttg gcaccaaaat caacgggact  120
```

-continued

```
ttccaaaatg tcgtaacaac tccgccccat tgacgcaaat gggcggtagg cgtgtacggt  180
gggaggtcta tataagcagc gcgttttgcc tgtactgggt ctctctggtt agaccagatc  240
tgagcctggg agctctctgg ctaactaggg aacccactgc ttaagcctca ataaagcttg  300
ccttgagtgc ttcaagtagt gtgtgcccgt ctgttgtgtg actctggtaa ctagagatcc  360
ctcagaccct tttagtcagt gtggaaaatc tctagcagtg gcgcccgaac agggacttga  420
aagcgaaagg gaaaccagag gagctctctc gacgcaggac tcggcttgct gaagcgcgca  480
cggcaagagg cgaggggcgg cgactggtga gtacgccaaa aattttgact agcggaggct  540
agaaggagag agatgggtgc gagagcgtca gtattaagcg ggggagaatt agatcgcgat  600
gggaaaaaat tcggttaagg ccagggggaa agaaaaaata taaattaaaa catatagtat  660
gggcaagcag ggagctagaa cgattcgcag ttaatcctgg cctgttagaa acatcagaag  720
gctgtagaca aatactggga cagctacaac catcccttca gacaggatca gaagaactta  780
gatcattata taatacagta gcaaccctct attgtgtgca tcaaaggata gagataaaag  840
acaccaagga agctttagac aagatagagg aagagcaaaa caaaagtaag accaccgcac  900
agcaagcggc cgctgatctt cagacctgga ggaggagata tgagggacaa ttggagaagt  960
gaattatata aatataaagt agtaaaaatt gaaccattag gagtagcacc caccaaggca  1020
aagagaagag tggtgcagag agaaaaaaga gcagtgggaa taggagcttt gttccttggg  1080
ttcttgggag cagcaggaag cactatgggc gcagcgtcaa tgacgctgac ggtacaggcc  1140
agacaattat tgtctggtat agtgcagcag cagaacaatt tgctgagggc tattgaggcg  1200
caacagcatc tgttgcaact cacagtctgg ggcatcaagc agctccaggc aagaatcctg  1260
gctgtggaaa gatacctaaa ggatcaacag ctcctgggga tttggggttg ctctggaaaa  1320
ctcatttgca ccactgctgt gccttggaat gctagttgga gtaataaatc tctggaacag  1380
atttggaatc acacgacctg gatggagtgg gacagagaaa ttaacaatta cacaagctta  1440
atacactcct taattgaaga atcgcaaaac cagcaagaaa agaatgaaca agaattattg  1500
gaattagata aatgggcaag tttgtggaat tggtttaaca taacaaattg gctgtggtat  1560
ataaaattat tcataatgat agtaggaggc ttggtaggtt taagaatagt ttttgctgta  1620
ctttctatag tgaatagagt taggcaggga tattcaccat tatcgtttca gacccacctc  1680
ccaaccccga ggggacccga caggcccgaa ggaatagaag aagaaggtgg agagagagac  1740
agagacagat ccattcgatt agtgaacgga tcggcactgc gtgcgccaat tctgcagaca  1800
aatggcagta ttcatccaca attttaaaag aaaagggggg attggggggt acagtgcagg  1860
ggaaagaata gtagacataa tagcaacaga catacaaact aaagaattac aaaaacaaat  1920
tacaaaaatt caaaattttc gggtttatta cagggacagc agagatccag tttggttaat  1980
taaggtaccg agggcctatt tcccatgatt ccttcatatt tgcatatacg atacaaggct  2040
gttagagaga taattagaat taatttgact gtaaacacaa agatattagt acaaaatacg  2100
tgacgtagaa agtaataatt tcttgggtag tttgcagttt taaaattatg ttttaaaatg  2160
gactatcata tgcttaccgt aacttgaaag tatttcgatt tcttggcttt atatatcttg  2220
tggaaaggac gaaacaccga tccattcatc atggtgtggg ttttagagct agaaatagca  2280
agttaaaata aggctagtcc gttatcaact tgaaaaagtg gcaccgagtc ggtgcttttt  2340
tgaattcgct agctaggtct tgaaaggagt gggaattggc tccggtgccc gtcagtgggc  2400
agagcgcaca tcgcccacag tccccgagaa gttgggggga ggggtcggca attgatccgg  2460
tgcctagaga aggtggcgcg gggtaaactg ggaaagtgat gtcgtgtact ggctccgcct  2520
ttttcccgag ggtgggggag aaccgtatat aagtgcagta gtcgccgtga acgttctttt  2580
tcgcaacggg tttgccgcca gaacacagga ccggttctag agcgctgcca ccatggacaa  2640
gaagtacagc atcggcctgg acatcggcac caactctgtg ggctgggccg tgatcaccga  2700
cgagtacaag gtgcccagca agaaattcaa ggtgctgggc aacaccgacc ggcacagcat  2760
caagaagaac ctgatcggag ccctgctgtt cgacagcggc gaaacagccg aggccacccg  2820
gctgaagaga accgccagaa gaagatacac cagacggaag aaccggatct gctatctgca  2880
agagatcttc agcaacgaga tggccaaggt ggacgacagc ttcttccaca gactggaaga  2940
gtccttcctg gtggaagagg ataagaagca cgagcggcac cccatcttcg gcaacatcgt  3000
ggacgaggtg gcctaccacg agaagtaccc caccatctac cacctgagaa agaaactggt  3060
ggacagcacc gacaaggccg acctgcggct gatctatctg gccctggccc acatgatcaa  3120
gttccggggc cacttcctga tcgagggcga cctgaacccc gacaacagcg acgtggacaa  3180
gctgttcatc cagctggtgc agacctacaa ccagctgttc gaggaaaacc ccatcaacgc  3240
cagcggcgtg gacgccaagg ccatcctgtc tgccagactg agcaagagca gacggctgga  3300
aaatctgatc gcccagctgc ccggcgagaa gaagaatggc ctgttcggaa acctgattgc  3360
cctgagcctg ggcctgaccc ccaacttcaa gagcaacttc gacctggccg aggatgccaa  3420
actgcagctg agcaaggaca cctacgacga cgacctggac aacctgctgg cccagatcgg  3480
cgaccagtac gccgacctgt ttctggccgc caagaacctg tccgacgcca tcctgctgag  3540
cgacatcctg agagtgaaca ccgagatcac caaggccccc ctgagcgcct ctatgatcaa  3600
gagatacgac gagcaccacc aggacctgac cctgctgaaa gctctcgtgc ggcagcagct  3660
gcctgagaag tacaaagaga ttttcttcga ccagagcaag aacggctacg ccggctacat  3720
tgacggcgga gccagccagg aagagttcta caagttcatc aagcccatcc tggaaaagat  3780
ggacggcacc gaggaactgc tcgtgaagct gaacagagag gacctgctgc ggaagcagcg  3840
gaccttcgac aacggcagca tcccccacca gatccacctg ggagagctgc acgccattct  3900
gcggcggcag gaagattttt acccattcct gaaggacaac cgggaaaaga tcgagaagat  3960
cctgaccttc cgcatcccct actacgtggg ccctctggcc aggggaaaca gcagattcgc  4020
ctggatgacc agaaagagcg aggaaaccat caccccctgg aacttcgagg aagtggtgga  4080
caagggcgct tccgcccaga gcttcatcga gcggatgacc aacttcgata agaacctgcc  4140
caacgagaag gtgctgccca agcacagcct gctgtacgag tacttcaccg tgtataacga  4200
gctgaccaaa gtgaaatacg tgaccgaggg aatgagaaag cccgccttcc tgagcggcga  4260
gcagaaaaag gccatcgtgg acctgctgtt caagaccaac cggaaagtga ccgtgaagca  4320
gctgaaagag gactacttca agaaaatcga gtgcttcgac tccgtggaaa tctccggcgt  4380
ggaagatcgg ttcaacgcct ccctgggcac ataccacgat ctgctgaaaa ttatcaagga  4440
caaggacttc ctggacaatg aggaaaacga ggacattctg gaagatatcg tgctgaccct  4500
gacactgttt gaggacagag agatgatcga ggaacggctg aaaacctatg cccacctgtt  4560
cgacgacaaa gtgatgaagc agctgaagcg gcggagatac accggctggg gcaggctgag  4620
ccggaagctg atcaacggca tccgggacaa gcagtccggc aagacaatcc tggatttcct  4680
gaagtccgac ggcttcgcca acagaaactt catgcagctg atccacgacg acagcctgac  4740
ctttaaagag gacatccaga aagcccaggt gtccggccag ggcgatagcc tgcacgagca  4800
cattgccaat ctggccggca gccccgccat taagaagggc atcctgcaga cagtgaaggt  4860
```

```
ggtggacgag ctcgtgaaag tgatgggccg gcacaagccc gagaacatcg tgatcgaaat  4920
ggccagagag aaccagacca cccagaaggg acagaagaac agccgcgaga gaatgaagcg  4980
gatcgaagag ggcatcaaag agctgggcag ccagatcctg aaagaacacc ccgtggaaaa  5040
cacccagctg cagaacgaga agctgtacct gtactacctg cagaatgggc gggatatgta  5100
cgtggaccag gaactggaca tcaaccggct gtccgactac gatgtggacc atatcgtgcc  5160
tcagagcttt ctgaaggacg actccatcga caacaaggtg ctgaccagaa gcgacaagaa  5220
ccggggcaag agcgacaacg tgccctccga agaggtcgtg aagaagatga agaactactg  5280
gcggcagctg ctgaacgcca agctgattac ccagagaaag ttcgacaatc tgaccaaggc  5340
cgagagaggc ggcctgagcg aactggataa ggccggcttc atcaagagac agctggtgga  5400
aacccggcag atcacaaagc acgtggcaca gatcctggac tcccggatga acactaagta  5460
cgacgagaat gacaagctga tccgggaagt gaaagtgatc accctgaagt ccaagctggt  5520
gtccgatttc cggaaggatt tccagtttta caaagtgcgc gagatcaaca actaccacca  5580
cgcccacgac gcctacctga acgccgtcgt gggaaccgcc ctgatcaaaa agtaccctaa  5640
gctggaaagc gagttcgtgt acggcgacta caaggtgtac gacgtgcgga agatgatcgc  5700
caagagcgag caggaaatcg gcaaggctac cgccaagtac ttcttctaca gcaacatcat  5760
gaactttttc aagaccgaga ttaccctggc caacggcgag atccggaagc ggcctctgat  5820
cgagacaaac ggcgaaaccg gggagatcgt gtgggataag ggccgggatt ttgccaccgt  5880
gcggaaagtg ctgagcatgc cccaagtgaa tatcgtgaaa aagaccgagg tgcagacagg  5940
cggcttcagc aaagagtcta tcctgcccaa gaggaacagc gataagctga tcgccagaaa  6000
gaaggactgg gaccctaaga agtacggcgg cttcgacagc cccaccgtgg cctattctgt  6060
gctggtggtg gccaaagtgg aaaagggcaa gtccaagaaa ctgaagagtg tgaaagagct  6120
gctggggatc accatcatgg aaagaagcag cttcgagaag aatcccatcg actttctgga  6180
agccaagggc tacaaagaag tgaaaaagga cctgatcatc aagctgccta agtactccct  6240
gttcgagctg gaaaacggcc ggaagagaat gctggcctct gccggcgaac tgcagaaggg  6300
aaacgaactg gccctgccct ccaaatatgt gaacttcctg tacctggcca gccactatga  6360
gaagctgaag ggctcccccg aggataatga gcagaaacag ctgtttgtgg aacagcacaa  6420
gcactacctg gacgagatca tcgagcagat cagcgagttc tccaagagag tgatcctggc  6480
cgacgctaat ctggacaaag tgctgtccgc ctacaacaag caccgggata agcccatcag  6540
agagcaggcc gagaatatca tccacctgtt taccctgacc aatctgggag cccctgccgc  6600
cttcaagtac tttgacacca ccatcgaccg gaagaggtac accagcacca aagaggtgct  6660
ggacgccacc ctgatccacc agagcatcac cggcctgtac gagacacgga tcgacctgtc  6720
tcagctggga ggcgacaagc gacctgccgc cacaaagaag gctggacagg ctaagaagaa  6780
gaaagattac aaagacgatg acgataaggg atccggcgca acaaacttct ctctgctgaa  6840
acaagccgga gatgtcgaag agaatcctgg accgaccgag tacaagccca cggtgcgcct  6900
cgccacccgc gacgacgtcc ccagggccgt acgcaccctc gccgccgcgt tcgccgacta  6960
ccccgccacg cgccacaccg tcgatccgga ccgccacatc gagcgggtca ccgagctgca  7020
agaactcttc ctcacgcgcg tcgggctcga catcggcaag gtgtgggtcg cggacgacgg  7080
cgccgcggtg gcggtctgga ccacgccgga gagcgtcgaa gcgggggcgg tgttcgccga  7140
gatcggcccg cgcatggccg agttgagcgg ttcccggctg gccgcgcagc aacagatgga  7200
aggcctcctg gcgccgcacc ggcccaagga gcccgcgtgg ttcctggcca ccgtcggagt  7260
ctcgcccgac caccagggca agggtctggg cagcgccgtc gtgctccccg gagtggaggc  7320
ggccgagcgc gccggggtgc ccgccttcct ggagacctcc gcgccccgca acctcccctt  7380
ctacgagcgg ctcggcttca ccgtcaccgc cgacgtcgag gtgcccgaag gaccgcgcac  7440
ctggtgcatg acccgcaagc ccggtgcctg aacgcgttaa gtcgacaatc aacctctgga  7500
ttacaaaatt tgtgaaagat tgactggtat tcttaactat gttgctcctt ttacgctatg  7560
tggatacgct gctttaatgc ctttgtatca tgctattgct tcccgtatgg ctttcatttt  7620
ctcctccttg tataaatcct ggttgctgtc tctttatgag gagttgtggc ccgttgtcag  7680
gcaacgtggc gtggtgtgca ctgtgtttgc tgacgcaacc cccactggtt ggggcattgc  7740
caccacctgt cagctccttt ccgggacttt cgctttcccc ctccctattg ccacggcgga  7800
actcatcgcc gcctgccttg cccgctgctg gacaggggct cggctgttgg gcactgacaa  7860
ttccgtggtg ttgtcgggga aatcatcgtc ctttccttgg ctgctcgcct gtgttgccac  7920
ctggattctg cgcgggacgt ccttctgcta cgtcccttcg gccctcaatc cagcggacct  7980
tccttcccgc ggcctgctgc cggctctgcg gcctcttccg cgtcttcgcc ttcgccctca  8040
gacgagtcgg atctcccttt gggccgcctc cccgcgtcga ctttaagacc aatgacttac  8100
aaggcagctg tagatcttag ccacttttta aaagaaaagg ggggactgga agggctaatt  8160
cactcccaac gaagacaaga tctgcttttt gcttgtactg ggtctctctg gttagaccag  8220
atctgagcct gggagctctc tggctaacta gggaacccac tgcttaagcc tcaataaagc  8280
ttgccttgag tgcttcaagt agtgtgtgcc cgtctgttgt gtgactctgg taactagaga  8340
tccctcagac ccttttagtc agtgtggaaa atctctagca gggcccgttt aaacccgctg  8400
atcagcctcg actgtgcctt ctagttgcca gccatctgtt gtttgcccct cccccgtgcc  8460
ttccttgacc ctggaaggtg ccactcccac tgtcctttcc taataaaatg aggaaattgc  8520
atcgcattgt ctgagtaggt gtcattctat tctggggggt ggggtggggc aggacagcaa  8580
gggggaggat tgggaagaca atagcaggca tgctggggat gcggtgggct ctatggcttc  8640
tgaggcggaa agaaccagct ggggctctag ggggtatccc cacgcgccct gtagcggcgc  8700
attaagcgcg gcgggtgtgg tggttacgcg cagcgtgacc gctacacttg ccagcgccct  8760
agcgcccgct cctttcgctt tcttcccttc ctttctcgcc acgttcgccg gctttccccg  8820
tcaagctcta aatcgggggc tccctttagg gttccgattt agtgctttac ggcacctcga  8880
ccccaaaaaa cttgattagg gtgatggttc acgtagtggg ccatcgccct gatagacggt  8940
ttttcgccct ttgacgttgg agtccacgtt ctttaatagt ggactcttgt tccaaactgg  9000
aacaacactc aaccctatct cggtctattc ttttgattta taagggattt tgccgatttc  9060
ggcctattgg ttaaaaaatg agctgattta acaaaaattt aacgcgaatt aattctgtgg  9120
aatgtgtgtc agttagggtg tggaaagtcc ccaggctccc cagcaggcag aagtatgcaa  9180
agcatgcatc tcaattagtc agcaaccagg tgtggaaagt ccccaggctc cccagcaggc  9240
agaagtatgc aaagcatgca tctcaattag tcagcaacca tagtcccgcc cctaactccg  9300
cccatcccgc ccctaactcc gcccagttcc gcccattctc cgccccatgg ctgactaatt  9360
ttttttattt atgcagaggc cgaggccgcc tctgcctctg agctattcca gaagtagtga  9420
ggaggctttt ttggaggcct aggcttttgc aaaaagctcc cgggagcttg tatatccatt  9480
ttcggatctg atcagcacgt gttgacaatt aatcatcggc atagtatatc ggcatagtat  9540
aatacgacaa ggtgaggaac taaaccatgg ccaagttgac cagtgccgtt ccggtgctca  9600
```

-continued

```
ccgcgcgcga cgtcgccgga gcggtcgagt tctggaccga ccggctcggg ttctcccggg  9660
acttcgtgga ggacgacttc gccggtgtgg tccgggacga cgtgaccctg ttcatcagcg  9720
cggtccagga ccaggtggtg ccggacaaca ccctggcctg ggtgtgggtg cgcggcctgg  9780
acgagctgta cgccgagtgg tcggaggtcg tgtccacgaa cttccgggac gcctccgggc  9840
cggccatgac cgagatcggc gagcagccgt gggggcggga gttcgccctg cgcgacccgg  9900
ccggcaactg cgtgcacttc gtggccgagg agcaggactg acacgtgcta cgagatttcg  9960
attccaccgc cgccttctat gaaaggttgg gcttcggaat cgttttccgg gacgccggct  10020
ggatgatcct ccagcgcggg gatctcatgc tggagttctt cgcccacccc aacttgttta  10080
ttgcagctta taatggttac aaataaagca atagcatcac aaatttcaca aataaagcat  10140
tttttcact gcattctagt tgtggtttgt ccaaactcat caatgtatct tatcatgtct  10200
gtataccgtc gacctctagc tagagcttgg cgtaatcatg gtcatagctg tttcctgtgt  10260
gaaattgtta tccgctcaca attccacaca acatacgagc cggaagcata aagtgtaaag  10320
cctggggtgc ctaatgagtg agctaactca cattaattgc gttgcgctca ctgcccgctt  10380
tccagtcggg aaacctgtcg tgccagctgc attaatgaat cggccaacgc gcggggagag  10440
gcggtttgcg tattgggcgc tcttccgctt cctcgctcac tgactcgctg cgctcggtcg  10500
ttcggctgcg gcgagcggta tcagctcact caaaggcggt aatacggtta tccacagaat  10560
caggggataa cgcaggaaag aacatgtgag caaaaggcca gcaaaaggcc aggaaccgta  10620
aaaaggccgc gttgctggcg tttttccata ggctccgccc ccctgacgag catcacaaaa  10680
atcgacgctc aagtcagagg tggcgaaacc cgacaggact ataaagatac caggcgtttc  10740
cccctggaag ctccctcgtg cgctctcctg ttccgaccct gccgcttacc ggatacctgt  10800
ccgcctttct cccttcggga agcgtggcgc tttctcatag ctcacgctgt aggtatctca  10860
gttcggtgta ggtcgttcgc tccaagctgg gctgtgtgca cgaacccccc gttcagcccg  10920
accgctgcgc cttatccggt aactatcgtc ttgagtccaa cccggtaaga cacgacttat  10980
cgccactggc agcagccact ggtaacagga ttagcagagc gaggtatgta ggcggtgcta  11040
cagagttctt gaagtggtgg cctaactacg gctacactag aagaacagta tttggtatct  11100
gcgctctgct gaagccagtt accttcggaa aaagagttgg tagctcttga tccggcaaac  11160
aaaccaccgc tggtagcggt ggtttttttg tttgcaagca gcagattacg cgcagaaaaa  11220
aaggatctca agaagatcct ttgatctttt ctacggggtc tgacgctcag tggaacgaaa  11280
actcacgtta agggattttg gtcatgagat tatcaaaaag gatcttcacc tagatccttt  11340
taaattaaaa atgaagtttt aaatcaatct aaagtatata tgagtaaact tggtctgaca  11400
gttaccaatg cttaatcagt gaggcaccta tctcagcgat ctgtctattt cgttcatcca  11460
tagttgcctg actccccgtc gtgtagataa ctacgatacg ggagggctta ccatctggcc  11520
ccagtgctgc aatgataccg cgagacccac gctcaccggc tccagattta tcagcaataa  11580
accagccagc cggaagggcc gagcgcagaa gtggtcctgc aactttatcc gcctccatcc  11640
agtctattaa ttgttgccgg gaagctagag taagtagttc gccagttaat agtttgcgca  11700
acgttgttgc cattgctaca ggcatcgtgg tgtcacgctc gtcgtttggt atggcttcat  11760
tcagctccgg ttcccaacga tcaaggcgag ttacatgatc ccccatgttg tgcaaaaaag  11820
cggttagctc cttcggtcct ccgatcgttg tcagaagtaa gttggccgca gtgttatcac  11880
tcatggttat ggcagcactg cataattctc ttactgtcat gccatccgta agatgctttt  11940
ctgtgactgg tgagtactca accaagtcat tctgagaata gtgtatgcgg cgaccgagtt  12000
gctcttgccc ggcgtcaata cgggataata ccgcgccaca tagcagaact ttaaaagtgc  12060
tcatcattgg aaaacgttct tcggggcgaa aactctcaag gatcttaccg ctgttgagat  12120
ccagttcgat gtaacccact cgtgcaccca actgatcttc agcatctttt actttcacca  12180
gcgtttctgg gtgagcaaaa acaggaaggc aaaatgccgc aaaaaaggga ataagggcga  12240
cacggaaatg ttgaatactc atactcttcc tttttcaata ttattgaagc atttatcagg  12300
gttattgtct catgagcgga tacatatttg aatgtattta gaaaaataaa caaatagggg  12360
ttccgcgcac atttccccga aaagtgccac ctgacgtcga cggatcggga gatctcccga  12420
tcccctatgg tgcactctca gtacaatctg ctctgatgcc gcatagttaa gccagtatct  12480
gctccctgct tgtgtgttgg aggtcgctga gtagtgcgcg agcaaaattt aagctacaac  12540
aaggcaaggc ttgaccgaca attgcatgaa gaatctgctt agggttaggc gttttgcgct  12600
gcttcgcgat gtacgggcca gatatacgcg ttgacattga ttattgacta gttattaata  12660
gtaatcaatt acggggtcat tagttcatag cccatatatg gagttccgcg ttacataact  12720
tacggtaaat ggcccgcctg gctgaccgcc caacgacccc cgcccattga cgtcaataat  12780
gacgtatgtt cccatagtaa cgccaatagg gactttccat tgacgtcaat gggtggagta  12840
tttacggtaa actgcccact tggcagtaca tcaagtgtat catatgccaa gtacgccccc  12900
tattgacgtc aatgacggta aatggcccgc ctggcattat gcccagtaca tgaccttatg  12960
ggactttcct acttggcagt acatctacgt attagtcatc gctattacca tgg         13013

SEQ ID NO: 21          moltype = DNA  length = 22
FEATURE                Location/Qualifiers
misc_feature           1..22
                       note = synthetic
source                 1..22
                       mol_type = other DNA
                       organism = synthetic construct
SEQUENCE: 21
aggaacggag tgacctgttt cc                                            22

SEQ ID NO: 22          moltype = DNA  length = 22
FEATURE                Location/Qualifiers
misc_feature           1..22
                       note = synthetic
source                 1..22
                       mol_type = other DNA
                       organism = synthetic construct
SEQUENCE: 22
ttcctccatg gtaaccacgc at                                            22

SEQ ID NO: 23          moltype = DNA  length = 22
```

```
FEATURE                Location/Qualifiers
misc_feature           1..22
                       note = synthetic
source                 1..22
                       mol_type = other DNA
                       organism = synthetic construct
SEQUENCE: 23
tggggaagcc acatgttgta ca                                            22

SEQ ID NO: 24          moltype = DNA  length = 22
FEATURE                Location/Qualifiers
misc_feature           1..22
                       note = synthetic
source                 1..22
                       mol_type = other DNA
                       organism = synthetic construct
SEQUENCE: 24
atgttttggt gggccatttg gt                                            22

SEQ ID NO: 25          moltype = DNA  length = 26
FEATURE                Location/Qualifiers
misc_feature           1..26
                       note = synthetic
source                 1..26
                       mol_type = other DNA
                       organism = synthetic construct
SEQUENCE: 25
aaattatggg tgttctgcaa tcttgg                                        26

SEQ ID NO: 26          moltype = DNA  length = 23
FEATURE                Location/Qualifiers
misc_feature           1..23
                       note = synthetic
source                 1..23
                       mol_type = other DNA
                       organism = synthetic construct
SEQUENCE: 26
acttgtgtta cagcacagct gtc                                           23

SEQ ID NO: 27          moltype = DNA  length = 21
FEATURE                Location/Qualifiers
misc_feature           1..21
                       note = synthetic
source                 1..21
                       mol_type = other DNA
                       organism = synthetic construct
SEQUENCE: 27
gccctccaga agtattggct t                                             21

SEQ ID NO: 28          moltype = DNA  length = 21
FEATURE                Location/Qualifiers
misc_feature           1..21
                       note = synthetic
source                 1..21
                       mol_type = other DNA
                       organism = synthetic construct
SEQUENCE: 28
gtcagggcct tgctctacaa a                                             21

SEQ ID NO: 29          moltype = DNA  length = 20
FEATURE                Location/Qualifiers
misc_feature           1..20
                       note = synthetic
source                 1..20
                       mol_type = other DNA
                       organism = synthetic construct
SEQUENCE: 29
cgcaaaaact ggctgcgtat                                               20

SEQ ID NO: 30          moltype = DNA  length = 20
FEATURE                Location/Qualifiers
misc_feature           1..20
                       note = synthetic
source                 1..20
                       mol_type = other DNA
                       organism = synthetic construct
SEQUENCE: 30
tgtaggcgca catgcagaag                                               20
```

-continued

```
SEQ ID NO: 31          moltype = DNA  length = 21
FEATURE                Location/Qualifiers
misc_feature           1..21
                       note = synthetic
source                 1..21
                       mol_type = other DNA
                       organism = synthetic construct
SEQUENCE: 31
caggtagagc gtggaaactc a                                            21

SEQ ID NO: 32          moltype = DNA  length = 20
FEATURE                Location/Qualifiers
misc_feature           1..20
                       note = synthetic
source                 1..20
                       mol_type = other DNA
                       organism = synthetic construct
SEQUENCE: 32
tgtgcgcatt aggaccagat                                              20

SEQ ID NO: 33          moltype = DNA  length = 20
FEATURE                Location/Qualifiers
misc_feature           1..20
                       note = synthetic
source                 1..20
                       mol_type = other DNA
                       organism = synthetic construct
SEQUENCE: 33
cacctgacaa tgctgtccca                                              20

SEQ ID NO: 34          moltype = DNA  length = 21
FEATURE                Location/Qualifiers
misc_feature           1..21
                       note = synthetic
source                 1..21
                       mol_type = other DNA
                       organism = synthetic construct
SEQUENCE: 34
agacaaggtc tgtctccttg c                                            21

SEQ ID NO: 35          moltype = DNA  length = 20
FEATURE                Location/Qualifiers
misc_feature           1..20
                       note = synthetic
source                 1..20
                       mol_type = other DNA
                       organism = synthetic construct
SEQUENCE: 35
ccaactcttt gcttaggggc                                              20

SEQ ID NO: 36          moltype = DNA  length = 20
FEATURE                Location/Qualifiers
misc_feature           1..20
                       note = synthetic
source                 1..20
                       mol_type = other DNA
                       organism = synthetic construct
SEQUENCE: 36
atcgtccctg gtgcattctc                                              20

SEQ ID NO: 37          moltype = DNA  length = 20
FEATURE                Location/Qualifiers
misc_feature           1..20
                       note = synthetic
source                 1..20
                       mol_type = other DNA
                       organism = synthetic construct
SEQUENCE: 37
ggaaaaccag gtagaggggg                                              20

SEQ ID NO: 38          moltype = DNA  length = 20
FEATURE                Location/Qualifiers
misc_feature           1..20
                       note = synthetic
source                 1..20
                       mol_type = other DNA
                       organism = synthetic construct
SEQUENCE: 38
tctctggctc gagggtacat                                              20
```

```
SEQ ID NO: 39           moltype = DNA  length = 20
FEATURE                 Location/Qualifiers
misc_feature            1..20
                        note = synthetic
source                  1..20
                        mol_type = other DNA
                        organism = synthetic construct
SEQUENCE: 39
ctgcatgcca tgggtaggta                                              20

SEQ ID NO: 40           moltype = DNA  length = 19
FEATURE                 Location/Qualifiers
misc_feature            1..19
                        note = synthetic
source                  1..19
                        mol_type = other DNA
                        organism = synthetic construct
SEQUENCE: 40
caggctgttt cgggtcctt                                               19

SEQ ID NO: 41           moltype = DNA  length = 21
FEATURE                 Location/Qualifiers
misc_feature            1..21
                        note = synthetic
source                  1..21
                        mol_type = other DNA
                        organism = synthetic construct
SEQUENCE: 41
agactcttct ccgattccag c                                            21

SEQ ID NO: 42           moltype = DNA  length = 20
FEATURE                 Location/Qualifiers
misc_feature            1..20
                        note = synthetic
source                  1..20
                        mol_type = other DNA
                        organism = synthetic construct
SEQUENCE: 42
tccagcacga tctggtaggc                                              20

SEQ ID NO: 43           moltype = DNA  length = 22
FEATURE                 Location/Qualifiers
misc_feature            1..22
                        note = synthetic
source                  1..22
                        mol_type = other DNA
                        organism = synthetic construct
SEQUENCE: 43
agtgcttttc tttgcctttg ct                                           22

SEQ ID NO: 44           moltype = DNA  length = 20
FEATURE                 Location/Qualifiers
misc_feature            1..20
                        note = synthetic
source                  1..20
                        mol_type = other DNA
                        organism = synthetic construct
SEQUENCE: 44
tgctcgggag gtgtttctac                                              20

SEQ ID NO: 45           moltype = DNA  length = 20
FEATURE                 Location/Qualifiers
misc_feature            1..20
                        note = synthetic
source                  1..20
                        mol_type = other DNA
                        organism = synthetic construct
SEQUENCE: 45
aacaaggcag ctcctcaact                                              20

SEQ ID NO: 46           moltype = DNA  length = 21
FEATURE                 Location/Qualifiers
misc_feature            1..21
                        note = synthetic
source                  1..21
                        mol_type = other DNA
                        organism = synthetic construct
SEQUENCE: 46
```

```
gacgtcagaa ttgagggtgg a                                            21

SEQ ID NO: 47          moltype = DNA  length = 22
FEATURE                Location/Qualifiers
misc_feature           1..22
                       note = synthetic
source                 1..22
                       mol_type = other DNA
                       organism = synthetic construct
SEQUENCE: 47
ccagcgggat gaactggtaa ga                                           22

SEQ ID NO: 48          moltype = DNA  length = 22
FEATURE                Location/Qualifiers
misc_feature           1..22
                       note = synthetic
source                 1..22
                       mol_type = other DNA
                       organism = synthetic construct
SEQUENCE: 48
cccaggtcac cttaaggagc aa                                           22

SEQ ID NO: 49          moltype = DNA  length = 22
FEATURE                Location/Qualifiers
misc_feature           1..22
                       note = synthetic
source                 1..22
                       mol_type = other DNA
                       organism = synthetic construct
SEQUENCE: 49
gagagagttg gaggccttga gg                                           22

SEQ ID NO: 50          moltype = DNA  length = 22
FEATURE                Location/Qualifiers
misc_feature           1..22
                       note = synthetic
source                 1..22
                       mol_type = other DNA
                       organism = synthetic construct
SEQUENCE: 50
aaccacagtg acaagtggct ct                                           22

SEQ ID NO: 51          moltype = DNA  length = 22
FEATURE                Location/Qualifiers
misc_feature           1..22
                       note = synthetic
source                 1..22
                       mol_type = other DNA
                       organism = synthetic construct
SEQUENCE: 51
gtgaatgcgt ctgttccaag gg                                           22

SEQ ID NO: 52          moltype = DNA  length = 22
FEATURE                Location/Qualifiers
misc_feature           1..22
                       note = synthetic
source                 1..22
                       mol_type = other DNA
                       organism = synthetic construct
SEQUENCE: 52
gctgctggga ctatctggga at                                           22

SEQ ID NO: 53          moltype = DNA  length = 22
FEATURE                Location/Qualifiers
misc_feature           1..22
                       note = synthetic
source                 1..22
                       mol_type = other DNA
                       organism = synthetic construct
SEQUENCE: 53
ttttaggggc tcgaccttcc ag                                           22

SEQ ID NO: 54          moltype = DNA  length = 22
FEATURE                Location/Qualifiers
misc_feature           1..22
                       note = synthetic
source                 1..22
                       mol_type = other DNA
                       organism = synthetic construct
```

```
SEQUENCE: 54
tgcactaatt tcccagggct ca                                          22

SEQ ID NO: 55           moltype = DNA  length = 30
FEATURE                 Location/Qualifiers
misc_feature            1..30
                        note = synthetic
source                  1..30
                        mol_type = other DNA
                        organism = synthetic construct
SEQUENCE: 55
cacatccatc catcatggcg tggtggaggt                                  30

SEQ ID NO: 56           moltype = DNA  length = 30
FEATURE                 Location/Qualifiers
misc_feature            1..30
                        note = synthetic
source                  1..30
                        mol_type = other DNA
                        organism = synthetic construct
SEQUENCE: 56
tcttggagag atggcgctcc tctggggtca                                  30

SEQ ID NO: 57           moltype = DNA  length = 30
FEATURE                 Location/Qualifiers
misc_feature            1..30
                        note = synthetic
source                  1..30
                        mol_type = other DNA
                        organism = synthetic construct
SEQUENCE: 57
ctcatatccg ttctgctgca tcttggagag                                  30

SEQ ID NO: 58           moltype = DNA  length = 303
FEATURE                 Location/Qualifiers
source                  1..303
                        mol_type = genomic DNA
                        organism = Mus musculus
SEQUENCE: 58
atggatgcag aattcggaca tgattcagga tttgaagtcc gccatcaaaa actggtgttc  60
tttgctgaag atgtgggttc gaacaaaggc gccatcatcg gactcatggt gggcggcgtt  120
gtcatagcaa ccgtgattgt catcaccctg gtgatgttga agaagaaaca gtacacatcc  180
atccatcatg gcgtggtgga ggtcgacgcc gccgtgaccc cagaggagcg ccatctctcc  240
aagatgcagc agaacggata tgagaatcca acttacaagt tctttgagca aatgcagaac  300
taa                                                                303

SEQ ID NO: 59           moltype = AA  length = 100
FEATURE                 Location/Qualifiers
source                  1..100
                        mol_type = protein
                        organism = Mus musculus
SEQUENCE: 59
MDAEFGHDSG FEVRHQKLVF FAEDVGSNKG AIIGLMVGGV VIATVIVITL VMLKKKQYTS  60
IHHGVVEVDA AVTPEERHLS KMQQNGYENP TYKFFEQMQN                        100

SEQ ID NO: 60           moltype = DNA  length = 66
FEATURE                 Location/Qualifiers
misc_feature            1..66
                        note = synthetic
source                  1..66
                        mol_type = other DNA
                        organism = synthetic construct
SEQUENCE: 60
gaagaagaaa cagtacacat ccatccatca tggcgtggtg gaggtaggta aacctggagg  60
cttgtc                                                            66

SEQ ID NO: 61           moltype = DNA  length = 46
FEATURE                 Location/Qualifiers
misc_feature            1..46
                        note = synthetic
source                  1..46
                        mol_type = other DNA
                        organism = synthetic construct
SEQUENCE: 61
aacagtacac atccatccat catggcgtgg tggaggtagg taaacc                46

SEQ ID NO: 62           moltype = DNA  length = 41
FEATURE                 Location/Qualifiers
misc_feature            1..41
```

```
                        note = synthetic
source                  1..41
                        mol_type = other DNA
                        organism = synthetic construct
SEQUENCE: 62
aacagtacac atccatccat catggtggag gtaggtaaac c                       41

SEQ ID NO: 63           moltype = DNA  length = 41
FEATURE                 Location/Qualifiers
misc_feature            1..41
                        note = synthetic
source                  1..41
                        mol_type = other DNA
                        organism = synthetic construct
SEQUENCE: 63
aacagtacac atccatccat catggcggag gtaggtaaac c                       41

SEQ ID NO: 64           moltype = DNA  length = 38
FEATURE                 Location/Qualifiers
misc_feature            1..38
                        note = synthetic
source                  1..38
                        mol_type = other DNA
                        organism = synthetic construct
SEQUENCE: 64
aacagtacac atccatccat catggaggta ggtaaacc                           38

SEQ ID NO: 65           moltype = DNA  length = 44
FEATURE                 Location/Qualifiers
misc_feature            1..44
                        note = synthetic
source                  1..44
                        mol_type = other DNA
                        organism = synthetic construct
SEQUENCE: 65
aacagtacac atccatccat catggcggtg gaggtaggta aacc                    44

SEQ ID NO: 66           moltype = DNA  length = 44
FEATURE                 Location/Qualifiers
misc_feature            1..44
                        note = synthetic
source                  1..44
                        mol_type = other DNA
                        organism = synthetic construct
SEQUENCE: 66
aacagtacac atccatccat catggtggtg gaggtaggta aacc                    44

SEQ ID NO: 67           moltype = DNA  length = 23
FEATURE                 Location/Qualifiers
source                  1..23
                        mol_type = genomic DNA
                        organism = Mus musculus
SEQUENCE: 67
atccatccat catggcgtgg tgg                                           23

SEQ ID NO: 68           moltype = DNA  length = 23
FEATURE                 Location/Qualifiers
source                  1..23
                        mol_type = genomic DNA
                        organism = Homo sapiens
SEQUENCE: 68
atccattcat catggtgtgg tgg                                           23

SEQ ID NO: 69           moltype = DNA  length = 66
FEATURE                 Location/Qualifiers
misc_feature            1..66
                        note = synthetic
source                  1..66
                        mol_type = other DNA
                        organism = synthetic construct
SEQUENCE: 69
gaagaagaaa cagtacacat ccattcatca tggtgtggtg gaggtaggta aacttgactg  60
catgtt                                                              66

SEQ ID NO: 70           moltype = DNA  length = 45
FEATURE                 Location/Qualifiers
misc_feature            1..45
                        note = synthetic
source                  1..45
```

```
                        mol_type = other DNA
                        organism = synthetic construct
SEQUENCE: 70
aacagtacac atccattcat catggtgtgg tggaggtagg taaac                  45

SEQ ID NO: 71           moltype = DNA  length = 40
FEATURE                 Location/Qualifiers
misc_feature            1..40
                        note = synthetic
source                  1..40
                        mol_type = other DNA
                        organism = synthetic construct
SEQUENCE: 71
aacagtacac atccattcat catggtggag gtaggtaaac                        40

SEQ ID NO: 72           moltype = DNA  length = 43
FEATURE                 Location/Qualifiers
misc_feature            1..43
                        note = synthetic
source                  1..43
                        mol_type = other DNA
                        organism = synthetic construct
SEQUENCE: 72
aacagtacac atccattcat catggtggtg gaggtaggta aac                    43

SEQ ID NO: 73           moltype = DNA  length = 41
FEATURE                 Location/Qualifiers
misc_feature            1..41
                        note = synthetic
source                  1..41
                        mol_type = other DNA
                        organism = synthetic construct
SEQUENCE: 73
aacagtacac atccattcat cattggtgga ggtaggtaaa c                      41

SEQ ID NO: 74           moltype = DNA  length = 44
FEATURE                 Location/Qualifiers
misc_feature            1..44
                        note = synthetic
source                  1..44
                        mol_type = other DNA
                        organism = synthetic construct
SEQUENCE: 74
aacagtacac atccattcat catggtgggt ggaggtaggt aaac                   44

SEQ ID NO: 75           moltype = DNA  length = 39
FEATURE                 Location/Qualifiers
misc_feature            1..39
                        note = synthetic
source                  1..39
                        mol_type = other DNA
                        organism = synthetic construct
SEQUENCE: 75
aacagtacac atccattcat ctggtggagg taggtaaac                         39

SEQ ID NO: 76           moltype = AA  length = 46
FEATURE                 Location/Qualifiers
REGION                  1..46
                        note = synthetic
source                  1..46
                        mol_type = protein
                        organism = synthetic construct
SEQUENCE: 76
GGVVIATVIV ITLVMLKKKQ YTSIHHGVVE VDAAVTPEER HLSKMQ                 46

SEQ ID NO: 77           moltype = AA  length = 29
FEATURE                 Location/Qualifiers
REGION                  1..29
                        note = synthetic
source                  1..29
                        mol_type = protein
                        organism = synthetic construct
SEQUENCE: 77
GGVVIATVIV ITLVMLKKKQ YTSIHHGGG                                    29

SEQ ID NO: 78           moltype = AA  length = 30
FEATURE                 Location/Qualifiers
REGION                  1..30
                        note = synthetic
```

```
source                1..30
                      mol_type = protein
                      organism = synthetic construct
SEQUENCE: 78
GGVVIATVIV ITLVMLKKKQ YTSIHHGGGG                                    30

SEQ ID NO: 79         moltype = AA  length = 26
FEATURE               Location/Qualifiers
REGION                1..26
                      note = synthetic
source                1..26
                      mol_type = protein
                      organism = synthetic construct
SEQUENCE: 79
GGVVIATVIV ITLVMLKKKQ YTSIHH                                        26

SEQ ID NO: 80         moltype = AA  length = 27
FEATURE               Location/Qualifiers
REGION                1..27
                      note = synthetic
source                1..27
                      mol_type = protein
                      organism = synthetic construct
SEQUENCE: 80
GGVVIATVIV ITLVMLKKKQ YTSIHHG                                       27

SEQ ID NO: 81         moltype = AA  length = 44
FEATURE               Location/Qualifiers
REGION                1..44
                      note = synthetic
source                1..44
                      mol_type = protein
                      organism = synthetic construct
SEQUENCE: 81
GGVVIATVIV ITLVMLKKKQ YTSIHLVEVD AAVTPEERHL SKMQ                    44

SEQ ID NO: 82         moltype = AA  length = 37
FEATURE               Location/Qualifiers
REGION                1..37
                      note = synthetic
source                1..37
                      mol_type = protein
                      organism = synthetic construct
SEQUENCE: 82
GVVEVDAAVT PEERHLSKMQ QNGYENPTYK FFEQMQN                            37

SEQ ID NO: 83         moltype = DNA  length = 45
FEATURE               Location/Qualifiers
misc_feature          1..45
                      note = synthetic
source                1..45
                      mol_type = other DNA
                      organism = synthetic construct
SEQUENCE: 83
aacagtacac atccattcat catggtgtgg tggaggtagg taaac                   45

SEQ ID NO: 84         moltype = DNA  length = 40
FEATURE               Location/Qualifiers
misc_feature          1..40
                      note = synthetic
source                1..40
                      mol_type = other DNA
                      organism = synthetic construct
SEQUENCE: 84
aacagtacac atccattcat catggtggag gtaggtaaac                         40

SEQ ID NO: 85         moltype = DNA  length = 43
FEATURE               Location/Qualifiers
misc_feature          1..43
                      note = synthetic
source                1..43
                      mol_type = other DNA
                      organism = synthetic construct
SEQUENCE: 85
aacagtacac atccattcat catggtggtg gaggtaggta aac                     43

SEQ ID NO: 86         moltype = DNA  length = 44
FEATURE               Location/Qualifiers
misc_feature          1..44
```

```
                        note = synthetic
source                  1..44
                        mol_type = other DNA
                        organism = synthetic construct
SEQUENCE: 86
aacagtacac atccattcat catggtgggt ggaggtaggt aaac                     44

SEQ ID NO: 87           moltype = DNA  length = 41
FEATURE                 Location/Qualifiers
misc_feature            1..41
                        note = synthetic
source                  1..41
                        mol_type = other DNA
                        organism = synthetic construct
SEQUENCE: 87
aacagtacac atccattcat cattggtgga ggtaggtaaa c                        41

SEQ ID NO: 88           moltype = DNA  length = 42
FEATURE                 Location/Qualifiers
misc_feature            1..42
                        note = synthetic
source                  1..42
                        mol_type = other DNA
                        organism = synthetic construct
SEQUENCE: 88
aacagtacac atccattcat catgtggtgg aggtaggtaa ac                       42

SEQ ID NO: 89           moltype = DNA  length = 45
FEATURE                 Location/Qualifiers
misc_feature            1..45
                        note = synthetic
source                  1..45
                        mol_type = other DNA
                        organism = synthetic construct
SEQUENCE: 89
tgctgcatct tggacaggtg gcgctcctct ggggtgacag cggcg                    45

SEQ ID NO: 90           moltype = DNA  length = 46
FEATURE                 Location/Qualifiers
misc_feature            1..46
                        note = synthetic
misc_feature            28
                        note = n is a, c, g, or t
source                  1..46
                        mol_type = other DNA
                        organism = synthetic construct
SEQUENCE: 90
tgctgcatct tggacaggtg gcgctccntc tggggtgaca gcggcg                   46

SEQ ID NO: 91           moltype = DNA  length = 43
FEATURE                 Location/Qualifiers
misc_feature            1..43
                        note = synthetic
source                  1..43
                        mol_type = other DNA
                        organism = synthetic construct
SEQUENCE: 91
tgctgcatct tggacaggtg gcgcttctgg ggtgacagcg gcg                      43

SEQ ID NO: 92           moltype = DNA  length = 40
FEATURE                 Location/Qualifiers
misc_feature            1..40
                        note = synthetic
source                  1..40
                        mol_type = other DNA
                        organism = synthetic construct
SEQUENCE: 92
tgctgcatct tggacaggtg gctctggggt gacagcggcg                          40

SEQ ID NO: 93           moltype = DNA  length = 42
FEATURE                 Location/Qualifiers
misc_feature            1..42
                        note = synthetic
source                  1..42
                        mol_type = other DNA
                        organism = synthetic construct
SEQUENCE: 93
tgctgcatct tggacaggtg gcgctctggg gtgacagcgg cg                       42
```

```
SEQ ID NO: 94          moltype = DNA  length = 44
FEATURE                Location/Qualifiers
misc_feature           1..44
                       note = synthetic
source                 1..44
                       mol_type = other DNA
                       organism = synthetic construct
SEQUENCE: 94
tgctgcatct tggacaggtg gcgctctctg gggtgacagc ggcg                    44

SEQ ID NO: 95          moltype = DNA  length = 45
FEATURE                Location/Qualifiers
misc_feature           1..45
                       note = synthetic
source                 1..45
                       mol_type = other DNA
                       organism = synthetic construct
SEQUENCE: 95
ttggattttc gtagccgttc tgctgcatct tggacaggtg gcgct                   45

SEQ ID NO: 96          moltype = DNA  length = 46
FEATURE                Location/Qualifiers
misc_feature           1..46
                       note = synthetic
misc_feature           28
                       note = n is a, c, g, or t
source                 1..46
                       mol_type = other DNA
                       organism = synthetic construct
SEQUENCE: 96
ttggattttc gtagccgttc tgctgcantc ttggacaggt ggcgct                  46

SEQ ID NO: 97          moltype = DNA  length = 36
FEATURE                Location/Qualifiers
misc_feature           1..36
                       note = synthetic
source                 1..36
                       mol_type = other DNA
                       organism = synthetic construct
SEQUENCE: 97
ttggattttc gtagccgttc ttggacaggt ggcgct                             36

SEQ ID NO: 98          moltype = DNA  length = 44
FEATURE                Location/Qualifiers
misc_feature           1..44
                       note = synthetic
source                 1..44
                       mol_type = other DNA
                       organism = synthetic construct
SEQUENCE: 98
ttggattttc gtagccgttc tgctgctctt ggacaggtgg cgct                    44

SEQ ID NO: 99          moltype = DNA  length = 42
FEATURE                Location/Qualifiers
misc_feature           1..42
                       note = synthetic
source                 1..42
                       mol_type = other DNA
                       organism = synthetic construct
SEQUENCE: 99
ttggattttc gtagccgttc tgcttcttgg acaggtggcg ct                      42

SEQ ID NO: 100         moltype = DNA  length = 39
FEATURE                Location/Qualifiers
misc_feature           1..39
                       note = synthetic
source                 1..39
                       mol_type = other DNA
                       organism = synthetic construct
SEQUENCE: 100
ttggattttc gtagccgttc ttcttggaca ggtggcgct                          39

SEQ ID NO: 101         moltype = AA  length = 46
FEATURE                Location/Qualifiers
REGION                 1..46
                       note = synthetic
source                 1..46
                       mol_type = protein
                       organism = synthetic construct
```

```
SEQUENCE: 101
GGVVIATVIV ITLVMLKKKQ YTSIHHGVVE VDAAVTPEER HLSKMQ                46

SEQ ID NO: 102         moltype = AA  length = 29
FEATURE                Location/Qualifiers
REGION                 1..29
                       note = synthetic
source                 1..29
                       mol_type = protein
                       organism = synthetic construct
SEQUENCE: 102
GGVVIATVIV ITLVMLKKKQ YTSIHHGGG                                   29

SEQ ID NO: 103         moltype = AA  length = 30
FEATURE                Location/Qualifiers
REGION                 1..30
                       note = synthetic
source                 1..30
                       mol_type = protein
                       organism = synthetic construct
SEQUENCE: 103
GGVVIATVIV ITLVMLKKKQ YTSIHHGGGG                                  30

SEQ ID NO: 104         moltype = AA  length = 27
FEATURE                Location/Qualifiers
REGION                 1..27
                       note = synthetic
source                 1..27
                       mol_type = protein
                       organism = synthetic construct
SEQUENCE: 104
GGVVIATVIV ITLVMLKKKQ YTSIHHG                                     27

SEQ ID NO: 105         moltype = AA  length = 26
FEATURE                Location/Qualifiers
REGION                 1..26
                       note = synthetic
source                 1..26
                       mol_type = protein
                       organism = synthetic construct
SEQUENCE: 105
GGVVIATVIV ITLVMLKKKQ YTSIHH                                      26

SEQ ID NO: 106         moltype = AA  length = 45
FEATURE                Location/Qualifiers
REGION                 1..45
                       note = synthetic
source                 1..45
                       mol_type = protein
                       organism = synthetic construct
SEQUENCE: 106
GGVVIATVIV ITLVMLKKKQ YTSIHHVVAV DAAVTPEERH LSKMQ                 45

SEQ ID NO: 107         moltype = AA  length = 46
FEATURE                Location/Qualifiers
REGION                 1..46
                       note = synthetic
source                 1..46
                       mol_type = protein
                       organism = synthetic construct
SEQUENCE: 107
KKQYTSIHHG VVEVDAAVTP EERHLSKMQQ NGYENPTYKF FEQMQN                46

SEQ ID NO: 108         moltype = AA  length = 41
FEATURE                Location/Qualifiers
REGION                 1..41
                       note = synthetic
SITE                   21
                       note = MISC_FEATURE - X is D or E
source                 1..41
                       mol_type = protein
                       organism = synthetic construct
SEQUENCE: 108
KKQYTSIHHG VVEVDAAVTP XGAPPVQDAA ERLRKSNLQV L                     41

SEQ ID NO: 109         moltype = AA  length = 41
FEATURE                Location/Qualifiers
REGION                 1..41
                       note = synthetic
```

```
source                1..41
                      mol_type = protein
                      organism = synthetic construct
SEQUENCE: 109
KKQYTSIHHG VVEVDAAVTP EARPPVQDAA ERLRKSNLQV L                 41

SEQ ID NO: 110        moltype = AA  length = 39
FEATURE               Location/Qualifiers
REGION                1..39
                      note = synthetic
source                1..39
                      mol_type = protein
                      organism = synthetic construct
SEQUENCE: 110
KKQYTSIHHG VVEVDAAVTP EPPVQDAAER LRKSNLQVL                    39

SEQ ID NO: 111        moltype = AA  length = 45
FEATURE               Location/Qualifiers
REGION                1..45
                      note = synthetic
source                1..45
                      mol_type = protein
                      organism = synthetic construct
SEQUENCE: 111
KKQYTSIHHG VVEVDAAVTP ERHLSKMQQN SYENPTYKFF EQMQN             45

SEQ ID NO: 112        moltype = AA  length = 20
FEATURE               Location/Qualifiers
REGION                1..20
                      note = synthetic
source                1..20
                      mol_type = protein
                      organism = synthetic construct
SEQUENCE: 112
KKQYTSIHHG VVEVDAAVTP                                         20

SEQ ID NO: 113        moltype = AA  length = 27
FEATURE               Location/Qualifiers
REGION                1..27
                      note = synthetic
source                1..27
                      mol_type = protein
                      organism = synthetic construct
SEQUENCE: 113
KKQYTSIHHG VVEVDAAVTP EERHLSK                                 27

SEQ ID NO: 114        moltype = AA  length = 43
FEATURE               Location/Qualifiers
REGION                1..43
                      note = synthetic
source                1..43
                      mol_type = protein
                      organism = synthetic construct
SEQUENCE: 114
KKQYTSIHHG VVEVDAAVTP EERHLSKNGY ENPTYKFFEQ MQN               43

SEQ ID NO: 115        moltype = AA  length = 27
FEATURE               Location/Qualifiers
REGION                1..27
                      note = synthetic
source                1..27
                      mol_type = protein
                      organism = synthetic construct
SEQUENCE: 115
KKQYTSIHHG VVEVDAAVTP EERHLSK                                 27

SEQ ID NO: 116        moltype = AA  length = 45
FEATURE               Location/Qualifiers
REGION                1..45
                      note = synthetic
source                1..45
                      mol_type = protein
                      organism = synthetic construct
SEQUENCE: 116
KKQYTSIHHG VVEVDAAVTP EERHLSKKQN GYENPTYKFF EQMQN             45

SEQ ID NO: 117        moltype = AA  length = 44
FEATURE               Location/Qualifiers
REGION                1..44
```

```
                        note = synthetic
source                  1..44
                        mol_type = protein
                        organism = synthetic construct
SEQUENCE: 117
KKQYTSIHHG VVEVDAAVTP EERHLSKKNG YENPTYKFFE QMQN                  44

SEQ ID NO: 118          moltype = AA  length = 46
FEATURE                 Location/Qualifiers
REGION                  1..46
                        note = synthetic
source                  1..46
                        mol_type = protein
                        organism = synthetic construct
SEQUENCE: 118
GGVVIATVIV ITLVMLKKKQ YTSIHHGVVE VDAAVTPEER HLSKMQ                46

SEQ ID NO: 119          moltype = AA  length = 48
FEATURE                 Location/Qualifiers
REGION                  1..48
                        note = synthetic
source                  1..48
                        mol_type = protein
                        organism = synthetic construct
SEQUENCE: 119
GGVVIATVIV ITLVMLKKKQ YTSIHHGGGR RRRDPRGAPS LQDAAERI              48

SEQ ID NO: 120          moltype = AA  length = 47
FEATURE                 Location/Qualifiers
REGION                  1..47
                        note = synthetic
source                  1..47
                        mol_type = protein
                        organism = synthetic construct
SEQUENCE: 120
GGVVIATVIV ITLVMLKKKQ YTSIHHGGRR RRDPRGAPSL QDAAERI               47

SEQ ID NO: 121          moltype = AA  length = 49
FEATURE                 Location/Qualifiers
REGION                  1..49
                        note = synthetic
source                  1..49
                        mol_type = protein
                        organism = synthetic construct
SEQUENCE: 121
GGVVIATVIV ITLVMLKKKQ YTSIHHGGGG RRRRDPRGAP SLQDAAERI             49

SEQ ID NO: 122          moltype = DNA  length = 20
FEATURE                 Location/Qualifiers
misc_feature            1..20
                        note = synthetic
source                  1..20
                        mol_type = other DNA
                        organism = synthetic construct
SEQUENCE: 122
gtccatccat catggcctgg                                             20

SEQ ID NO: 123          moltype = DNA  length = 20
FEATURE                 Location/Qualifiers
misc_feature            1..20
                        note = synthetic
source                  1..20
                        mol_type = other DNA
                        organism = synthetic construct
SEQUENCE: 123
ttccatccat catggcttgg                                             20

SEQ ID NO: 124          moltype = DNA  length = 20
FEATURE                 Location/Qualifiers
misc_feature            1..20
                        note = synthetic
source                  1..20
                        mol_type = other DNA
                        organism = synthetic construct
SEQUENCE: 124
gtccctccat catggcctgg                                             20

SEQ ID NO: 125          moltype = DNA  length = 20
FEATURE                 Location/Qualifiers
```

```
misc_feature          1..20
                      note = synthetic
source                1..20
                      mol_type = other DNA
                      organism = synthetic construct
SEQUENCE: 125
ggccatcatt catggcgtgg                                             20

SEQ ID NO: 126        moltype = DNA  length = 20
FEATURE               Location/Qualifiers
misc_feature          1..20
                      note = synthetic
source                1..20
                      mol_type = other DNA
                      organism = synthetic construct
SEQUENCE: 126
ataaatatat catggcgtgg                                             20

SEQ ID NO: 127        moltype = DNA  length = 20
FEATURE               Location/Qualifiers
misc_feature          1..20
                      note = synthetic
source                1..20
                      mol_type = other DNA
                      organism = synthetic construct
SEQUENCE: 127
ctcccttcat cttggtgtgg                                             20

SEQ ID NO: 128        moltype = DNA  length = 20
FEATURE               Location/Qualifiers
misc_feature          1..20
                      note = synthetic
source                1..20
                      mol_type = other DNA
                      organism = synthetic construct
SEQUENCE: 128
atgcaatcag catggtgtgg                                             20

SEQ ID NO: 129        moltype = DNA  length = 20
FEATURE               Location/Qualifiers
misc_feature          1..20
                      note = synthetic
source                1..20
                      mol_type = other DNA
                      organism = synthetic construct
SEQUENCE: 129
ttctgttcag catggtgtgg                                             20

SEQ ID NO: 130        moltype = DNA  length = 20
FEATURE               Location/Qualifiers
misc_feature          1..20
                      note = synthetic
source                1..20
                      mol_type = other DNA
                      organism = synthetic construct
SEQUENCE: 130
ttaaattcaa catggtgtgg                                             20

SEQ ID NO: 131        moltype = DNA  length = 20
FEATURE               Location/Qualifiers
misc_feature          1..20
                      note = synthetic
source                1..20
                      mol_type = other DNA
                      organism = synthetic construct
SEQUENCE: 131
agccatttat caaggtgtgg                                             20

SEQ ID NO: 132        moltype = DNA  length = 23
FEATURE               Location/Qualifiers
misc_feature          1..23
                      note = synthetic
source                1..23
                      mol_type = other DNA
                      organism = synthetic construct
SEQUENCE: 132
atccatccat catggcgtgg tgg                                         23

SEQ ID NO: 133        moltype = DNA  length = 23
```

-continued

```
FEATURE                 Location/Qualifiers
misc_feature            1..23
                        note = synthetic
source                  1..23
                        mol_type = other DNA
                        organism = synthetic construct
SEQUENCE: 133
gactatcagc catggagtgg tgg                                               23

SEQ ID NO: 134          moltype = DNA  length = 23
FEATURE                 Location/Qualifiers
misc_feature            1..23
                        note = synthetic
source                  1..23
                        mol_type = other DNA
                        organism = synthetic construct
SEQUENCE: 134
atccatccat catggcgtgg tgg                                               23

SEQ ID NO: 135          moltype = DNA  length = 23
FEATURE                 Location/Qualifiers
misc_feature            1..23
                        note = synthetic
source                  1..23
                        mol_type = other DNA
                        organism = synthetic construct
SEQUENCE: 135
caccatcagc cacgggattg tgg                                               23

SEQ ID NO: 136          moltype = DNA  length = 23
FEATURE                 Location/Qualifiers
misc_feature            1..23
                        note = synthetic
source                  1..23
                        mol_type = other DNA
                        organism = synthetic construct
SEQUENCE: 136
atccattcat catggtgtgg tgg                                               23

SEQ ID NO: 137          moltype = DNA  length = 23
FEATURE                 Location/Qualifiers
misc_feature            1..23
                        note = synthetic
source                  1..23
                        mol_type = other DNA
                        organism = synthetic construct
SEQUENCE: 137
ggctatcagc catggcgtgg tgg                                               23

SEQ ID NO: 138          moltype = DNA  length = 23
FEATURE                 Location/Qualifiers
misc_feature            1..23
                        note = synthetic
source                  1..23
                        mol_type = other DNA
                        organism = synthetic construct
SEQUENCE: 138
atccattcat catggtgtgg tgg                                               23
```

GENE EDITING-BASED METHOD OF ATTENUATING THE BETA-AMYLOID PATHWAY

CROSS-REFERENCE TO RELATED APPLICATIONS

This application is a continuation of U.S. application Ser. No. 17/494,457, filed on Oct. 5, 2021, which is a divisional of U.S. application Ser. No. 16/251,970, filed on Jan. 18, 2019, now U.S. Pat. No. 11,173,216, which claims priority to U.S. Provisional Patent Application No. 62/618,694, filed Jan. 18, 2018, which are incorporated herein by reference in their entirety.

STATEMENT REGARDING FEDERALLY SPONSORED RESEARCH

This invention was made with government support under AG048218 awarded by the National Institutes of Health. The government has certain rights in the invention.

SEQUENCE LISTING

The Instant Application contains a Sequence Listing which has been submitted electronically in XML format and is hereby incorporated by reference in its entirety. Said XML copy, created on Jun. 5, 2023, is named "Replacement Sequence List WIS0059USC" and is 218,039 bytes in size. The Sequence Listing does not go beyond the disclosure in the application as filed.

BACKGROUND

The gradual accumulation of Aβ in brains is a neuropathologic hallmark of Alzheimer's disease (AD). Aβ is generated by the sequential cleavage of the amyloid precursor protein (APP) by β- and γ-secretases (β-secretase aka BACE-1, and γ-secretase), with BACE-1-cleavage as the rate-limiting step. Substantial evidence indicates that accrual of APP-cleavage products plays a key role in AD, making the "amyloidogenic pathway" an important therapeutic target (1-3).

CRISPR/Cas9 gene editing is emerging as a promising tool to disrupt the expression of disease-causing genes or edit pathogenic mutations (4). Originally discovered in bacteria as part of a natural self-defense mechanism, the Cas9 nuclease—guided by a short guide RNA (sgRNA)—generates double-stranded breaks (DSB) at targeted genomic loci (5).

However, to date, the application of gene editing to neurologic diseases has been limited (6). For instance, CRISPR/Cas9 has been used in cell-based models to edit triplet-repeat expansions of Huntington's and Fragile X syndrome (7, 8). Besides significant technical caveats such as low editing efficiency and limited in vivo validation (6), such canonical approaches would only be applicable to the small fraction of cases that are inherited (i.e. <10% of AD, Parkinson's, ALS); with a different approach required for each gene. Moreover, the feasibility of CRISPR/Cas9 as a therapeutic possibility in AD has not been reported.

Needed in the art of Alzheimer's disease treatment is an improved method of using gene editing methods to treat or prevent the disease.

SUMMARY OF THE INVENTION

In a first aspect, provided herein is a method of treating or preventing Alzheimer's disease (AD) caused by formation of amyloid plaques composed of amyloid beta (Aβ) peptides, wherein the method comprises the steps of (a) obtaining a gene-editing construct specific for the amyloid precursor protein (APP), wherein the construct facilitates truncation of the APP C-terminus when combined with a Cas9 nuclease, and (b) delivering the construct and a construct encoding the Cas9 nuclease to a patient in need of AD therapy, wherein the APP molecule is truncated and production of Aβ peptides is decreased in the patient's brain. In some embodiments, the truncation of the APP C-terminus occurs at an APP residue selected from the group consisting of 659, 670, 676, and 686. In some embodiments, the gene-editing construct comprises a gRNA sequence selected from the group consisting of SEQ ID NOs:1-10. In some embodiments, the construct and the nuclease are delivered in a composition comprising an adeno-associated viral vector and a nanocarrier delivery vehicle. In some embodiments, the composition is delivered intravenously or intrathecally.

In a second aspect, provided herein is a method of reducing the formation of amyloid plaques in a patient's brain, wherein the plaques are comprise amyloid beta (Aβ) peptides, the method comprises the steps of (a) obtaining a gene-editing construct specific for the amyloid precursor protein (APP), wherein the construct facilitates truncation of the APP C-terminus when combined with a Cas9 nuclease, and (b) delivering the construct and nuclease to a patient in need of AD therapy, wherein the APP molecule is truncated and production of Aβ peptides is decreased in the patient's brain. In some embodiments, the truncation of the APP C-terminus occurs at an APP residue selected from the group consisting of 659, 670, 676, and 686. In some embodiments, the gene-editing construct comprises a gRNA sequence selected from the group consisting of SEQ ID NO:1-10. In some embodiments, the construct and the nuclease are delivered in a composition comprising an adeno-associated viral vector and a nanocarrier delivery vehicle. In some embodiments, the composition is delivered intravenously or intrathecally.

In a third aspect, provided herein is a genetic construct comprising, a sequence encoding for a Cas9 nuclease and a sequence encoding a gRNA specific to amyloid precursor protein (APP). In some embodiments, the construct is packaged in a viral vector selected from the group consisting of a lentiviral vector and an adeno-associated viral (AAV) vector. In some embodiments, the construct further comprises at least one neuron specific promoter. In some embodiments, the neuron specific promoter is selected from the group consisting of human synapsin 1 (hSyn1) promoter, and mouse Mecp2 promoter (pMecp2). In some embodiments, the construct further comprises an RNA Pol III promoter. In some embodiments, the RNA Pol III promoter is a U6 promoter. In some embodiments, the sequence of the gRNA is selected from the group consisting of SEQ ID NOs:1-10. In some embodiments, the sequence of the Cas9 nuclease consists of SEQ ID NO:15. In some embodiments, the construct comprises the sequence of SEQ ID NO:17, SEQ ID NO:18, SEQ ID NO:19, or SEQ ID NO:20. In some embodiments, the sequence encoding for a Cas9 nuclease in packaged on a first AAV vector and the sequence encoding a gRNA specific to amyloid precursor protein (APP) is packaged on a second AAV vector.

In a fourth aspect, provided herein is a kit for reducing the formation of amyloid plaques in a patient's brain, the kit comprising a first viral vector encoding a gRNA selected from the group consisting of SEQ ID NOs:1-10 and a second viral vector encoding a Cas9 nuclease. In some embodiments, the viral vector is selected from the group consisting of a lentiviral vector and an adeno-associated viral (AAV) vector. In some embodiments, the first or second viral vector further comprises at least one neuron specific promoter. In some embodiments, the neuron specific promoter is selected from the group consisting of human synapsin 1 (hSyn1) promoter, and mouse Mecp2 promoter (pMecp2). In some embodiments, the first or second viral vector further comprises an RNA Pol III promoter. In some embodiments, the RNA Pol III promoter is a U6 promoter. In some embodiments, the kit comprises a viral vector encoding both a gRNA selected from the group consisting of SEQ ID NOs: 1-10 and a Cas9 nuclease.

BRIEF DESCRIPTION OF THE DRAWINGS

The patent or application file contains at least one drawing executed in color. Copies of this patent or patent application publication with color drawings will be provided by the Office upon request and payment of the necessary fee.

(FIG. 1A) Schematic and C-terminal sequence of mouse APP showing PAM sites (yellow) and genomic targets for the three APP-sgRNAs (APP-659 sgRNA used henceforth and referred to as 'APP-sgRNA'—see text). Note that the C-terminal antibody Y188 recognizes the last 20 amino acids of APP. (FIG. 1B) Neuro2A cells were transfected with APP-sgRNA and Cas9 (or Cas9 only), and immunostained with the Y188 antibody (after 5 days; mCherry labels transfected cells). Note decreased APP (Y188) fluorescence, indicating APP editing (quantified on right, mean±SEM of 39 cells from two independent experiments per condition, $p<0.0001$). (FIGS. 1C-1D) Neuro2A cells were transduced by lentiviral vectors carrying APP-sgRNA and Cas9 (or non-targeting control-sgRNA/Cas9 as control) and immunoblotted with Y188 and 22C11 antibodies (latter recognizes APP N-terminus). A gamma secretase inhibitor (GSI) was added to allow detection of accumulated APP CTF's (see methods, GAPDH used as loading controls). Note attenuated signal with the Y188 antibody in APP-sgRNA treated samples, but no change in 22C11 signal. Blots quantified in (d), mean±SEM of six independent experiments, $p<0.0001$. (FIG. 1E) Time course of APP-editing in neuro2a cells. Cells were transfected with a vector carrying APP-sgRNA and Cas9, and APP-CTFs were analyzed by Western blotting (in the presence of GSI). (FIG. 1F) Deep sequencing of APP C-terminus in neuro2A cells. Top: Frequency of base-pair matches between gRNA-edited and WT mouse sequence. Red underline marks the sgRNA target sequence and arrowhead denotes predicted cut-site. Note extensive mismatch around predicted cut-site, indicating robust editing. Bottom: Major mutated APP loci resulting from sgRNA-editing, and their frequencies.

(FIG. 2A) Comparison of mouse and human APP-sgRNA targeting sequences (red arrowheads indicate differences; yellow bar denotes the PAM site). (FIG. 2B) Human iPSC-derived NPCs were transduced by lentiviral vectors carrying APP-sgRNA and Cas9 (or non-targeting control-sgRNA/Cas9 as control) and differentiated into neurons. After 3 weeks of differentiation, cells were immunostained with the Y188 and Tuj1 (tubulin) antibodies. Note decreased APP (Y188) fluorescence, indicating APP editing. (FIG. 2C) The iPSC-derived neurons above (or isogenic APPV717I London-mutant knock-in iPSC-neurons) were transduced and differentiated as above and immunoblotted with C- and N-terminus antibodies (GSI was added to allow detection of accumulated APP CTFs). Note attenuation of APP signal with Y188 after APP-sgRNA treatment in both wild type and isogenic APP London iPSCs (quantified on right, mean±SEM of three independent experiments, $^{}p<0.01$, $^{*}p<0.001$, $^{**}p<0.0001$). (FIG. 2D) Media from the iPSC-derived neurons above was immunoblotted for secreted sAPPα (6E10 antibody). Note increased sAPPα in sgRNA-treated samples, indicating upregulation of the non-amyloidogenic pathway. (FIG. 2E) ELISA of media from iPSC derived neurons. Note decreased Aβ in the sgRNA-treated samples (mean±SEM of three independent experiments, $^{}p<0.01$, $^{*}p<0.001$, $^{}p<0.0001$). (FIG. 2F) Deep sequencing of APP C-terminus in human ESCs. Red underline marks the sgRNA target sequence and arrowhead denotes predicted cut-site. Note extensive mismatch around predicted cut-site, indicating robust editing. (FIG. 2G) Major mutated APP-loci resulting from CRISPR editing, and their frequencies. (FIG. 2H) Predicted APP translational products (post-editing) for the major mutant alleles observed in deep sequencing. Note that after editing, APP is translated up-to amino acid 659 (red arrowheads; similar results were seen in HEK cells, see FIG. 6**E).

(FIG. 3A) AAV9-sgRNA and AAV9-Cas9 expression vectors. Note that the sgRNA vector co-expresses GFP and the Cas9 is tagged to HA, for identification of transduced neurons. (FIG. 3B) Cultured hippocampal neurons were transduced with AAV9s carrying APP-sgRNA/Cas9 (or Cas9 only) and immunoblotted with the Y188 and 22C11 antibodies (in the presence of GSI). Note attenuation of CTFs by the APP-sgRNA. (FIG. 3C) Neurons were transfected (at the time of plating) with a vector expressing APP-sgRNA and Cas9. Neuritic/axon outgrowth was analyzed after 5-6 days. Neurons were transfected or infected at DIV7 with APP CRISPR, and synapse structure/function was analyzed after 14-17 days. (FIG. 3D) Top: Representative images of neurons transfected with the APP-sgRNA/Cas9 (or Cas9 alone). Bottom: Axon length and number of neurites/branches in the APP-sgRNA/Cas9 (or Cas9 alone) groups; note that there was no significant difference (mean±SEM; axon length: 30 cells for Cas9 only and 27 cells for moAPP-sgRNA from two independent experiments, $p=0.2462$; neurite number: 35 cells for Cas9 only and 31 cells for moAPP-sgRNA from two independent experiments, $p=0.2289$; branch number: 27 cells for both conditions from two independent experiments, $p=0.6008$). (FIG. 3E) Neurons were infected with AAV9 viruses carrying APP-sgRNA/Cas9 (or Cas9 only as controls), and fixed/stained with the presynaptic marker VAMP2. Note that the presynaptic density (VAMP2 puncta) was similar in both groups (quantified on right, mean±SEM of VAMP2 staining along 27 dendrites for Cas9 only and 25 dendrites for moAPP-sgRNA from two independent experiments, $p=0.3132$). (FIG. 3F) Neurons were transfected with APP-sgRNA/Cas9 (or Cas9 only as controls). Spine density in the APP-sgRNA/Cas9 (or Cas9 only) groups was also similar, quantified on right (mean±SEM of 18 dendrites for Cas9 only and 16 dendrites for moAPP-sgRNA from two independent experiments, $p=0.7456$). (FIG. 3G) Miniature excitatory postsynaptic currents (mEPSC) were recorded from neurons infected with AAV9-APP-sgRNA/Cas9 or AAV9-Cas9 alone. Top: Representative mEPSC traces in control and APP-sgRNA transduced neurons. Corresponding alignments of mEPSCs with average (white traces) are shown on right. Bottom: Cumulative histograms of mEPSC amplitude, 20-80% rise-time and inter-event interval in APP-sgRNA/Cas9 and the Cas9-only infected neurons (note no significant differences).

(FIG. 4A) AAV9-sgRNA and AAV9-Cas9 were stereotactically co-injected into dentate gyrus of 8-week old mouse brains (bottom). Two weeks after viral delivery, brains were perfused, fixed, and immunostained with anti-GFP, anti-HA and anti-APP(Y188) antibodies. (FIG. 4B) Co-expression of AAV9-sgRNA-GFP and AAV9-HA-Cas9 in the dentate gyrus. Note that majority of neurons are positive for both GFP and HA (~87% of the cells were positive for both; sampling from 3 brains). (FIGS. 4C-4D) Coronal section of a mouse hippocampi injected on one side (marked by arrow) with the AAV viruses as described above. Note attenuated Y188 staining of neurons on the injected side, indicating APP-editing. The image of mouse hippocampus injected with Cas9 only is not shown. Fluorescence quantified in (d), mean±SEM, data from three brains. One-way ANOVA: p<0.0001. Tukey's multiple comparisons: p=0.4525 (Un-injected vs Cas9 only); p<0.0001 (Un-injected vs APP-sgRNA); p<0.0001 (Cas9 only vs APP-sgRNA). (FIG. 4E) Intracerebroventrical injection of the AAV9 viruses into P0 pups. Note widespread delivery of gRNA into brain, as evident by GFP fluorescence. (FIG. 4F) Brain sections from above were immunostained with the Y188 antibody. Note attenuated Y188 staining in the APP-sgRNA/Cas9 transduced sample, suggesting APP-editing. (FIG. 4G) Western blots of the brains from (e). Note decreased expression of CTFs in the APP-sgRNA/Cas9 transduced brains; blots quantified on right (mean±SEM of three independent experiments, **p<0.01).

(FIG. 5A) APP/BACE-1 interaction—as evaluated by fluorescence complementation in cultured hippocampal neurons—was attenuated in neurons transfected with an APP C-terminus truncation mimicking the post-edited translational product (APP659:VN; quantified below, mean±SEM of 12 cells for APP(WT) and 13 cells for APP(659) from two independent experiments, p<0.0001). (FIG. 5B) APP β-cleavage is also attenuated in cells transfected with APP659. HEK cells were co-transfected with APPWT (or APP659) tagged to VN, and BACE-1:VC; and immunoblotted with the 6E10 antibody. Note decreased 3-CTFs in cells carrying the truncated APP plasmid. (FIG. 5C) Schematic showing the CRISPR-edited C-terminus portion of APP. Note that the threonine at 668 position, and the endocytic YENPTY motif (dashed boxes) are thought to play roles in Aβ production (see text). (FIG. 5D) APP/BACE-1 interaction—as evaluated by fluorescence complementation in cultured hippocampal neurons—was most markedly attenuated in neurons transfected with mutant YENPTY (mean±SEM of 32 cells for APP(WT), 37 cells for APP(T668A), 45 cells for APP(YENPTY) and 49 cells for APP(T668A+YENPTY) from two independent experiments). One-way ANOVA: p<0.0001. Tukey's multiple comparisons: p=0.0022 (APP vs APPT668A); p<0.0001 (APP vs APPYENPTY); p<0.0001 (APP vs APPT668A+YENPTY); p<0.0001 (APPT668A vs APPYENPTY); p<0.0001 (APPT668A vs APPT668A+YENPTY); p=0.7568 (APPYENPTY vs APPT668A+YENPTY). (FIG. 5E) Strategy of APP internalization assay. Neuro 2a cells are transfected with APP:GFP or APP659:GFP. After incubation with anti N-terminal APP antibody (22C11) for 10 min, the cells were fixed and stained with secondary antibody to visualize the cell surface and internalized APP. Note the cell surface accumulation and decreased internalization of APP659 (mean±SEM of 21 cells from two independent experiments, p<0.0001).

(FIG. 6A) Strategy to integrate APP:VN and BACE-1:VC into the H4 genome and generation of a stable cell line expressing single copies of the two proteins (see results and methods for details). (FIG. 6B) APP and BACE-1 expression in the $H4^{single\ copy}$ cell line. Note negligible expression of endogenous proteins in native H4 cells. (FIG. 6C) The $H4^{single\ copy}$ cell line was transduced with lentiviral vectors carrying non-targeting control-sgRNA/Cas9 or various human APP C-terminus targeting sgRNAs/Cas9 (see Table 5 for targeting sequences). The APP/BACE-1 Venus complementation was visualized by fluorescence microscopy. Note attenuation of complementation, indicating editing by the APP-sgRNAs (quantified on right, mean±SEM of three independent experiments). One-way ANOVA: p<0.0001. Tukey's multiple comparisons: p<0.0001 (control-sgRNA vs APP659-sgRNA); p<0.0001 (control-sgRNA vs APP670-sgRNA); p<0.0001 (control-sgRNA vs APP676-sgRNA); p=0.0064 (APP659-sgRNA vs APP670-sgRNA); p=0.0015 (APP659-sgRNA vs APP676-sgRNA); p=0.6207 (APP670-sgRNA vs APP676-sgRNA). (FIG. 6D) ELISA of media from the $H4^{single\ copy}$ cell line (treated as above). Note decreased Aβ in the APP-sgRNAs treated samples (mean±SEM of three independent experiments). One-way ANOVA for Aβ 40 and 42: p<0.0001. Tukey's multiple comparisons for Aβ 40: p<0.0001 (control-sgRNA vs APP659-sgRNA; control-sgRNA vs APP670-sgRNA; control-sgRNA vs APP676-sgRNA); p=0.0331 (APP659-sgRNA vs APP670-sgRNA); p=0.0071 (APP659-sgRNA vs APP676-sgRNA); p=0.6673 (APP670-sgRNA vs APP676-sgRNA). Tukey's multiple comparisons for Aβ 42: p<0.0001 (control-sgRNA vs APP659-sgRNA; control-sgRNA vs APP670-sgRNA; control-sgRNA vs APP676-sgRNA); p=0.0068 (APP659-sgRNA vs APP670-sgRNA); p=0.0221 (APP659-sgRNA vs APP676-sgRNA); p=0.8079 (APP670-sgRNA vs APP676-sgRNA). (FIG. 6E) HEK cells were transduced by lentiviral vectors carrying APP-sgRNAs and Cas9 (or non-targeting control-sgRNA/Cas9 as control), and APP C-terminus was sequenced. Left: Deep sequencing of APP659-sgRNA treated cells, and Sanger sequencing followed by ICE analyses for APP670-sgRNA and APP676-sgRNA treated cells. Red underlines mark the sgRNA-targeting sequences and arrowheads denote predicted cut-sites. Right: Predicted APP translational products after CRISPR/Cas9 editing in human HEK cells for the major mutant alleles observed in sequencing analyses. Red arrowheads indicate the amino acids where APP genes were translated up to after editing.

(FIG. 7A) Neuro2a cells were co-transfected with a sgRNA that knocked out the entire APP gene and Cas9 (see Table 5 for APP targeting sequence), and immunostained with APP N-terminal and C-terminal antibodies (after 5 days in culture). Note attenuation of staining for both Y188 and 22C11. (FIG. 7B) Neuro2a cells were transfected with various APP C-terminus targeting sgRNAs (or non-targeting control-sgRNA), and immunostained with APP N-terminal and C-terminal antibodies (after 5 days in culture in the presence of GSI). Note attenuation of staining by Y188 but not 22C11, indicating selective editing of the APP C-terminus. (FIG. 7C) Neuro2A cells were transduced by lentiviral vectors carrying APP-sgRNA and Cas9 (or non-targeting control-sgRNA/Cas9 as control) and immunoblotted with the APP antibodies CT20 and M3.2 (CT20 recognizes last 20 aa; M3.2 recognizes an extracellular domain located upstream of the CRISPR/Cas9 targeting site). A GSI was added to allow detection of accumulated APP CTF's. Note attenuated signal with CT20- but not M3.2-antibody, indicating selective editing of the APP C-terminus. (FIG. 7D) Post-editing translational products in mouse (neuro 2a) cells. Note effective truncation of APP at aa 659.

FIGS. 8A-8G show APP C-terminus editing by CRISPR/Cas9. (FIG. 8A) HEK cells were transfected with human-specific APP-sgRNA and Cas9 (or Cas9 only), and immunostained with the Y188 antibody (after 5 days in culture). Note attenuation of staining, quantified on right (mean±SEM of 25 cells for Cas9 only and 43 cells for huAPP-sgRNA from two independent experiments, $p<0.0001$). (FIG. 8B) HEK cells were transduced by lentiviral vectors carrying APP-sgRNA and Cas9 (or non-targeting control-sgRNA/Cas9 as control) and immunoblotted with the Y188 and 22C11 antibodies (in the presence of GSI). Note attenuation of APP-CTFs in APP-sgRNA treated cells, indicating CRISPR-editing (mean±SEM of three independent experiments, $p<0.0001$). (FIG. 8C) HEK cells above were immunoblotted with CT20 and 2E9 antibodies (CT20 recognizes last 20 aa; 2E9 recognizes APP extracellular domain upstream of the CRISPR/Cas9 targeting site). Note attenuated signal with CT20- but not 2E9-antibody, indicating selective editing of the APP C-terminus. (FIGS. 8D-8E) Human ESCs were transduced by lentiviral vectors carrying human APP-sgRNA/Cas9 (or non-targeting sgRNA/Cas9). Samples were immunostained with the Y188 antibody (d) or immunoblotted with the Y188 and 22C11 antibodies (e). Note attenuation of APP-CTFs in sgRNA-transduced group (for immunostaining, mean±SEM of 17 colonies for control-sgRNA and 20 colonies for huAPP-sgRNA from two independent experiments, $p<0.0001$; for western blotting, mean±SEM of three independent experiments, $p=0.001$ for total APP and $p<0.0001$ for CTFs). (FIG. 8F) Media from iPSC derived neurons were immunoblotted for extracellular sAPPβ (in the absence of GSI). Note decrease in APP β-cleavage in the APP-sgRNA treated samples. (FIG. 8G) Media from $H4^{single\text{-}copy}$ cells were immunoblotted for extracellular sAPPα with 6E10 antibody and sAPPβ (in the absence of GSI). Note enhanced APP α-cleavage and attenuated APP β-cleavage in the APP-sgRNA treated samples.

(FIG. 9A) Strategy to evaluate γ-cleavage of post-edited APP. Neuro2a cells were transfected with either full length (FL) C99, or C99 truncated at aa 659 (to mimic the post-editing translational product; all constructs were GFP-tagged to confirm expression). γ-cleavage of the FL and 659 C99 was evaluated by western blotting (note that neuro2a cells have all components of the γ-secretase complex). (FIG. 9B) Schematic showing expected C99-cleavage patterns. Note that upon γ-cleavage, both C99-fragments will be further truncated. However, if the 'CRISPR-mimic' (659) fragment did not undergo γ-cleavage, this truncation would not occur. (FIG. 9C) Western blotting of the cells from (a) indicates that both C99 fragments (FL and 659) undergo γ-cleavage—as indicated by the shift upon inhibiting γ-cleavage by GSI. These data suggest that gene editing by the APP-gRNA likely does not affect APP γ-cleavage, and that the effects seen on the amyloid pathway are likely due to modulation of APP-β-cleavage.

(FIG. 10A) Computationally predicted top five off-target (OT) sites in the genome, that can be potentially targeted by the mouse and human APP-sgRNAs (mismatched nucleotides in the targeting sequence are marked in red). Genomic locations corresponding to the sequences is shown on the right column (note most are in non-coding regions). (FIG. 10B) Strategy of T7 endonuclease digestion assay to detect genome-editing events. Genomic DNA was PCR amplified with primers bracketing the modified locus. PCR products were then rehybridized, yielding three possible structures. Duplexes containing a mismatch were digested by T7 endonuclease I. DNA gel analysis was used to calculate targeting efficiency. Note digested fragments in the gel indicates cleavage. (FIG. 10C) Gene edits at the APP locus by the APP-sgRNA, as seen by T7 endonuclease digestion. Note two digested fragments were recognized after T7 endonuclease digestion. (FIGS. 10D-10E) T7 endonuclease assays of potential off-target sites (mouse and human). No digested fragments are seen, indicating that the sgRNAs do not generate detectable gene edits at these sites. (FIG. 10F) Comparison of APLP1 and 2 sequences with APP at the sgRNA targeting site. Asterisks mark conserved nucleotide sequences, and the PAM sites are underlined. Nucleotide mis-matches are highlighted in yellow. Note extensive mismatch of the mouse and human sequences at the sgRNA targeting site. (FIG. 10G) Left: Off-target TIDE analysis of APP family members APLP1 and 2 in mouse (neuro 2a) and human (HEK) cell lines following lentiviral integration of Cas9 using TIDE. No modifications were detected below the TIDE limit of detection (dotted line) in either of the populations, indicating that the APP-gRNA was unable to edit APLP 1/2. Right: TIDE analysis of APLP1 and 2 loci in mouse and human cell lines. Neither of the populations had significant editing at either of the two loci, and all sequences had a near perfect correlation to the model.

(FIG. 11A) Cultured hippocampal neurons were transfected with APP(WT):GFP or APP(659):GFP, and kinetics of APP particles were imaged live in axons and dendrites. (FIG. 11B) Representative kymographs and quantification of APP kinetics in axons. Note that there was no change in frequency of transport, and only a modest reduction in run-length and velocity. Error bars, mean±SEM of 325 APP(WT):GFP and 310 APP(659):GFP vesicles in 10-12 neurons from two independent experiments. Frequency: $p=0.4635$ (APP_antero vs APP659_antero); $p=0.6650$ (APP_retro vs APP659_retro); $p=0.7420$ (APP-_stat vs APP659_stat). Velocity: $P<0.0001$ (APP_antero vs APP659_antero); $p=0.9419$ (APP_retro vs APP659_retro). Run length: $p<0.0001$ (APP_antero vs APP659_antero); $p=0.2433$ (APP_retro vs APP659_retro). (FIG. 11C) Representative kymographs and quantification of APP kinetics in dendrites. Error bars, mean±SEM of 130 APP(WT):GFP and 115 APP(659):GFP particles in 10-12 neurons from two independent experiments. Frequency: $p=0.3245$ (AP-P_antero vs APP659_antero); $p=0.5438$ (APP_retro vs APP659_retro); $p=0.2394$ (APP_stat vs APP659_stat). Velocity: $p=0.0120$ (APP_antero vs APP659_antero); $p=0.6248$ (APP_retro vs APP659_retro). Run length: $p=0.1352$ (APP_antero vs APP659_antero); $p=0.4284$ (AP-P_retro vs APP659_retro).

(FIGS. 12A-12B) Neuro2a cells were co-transfected with untagged APP-659-GG and mCherry (or untagged WT APP and mCherry as control). After incubation with anti N-terminal APP antibody (22C11) for 10 min, the cells were fixed and stained with secondary antibody to visualize surface and internalized APP (mCherry labels transfected cells). Note accumulation of APP-659-GG on the cell surface, along with decreased internalization; quantified in FIG. 12B. Mean±SEM of 25 cells for APP(WT) and 26 cells for APP-659-GG from two independent experiments, $p<0.0001$. (FIG. 12C) Expression levels of exogenous APP constructs. Note that WT and APP-659-GG were expressed at similar levels in the Neuro2a cells above.

FIG. 13 shows the sequence of human APP (nucleotide sequence SEQ ID NO:11, amino acid sequence SEQ ID NO:12) and mouse APP (nucleotide sequence SEQ ID NO:13, amino acid sequence SEQ ID NO:14) along with the corresponding sequences of the gRNA used in select gene editing embodiments described herein.

FIG. 14 shows the sequence of the Cas9 nuclease gene sequence.

FIG. 15 shows the sequence and vector map of an exemplary vector (SEQ ID NO:17) for APP truncation at amino acid 659. The vector includes the gRNA sequence (lowercase italics) and the Cas9 nuclease sequence.

FIG. 16 shows the sequence and vector map of an exemplary Cas9 vector (SEQ ID NO:18).

FIG. 17 shows the sequence and vector map of an exemplary APP sgRNA vector (SEQ ID NO:19).

INCORPORATION BY REFERENCE

Figures 1A, 1B, 1C, 1D, 1E, 1F:
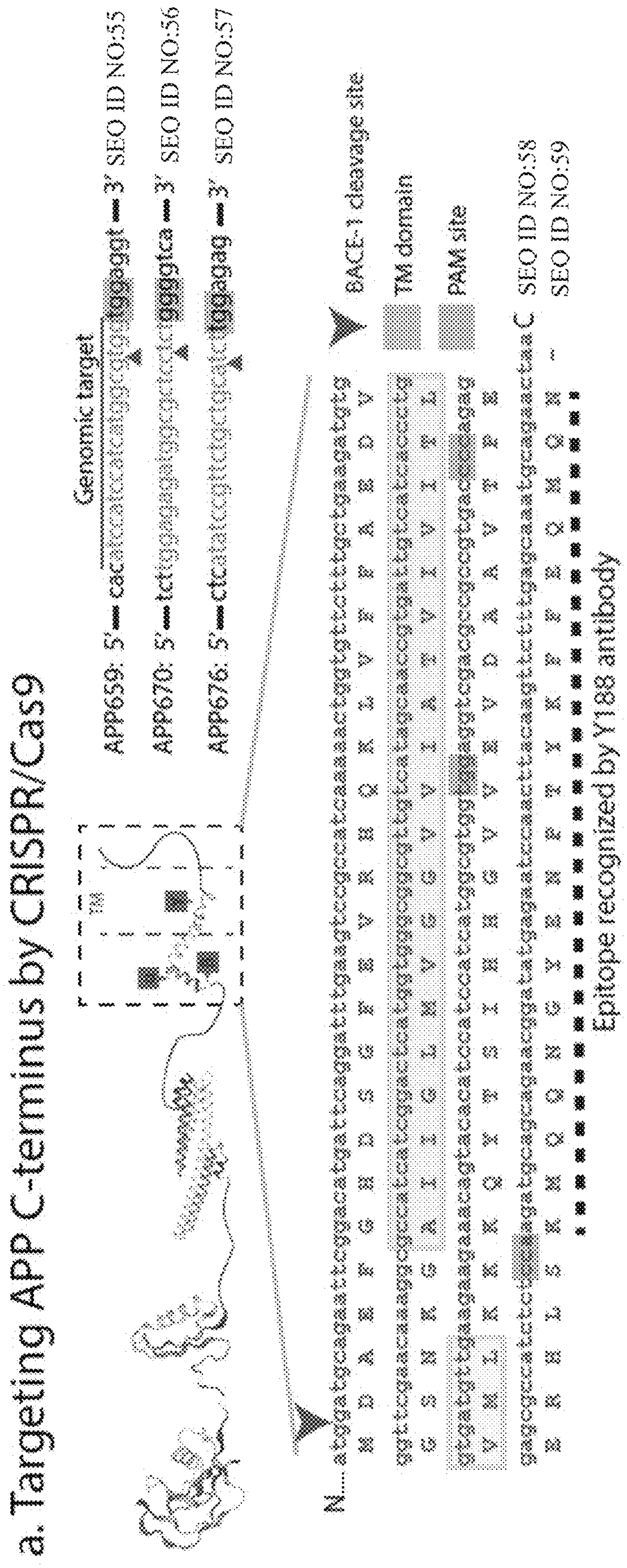
FIGS. 1A-1F show manipulation of the amyloid pathway by CRISPR/Cas9 editing.
Figures 1A, 1B, 1C, 1D, 1E, 1F:
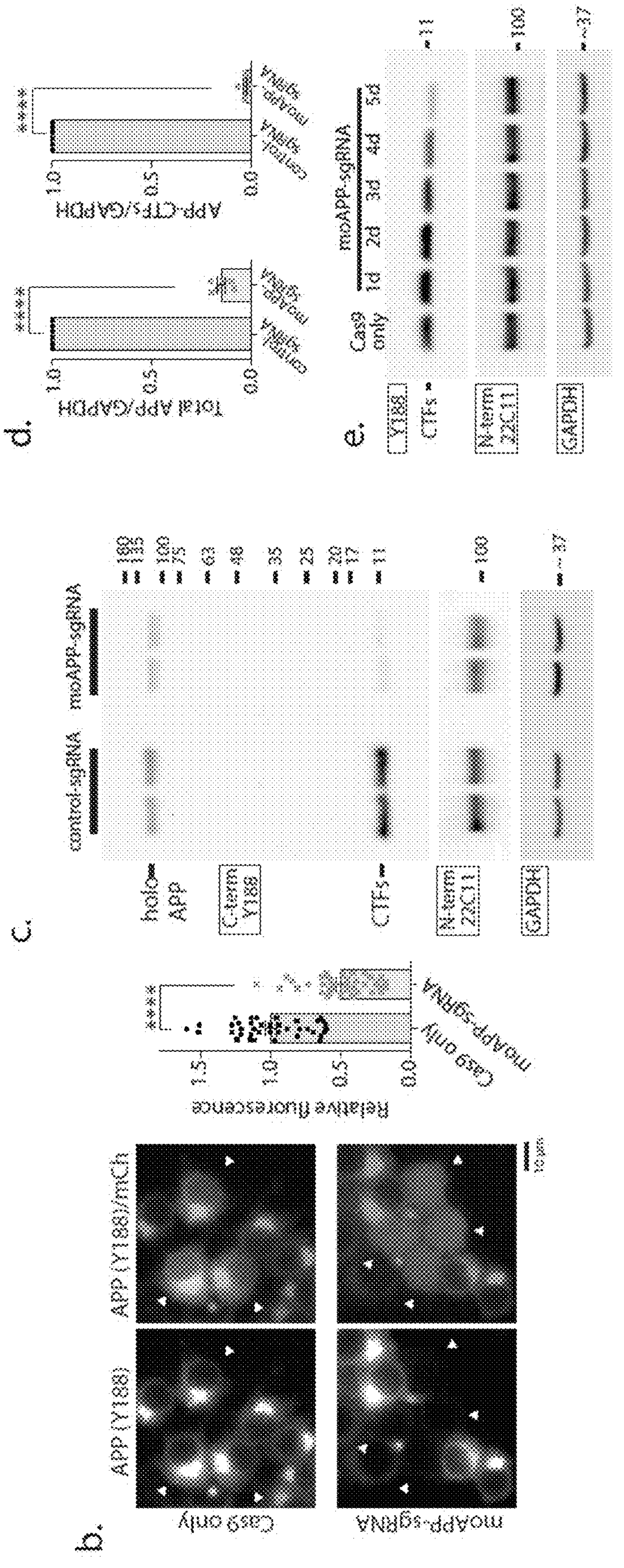
Figures 1A, 1B, 1C, 1D, 1E, 1F:
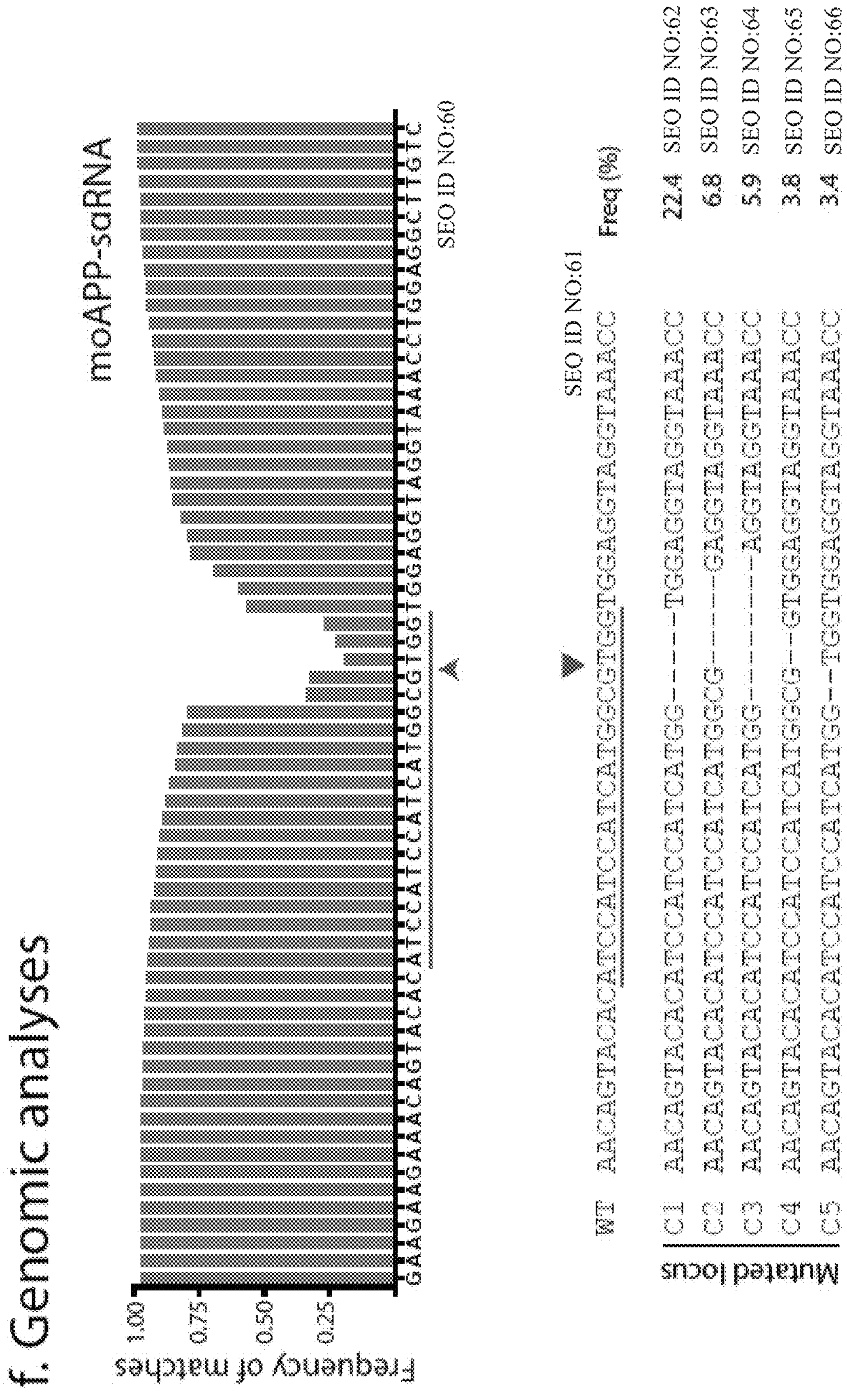

All publications, including but not limited to patents and patent applications, cited in this specification are herein incorporated by reference as though set forth in their entirety in the present application.

DETAILED DESCRIPTION OF THE INVENTION

In General

Gene-editing methods, such as CRISPR/Cas9 guided gene-editing, hold promise as a therapeutic tool. However, few studies have applied the technology to neurodegenerative diseases. Moreover, the conventional approach of mutation-correction is limited in scope to inherited diseases which are a small fraction of neurodegenerative disease cases. The present invention introduces a strategy to edit endogenous amyloid precursor protein (APP) at the extreme C-terminus and selectively attenuate the amyloidogenic pathway—a key pathologic cascade in Alzheimer's disease (AD). In the method of the present invention, the APP N-terminus remains intact and protective α-cleavage is up-regulated.

The Examples below demonstrate that robust APP-editing is demonstrated in cell lines, human stem cells, cultured neurons, and in mouse brains. Physiologic parameters remain unaffected. Without being bound by any particular theory, the present invention works by restricting the physical interaction of APP and BACE-1, said interaction being the rate-limiting step in amyloid-β (Aβ) production. The Examples below delineate underlying mechanisms that abrogate APP/BACE-1 interaction in this setting. The invention offers an innovative 'cut and silence' gene-editing strategy that could be a new therapeutic paradigm for AD.

CRISPR/Cas9 works by inducing sequence-specific double-stranded breaks (DSBs) in DNA. After such breaks, the cell undergoes an error-prone repair process called non-homologous end joining, leading to a disruption in the translational reading frame, often resulting in frameshift mutations and premature stop codons. For the system to work, at least two components must be introduced in cells: a Cas9 nuclease and a guide RNA. Described herein are CRISPR/Cas9 constructs suitable for truncation of the APP protein and disruption of amyloid-β production.

Constructs of the Present Invention

In a first aspect, the present invention provides a construct for CRISPR mediated cleavage of the APP gene. The constructs of the present invention include a nucleotide sequence encoding a Cas9 nuclease and a guide RNA (gRNA). In some embodiments the sequence encoding the Cas9 nuclease and the gRNA are included on a single vector construct. In some embodiments the sequence encoding the Cas9 nuclease is included in a vector construct separate from a vector construct encoding for the gRNA. Additionally, the construct may include a promoter, a poly(A) tail, an optional reporter element, and an optional selection marker such as an ampicillin selection marker.

As used herein "Cas9 nuclease" refers to the RNA-guided DNA endonuclease enzyme associated with the CRISPR adaptive immunity system in *Streptococcus pyogenes* and other bacteria. The Cas9 nuclease includes two nuclease domains, a RuvC-like nuclease domain located at the amino terminus, and a HNH-like nuclease domain. In some embodiments, the sequence of the Cas9 nuclease is the sequence included in FIG. 14 (SEQ ID NO:15).

In some embodiments, the Cas nuclease is expressed under the control of a neuron specific promoter or ubiquitous promoter. The neuron specific promoter may be any neuron specific promoter known in the art (see for example, Swiech L et al., In vivo interrogation of gene function in the mammalian brain using CRISPR-Cas9. Nature Biotechnology 2015 January; 33(1): 102-6). In some embodiments the neuron specific promoter is the human synapsin 1 (hSyn1) promoter. In some embodiments the neuron specific promoter is the mouse Mecp2 promoter (pMecp2). In some embodiments the ubiquitous promoter is the chicken 3-actin promoter. In some embodiments, the ubiquitous promoter is an EFS promoter.

In one embodiment of the present invention, the construct is specific for the extreme C-terminus of the APP gene. By "APP gene" or "amyloid precursor protein", we mean to include the human APP gene as disclosed in Hendricks et al (Hendriks L et al. Presenile dementia and cerebral haemorrhage linked to a mutation at codon 692 of the beta-amyloid precursor protein gene. Nature Genetics 1992 June; 1(3): 218-21) and recited herein as SEQ ID NO:11. The amino acid sequence of the APP gene is recited as SEQ ID NO:12.

As used herein "extreme C-terminus," refers of a portion of the C-terminus of the APP protein which, when absent, is sufficient to disrupt the interaction between APP and BACE. The truncated APP lacking the extreme C-terminus will still include its native N-terminus, the transmembrane domain and the residual C-terminal region. Typically, the extreme C-terminus of the APP protein will mean 8 or more amino acids at the C-terminus of the APP protein. This may be accomplished by CRISPR/Cas9 mediated cleavage of the APP gene such that the expressed APP protein is truncated to a length selected from the group consisting of 659, 670, 676, or 686, relative to SEQ ID NO:12 (human) or SEQ ID NO:14 (mouse). In some embodiments, the APP gene is cleaved following a nucleotide selected from the group consisting of 1978, 2009, 2010, 2029, and 2058 relative to SEQ ID NO:11 (human) or SEQ ID NO:14 (mouse). A list of these cleavage sites is included in the table below.

As used herein "guide RNA (gRNA)" refers to the 20 nucleotide target sequence which directs Cas9 mediated cleavage within the APP gene. The gRNA will be encoded on a synthetic RNA construct which additionally includes the tracrRNA sequence. While the gRNA sequence is variable and will be specific for the cleavage site of interest, the tracrRNA is the same for all gRNA sequences used. The tracrRNA sequence is SEQ ID NO:16 The gRNA described herein are specific for the truncation of the C-terminal segment of APP. Suitable target sequences within the APP gene for design of gRNA sequences are recited below, which includes the sequence of the gRNA.

tracrRNA (SEQ ID NO:16):
5'-GTTTTAGAGCTAGAAATAGCAAGTTAAAATAAGGCTAGTC

CGTTATCAACTTGAAAAAGTGGCACCGAGTCGGTGCTTTT -3

TABLE 1

| HUMAN APP (FULL LENGTH 695 AA) | | | | | |
|---|---|---|---|---|---|
| sgRNA name | sgRNA sequence (5'-3') | SEQ ID NO: | Position relative to APP | Cas9 cleavage between nucleotides | Length of truncated protein |
| sgRNA 1 | atccattcatcatggtgtgg | 1 | 1962-1981 | 1978/1979 | 659 aa |
| sgRNA 2 | tggacaggtggcgctcctct | 2 | 2007-2026 | 2009/2010 | 670 aa |
| sgRNA 3 | ttggacaggtggcgctcctc | 3 | 2008-2027 | 2010/2011 | 670 aa |
| sgRNA 4 | gtagccgttctgctgcatct | 4 | 2027-2046 | 2029/2030 | 676 aa |
| sgRNA 5 | tgctcaaagaacttgtaggt | 5 | 2056-2075 | 2058/2059 | 686 aa |

TABLE 2

| MOUSE APP (FULL LENGTH 695 AA) | | | | | |
|---|---|---|---|---|---|
| sgRNA name | sgRNA sequence (5'-3') | SEQ ID NO: | Position relative to APP | Cas9 cleavage between nucleotides | Length of truncated protein |
| sgRNA 1 | atccatccatcatggcgtgg | 6 | 1962-1981 | 1978/1979 | 659 aa |
| sgRNA 2 | tggagagatggcgctcctct | 7 | 2007-2026 | 2009/2010 | 670 aa |
| sgRNA 3 | ttggagagatggcgctcctc | 8 | 2008 -2027 | 2010/2011 | 670 aa |
| sgRNA 4 | atatccgttctgctgcatct | 9 | 2027-2046 | 2029/2030 | 676 aa |
| sgRNA 5 | tgctcaaagaacttgtaagt | 10 | 2056-2075 | 2058/2059 | 686 aa |

III promoters include, but are not limited to, U6 and H1 promoters. A promoter, generally, is a region of nucleic acid that initiates transcription of a nucleic acid encoding a product. A promoter may be located upstream (e.g., 0 bp to −100 bp, −30 bp, −75 bp, or −90 bp) from the transcriptional start site of a nucleic acid encoding a product, or a transcription start site may be located within a promoter. A promoter may have a length of 100-1000 nucleotide base pairs, or 50-2000 nucleotide base pairs. In some embodiments, promoters have a length of at least 2 kilobases (e.g., 2-5 kb, 2-4 kb, or 2-3 kb).

In some embodiments, the construct comprises an optional reporter element. The reporter element may be any reporter known in the art including, but not limited to, mCherry, green fluorescent protein, and human influenza hemagglutinin (HA).

Cleavage of the APP gene will occur between the 3rd and 4th nucleotides from the PAM site associated with the target sequence in the APP gene. For the sgRNA 1, the PAM site is on the sense strand of the APP gene, the sgRNA of SEQ ID NOs:1 and 6 are complementary to the antisense strand of the APP gene, and the cleavage will occur between nucleotides 1978 and 1979 relative to SEQ ID NO:11 (human) or SEQ ID NO:14 (mouse). For sgRNA 2, 3, 4 and 5, the PAM site is on the antisense strand of the APP gene, the sgRNA of SEQ ID NOs:2-5 and 7-10 are complementary to the sense strand of the APP gene, and the cleavage site is between nucleotides 2009 and 2010 for sgRNA 2, between nucleotides 2010 and 2011 for sgRNA 3, between nucleotides 2029 and 2030 for sgRNA 4 and between nucleotides 2058 and 2059 for sgRNA 5, relative to SEQ ID NO:11 (human) or SEQ ID NO:14 (mouse).

In some embodiments, the gRNA or tracrRNA is modified by any means known in the art. Common methods for gRNA or tracrRNA modification include chemical modifications or modifications to axillary sequences appended to the RNA to increase efficiency known in the art.

In some embodiments, the gRNA is expressed under the control of an RNA Pol III promoter. Examples of RNA Pol In some embodiments, the constructs are packaged in a vector suitable for delivery into a mammalian cell, including but not limited to, an adeno-associated viral (AAV) vector, a lentiviral vector, or a vector suitable for transient transfection. Suitable vector backbones are known and commercially available in the art. For example, see Deverman et al. (Cre-dependent selection yields AAV variants for widespread gene transfer to the adult brain, Nature Biotechnology, 34(2):204-209, 2016) and Chan et al. (Engineered AAVs for efficient noninvasive gene delivery to the central and peripheral nervous system, Nature Neuroscience, 20(8): 1172-1179, 2017) which are incorporated herein by reference in their entirety. In some embodiments, the vector is an AAV vector and the gRNA and Cas9 constructs are encoded on separate vectors. In some embodiments, the vector is a lentiviral vector and the gRNA and Cas9 constructs are encoded on a single vector. In some embodiments, the vector is a vector suitable for transient transfection and the gRNA and Cas9 constructs are encoded on a single vector. In one embodiment the vector includes the sequence of SEQ ID NO:17. In some embodiment, the gRNA and Cas9 constructs are encoded on separate AAV vectors wherein the gRNA is encoded on a vector comprising SEQ ID NO:19 and the Cas9 construct is encoded on a vector comprising SEQ ID NO:18. In some embodiments, the vector is a lentiviral vector and comprises the sequence of SEQ ID NO:20. The vectors of SEQ ID NOs:17-20 are included in FIGS. 15-18.

In some embodiments, the vectors encoding the constructs described herein may optionally include a monoclonal antibody tag (e.g., FLAG), one or more origins of replication (e.g., fl ori), one or more terminator sequences (e.g., bGH), one or more polyadenylation tags (bGH poly (A)), and one or more inverted terminal repeats (ITR). The vector may also include one or more selectable markers, such as an antibacterial resistance marker such as an ampicillin selectable marker. A skilled artisan will be familiar with the elements and configurations necessary for vector construction to encode the constructs described herein.

Methods of the Present Invention

The constructs described herein may be formulated with a pharmaceutically acceptable carrier for administration to a patient in need thereof. A pharmaceutically acceptable carrier may be, but is not limited to, a nanoparticle cage including the one or more vectors of the present invention.

To function as therapeutic agents, the constructs described herein are delivered into neurons in the patient's brain, crossing the blood brain barrier (BBB). In one embodiment, one would attach or associate the CRISPR components with a delivery system, such as a nanoparticle delivery system. In some embodiments, the constructs are formulated using an AAV vector and are delivered intravenously. In some embodiments, the constructs are delivered intrathecally into the spinal fluid of the patient. In some embodiments, the constructs are delivered directly into the brain of the patient.

As used herein, the terms "treat" and "treating" refer to therapeutic measures, wherein the object is to slow down or alleviate (lessen) an undesired physiological change or pathological disorder resulting from Alzheimer's disease. For purposes of this invention, treating the disease, condition, or injury includes, without limitation, alleviating one or more clinical indications, reducing the severity of one or more clinical indications of Alzheimer's disease, diminishing the extent of the condition, stabilizing the subject's Alzheimer's disease (i.e., not worsening), delay or slowing, halting, or reversing Alzheimer's disease and bringing about partial or complete remission Alzheimer's disease. Treating Alzheimer's disease also includes prolonging survival by days, weeks, months, or years as compared to prognosis if treated according to standard medical practice not incorporating treatment with the constructs described herein.

Subjects in need of treatment can include those already having or diagnosed with Alzheimer's disease as well as those prone to, likely to develop, or suspected of having Alzheimer's disease, such as a subject with a genetic predisposition to or family history of Alzheimer's disease. Subjects in need to treatment may be those with a familial AD mutation or wild-type patients without a mutation. In some embodiments, a subject in need of treatment may be a subject who had been diagnosed by a positron emission tomography (PET) scan, a blood test or other means known in the art to have AD or to be predisposed to AD. Pre-treating or preventing Alzheimer's disease according to a method of the present invention includes initiating the administration of a therapeutic (e.g., the APP gRNA and Cas9 constructs described herein) at a time prior to the appearance or existence of the disease or injury, or prior to the exposure of a subject to factors known to induce Alzheimer's disease. Pre-treating the disorder is particularly applicable to subjects at risk of having or acquiring the disease injury.

As used herein, the terms "prevent" and "preventing" refer to prophylactic or preventive measures intended to inhibit undesirable physiological changes or the development of Alzheimer's disease. In exemplary embodiments, preventing Alzheimer's disease comprises initiating the administration of a therapeutic (e.g., the APP gRNA and Cas9 constructs described herein) at a time prior to the appearance or existence of Alzheimer's disease such that the disease, or its symptoms, pathological features, consequences, or adverse effects do not occur. In such cases, a method of the invention for preventing Alzheimer's disease comprises administering the APP gRNA and Cas9 constructs described herein to a subject in need thereof prior to the onset or development of Alzheimer's disease in a patient at risk for Alzheimer's disease such as a patient with a genetic risk factor or a patient with a family history of Alzheimer's disease.

As used herein, the terms "subject" or "patient" are used interchangeably and can encompass a human or mouse. As used herein, the phrase "in need thereof" indicates the state of the subject, wherein therapeutic or preventative measures are desirable. Such a state can include, but is not limited to, subjects having Alzheimer's disease or a pathological symptom or feature associated with Alzheimer's disease.

Examples

The embodiment described in this example demonstrates truncation of the C-terminus of the APP protein, attenuation of APP-β-cleavage and Aβ production, and manipulation of the amyloid pathway using CRISPR/Cas9 gene editing.

A common theme in neurodegenerative diseases is that proteins normally present in the brain (APP, tau, α-synuclein, TDP-43, etc.) acquire toxic properties—or trigger pathologic cascades—that ultimately lead to synaptic loss and neurodegeneration. Our broad idea is to rationally edit small segments of endogenous proteins known to play key roles in the progression of disease, with the ultimate goal of attenuating their pathologic activity. As endogenous proteins expectedly play physiologic roles, it is also important to conserve their normal function, as far as possible. Here we show conceptual proof of this 'selective silencing' approach for APP. APP is a single-pass transmembrane protein, cleaved by the enzymes β- and γ-secretases to ultimately generate Aβ—a neuropathologic hallmark of AD. APP cleavage by the β-secretase BACE-1 is the rate limiting step in this 'amyloidogenic' pathway. Alternatively, APP is cleaved by α-secretases—the 'non-amyloidogenic' pathway—that is thought to be neuroprotective because it precludes β-cleavage of APP (6,7); and studies have highlighted neuroprotective effects of APP-α-cleavage products in vivo (8,9).

We recently developed a Bi-molecular fluorescence complementation (BifC) assay to visualize the physical approximation of APP and BACE-1 in neurons (10). As a control for validation, we found that a C-terminal deletion also abrogated APP/BACE-1 complementation (10); in line with previous studies showing that deletions/mutations of the APP C-terminus can attenuate Aβ production (11-13). Collectively, these observations originally gave us the idea of using CRISPR/Cas9-mediated truncation of native APP to attenuate APP-β-cleavage and Aβ production in AD. Using CRISPR-tools, cell/molecular biology, live imaging, deep sequencing, electrophysiology and in vivo animal studies, here we highlight a strategy to favorably manipulate the amyloid pathway by gene editing.

Results and Discussion

Figures 6A, 6B, 6C, 6D, 6E:
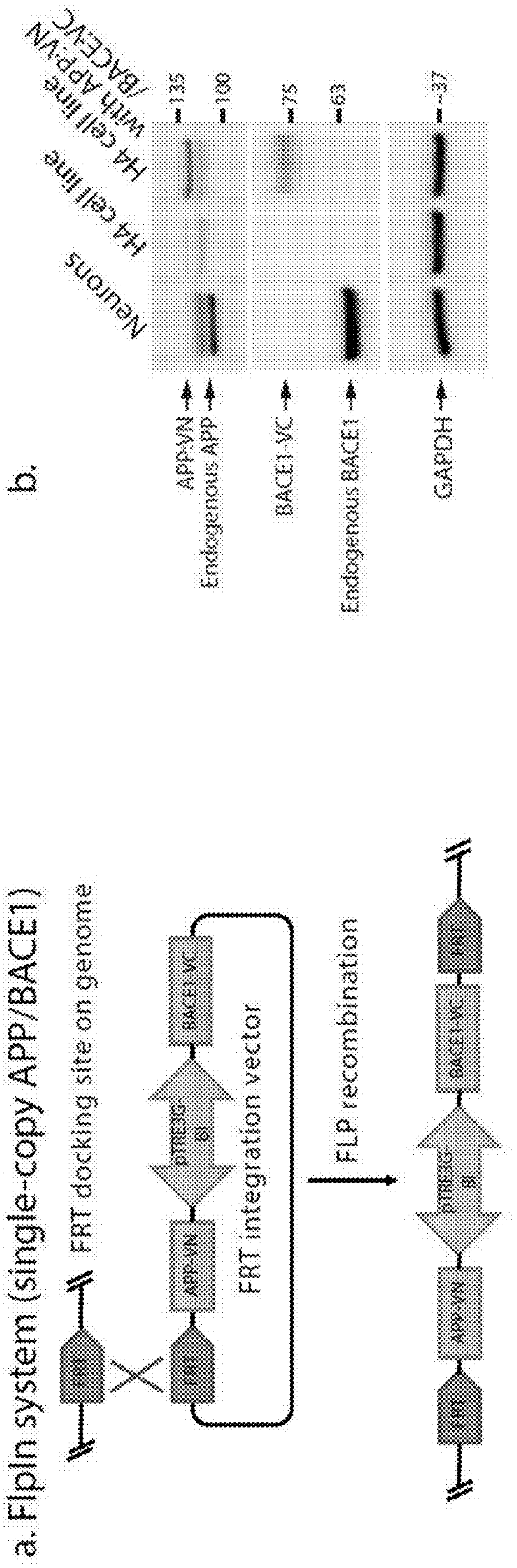
FIGS. 6A-6E show the choice of CRISPR editing site at APP C-terminus.

CRISPR/Cas9 editing of APP C-terminus—The CRISPR/Cas9 system consists of a Cas9 nuclease enzyme that generates double-stranded breaks in DNA, and a custom-designed single guide-RNA (sgRNA) that targets the Cas9 to specific sites in the host genomic DNA. Typically, the synthetic sgRNAs are complementary to stretches of genomic DNA containing 3-nt PAM (protospacer adjacent motif) and flanking 20-nt sequences. Since subsequent repair after DNA-breaks is naturally error-prone, insertions and deletions (indels) are generated at the cut-sites, leading to disruption of the translational reading frame and effectively truncated proteins (reviewed in 14). We identified three PAM sites at the APP C-terminus that are conserved in both human and mouse, and synthesized sgRNAs targeting these regions (FIG. 1A). To compare the editing efficiency of these sgRNAs, we engineered a stable H4 neuroglioma cell line expressing single copies of APP:VN and BACE-1:VC (APP/BACE$^{single_copy}$), where editing efficiency of a given sgRNA could be determined as a simple fluorescence on/off readout and the effect of APP truncation could be assessed by evaluating secreted Aβ (for details, see FIGS. 6A and 6B and methods). The APP-sgRNA predicted to cut human APP at the 659 aa. (amino acid) position was the most efficient—both in editing APP as well as in attenuating Aβ- and also led to minimal indels (FIGS. 6C-6E). Accordingly, we used the APP659-sgRNA for further characterization (henceforth called 'mo-APP-sgRNA' or 'hu-APP-sgRNA' representing mouse and human specific sequences).

Figures 7A, 7B, 7C, 7D:
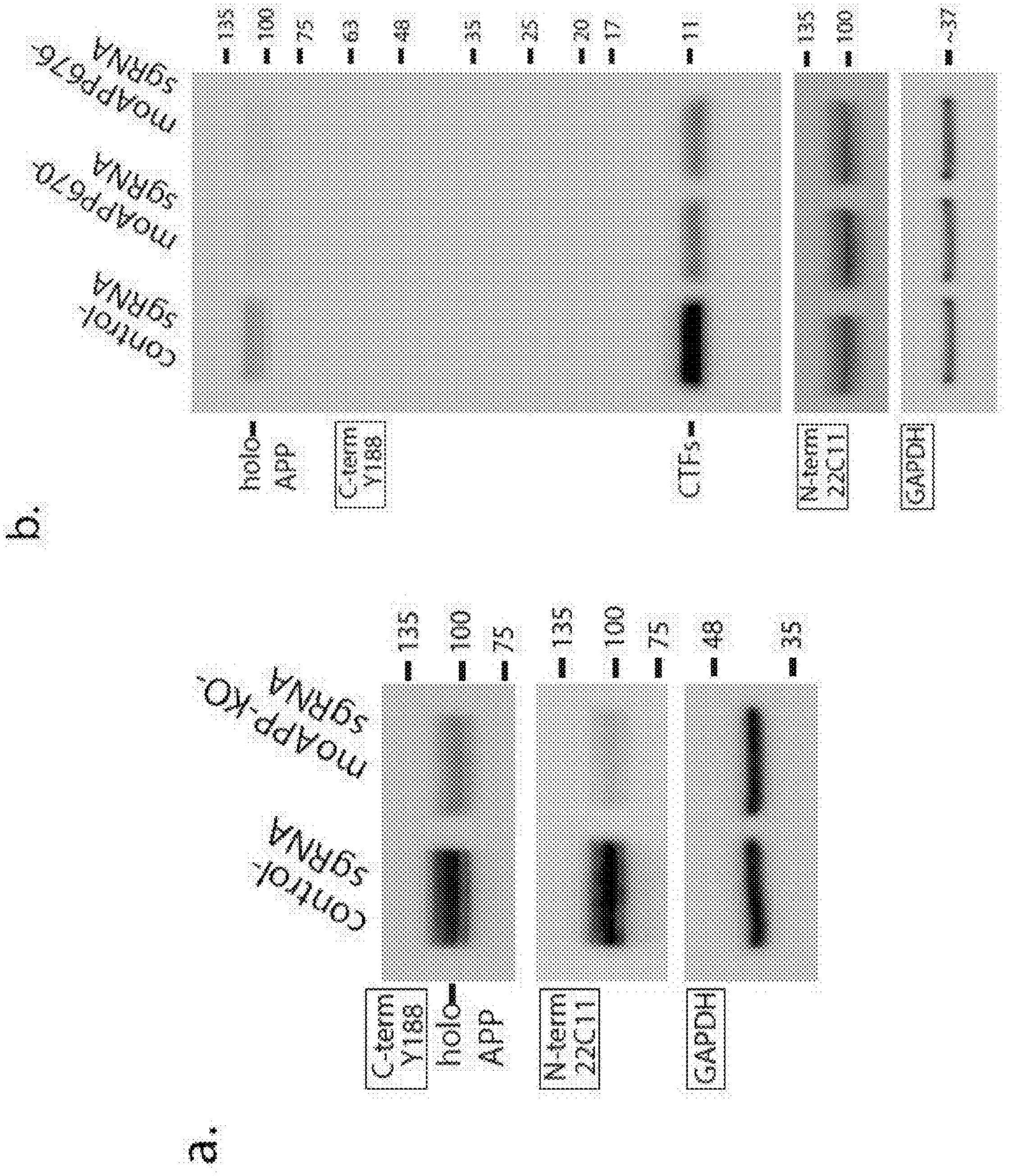
FIGS. 7A-7D show evaluation of CRISPR editing by immunoblotting in mouse Neuro2a cells.

The TGG PAM and preceding 20-nt genomic target sequence recognized by the mo-APP-sgRNA is shown in FIG. 1A (top right); and FIGS. 1B-1F shows gene editing by this sgRNA in mouse cells. Note that upon editing, the Y188 antibody—recognizing the last 20 amino acids. of APP—would not be able to identify the resultant translational product. Robust editing of endogenous APP was seen in mouse neuroblastoma cells, as determined by attenuation of immunofluorescence with the Y188 antibody (FIG. 1B), and decreased Y188-signal in western blots (FIGS. 1C-1D; FIG. 1E shows time-course of editing). Note that the edited APP is recognized by antibodies to the N-terminus, indicating selective editing of the C-terminus by the APP-sgRNA (FIGS. 1C and 1E). However, the N-terminus antibody was unable to detect APP when the entire gene was deleted (FIG. 7A). Similar results were obtained with other sgRNAs targeting APP C-terminus and other C- and N-terminus APP antibodies (FIGS. 7B and 7C). Genomic deep-sequencing confirmed efficient editing of mouse APP at the expected loci, APP-659 (FIG. 1F). Post-editing translational products show that the last 36 amino acids. are effectively truncated by APP-sgRNA (FIG. 7D). Though the TGG PAM at this site is conserved in both mouse and human APP, and the upstream sgRNA-targeting sequences only differ by two nucleotides (FIG. 2A, arrowheads); the mouse APP-sgRNA was unable to edit human APP (not shown). However, a sgRNA specific to the human APP targeting sequence robustly edited APP in HEK293 (FIGS. 8A-8C), as well as in human embryonic stem cells (FIGS. 8D-8E). CRISPR editing of APP did not alter the steady-state levels of holo-APP (note data throughout with multiple N-terminus antibodies in various cell lines).

Figures 2A, 2B, 2C, 2D, 2E, 2F, 2G, 2H:
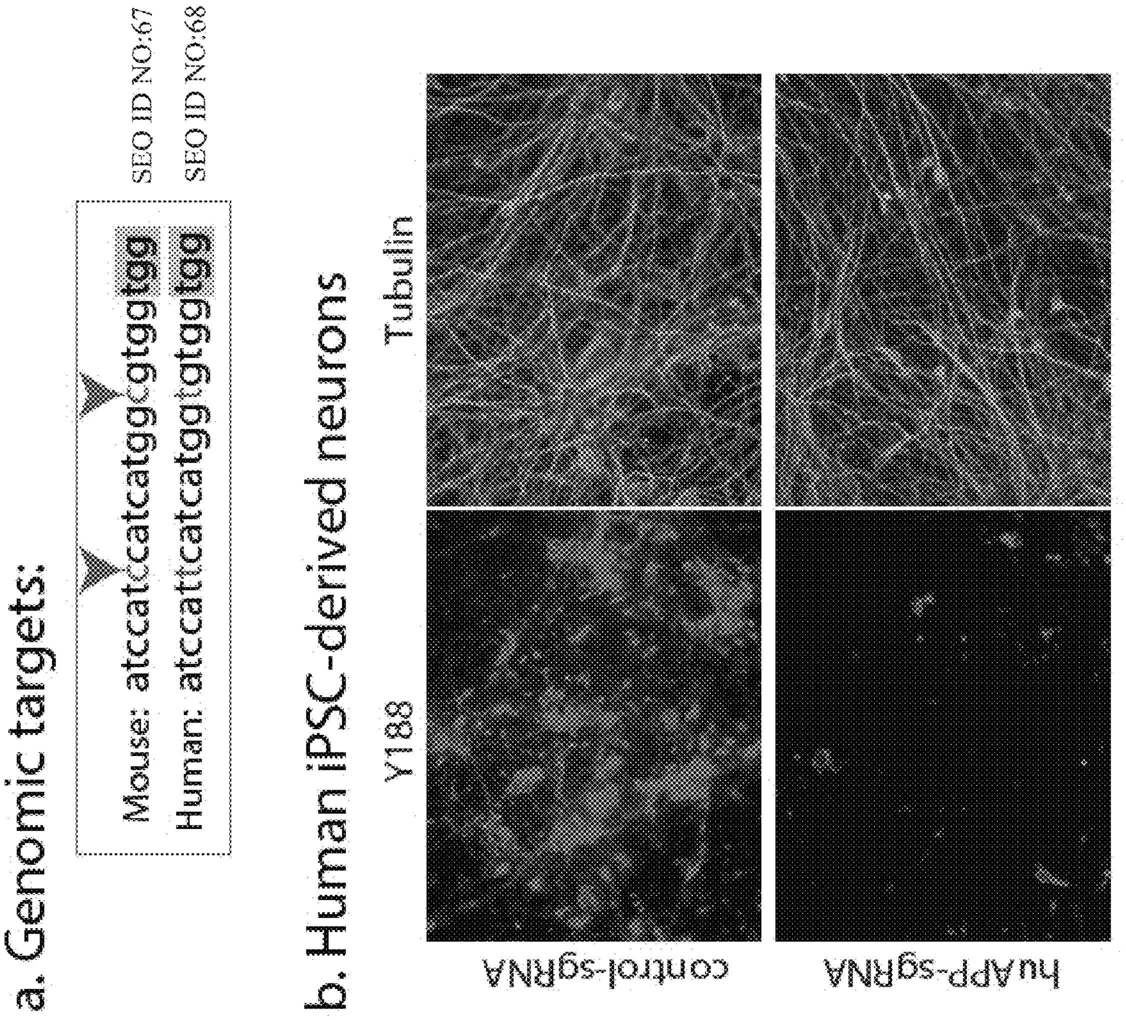
FIGS. 2A-2H show gene editing of APP C-terminus and effects on APP processing in human cells.
Figures 2A, 2B, 2C, 2D, 2E, 2F, 2G, 2H:
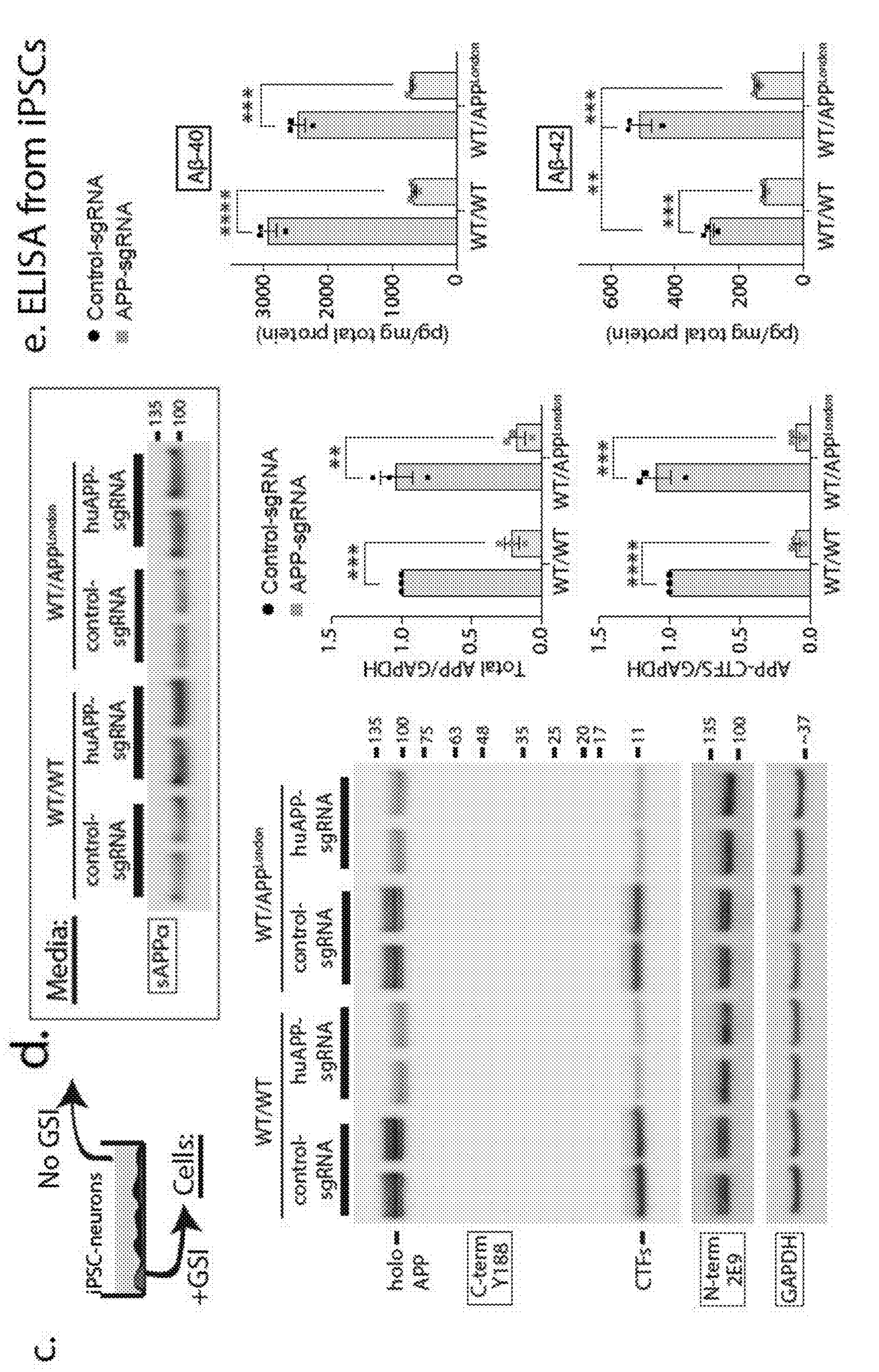

Reciprocal manipulation of the APP β/α pathway by CRISPR/Cas9 editing—Next, we examined APP editing in human iPSC-derived neurons. As shown in FIG. 2B, immunostaining with the Y188 antibody was attenuated in iPSC-neurons transduced by the hu-APP-sgRNA. To examine effects of APP editing in an "AD-like setting", we also tested the hu-APP-sgRNA in a heterozygous knock-in iPSC line carrying the most common familial AD mutation (APPV717I, also called the 'London mutation'; see methods for details of iPSC line). Both cell-lysates and supernatants were examined, to look for cellular and secreted APP products (see schematic in FIG. 2C). Immunoblotting with the Y188 antibody confirmed robust—and C-terminus selective—APP editing in both WT and APP-London iPSC lines (FIG. 2C). Examination of supernatants revealed that interestingly, APP-editing also led to increased sAPPα in both WT and London lines (FIG. 2D); suggesting upregulation of the neuroprotective α-cleavage pathway. ELISAs and western blot showed attenuated secretion of Aβ40/42 (FIG. 2E) and sAPPβ (FIG. 8F), confirming inhibition of the amyloidogenic pathway in these neurons. Genomic deep sequencing showed efficient editing of human APP by the sgRNA, with truncation of the last 36 amino acids. in human embryonic stem cells (FIGS. 2F-2H).

Figures 9A, 9B, 9C:
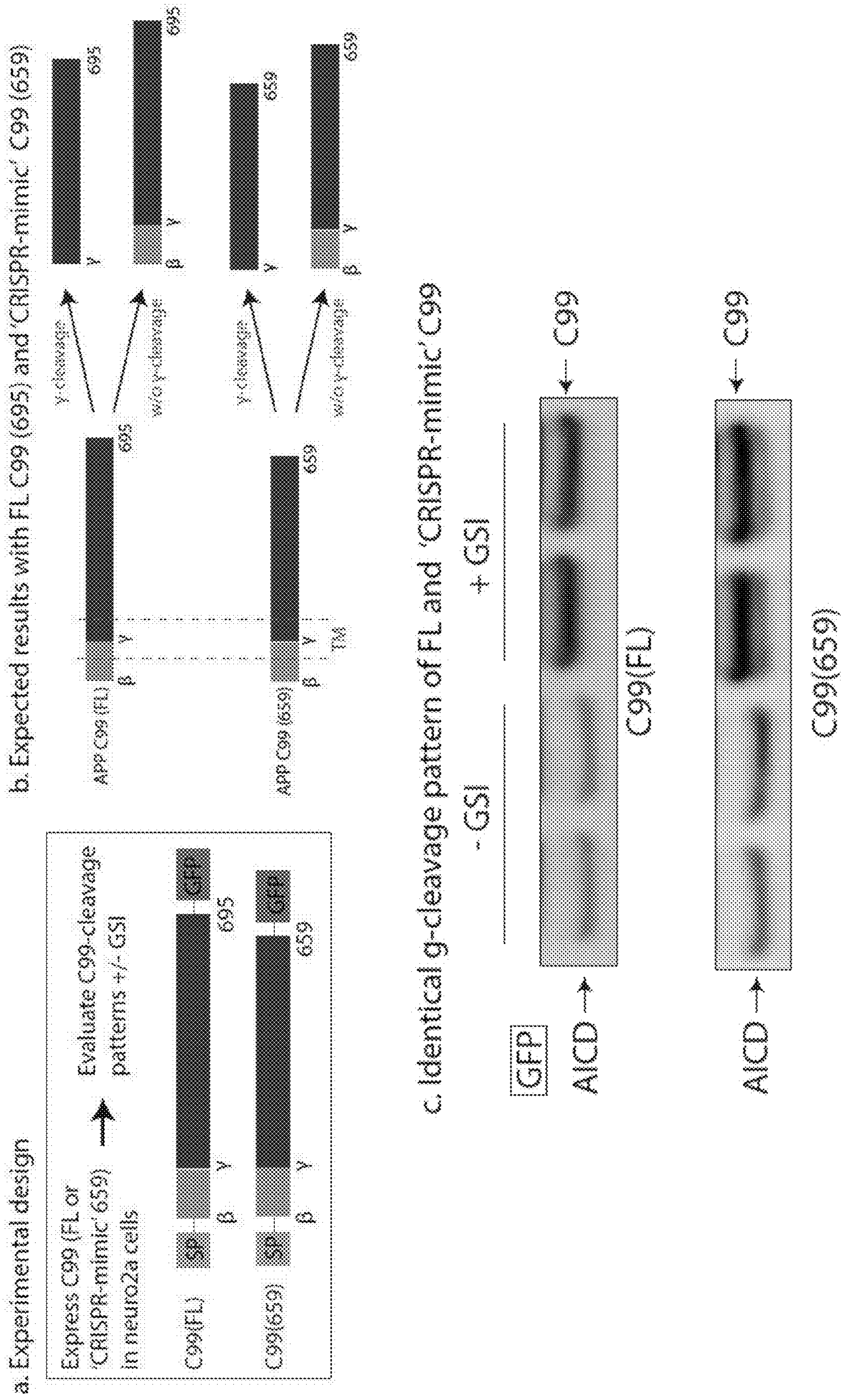
FIGS. 9A-9C show gene editing by APP-sgRNA likely does not influence APP γ-cleavage.

The data from iPSC-neurons suggest that the APP-sgRNA has reciprocal effects on APP β- and α-cleavage. To validate this in a more controlled setting, we tested the effects of APP editing in the H4 APP/BACE$^{single_copy}$ cell line, where APP-cleavage is tightly regulated. In line with the data from iPSC-neurons, the hu-APP-sgRNA had reciprocal effects on APP β- and α-cleavage in APP/BACE$^{single_copy}$ cells as well, confirming that our editing strategy has reciprocal effects on β/α cleavage (FIG. 8G). Further experiments using an APP-C99 construct (wild-type and truncated construct mimicking the CRISPR-product, APP-659) precludes an effect of the sgRNA on APP-γ-cleavage (FIGS. 9A-9C), indicating that our editing strategy is selectively affecting APP β-cleavage. Collectively, the available data strongly suggest that our gene editing strategy targeting the APP C-terminus is favorably manipulating the amyloid pathway by attenuating APP β-cleavage, while reciprocally up-regulating protective α-cleavage.

Figures 10A, 10B, 10C, 10D, 10E, 10F, 10G:
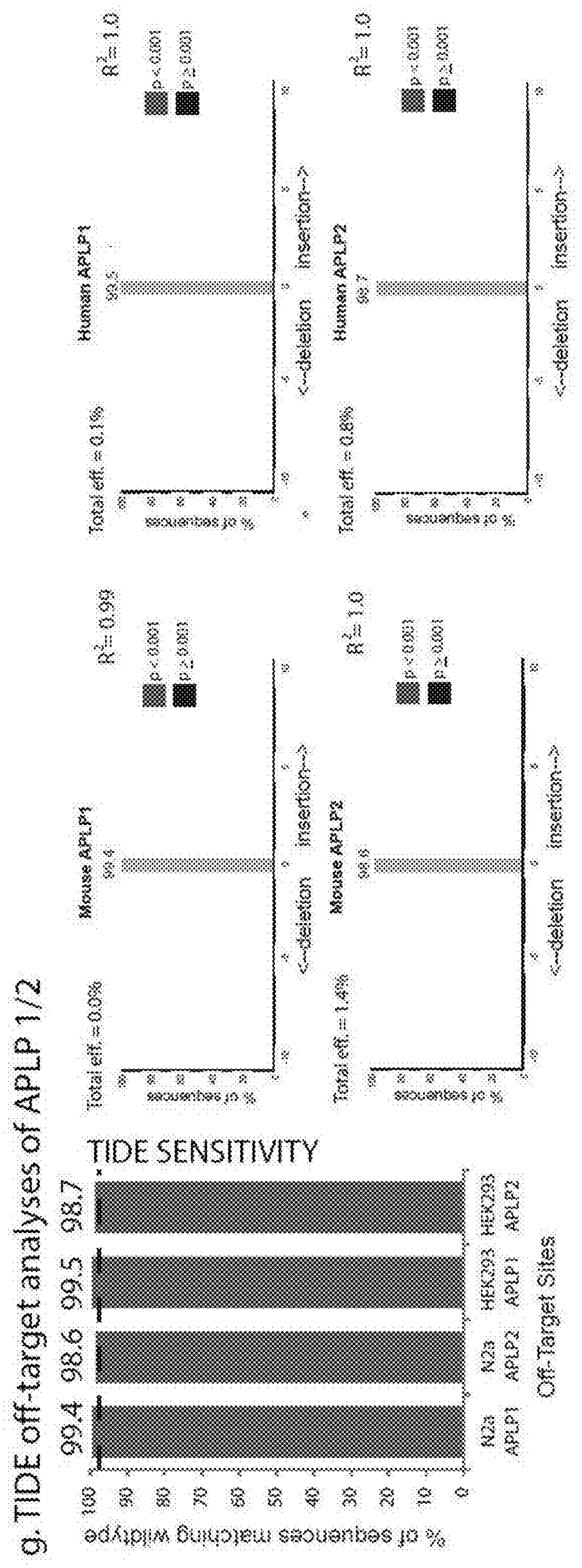
FIGS. 10A-10G show off target analyses of APP-sgRNA.

Off-target analysis and effect of APP C-terminus editing on neuronal physiology—Off-target effects of CRISPR/Cas9, due to unwanted editing of DNA-stretches resembling the targeted region, are a concern. Towards this, we asked if our mouse and human APP-sgRNA were able to edit the top five computationally predicted off-target sites (FIG. 10A; also see Table 3). No editing was seen using T7 endonuclease assays (FIGS. 10B-10E). Though APP null mice are viable, there is compensation by the two APP homologues APLP1 and 2 that undergo similar processing as APP (15,16). APLP1 and 2 were not amongst the top 50 predicted off-target sites, as their corresponding sgRNA-target sites were substantially different from APP (see sequences in FIG. 10F). For further assurance that our sgRNA was not editing the APP homologues, we performed specific off-target TIDE (Tracking of Indels by DEcomposition) analyses (17) on cells carrying the sgRNA. As shown in FIG. 10G, TIDE analyses showed no editing of APLP 1/2 by the sgRNA.

Figures 3A, 3B, 3C, 3D, 3E, 3F, 3G:
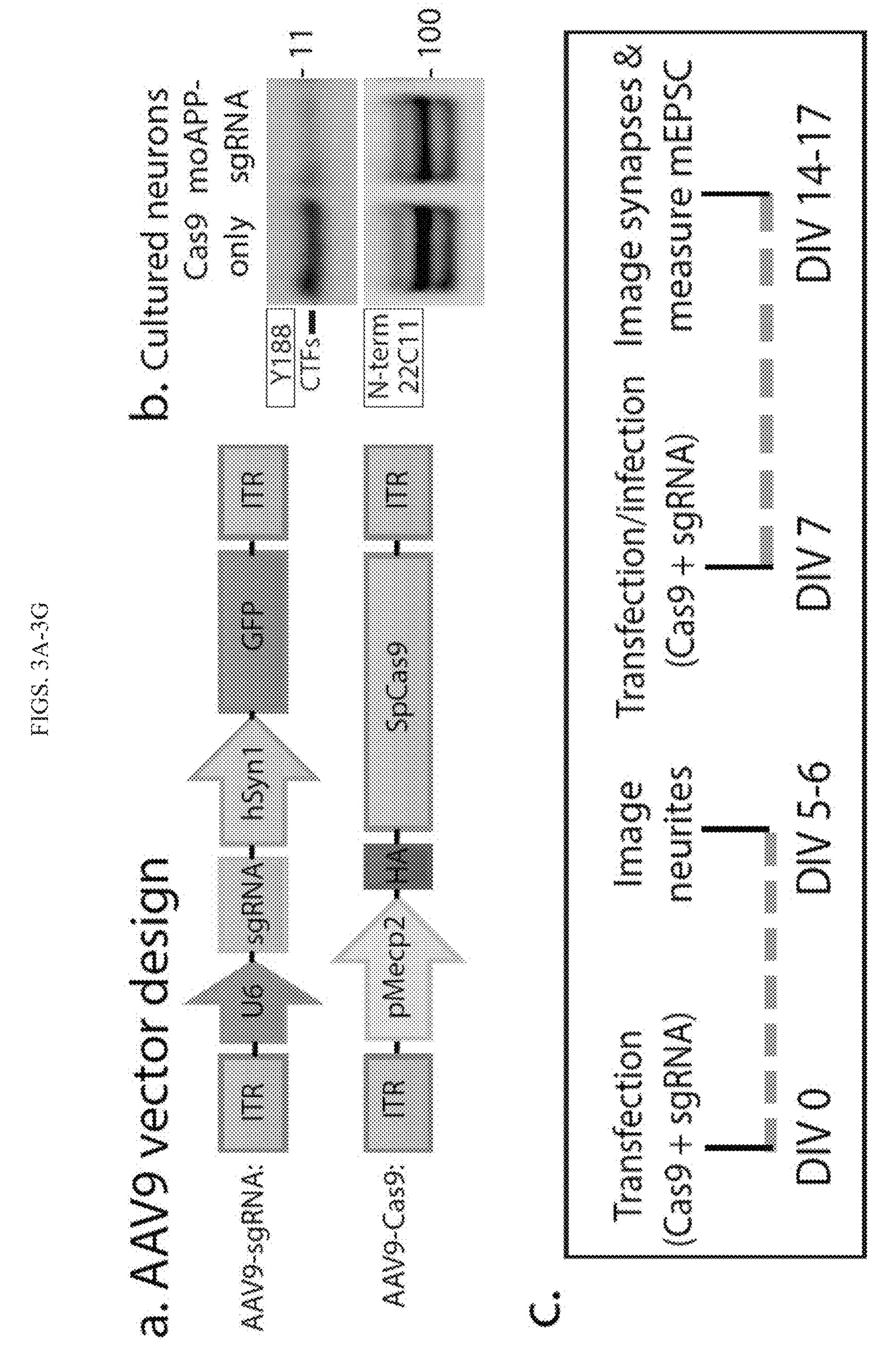
FIGS. 3A-3G show the effect of APP C-terminus editing on neuronal physiology.

APP has known physiologic roles in axon growth and signaling (18). As noted above, the N-terminus of APP—thought to play roles in axon growth and differentiation—is entirely preserved in our setting. The C-terminal APP intracellular domain (AICD) has been implicated in gene transcription, though the effect appears to be both physiologic and pathologic (19,20.) To examine potential deleterious effects of editing the extreme C-terminus of APP, we turned to cultured hippocampal neurons where various parameters like neurite outgrowth and synaptic structure/function can be confidently evaluated. To study pre-synapse structure and neuronal activity, we generated AAV9 viruses carrying the mo-APP-sgRNA and Cas9, tagged with GFP and HA respectively (see vector design in FIG. 3A) that transduced almost all cultured neurons (FIG. 3B and data not shown). In blinded analyses, we found no significant effect of the mo-APP-sgRNA on neurite outgrowth, axon-length, synaptic organization, or neuronal activity (FIGS. 3C-3G). We reason that the lack of deleterious effects upon editing is likely because: 1) most of the APP molecule remains intact after editing; 2) the APP homologues APLP1/2—that undergo similar processing as APP, generate CTFs, and are known to compensate for APP function—remain unedited; and 3) APP-cleavage is not entirely blocked by our approach.

Figures 4A, 4B, 4C, 4D, 4E, 4F, 4G:
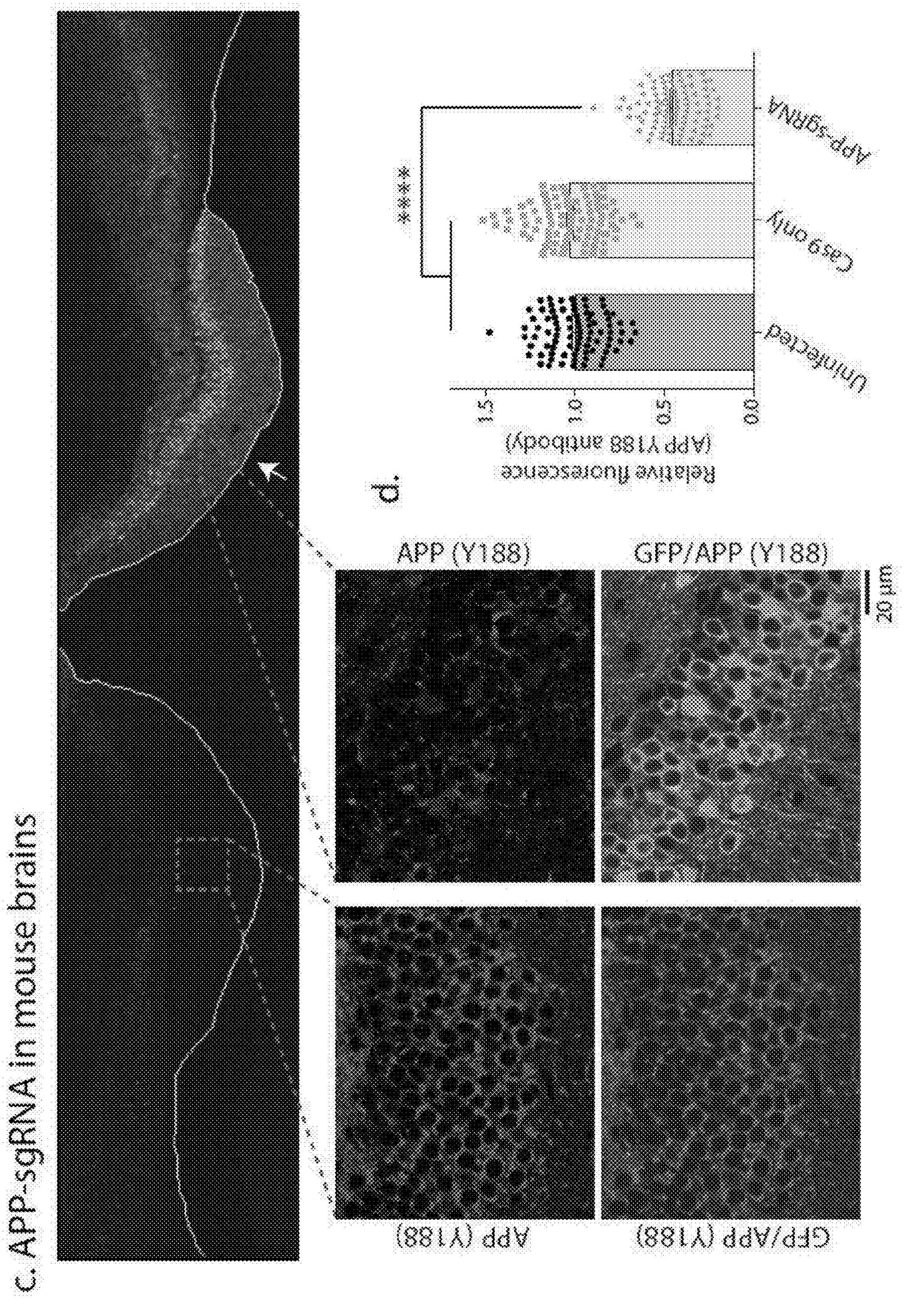
FIGS. 4A-4G show gene editing of APP C-terminus in vivo.

Editing of APP C-terminus in vivo and mechanistic details of APP β/α manipulation—Next we asked if the APP-sgRNA could edit endogenous APP in mouse brains. Injection of the AAV9s into mouse hippocampi (FIG. 4A) led to efficient transduction of both sgRNA and Cas9 in dentate neurons (86.87±2.83% neurons carrying the sgRNA also had Cas9; see representative images in FIG. 4B). Immunostaining of transduced neurons with the APP Y188 antibody showed attenuated staining, suggesting editing of endogenous APP in vivo (FIGS. 4C and 4D). To achieve a more widespread expression of the sgRNA and Cas9 in mouse brains—and also evaluate editing by biochemistry—we injected the viruses into the ventricles of neonatal (P0) mice and examined the brain after 2-4 weeks (FIG. 4E). Previous studies have shown that when AAVs are injected into the ventricles of neonatal mice, there is widespread delivery of transgenes into the brain—also called somatic transgenesis (21,22). Indeed, APP Y188 immunostaining was attenuated in cortical regions (FIG. 4F) and immunoblotting with the Y188 antibody also showed a decreased signal (FIG. 4G); indicating that the APP-sgRNA can edit APP in vivo.

Figures 5A, 5B, 5C, 5D, 5E:
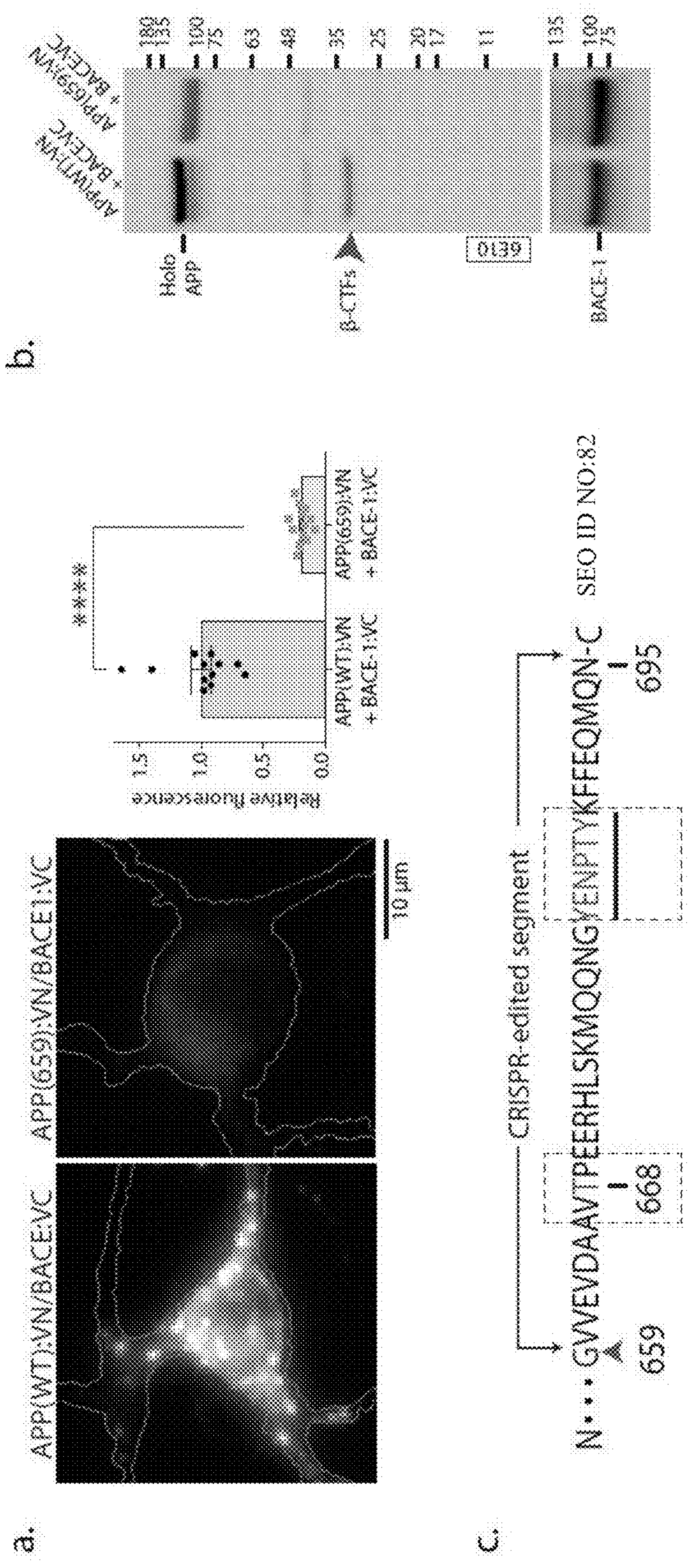
FIGS. 5A-5E show mechanistic details of CRISPR-guided APP editing.
Figures 5A, 5B, 5C, 5D, 5E:
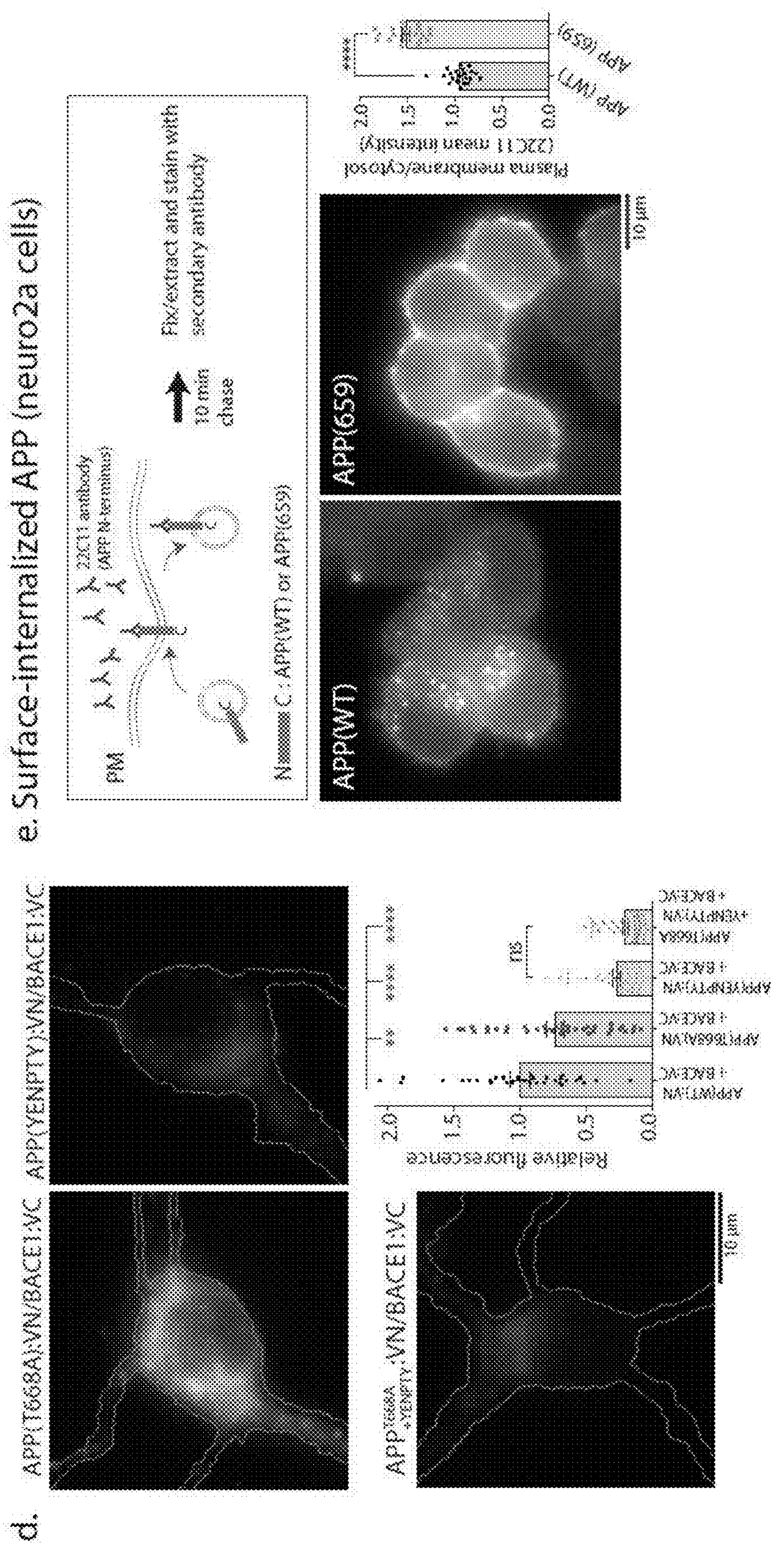
Figures 11A, 11B, 11C:
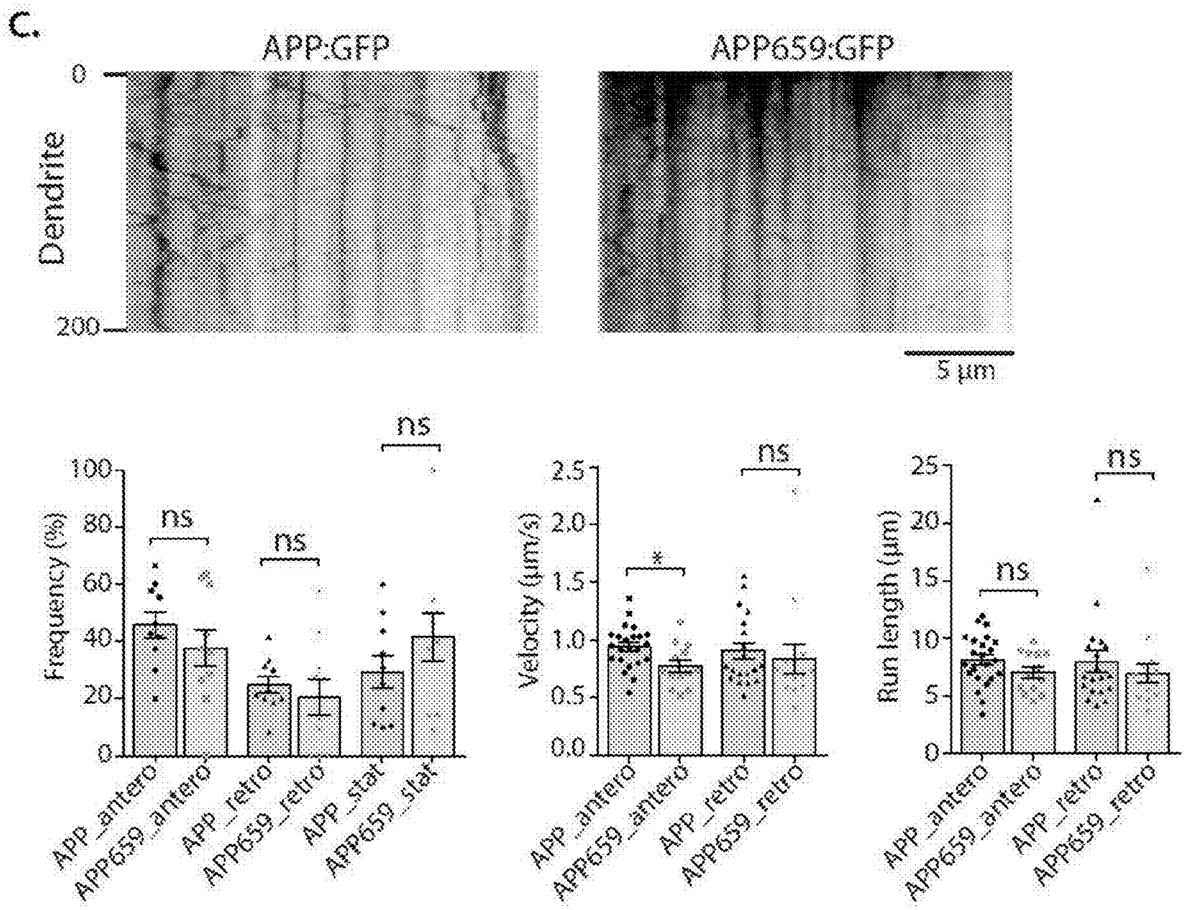
FIGS. 11A-11C show trafficking of vesicles carrying APP(WT) or APP(659).

To determine the mechanism by which the APP-sgRNA manipulates the amyloid pathway, we used a "CRISPR-mimic" truncated APP construct (APP-659) that is the major post-editing translational product in both mouse and human cells (see FIG. 2H, FIG. 6E, and FIG. 7D). Using our BifC assay (10), we first asked if the CRISPR-mimic APP-659 interacted with BACE-1. APP-659/BACE-1 approximation was greatly attenuated in cultured neurons (FIG. 5A), along with a decrease in β-CTF generation (FIG. 5B). Next, we visualized axonal and dendritic transport of APP-WT and APP-659. Although there were minor changes (FIGS. 11A-11C and Table 4), it seems unlikely that such small transport perturbations would lead to the dramatic attenuation of β-cleavage and Aβ-production seen in our experiments.

Figures 12A, 12B, 12C:
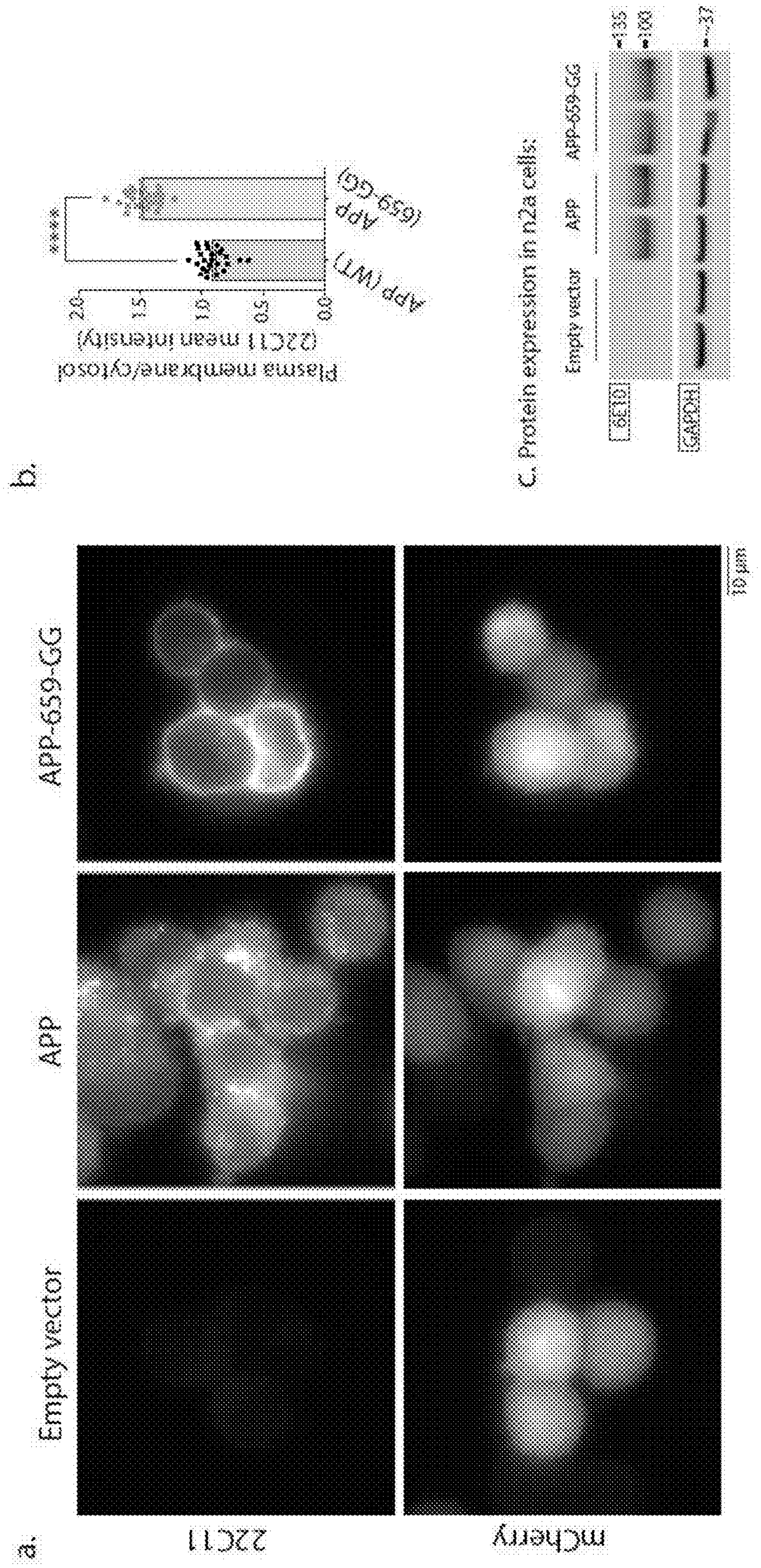
FIGS. 12A-12C show internalization of APP-659-GG (most common post-editing translational product).
Figure 18:
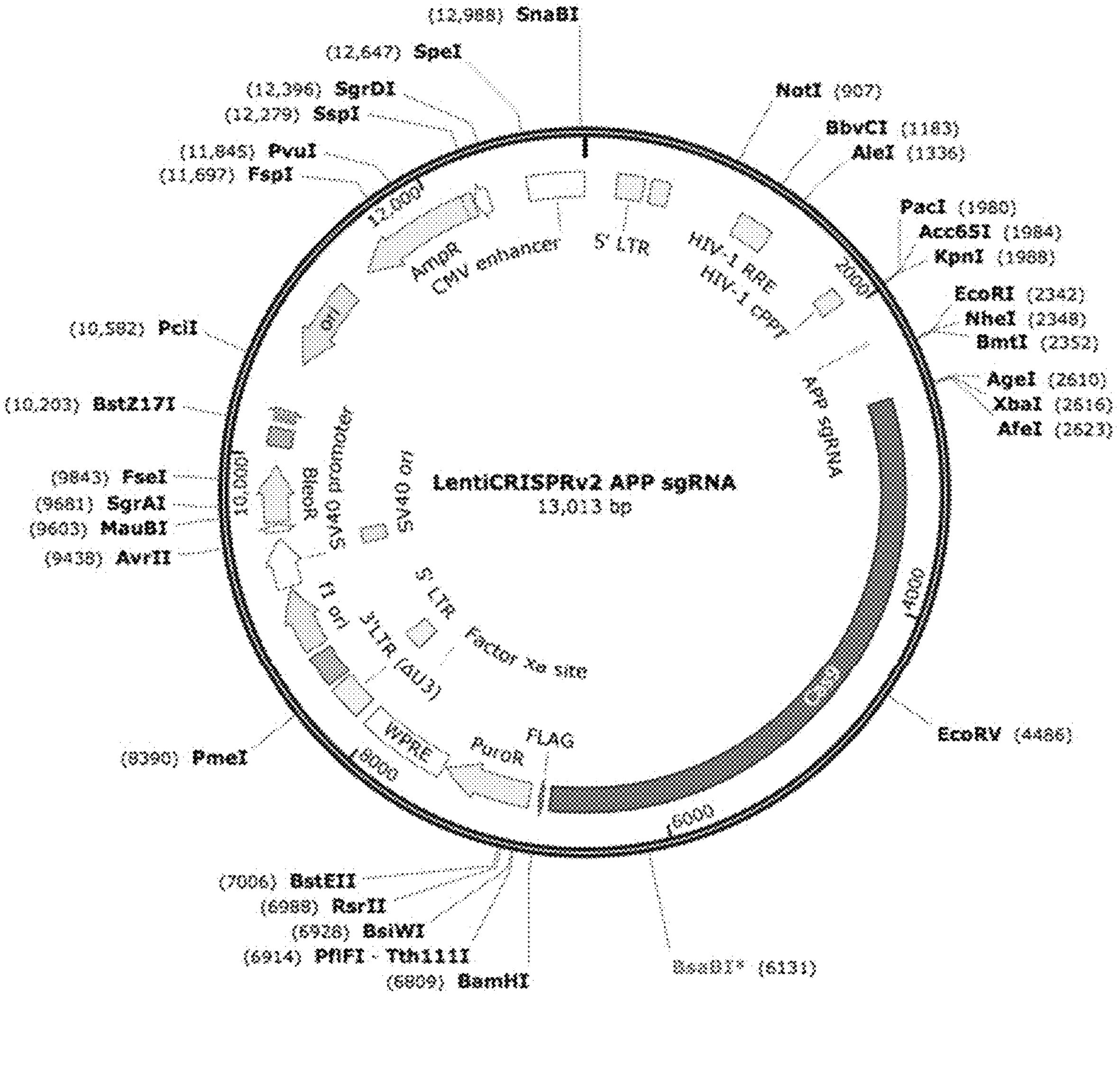
FIG. 18 shows the sequence and vector map of an exemplary lentiviral APP sgRNA vector (SEQ ID NO:20).

The CRISPR-edited segment of APP contains the residues T668 and Y682-Y687 (YENPTY motif, see FIG. 5C; also present in APLP1/2), that have been reported to play a role in Aβ production (12,23,24). Specifically, APP phosphorylated at T668 has been reported to colocalize with BACE-1 in endosomes (23), and the YENPTY motif is known to mediate APP internalization from the plasma membrane (25). Examining the effects of these residues in APP/BACE-1 BifC assays, we saw that the extent of APP/BACE-1 attenuation by the YENPTY mutation strongly resembled the decrease in fluorescence complementation by the APP-659 construct (FIG. 5D). A prediction from these experiments is that endocytosis of the CRISPR-mimic APP from the cell surface should be attenuated; and indeed, this was the case in internalization assays (FIG. 5E). Similar results were seen with an "APP-659-GG" construct that more closely resembles the most common post-editing translational product of our sgRNA (FIGS. 12A-12C; also see post-editing products from human cells in FIG. 2H and FIG. 6E).

Collectively, the data suggest that our gene-editing approach does not have a major effect on post-Golgi trafficking of APP, but attenuates its endocytosis from cell surface, and consequently, its interaction with BACE-1 in endosomes—though we cannot exclude a direct effect of editing on APP/BACE-1 interaction. This is also consistent with previous studies showing that surface APP is internalized into endosomes, where it is cleaved by BACE-1 (26-29). Since most of the APP α-cleavage is thought to occur at the cell surface (30), this may also explain why the non-amyloidogenic pathway is enhanced by our approach.

Using CRISPR/Cas9 technology, herein we provide conceptual proof for a strategy that selectively edits the C-terminus of APP and alters the balance of APP-cleavage—attenuating β-cleavage and Aβ, while upregulating neuroprotective α-cleavage. The N-terminus of APP—known to play physiologic roles—is unaffected, along with the compensatory APP homologues APLP1/2. No deleterious effects were seen in neurophysiologic parameters. Without wishing to be bound by any particular theory, our strategy likely works by editing the terminal YENPTY motif in APP that is responsible for its internalization, subsequent APP/BACE-1 association, and initiation of the amyloidogenic pathway; while retention of APP at the plasma membrane may facilitate the upregulation of APP α-cleavage.

APP processing is regulated by α-, β-, and γ-secretases; and the various cleavage products may play physiological functions that are not fully understood (31,32). Previous studies suggest that in vivo deletion of the APP C-terminus blocks APP β-cleavage without obvious effects on neuroanatomy, behavior and neuronal activity in adult mice (13). Notably, the APP homologues APLP 1/2 also have YENPTY motifs (15,16)—that can presumably undergo endocytosis and protein-protein interactions—and are expected to compensate for the loss of the C-terminus. The precise reasoning behind enhanced α-cleavage is unclear. We propose that retention of APP at the plasma membrane might be responsible, but we cannot rule out other causes, including off-target effects, and further detailed studies may provide clarity.

Methods

Constructs, antibodies and reagents—For transient co-expression of CRISPR/Cas9 components, APP sgRNA nucleotides were synthesized and cloned into pU6-(Bbs1)_CBh-Cas9-T2A-mCherry vector at Bbs1 site. For viral transduction, a dual vector system was used to deliver CRISPR/Cas9 components using AAV9 (33). For making the AAV9 vectors, the APP sgRNA was cloned into pAAV9-U6sgRNA(SapI)_hSyn-GFP-KASH-bGH vector at Sapl site. The CRISPR/Cas9 stable cell lines were generated by lentivirus infection as follows. The APP sgRNA was cloned into lentiCRISPR v2 vector at Bbs1 site to produce lentivirus (34). For making APP deletions and relevant constructs, the human APP659 truncation was PCR amplified and cloned at Hind3 and Sac2 sites of pVN to generate pAPP659:VN. The BBS-APP659 was PCR amplified and cloned into pBBS-APP:GFP at Hind3 and Sac2, replacing BBS-APP, to generate pBBS-APP659:GFP. The pBBS-APP$^{YENPTY}$:GFP was generated by site directed mutagenesis from pBBS-APP:GFP. The pAPP$^{T668A}$:VN and pAPP$^{T668A+YENPTY}$:VN were generated by site directed mutagenesis from pAPP:VN and pAPP$^{YENPTY}$:VN. Antibodies used were as follows: APP Y188 (ab32136; Abcam), APP 22C11 (MAB348; Millipore), APP 6E10 (803001; BioLegend), APP M3.2 (805701; BioLegend), APP 2E9 (MABN2295; Millipore), APP CT20 (171610; Millipore), sAPPβ (18957; IBL) BACE-1 (MAB931; R&D), GAPDH (MA5-15738, ThermoFisher), GFP (ab290, Abcam), GFP (A10262, Invitrogen), HA (901513, BioLegend), VAMP2 (104211, Synaptic Systems). Reagents were as follows: γ-secretase inhibitor BMS-299897 (Sigma), and Rho Kinase (ROCK)-inhibitor H-1152P (Calbiochem).

Cell cultures, transfections, viral production/infections, and biochemistry—HEK293 and neuro2a cells (ATCC) were maintained in DMEM with 10% FBS. Cells were transfected with Lipofectamine™ 2000 and collected 5 days after transfection for biochemical and immunostaining analysis. All the studies involving primary neuron culture were performed in accordance with University of Wisconsin guidelines. Primary hippocampal neurons were obtained from postnatal (P0-P1) CD1 mice (either sex), and transiently transfected using Lipofectamine™ 2000 or Amaxa™ 4D system (Lonza). Dissociated neurons were plated at a density of 30,000 cells/cm$^2$ on poly-D-lysine-coated glass-bottom culture dishes (Mattek) and maintained in Neurobasal™/B27 medium with 5% $CO_2$. For APP/BACE-1 interaction and APP transport studies, DIV 7 neurons were cultured for ~18-20 h after transfection. For spine density analysis, DIV7 neurons were transfected with Cas9, sgRNA and soluble marker, and cultured for 7 d before imaging. For testing the effect of CRISPR/Cas9 on neuronal development, neurons were electroporated with the respective constructs before plating using an Amaxa™ 4D-Nucleofector™ system with the P3 Primary Cell 4D-Nucleofector™ X kit S and program CL-133.

For western blotting, pre-synapse analyses and electrophysiology, DIV7 cultured neurons were infected with either AAV9-APP sgRNA-GFP (2.24×10$^{13}$ Vg/ml) and AAV9-Cas9 (2.4×10$^{14}$ Vg/ml), or AAV9-GFP (2.58×10$^{13}$ Vg/ml) and AAV9-Cas9 at a multiplicity of infection (MOI) of 1.5×10$^5$. Neurons were analyzed 7 days post-infection. Lentivirus was produced from HEK293FT cells as described (35). Briefly, HEK293FT cells (Life Technologies) were maintained in DMEM with 10% FBS, 0.1 mM NEAA, 1 mM sodium pyruvate and 2 mM Glutamine. Cells were transfected with lentiviral-target and helper plasmids at 80-90% confluency. 2 days after transfection, the supernatant was collected and filtered with 0.45 μm filter. For experiments with hESCs, cells were cultured on a Matrigel® substrate (BD Biosciences) and fed daily with TeSR-E8 culture media (StemCell Technologies). When the cells were around 60-70% confluent, they were infected with a 50/50 mixture of TeSR-E8 (with 1.0 μM H-1152P) and lentivirus supernatant. After 24 h, the virus was removed, and the cells were fed for 2 days (to recover). After 3 days, cells were treated with 0.33 μg/mL of puromycin for 72 h to select for virally-integrated hESCs. For HEK and neuro2a cell lines, cells were infected with the lentivirus carrying APP-sgRNA and Cas9 for 24 h. And then cells were fed for 1 day to recover. After 2 days, cells were treated with 1 μg/mL of puromycin for 72 h to select for virally-integrated cells.

Human NPCs were generated as has been described previously (36), using manual rosette selection and Matrigel® (Corning) to maintain them. Concentrated lentiviruses express control-sgRNA or APP-sgRNA were made as described previously (37), using Lenti-X™ concentrator (Clontech). The NPCs were transduced with either control-sgRNA or APP-sgRNA after Accutase® splitting and were submitted to puromycin selection the subsequent day. Polyclonal lines were expanded and treated with puromycin for 5 more days before banking. Neuronal differentiations were carried out by plating 165,000 cells/12 well-well in N2/B27 media (DMEM/F12 base) supplemented with BDNF (20 ng/mL; R&D) and laminin (1 ug/mL; Trevigen).

For biochemistry, cell lysates were prepared in PBS+0.15% Triton™ X-100 or RIPA supplemented with protease inhibitor cocktail, pH 7.4. After centrifuging at 12,000 g for 15 min at 4° C., supernatants were quantified and resolved by SDS-PAGE for western blot analysis. For sAPPα and sAPPβ detection, cell culture medium was collected and centrifuged at 2,000 g for 15 min at RT. The supernatants were resolved by SDS-PAGE for western blot analysis; band intensities were measured by ImageJ. Human Aβ40 and Aβ42 were detected using kits, according to the manufacturer's instructions (Thermo KHB3481 and KHB3544). Briefly, supernatants from H4$^{single\ copy}$ cells or human iPSC derived neurons were collected and diluted (×5 for H4 and ×2 for iPSC-neuron). The diluted supernatants and the human Aβ40/42 detection antibodies were then added into well and incubated for 3 h at RT with shaking. After washing (×4), the anti-Rabbit IgG HRP solution was added and incubated for 30 min at RT. The stabilized Chromogen was added after washing (×4) and incubated for another 30 min at RT in the dark. After addition of stop solution, absorbance at 450 nm was read using a luminescence microplate reader.

Developing a single-copy, stable APP/BACE-1 cell line—H4 tetOff FlpIn empty clone was maintained in OptiMEM® with 10% FBS, 200 μg/mL G418 and 300 μg/mL Zeocin. To generate an APP:VN/BACE-1:VC stable cell line carrying single copies of APP and BACE-1, the expressing plasmid and pOG44 plasmids were transfected with Lipofectamine™ 2000. 2 days after transfection, cells were selected with 200 μg/mL hygromycin B and 200 μg/mL G418 for 1 week. A monoclonal cell line with stable expression was selected. H4 stable cell lines were then infected with the lentivirus carrying APP-sgRNA and Cas9, as described above. After 24 h, the virus was removed, and cells were fed for 1 day to recover. After 2 days, cells were treated with 0.7 μg/mL of puromycin for 72 h to select for virally-integrated cells.

Generation of the APPLondon (V717I) knockin iPSC line—CRIPSR/Cas9 was used to knock in the APP V717I mutation (APPLon) into a commercially available control human iPSC line IMR90 (clone 4, WiCell). sgRNAs targeting Exon17 of APP were designed using the CRISPR design tool created by Feng Zhang's lab and subcloned into the MLM3636 vector (AddGene). Efficacy of multiple sgRNAs was first assessed in HEK293 cells (Geneart™ Genomic Cleavage Detection Kit, Life Technologies). The ssDNA HDR template was designed to include a silent CRISPR blocking mutation at the PAM site of most efficacious sgRNA in addition to the APPLon mutation. sgRNA, Cas9-2A-mCherry (generously provided by Hynek Wicterle), and ssDNA HDR template were electroporated (Lonza Nucleofector™) into feeder-free IMR90 iPSCs, followed by cell sorting on mCherry signal and plating at low density on MEFs (MTI-GlobalStem). Individual clones were manually picked into a 96 well format, subsequently split into duplicate plates, one of which were used to generate gDNA as had been done previously[38]. For each clone, exon 17 of APP was amplified and initially screened by restriction digest for the presence of a de novo Bell site introduce by the APPLon mutation. Sanger sequencing was used to confirm the mutation, and successful knockin clones were expanded and banked. Potential off-target effects of CRISPR/Cas9 cleavage were analyzed by Sanger sequencing of the top 5 predicted off-target genomic locations, which demonstrated a lack of indels for multiple clones. Clone 88 was picked for future studies.

Immunofluorescence, microscopy/image analysis, APP trafficking and endocytosis assays—For immunostaining of endogenous APP or VAMP2, cells were fixed in 4% PFA/sucrose solution in PBS for 10 min at room temperature (RT), extracted in PBS containing 0.2% Triton™ X-100 for 10 min at RT, blocked for 2 h at RT in 1% bovine serum albumin and 5% FBS, and then incubated with rabbit anti-APP (1:200) or mouse anti-VAMP2 (1:1000) diluted in blocking buffer for 2 h at RT. After removal of primary antibody, cells were blocked for 30 min at RT, incubated with goat anti-rabbit (Alexa Fluor 488) or goat anti-mouse (Alexa Fluor® 594) secondary antibody at 1:1000 dilution for 1 h at RT and then mounted for imaging. z-stack images (0.339 μm z-step) were acquired using an inverted epifluorescence microscope (Eclipse Ti-E) equipped with CFI S Fluor VC 40×NA 1.30 (Nikon). An electron-multiplying charge-coupled device camera (QuantEM: 512SC; Photometrics) and LED illuminator (SPECTRA X; Lumencor) were used for all image acquisition. The system was controlled by Elements software (NIS Elements Advanced Research). z-stacks were subjected to a maximum intensity projection. For APP Y188 staining, the average intensity of single cell body (neuro2A, HEK293 and neurons) or the whole colony (hESCs) was quantified. All the images were analyzed in Metamorph® and ImageJ.

Spine density experiments were done as described previously (39). Briefly, DIV 7 neurons were transfected with desired constructs for 7 days, and secondary dendrites were selected for imaging. z-stack images were captured using a 100× objective (0.2 μm z-step) and subjected to a maximum intensity projection for analysis. For the APP/BACE-1 complementation assay, DIV 7 neurons were transfected with desired constructs for ~15-18 h and fixed. z-stack images were captured using a 40× objective (0.339 μm z-step) and subjected to a maximum intensity projection. The average intensity within cell bodies was quantified.

For trafficking studies in axons and dendrites, imaging parameters were set at 1 frame/s and total 200 frames. Kymographs were generated in MetaMorph®, and segmental tracks were traced on the kymographs using a line tool. The resultant velocity (distance/time) and run length data were obtained for each track, frequencies of particle movements were calculated by dividing the number of individual particles moving in a given direction by the total number of analyzed particles in the kymograph, and numbers of particles per minute were calculated by dividing the number of particles moving in a given direction by the total imaging time.

APP endocytosis assay was done as described previously (40). Cells expressing APP-GFP, APP659-GFP, untagged APP or untagged APP-659-GG were starved with serum-free medium for 30 min and incubated with anti-APP (22C11) in complete medium with 10 mM HEPES for 10 min. And then, cells were fixed, permeabilized and immunostained for 22C11. The mean intensity of 22C11 along plasma membrane was calculated by dividing the total intensity along plasma membrane (=intensity of whole cell−intensity of cytoplasm) with area of plasma membrane (=area of whole cell−area of cytoplasm). The ratio of mean intensities between plasma membrane and cytoplasm was quantified.

Stereotactic injection of AAV9s into the mouse brain and histology—All the animal procedures were performed in accordance with University of Wisconsin guidelines. In vivo injection and immunofluorescence staining was done as described previously (41). Briefly, 1.5 μl of 1:2 AAV9 mixture of AAV9-APP sgRNA-GFP (or AAV9-GFP) and AAV9-Cas9 was injected into the dentate gyrus (−2.0, ±1.6, −1.9) of 8-week old male C57BL/6 mice (either sex). 2-weeks after surgery, the mice were sacrificed by transcardiac perfusion of saline, followed by 4% PFA. The brains were dissected, post-fixed with 4% PFA overnight, immersed in 30% sucrose until saturation, and sectioned at 40 μm. Sections were immunostained with the following antibodies: mouse anti-HA (1:1000, BioLegend, clone 16B12), chicken anti-GFP (1:1000, Invitrogen, polyclonal) and rabbit anti-APP (1:200, Abcam, clone Y188). Images were acquired using Zeiss LSM800 confocal microscope. Average intensities of APP staining in cell bodies were quantified using Metamorph®.

Intracerebroventricular injections and histology—All animal procedures were approved by the Mayo Institutional Animal Care and Use Committee and are in accordance with the NIH Guide for Care and Use of Laboratory animals. Free hand bilateral intracerebroventricular (ICV) injections were performed as previously described (42) in C57BL/6 mouse pups. On post-natal day 0, newborn pups were briefly cryoanesthetized on ice until no movement was observed. A 30-gauge needle attached to a 10 μl syringe (Hamilton) was used to pierce the skull of the pups just posterior to bregma and 2 mm lateral to the midline. The needle was held at a depth of approximately 2 millimeters, and 2 μl of a mixture of AAV9 viruses (ratio 1:2 of AAV9-APP sgRNA-GFP or AAV9-GFP+AAV9-Cas9) were injected into each cerebral ventricle. After 5 minutes of recovery on a heat pad, the pups were returned into their home cages. Mice were sacrificed 15 days after viral injection. Animals were deeply anesthetized with sodium pentobarbital prior to transcardial perfusion with phosphate buffered saline (PBS), and the brain was removed and bisected along the midline. The left hemisphere was drop-fixed in 10% neutral buffered formalin (Fisher Scientific, Waltham, MA) overnight at 4° C. for histology, whereas the right hemisphere of each brain was snap-frozen and homogenized for biochemical analysis. Formalin fixed brains were embedded in paraffin wax, sectioned in a sagittal plane at 5-micron thickness, and mounted on glass slides. Tissue sections were then deparaffinized in xylene and rehydrated. Antigen retrieval was performed by steaming in distilled water for 30 min, followed by permeabilization with 0.5% Triton™-X, and blocking with 5% goat serum for 1 hour. Sagittal sections were then incubated with primary anti-GFP antibody (1:250, Aves, chicken polyclonal) and anti-APP antibody (1:200, Abcam, clone Y188) overnight at 4° C. Sections were incubated with the secondary antibodies Alexa Fluor®-488-goat anti-chicken and Alexa Fluro®-568-goat anti rabbit (1:500, Invitrogen) for 2h at room temperature. Sections were washed and briefly dipped into 0.3% Sudan Black in 70% ethanol prior to mounting.

Electrophysiology—A coverslip with cultured cells at a density of 60,000 cells/$cm^2$ was placed in a continuously perfused bath, viewed under IR-DIC optics and whole-cell voltage clamp recordings were performed (−70 mV, room temp.). The extracellular solution consisted of (in mM): 145 NaCl, 2.5 KCl, 1 MgCl2, 2 CaCl2), 10 HEPES and 10 dextrose, adjusted to 7.3 pH with NaOH and 320 mOsm with sucrose. Whole-cell recordings were made with pipette solutions consisting of (in mM) 140 KCl, 10 EGTA, 10 HEPES, 2 Mg2ATP and 20 phosphocreatine, adjusted to pH 7.3 with KOH and 315 mOsm with sucrose. Excitatory synaptic events were isolated by adding 10 μM bicuculline to block GABA (subscript A) receptors. Miniature synaptic events were isolated by adding 100 nM tetrodotoxin to prevent action potentials. mEPSCs were detected using the template-matching algorithm in Axograph X, with a template that had 0.5 ms rise time and 5 ms decay. Statistics were computed using the Statistics Toolbox of Matlab.

T7 Endonuclease 1 Assay, Off-target, and ICE analyses—Genomic PCR was performed around each sgRNA target, and related off-target sites, following the manufacturer's instruction (using AccuPrime™ HiFi Taq using 500 ng of genomic DNA). Products were then purified using Wizard® SV Gel and PCR Clear-Up System (Promega) and quantified using a Qubit® 2.0 (Thermo Fischer). T7E1 assay was performed according to manufacturer's instructions (New England Biolabs). Briefly, 200 ng of genomic PCR was combined with 2 μL of NEBuffer™ 2 (New England Biolabs) and diluted to 19 μL. Products were then hybridized by denaturing at 95° C. for 5 minutes then ramped down to 85° C. at −2° C./second. This was followed by a second decrease to 25° C. at −0.1° C./second. To hybridized product, 1 μL T7E1 (M0302, New England Biolabs) was added and mixed well followed by incubation at 37° C. for 15 minutes. Reaction was stopped by adding 1.5 μL of 0.25M EDTA. Products were analyzed on a 3% agarose gel and quantified using a Gel Doc XR system (BioRad). Off-target sites were identified and scored using Benchling. The top 5 off-target sites—chosen on the basis of raw score and irrespective of being in a coding region—were identified and analyzed using T7E1 assay as previously described. For TIDE (43), PCR was performed on genomic DNA using Accuprime™ Taq HiFi (Thermo Fischer) according to manufacture specifications. Briefly, reactions were cycled at 2 min at 94° C. followed by 35 cycles of 98° C. for 30 seconds, 58° C. for 30 seconds, and 68° C. for 2 minutes 30 seconds and a final extension phase of 68° C. for 10 minutes. Products were then subjected to Sanger Sequencing and analyzed using the TIDE platform. The primers used for TIDE analyses are listed in Table 3. For analyses of indel after CRISPR editing with APP670-sgRNA and APP676-sgRNA, the edited regions of genomic DNA were PCR amplified and subjected to Sanger Sequencing. The results were analyzed using the ICE platform.

Deep Sequencing Sample Preparation and data analysis—Genomic PCR was performed using AccuPrime™ HiFi Taq (Life Technologies) following manufacturer's instructions. About 200-500 ng of genomic DNA was used for each PCR reaction. Products were then purified using AMPure® XP magnetic bead purification kit (Beckman Coulter) and quantified using a Nanodrop2000. Individual samples were pooled and run on an Illumina® HiSeq2500 High Throughput at a run length of 2×125 bp. A custom python script was developed to perform sequence analysis. For each sample, sequences with frequency of less than 100 reads were filtered from the data. Sequences in which the reads matched with primer and reverse complement subsequences classified as target sequences. These sequences were then aligned with corresponding wildtype sequence using global pairwise sequence alignment. Sequences that were misaligned through gaps or insertions around the expected cut site were classified as NHEJ events. The frequency, length, and position of matches, insertions, deletions, and mismatches were all tracked in the resulting aligned sequences.

Statistical analysis—Statistical analysis was performed and plotted using Prism software. Student's t-test (unpaired, two-tailed) was used to compare two groups. One-way ANOVA test was used to compare multiple groups, following with Tukey multiple comparison test of every pair. A P-value<0.05 was considered significant.

TABLE 3

PCR PRIMERS USED FOR ON- AND OFF- TARGET GENOMIC LOCI AMPLIFICATION

| | Forward primer sequence (5′-3′) | SEQ ID NO: | Reverse primer sequence (5′-3′) | SEQ ID NO: |
|---|---|---|---|---|
| Mouse APP (659) | AGGAACGGAGTGACCTGTTTCC | 21 | TTCCTCCATGGTAACCACGCAT | 22 |
| Human APP (659) | TGGGGAAGCCACATGTTGTACA | 23 | ATGTTTTGGTGGGCCATTTGGT | 24 |
| Human APP (670; 676) | AAATTATGGGTGTTCTGCAATCTTGG | 25 | ACTTGTGTTACAGCACAGCTGTC | 26 |
| Mouse OT1 | GCCCTCCAGAAGTATTGGCTT | 27 | GTCAGGGCCTTGCTCTACAAA | 28 |
| Mouse OT2 | CGCAAAAACTGGCTGCGTAT | 29 | TGTAGGCGCACATGCAGAAG | 30 |
| Mouse OT3 | CAGGTAGAGCGTGGAAACTCA | 31 | TGTGCGCATTAGGACCAGAT | 32 |
| Mouse OT4 | CACCTGACAATGCTGTCCCA | 33 | AGACAAGGTCTGTCTCCTTGC | 34 |
| Mouse OT5 | CCAACTCTTTGCTTAGGGGC | 35 | ATCGTCCCTGGTGCATTCTC | 36 |
| Human OT1 | GGAAAACCAGGTAGAGGGGG | 37 | TCTCTGGCTCGAGGGTACAT | 38 |
| Human OT2 | CTGCATGCCATGGGTAGGTA | 39 | CAGGCTGTTTCGGGTCCTT | 40 |
| Human OT3 | AGACTCTTCTCCGATTCCAGC | 41 | TCCAGCACGATCTGGTAGGC | 42 |
| Human OT4 | AGTGCTTTTCTTTGCCTTTGCT | 43 | TGCTCGGGAGGTGTTTCTAC | 44 |
| Human OT5 | AACAAGGCAGCTCCTCAACT | 45 | GACGTCAGAATTGAGGGTGGA | 46 |

TABLE 3-continued

| PCR PRIMERS USED FOR ON- AND OFF- TARGET GENOMIC LOCI AMPLIFICATION | | | | |
|---|---|---|---|---|
| | Forward primer sequence (5'-3') | SEQ ID NO: | Reverse primer sequence (5'-3') | SEQ ID NO: |
| Mouse APLP1 | CCAGCGGGATGAACTGGTAAGA | 47 | CCCAGGTCACCTTAAGGAGCAA | 48 |
| Mouse APLP2 | GAGAGAGTTGGAGGCCTTGAGG | 49 | AACCACAGTGACAAGTGGCTCT | 50 |
| Human APLP1 | GTGAATGCGTCTGTTCCAAGGG | 51 | GCTGCTGGGACTATCTGGGAAT | 52 |
| Human APLP2 | TTTTAGGGGCTCGACCTTCCAG | 53 | TGCACTAATTTCCCAGGGCTCA | 54 |

TABLE 4

| TRANSPORT PARAMETERS OF WT AND APP659 | | | | | | | |
|---|---|---|---|---|---|---|---|
| | % Anterograde | % Retrograde | % Stationary | Anterograde Run-length (μm) | Retrograde Run-length (μm) | Anterograde velocity (μm/sec), mean ± SEM | Retrograde velocity (μm/sec), mean ± SEM |
| Kinetics in axons | | | | | | | |
| APP659 | 53.88 ± 4.57 | 37.13 ± 4.36 | 8.97 ± 1.51 | 8.08 ± 0.31 | 6.8 ± 0.26 | 1.66 ± 0.03 | 1.52 ± 0.03 |
| APPWT | 57.84 ± 2.22 | 34.37 ± 4.46 | 10.42 ± 4.24 | 10.44 ± 0.42 | 6.35 ± 0.26 | 1.97 ± 0.03 | 1.52 ± 0.03 |
| Kinetics in dendrites | | | | | | | |
| APP659 | 37.81 ± 6.45 | 20.55 ± 6.21 | 41.64 ± 8.37 | 7.0 ± 0.48 | 6.94 ± 0.81 | 0.76 ± 0.05 | 0.83 ± 0.12 |
| APPWT | 45.83 ± 4.58 | 24.81 ± 2.97 | 29.35 ± 5.63 | 8.12 ± 0.46 | 7.98 ± 0.94 | 0.94 ± 0.03 | 0.9 ± 0.07 |

~115 APP659: GFP and ~130 APP: GFP vesicles analyzed in dendrites;
~310 APP659: GFP and ~325 APP: GFP vesicles in axons (from 10-12 neurons from 2 separate cultures.)

TABLE 5

| APP SGRNAS TARGETING SEQUENCES | | |
|---|---|---|
| | sgRNA targeting sequence | SEQ ID NO: |
| Human APP 659 | ATCCATTCATCATGGTGTGG | 1 |
| Human APP 670 | TGGACAGGTGGCGCTCCTCT | 2 |
| Human APP 676 | GTAGCCGTTCTGCTGCATCT | 4 |
| Mouse APP 659 | ATCCATCCATCATGGCGTGG | 6 |
| Mouse APP 670 | TGGAGAGATGGCGCTCCTCT | 7 |
| Mouse APP 676 | ATATCCGTTCTGCTGCATCT | 9 |

REFERENCES

1) Fellmann, C., Gowen, B. G., Lin, P. C., Doudna, J. A. & Corn, J. E. Cornerstones of CRISPR-Cas in drug discovery and therapy. *Nat Rev Drug Discov* 16, 89-100, doi: 10.1038/nrd.2016.238 (2017).

2) Yang, S. et al. CRISPR/C as 9-mediated gene editing ameliorates neurotoxicity in mouse model of Huntington's disease. *J Clin Invest* 127, 2719-2724, doi:10.1172/JCI92087 (2017).

3) Park, C. Y. et al. Reversion of FMR1 Methylation and Silencing by Editing the Triplet Repeats in Fragile X iPSC-Derived Neurons. *Cell Rep* 13, 234-241, doi: 10.1016/j.celrep.2015.08.084 (2015).

4) Gyorgy, B. et al. CRISPR/Cas9 Mediated Disruption of the Swedish APP Allele as a Therapeutic Approach for Early-Onset Alzheimer's Disease. *Mol Ther Nucleic Acids* 11, 429-440, doi:10.1016/j.omtn.2018.03.007 (2018).

5) McMahon, M. A. & Cleveland, D. W. Gene therapy: Gene-editing therapy for neurological disease. *Nat Rev Neurol* 13, 7-9, doi:10.1038/nrneurol.2016.190 (2017).

6) Mockett, B. G., Richter, M., Abraham, W. C. & Muller, U. C. Therapeutic Potential of Secreted Amyloid Precursor Protein APPsalpha. *Front Mol Neurosci* 10, 30, doi: 10.3389/fnmol.2017.00030 (2017).

7) O'Brien, R. J. & Wong, P. C. Amyloid precursor protein processing and Alzheimer's disease. *Annu Rev Neurosci* 34, 185-204, doi:10.1146/annurev-neuro-061010-113613 (2011).

8) Fol, R. et al. Viral gene transfer of APPsalpha rescues synaptic failure in an Alzheimer's disease mouse model. *Acta Neuropathol* 131, 247-266, doi:10.1007/s00401-015-1498-9 (2016).

9) Richter, M. C. et al. Distinct in vivo roles of secreted APP ectodomain variants APPsalpha and APPsbeta in regulation of spine density, synaptic plasticity, and cognition. *EMBO J* 37, doi:10.15252/embj.201798335 (2018).

10) Das, U. et al. Visualizing APP and BACE-1 approximation in neurons yields insight into the amyloidogenic pathway. *Nat Neurosci* 19, 55-64, doi:10.1038/nn.4188 (2016).

11) Citron, M., Teplow, D. B. & Selkoe, D. J. Generation of amyloid beta protein from its precursor is sequence specific. *Neuron* 14, 661-670, doi:0896-6273(95)90323-2 [pii] (1995).

12) Koo, E. H. & Squazzo, S. L. Evidence that production and release of amyloid beta-protein involves the endocytic pathway. *J Biol Chem* 269, 17386-17389 (1994).

13) Ring, S. et al. The secreted beta-amyloid precursor protein ectodomain APPs alpha is sufficient to rescue the anatomical, behavioral, and electrophysiological abnormalities of APP-deficient mice. *J Neurosci* 27, 7817-7826, doi:10.1523/JNEUROSCI.1026-07.2007 (2007).
14) Sander, J. D. & Joung, J. K. CRISPR-Cas systems for editing, regulating and targeting genomes. *Nat Biotechnol* 32, 347-355, doi:10.1038/nbt.2842 (2014).
15) Muller, U. C. & Zheng, H. Physiological functions of APP family proteins. *Cold Spring Harb Perspect Med* 2, a006288, doi:10.1101/cshperspect.a006288 (2012).
16) Muller, U. C., Deller, T. & Korte, M. Not just amyloid: physiological functions of the amyloid precursor protein family. *Nat Rev Neurosci* 18, 281-298, doi:10.1038/nrn.2017.29 (2017).
17) Carlson-Stevermer, J. et al. Assembly of CRISPR ribonucleoproteins with biotinylated oligonucleotides via an RNA aptamer for precise gene editing. *Nat Commun* 8, 1711, doi:10.1038/s41467-017-01875-9 (2017).
18) Deyts, C., Thinakaran, G. & Parent, A. T. APP Receptor? To Be or Not To Be. *Trends Pharmacol Sci* 37, 390-411, doi:10.1016/j.tips.2016.01.005 (2016).
19) Beckett, C., Nalivaeva, N. N., Belyaev, N. D. & Turner, A. J. Nuclear signalling by membrane protein intracellular domains: the AICD enigma. *Cell Signal* 24, 402-409, doi:10.1016/j.cellsig.2011.10.007 (2012).
20) Pardossi-Piquard, R. & Checler, F. The physiology of the beta-amyloid precursor protein intracellular domain AICD. *J Neurochem* 120 Suppl 1, 109-124, doi:10.1111/j.1471-4159.2011.07475.x (2012).
21) Passini, M. A. & Wolfe, J. H. Widespread gene delivery and structure-specific patterns of expression in the brain after intraventricular injections of neonatal mice with an adeno-associated virus vector. *J Virol* 75, 12382-12392, doi:10.1128/JVI.75.24.12382-12392.2001 (2001).
22) Kim, J. Y., Grunke, S. D. & Jankowsky, J. L. Widespread Neuronal Transduction of the Rodent CNS via Neonatal Viral Injection. *Methods Mol Biol* 1382, 239-250, doi:10.1007/978-1-4939-3271-9_17 (2016).
23) Lee, M. S. et al. APP processing is regulated by cytoplasmic phosphorylation. *J Cell Biol* 163, 83-95, doi:10.1083/jcb.200301115 (2003).
24) Perez, R. G. et al. Mutagenesis identifies new signals for beta-amyloid precursor protein endocytosis, turnover, and the generation of secreted fragments, including Abeta42. *J Biol Chem* 274, 18851-18856 (1999).
25) Lai, A., Sisodia, S. S. & Trowbridge, I. S. Characterization of sorting signals in the beta-amyloid precursor protein cytoplasmic domain. *J Biol Chem* 270, 3565-3573 (1995).
26) Thinakaran, G. & Koo, E. H. Amyloid precursor protein trafficking, processing, and function. *J Biol Chem* 283, 29615-29619, doi:10.1074/jbc.R800019200 (2008).
27) Vassar, R. et al. Function, therapeutic potential and cell biology of BACE proteases: current status and future prospects. *J Neurochem* 130, 4-28, doi:10.1111/jnc.12715 (2014).
28) Morel, E. et al. Phosphatidylinositol-3-phosphate regulates sorting and processing of amyloid precursor protein through the endosomal system. *Nat Commun* 4, 2250, doi:10.1038/ncomms3250 (2013).
29) Das, U. et al. Activity-induced convergence of APP and BACE-1 in acidic microdomains via an endocytosis-dependent pathway. *Neuron* 79, 447-460, doi:10.1016/j.neuron.2013.05.035 (2013).
30) Sisodia, S. S. Beta-amyloid precursor protein cleavage by a membrane-bound protease. *Proc Natl Acad Sci USA* 89, 6075-6079 (1992).
31) Chow, V. W., Mattson, M. P., Wong, P. C. & Gleichmann, M. An overview of APP processing enzymes and products. *Neuromolecular Med* 12, 1-12, doi:10.1007/s12017-009-8104-z (2010).
32) Sun, J. & Roy, S. The physical approximation of APP and BACE-1: A key event in alzheimer's disease pathogenesis. *Dev Neurobiol* 78, 340-347, doi:10.1002/dneu.22556 (2018).
33) Swiech, L. et al. In vivo interrogation of gene function in the mammalian brain using CRISPR-Cas9. *Nat Biotechnol* 33, 102-106, doi:10.1038/nbt.3055 (2015).
34) Sanjana, N. E., Shalem, O. & Zhang, F. Improved vectors and genome-wide libraries for CRISPR screening. *Nat Methods* 11, 783-784, doi:10.1038/nmeth.3047 (2014).
35) Joung, J. et al. Genome-scale CRISPR-Cas9 knockout and transcriptional activation screening. *Nat Protoc* 12, 828-863, doi:10.1038/nprot.2017.016 (2017).
36) Topol, A., Tran, N. N. & Brennand, K. J. A guide to generating and using hiPSC derived NPCs for the study of neurological diseases. *J Vis Exp*, e52495, doi:10.3791/52495 (2015).
37) Aime, P. et al. Trib3 Is Elevated in Parkinson's Disease and Mediates Death in Parkinson's Disease Models. *J Neurosci* 35, 10731-10749, doi:10.1523/JNEUROSCI.0614-15.2015 (2015).
38) Paquet, D. et al. Efficient introduction of specific homozygous and heterozygous mutations using CRISPR/Cas9. *Nature* 533, 125-+, doi:10.1038/nature17664 (2016).
39) Tang, Y. et al. Early and selective impairments in axonal transport kinetics of synaptic cargoes induced by soluble amyloid beta-protein oligomers. *Traffic* 13, 681-693, doi:10.1111/j.1600-0854.2012.01340.x (2012).
40) Ubelmann, F. et al. Bin1 and CD2AP polarise the endocytic generation of beta-amyloid. *EMBO Rep* 18, 102-122, doi:10.15252/embr.201642738 (2017).
41) Guo, W. et al. Fragile X Proteins FMRP and FXR2P Control Synaptic GluA1 Expression and Neuronal Maturation via Distinct Mechanisms. *Cell Rep* 11, 1651-1666, doi:10.1016/j.celrep.2015.05.013 (2015).
42) Chakrabarty, P. et al. Capsid serotype and timing of injection determines AAV transduction in the neonatal mice brain. *PLoS One* 8, e67680, doi:10.1371/journal.pone.0067680 (2013).
43) Brinkman, E. K., Chen, T., Amendola, M. & van Steensel, B. Easy quantitative assessment of genome editing by sequence trace decomposition. *Nucleic Acids Res* 42, e168, doi:10.1093/nar/gku936 (2014).

The invention claimed is:

1. A method of pre-treating a patient at risk of having or acquiring Alzheimer's disease (AD) caused by formation of amyloid plaques composed of amyloid beta (AB) peptides, wherein the method comprises the steps of (a) obtaining a gene-editing construct specific for the amyloid precursor protein (APP), wherein the gene-editing construct facilitates truncation of the APP C-terminus when combined with a Cas9 nuclease, and (b) delivering the gene-editing construct and a construct encoding the Cas9 nuclease to a patient in need of AD therapy, wherein the APP molecule is truncated and production of Aβ peptides is decreased in the patient's brain, wherein the truncation of the APP C-terminus occurs at an APP residue selected from the group consisting of 659, 670, 676, and 686 relative to SEQ ID NO: 12 (human) or SEO ID NO: 14 (mouse).

2. The method of claim 1, wherein the gene-editing construct comprises a gRNA sequence selected from the group consisting of SEQ ID NOs: 1-10.

3. The method of claim 1, wherein the gene-editing construct and the construct encoding the Cas9 nuclease are delivered in a composition comprising an adeno-associated viral vector and a nanocarrier delivery vehicle.

4. The method of claim 3, wherein the composition is delivered intravenously or intrathecally.

5. The method of claim 1, wherein the patient has a genetic risk factor for AD or a family history of AD.

6. The method of claim 5, wherein the patient has an APPV717I mutation.

* * * * *